US011185327B2

(12) United States Patent
Harris et al.

(10) Patent No.: US 11,185,327 B2
(45) Date of Patent: Nov. 30, 2021

(54) METHOD OF SURGICAL STAPLING WITH END EFFECTOR COMPONENT HAVING A CURVED TIP

(71) Applicant: Ethicon LLC, Guaynabo, PR (US)

(72) Inventors: Jason L. Harris, Lebanon, OH (US); Gregory J. Bakos, Mason, OH (US); Chester O. Baxter, III, Loveland, OH (US); Frederick E. Shelton, IV, Hilsboro, OH (US); Hilary A. Reinhardt, Cincinnati, OH (US); Christopher J. Hess, Blue Ash, OH (US); Taylor W. Aronhalt, Loveland, OH (US); Daniel L. Baber, West Chester, OH (US)

(73) Assignee: Cilag GmbH International, Zug (CH)

( * ) Notice: Subject to any disclaimer, the term of this patent is extended or adjusted under 35 U.S.C. 154(b) by 80 days.

(21) Appl. No.: 16/212,868

(22) Filed: Dec. 7, 2018

(65) Prior Publication Data
US 2019/0175173 A1    Jun. 13, 2019

Related U.S. Application Data

(63) Continuation of application No. 16/035,893, filed on Jul. 16, 2018, which is a continuation-in-part of (Continued)

(51) Int. Cl.
*A61B 17/072* (2006.01)
*A61B 17/068* (2006.01)
(Continued)

(52) U.S. Cl.
CPC .... *A61B 17/07207* (2013.01); *A61B 17/0686* (2013.01); *A61B 17/07292* (2013.01);
(Continued)

(58) Field of Classification Search
CPC .......... A61B 17/07207; A61B 17/0686; A61B 17/07292; A61B 17/368; A61B 17/0218;
(Continued)

(56) References Cited

U.S. PATENT DOCUMENTS 4,805,823 A   2/1989   Rothfuss
5,014,899 A   5/1991   Presty et al.
(Continued)

FOREIGN PATENT DOCUMENTS

EP   2772202   9/2014
WO   WO 2004/096057   11/2004
(Continued)

OTHER PUBLICATIONS

European Search Report, Partial, and Written Opinion dated Dec. 9, 2019 for Application No. EP 19186224.2, 11 pgs.
(Continued)

*Primary Examiner* — Chelsea E Stinson
*Assistant Examiner* — Mary C Hibbert-Copeland
(74) *Attorney, Agent, or Firm* — Frost Brown Todd LLC

(57) ABSTRACT

A method of surgical stapling that uses a surgical instrument operable to compress, staple, and cut tissue. The instrument includes a body, a shaft, and an end effector with a pair of jaws. A placement tip extends distally from one of the jaws of the end effector. The method includes positioning the end effector at a desired site for surgical stapling. The method also includes controlling one or more of the jaws of the end effector to place the end effector in an open position. The method also includes positioning the end effector such that tissue is located between the jaws. The method also includes clamping the tissue between the jaws by moving at least one of the jaws toward the other jaw. The method also includes advancing a firing beam of the apparatus from a proximal position to a distal position.

20 Claims, 77 Drawing Sheets

Related U.S. Application Data application No. 15/435,573, filed on Feb. 17, 2017, now Pat. No. 10,828,031.

(51) Int. Cl.
   *A61B 17/34* (2006.01)
   *A61B 17/00* (2006.01)
   *A61B 17/02* (2006.01)
   *A61B 17/29* (2006.01)
   *A61B 17/32* (2006.01)

(52) U.S. Cl.
   CPC ...... *A61B 17/3468* (2013.01); *A61B 17/0218* (2013.01); *A61B 2017/0046* (2013.01); *A61B 2017/00398* (2013.01); *A61B 2017/00526* (2013.01); *A61B 2017/00845* (2013.01); *A61B 2017/00862* (2013.01); *A61B 2017/00893* (2013.01); *A61B 2017/00946* (2013.01); *A61B 2017/07221* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2927* (2013.01); *A61B 2017/320044* (2013.01)

(58) Field of Classification Search
   CPC .. A61B 2017/00398; A61B 2017/0046; A61B 2017/00526; A61B 2017/00845; A61B 2017/008862; A61B 2017/00893; A61B 2017/00946; A61B 2017/07221; A61B 2017/07257; A61B 2017/07264; A61B 2017/07271; A61B 2017/07278; A61B 2017/07285; A61B 2017/2927; A61B 2017/320044
   USPC ...................................................... 227/176.1
   See application file for complete search history.

(56) References Cited

U.S. PATENT DOCUMENTS

| | | | |
|---|---|---|---|
| 5,415,334 A | | 5/1995 | Williamson et al. |
| 5,465,895 A | | 11/1995 | Knodel et al. |
| 5,597,107 A | | 1/1997 | Knodel et al. |
| 5,632,432 A | | 5/1997 | Schulze et al. |
| 5,673,840 A | | 10/1997 | Schulze et al. |
| 5,704,534 A | | 1/1998 | Huitema et al. |
| 5,752,965 A | | 5/1998 | Francis et al. |
| 5,792,135 A | | 8/1998 | Madhani et al. |
| 5,814,055 A | | 9/1998 | Knodel et al. |
| 5,817,084 A | | 10/1998 | Jensen |
| 5,878,193 A | | 3/1999 | Wang et al. |
| 6,231,565 B1 | | 5/2001 | Tovey et al. |
| 6,364,888 B1 | | 4/2002 | Niemeyer et al. |
| 6,783,524 B2 | | 8/2004 | Anderson et al. |
| 6,939,358 B2 | | 9/2005 | Palacios et al. |
| 6,978,921 B2 | | 12/2005 | Shelton et al. |
| 7,000,818 B2 | | 2/2006 | Shelton et al. |
| 7,143,923 B2 | | 12/2006 | Shelton et al. |
| 7,303,108 B2 | | 12/2007 | Shelton |
| 7,367,485 B2 | | 5/2008 | Shelton et al. |
| 7,380,695 B2 | | 6/2008 | Doll et al. |
| 7,380,696 B2 | | 6/2008 | Shelton et al. |
| 7,404,508 B2 | | 7/2008 | Smith et al. |
| 7,434,715 B2 | | 10/2008 | Shelton et al. |
| 7,524,320 B2 | | 4/2009 | Tierney et al. |
| 7,644,848 B2 | | 1/2010 | Swayze et al. |
| 7,691,098 B2 | | 4/2010 | Wallace et al. |
| 7,721,930 B2 | | 5/2010 | McKenna et al. |
| 7,806,891 B2 | | 10/2010 | Nowlin et al. |
| 8,066,166 B2 | | 11/2011 | Demmy et al. |
| 8,136,711 B2 | | 3/2012 | Beardsley et al. |
| 8,210,411 B2 | | 7/2012 | Yates et al. |
| 8,348,123 B2 | | 1/2013 | Scirica et al. |
| 8,403,195 B2 | | 3/2013 | Beardsley et al. |
| 8,403,196 B2 | | 3/2013 | Beardsley et al. |
| 8,408,439 B2 | | 4/2013 | Huang et al. |
| 8,453,914 B2 | | 6/2013 | Laurent et al. |
| 8,479,969 B2 | | 7/2013 | Shelton |
| 8,496,153 B2 | | 7/2013 | Demmy et al. |
| 8,573,461 B2 | | 11/2013 | Shelton et al. |
| 8,573,465 B2 | | 11/2013 | Shelton |
| 8,602,288 B2 | | 12/2013 | Shelton et al. |
| 8,616,431 B2 | | 12/2013 | Timm et al. |
| 8,690,039 B2 | | 4/2014 | Beardsley et al. |
| 8,714,429 B2 | | 5/2014 | Demmy |
| 8,783,541 B2 | | 7/2014 | Shelton et al. |
| 8,800,838 B2 | | 8/2014 | Shelton |
| 8,820,605 B2 | | 9/2014 | Shelton |
| 8,844,789 B2 | | 9/2014 | Shelton et al. |
| 8,844,790 B2 | | 9/2014 | Demmy et al. |
| 9,016,546 B2 | | 4/2015 | Demmy et al. |
| 9,039,736 B2 | | 5/2015 | Scirica et al. |
| 9,186,142 B2 | | 11/2015 | Fanelli et al. |
| 9,301,759 B2 | | 4/2016 | Spivey et al. |
| 9,433,416 B2 | | 9/2016 | Beardsley et al. |
| 9,517,065 B2 | | 12/2016 | Simms et al. |
| 9,522,004 B2 | | 12/2016 | Demmy |
| 9,597,078 B2 | | 3/2017 | Scirica et al. |
| 9,622,746 B2 | | 4/2017 | Simms et al. |
| 9,713,470 B2 | | 7/2017 | Scirica et al. |
| 9,717,497 B2 | | 8/2017 | Zerkle et al. |
| 9,795,379 B2 | | 10/2017 | Leimbach et al. |
| 9,808,248 B2 | | 11/2017 | Hoffman |
| 9,839,421 B2 | | 12/2017 | Zerkle et al. |
| 9,913,642 B2 | | 3/2018 | Leimbach et al. |
| 9,936,952 B2 | | 4/2018 | Demmy |
| 9,936,968 B2 | | 4/2018 | Demmy et al. |
| 9,943,311 B2 | | 4/2018 | Scirica et al. |
| 10,080,564 B2 | | 9/2018 | Beardsley et al. |
| 10,111,660 B2 | | 10/2018 | Hemmann |
| D833,010 S | | 11/2018 | Harris et al. |
| D836,198 S | | 12/2018 | Harris et al. |
| D836,199 S | | 12/2018 | Schowalter et al. |
| 10,166,023 B2 | | 1/2019 | Vendely et al. |
| 10,182,813 B2 | | 1/2019 | Leimbach et al. |
| 10,349,940 B2 | | 7/2019 | Zeiner et al. |
| 2004/0243151 A1 | | 12/2004 | Demmy et al. |
| 2005/0070929 A1* | | 3/2005 | Dalessandro .... A61B 17/07292 606/151 |
| 2005/0216055 A1 | | 9/2005 | Scirica et al. |
| 2009/0095791 A1* | | 4/2009 | Eskaros ............... A61B 17/072 227/175.1 |
| 2009/0206143 A1* | | 8/2009 | Huitema .......... A61B 17/07207 227/176.1 |
| 2012/0241492 A1* | | 9/2012 | Shelton, IV ......... A61L 17/005 227/175.1 |
| 2012/0289979 A1 | | 11/2012 | Eskaros et al. |
| 2013/0068818 A1 | | 3/2013 | Kasvikis |
| 2013/0334280 A1 | | 12/2013 | Krehel et al. |
| 2014/0166723 A1 | | 6/2014 | Beardsley et al. |
| 2014/0239036 A1 | | 8/2014 | Zerkle et al. |
| 2014/0239037 A1 | | 8/2014 | Boudreaux et al. |
| 2014/0239038 A1 | | 8/2014 | Leimbach et al. |
| 2014/0239041 A1 | | 8/2014 | Zerkle |
| 2014/0239043 A1 | | 8/2014 | Simms et al. |
| 2014/0239044 A1 | | 8/2014 | Hoffman |
| 2015/0173752 A1 | | 6/2015 | Demmy et al. |
| 2015/0272575 A1 | | 10/2015 | Leimbach et al. |
| 2015/0282809 A1 | | 10/2015 | Shelton, IV et al. |
| 2016/0143659 A1 | | 5/2016 | Glutz et al. |
| 2016/0278774 A1 | | 9/2016 | Shelton, IV et al. |
| 2017/0055981 A1 | | 3/2017 | Vendely et al. |
| 2017/0086823 A1 | | 3/2017 | Leimbach et al. |
| 2017/0156725 A1 | | 6/2017 | Hemmann |
| 2018/0235609 A1 | | 8/2018 | Harris et al. |
| 2018/0235610 A1 | | 8/2018 | Harris et al. |
| 2018/0235611 A1 | | 8/2018 | Harris et al. |
| 2018/0235619 A1 | | 8/2018 | Harris et al. |
| 2018/0325514 A1 | | 11/2018 | Harris et al. |
| 2018/0325515 A1 | | 11/2018 | Harris et al. |

(56) References Cited

U.S. PATENT DOCUMENTS

| | | | |
|---|---|---|---|
| 2018/0325516 A1 | 11/2018 | Harris et al. | |
| 2019/0000481 A1 | 1/2019 | Harris et al. | |
| 2019/0076143 A1* | 3/2019 | Smith | A61B 34/37 |

FOREIGN PATENT DOCUMENTS

| | | |
|---|---|---|
| WO | WO 2013/151888 A1 | 10/2013 |
| WO | WO 2017/083129 | 5/2017 |

OTHER PUBLICATIONS

European Search Report, Extended, and Written Opinion dated Dec. 10, 2019 for Application No. EP 19186231.7, 7 pgs.

European Search Report, Partial, and Provisional Written Opinion dated Oct. 31, 2019 for Application No. EP 119186252.3, 16 pgs.

European Search Report, Extended, and Written Opinion dated Jan. 31, 2020 for Application No. EP 119186252.3, 14 pgs.

International Search Report and Written Opinion dated Dec. 6, 2019 for Application No. PCT/IB2019/055980, 13 pgs.

International Search Report and Written Opinion dated Feb. 27, 2020 for Application No. PCT/IB2019/055983, 20 pgs.

Declaration of Non-Establishment of International Search Report and Written Opinion dated Dec. 13, 2019 for Application PCT/IB2019/055964, 6 pgs.

European Search Report dated Aug. 7, 2018 for Application No. 18157228.0, 8 pages.

International Search Report and Written Opinion dated Apr. 19, 2018 for International Application No. PCT/US2018/017751, 17 pages.

U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
U.S. Appl. No. 16/035,872, filed Jul. 16, 2018.

European Examination Report dated Aug. 3, 2020 for Application No. EP 19186244.0, 4 pgs.

European Examination Report dated Mar. 15, 2021 for Application No. EP 19186244.0, 4 pgs.

European Search Rpeport and Written Opinion dated Nov. 12, 2019 for Application No. EP 19186244.0, 7 pgs.

International Search Report and Written Opinion dated Jan. 2, 2020 for Application No. PCT/IB2019/056041, 11 pgs.

* cited by examiner

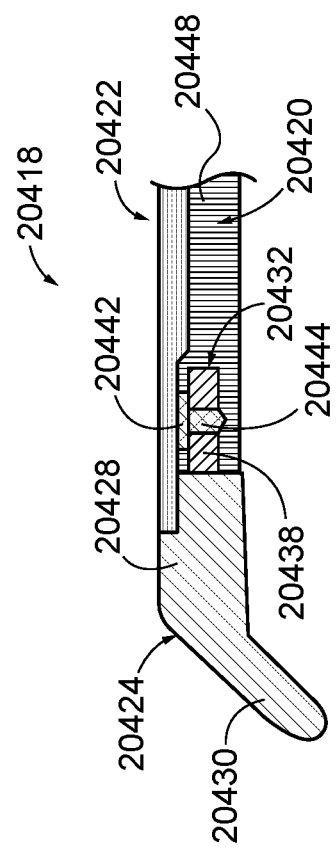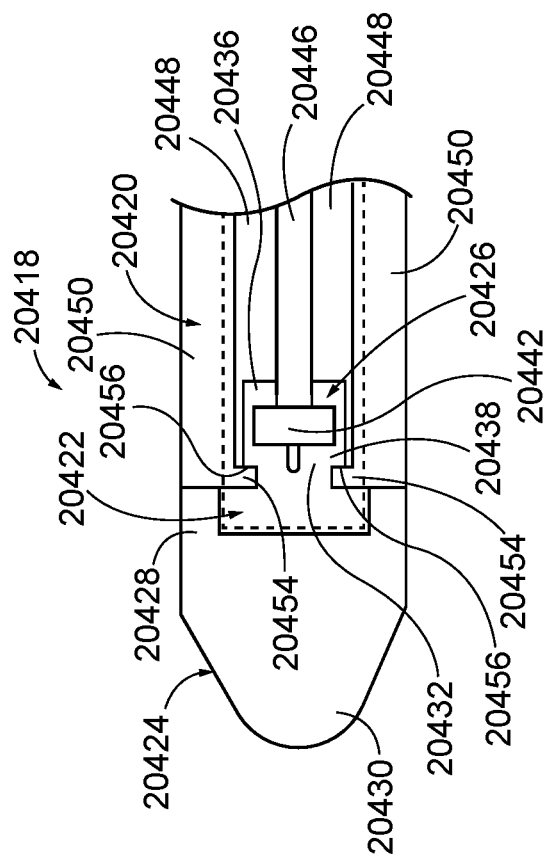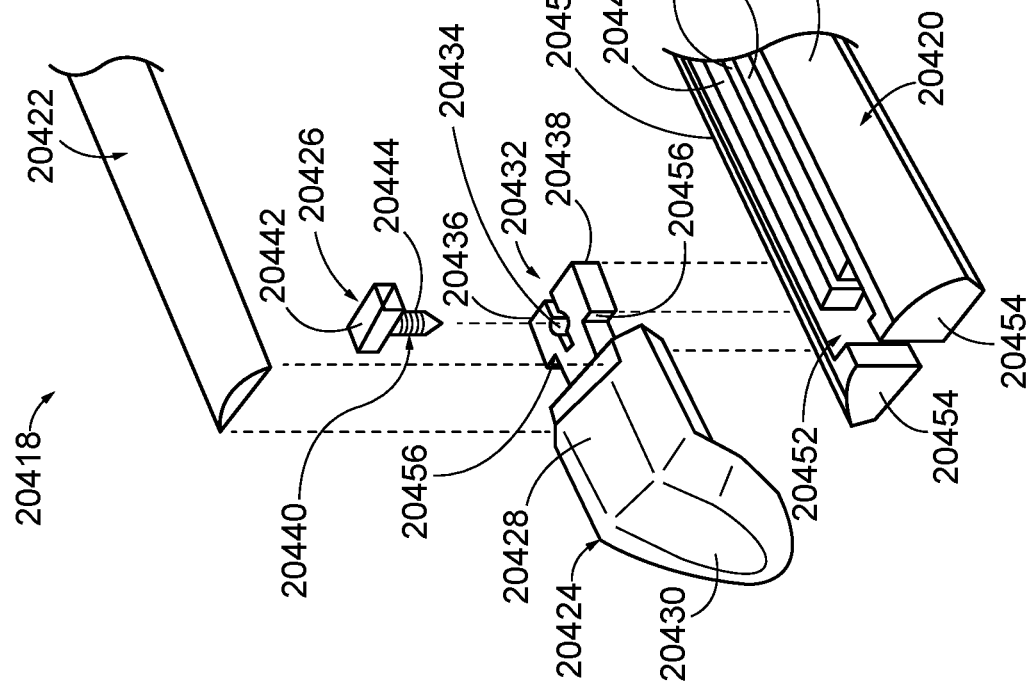

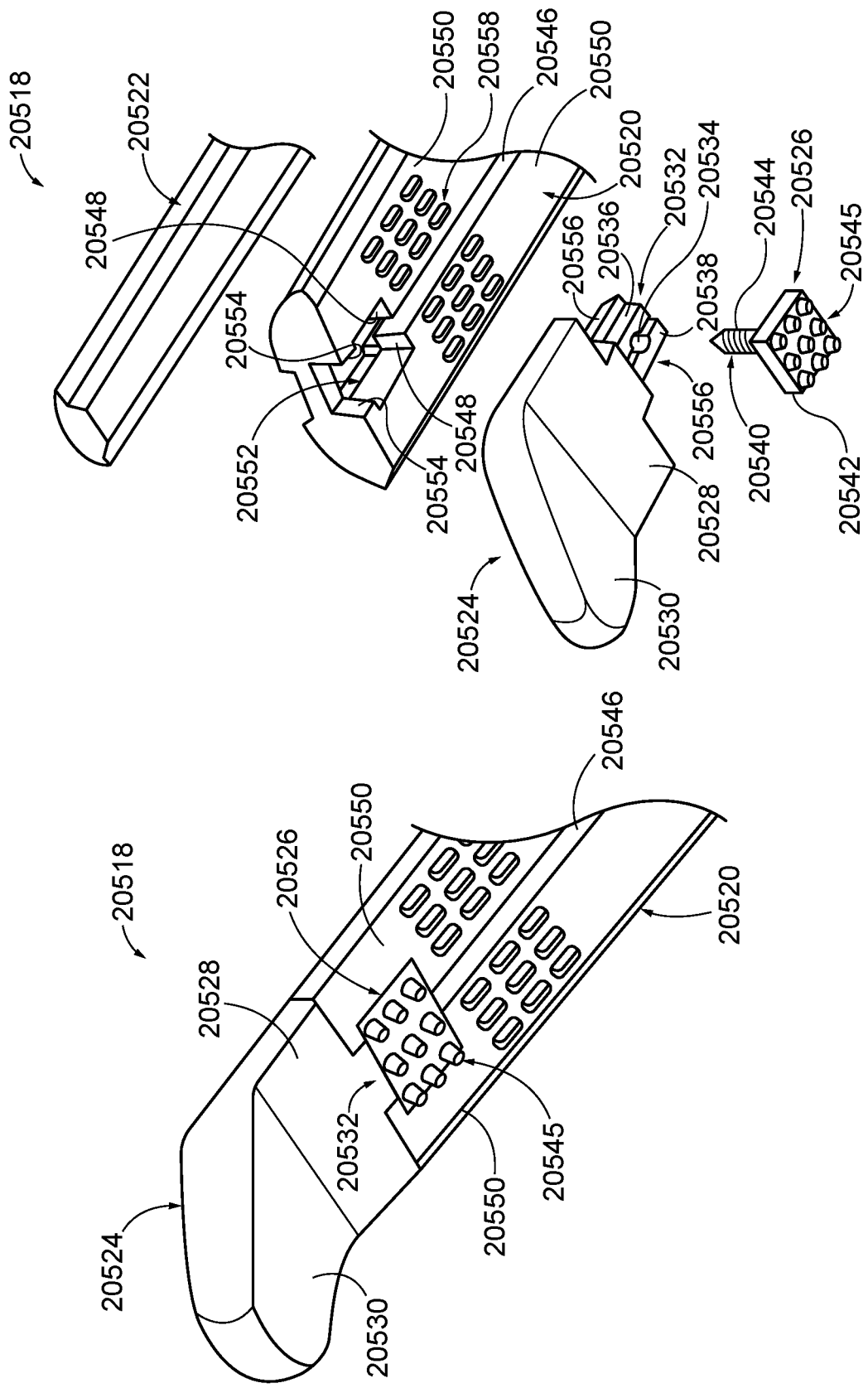

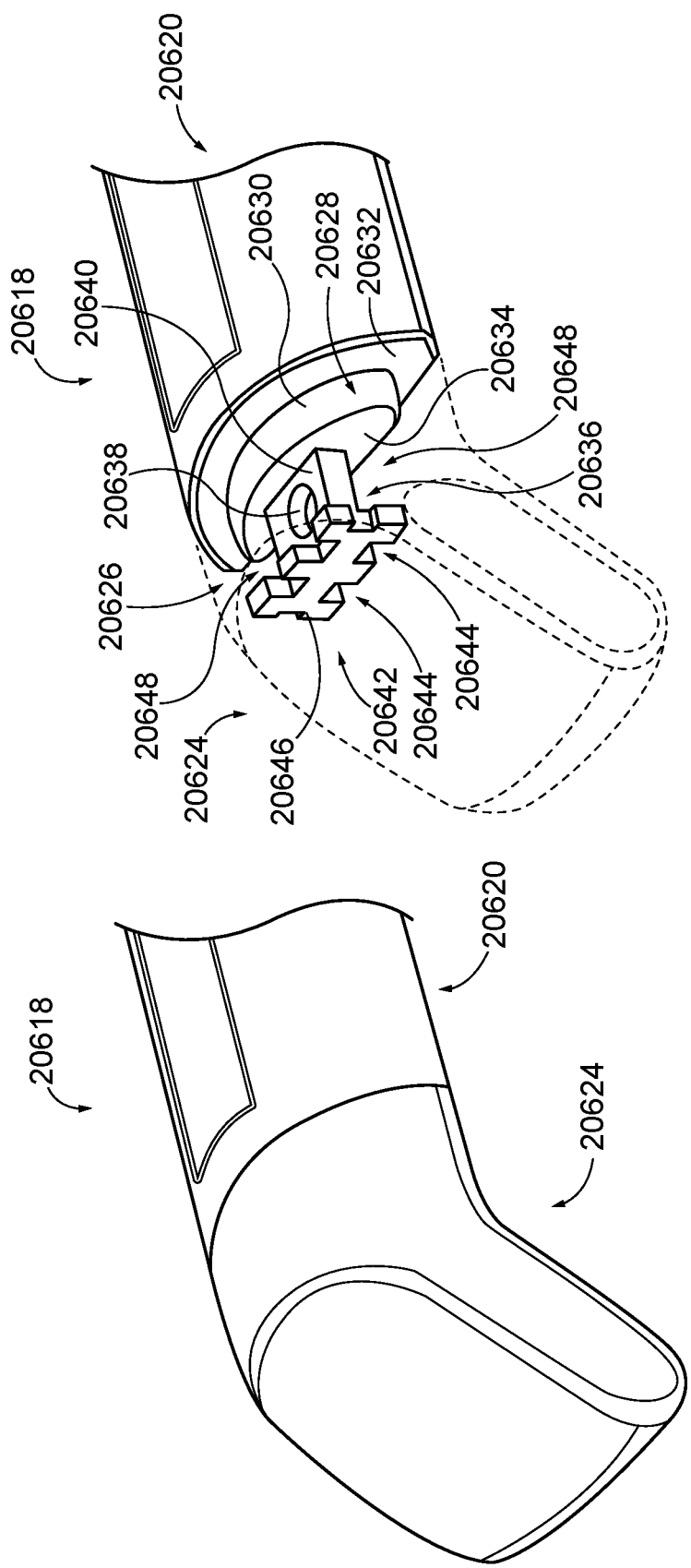

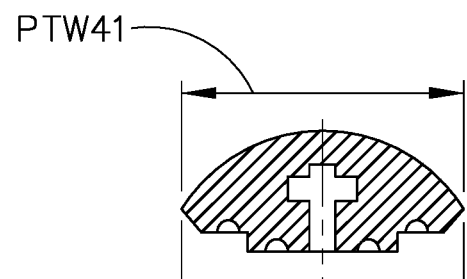
Fig.71
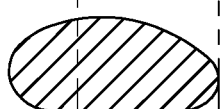
Fig.72
Fig.73
Fig.74
Fig.75
Fig.76
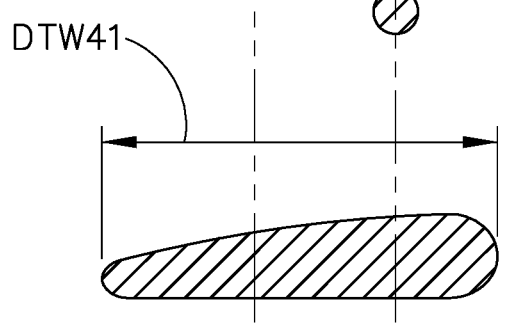
Fig.77

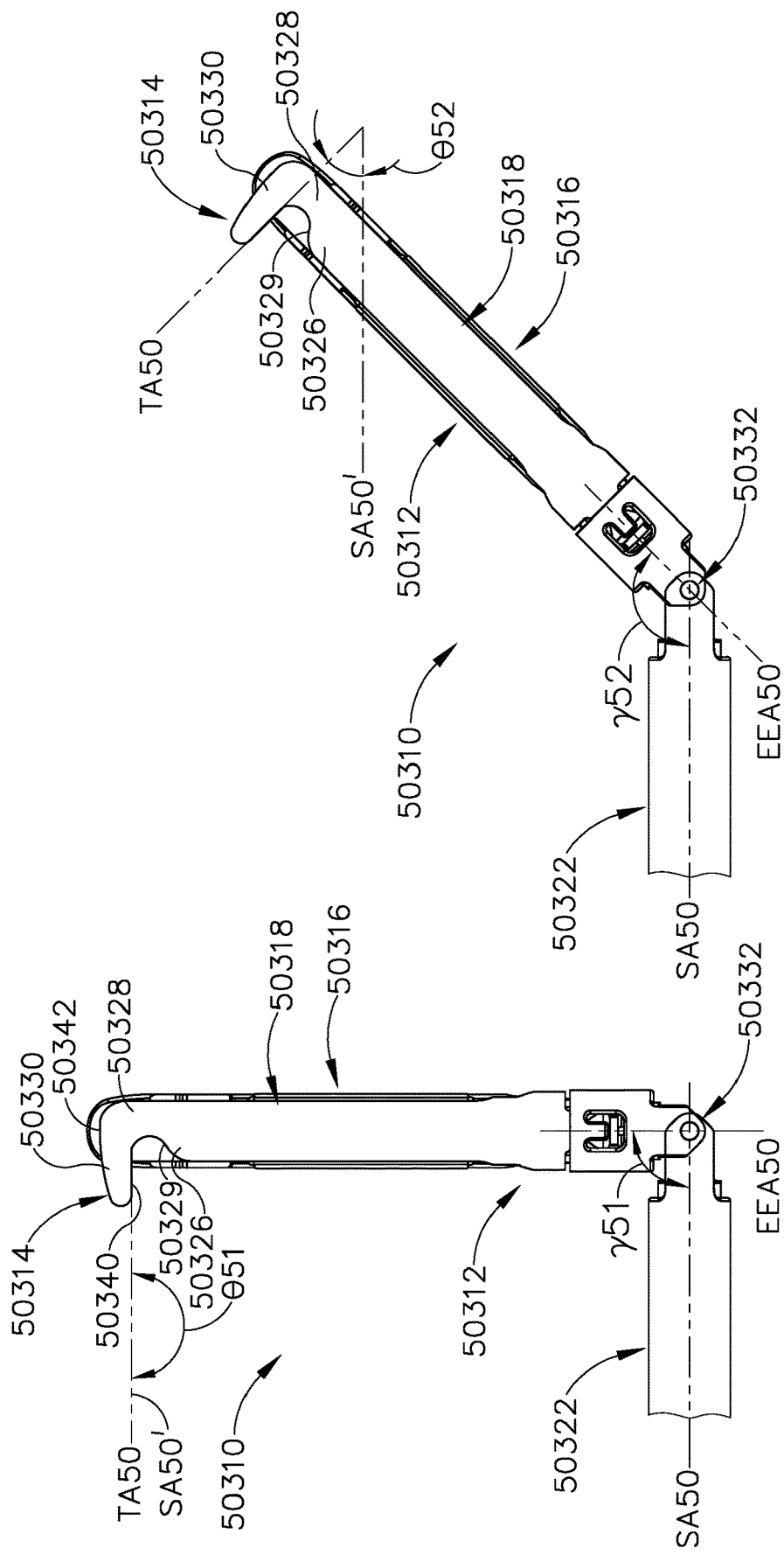

METHOD OF SURGICAL STAPLING WITH END EFFECTOR COMPONENT HAVING A CURVED TIP

PRIORITY

This application is a continuation of U.S. patent application Ser. No. 16/035,893, filed Jul. 16, 2018 and published as U.S. Pat. Pub. No. 2019/0000481 on Jan. 3, 2019, which is a continuation-in-part of U.S. Non-Provisional patent application Ser. No. 15/435,573, filed Feb. 17, 2017, issued as U.S. Pat. No. 10,828,031 on Nov. 10, 2020, entitled "SURGICAL STAPLER WITH ELASTICALLY DEFORMABLE TIP," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 47 depicts an exploded perspective view of an enlarged portion of an exemplary end effector having a deflectable tip;

FIG. 48 depicts a side cross-sectional view of the end effector of FIG. 47;

FIG. 49 depicts a top view of the end effector of FIG. 47, shown with a portion in phantom to reveal internal components;

FIG. 50 depicts an exploded perspective view of an enlarged portion of an exemplary end effector having a deflectable tip;

FIG. 51 depicts a perspective view of the end effector of FIG. 50;

FIG. 52 depicts a perspective view of an enlarged portion of an exemplary end effector having a deflectable tip;

FIG. 53 depicts a perspective view of the end effector of FIG. 52, shown with the deflectable tip in phantom to show other components of the end effector

FIG. 71 depicts a cross-sectional view of the anvil of the end effector of FIG. 67, taken along line 71-71 of FIG. 70;

FIG. 72 depicts a cross-sectional view of the placement tip of the end effector of FIG. 67, taken along line 72-72 of FIG. 70;

FIG. 73 depicts a cross-sectional view of the placement tip of the end effector of FIG. 67, taken along line 73-73 of FIG. 70;

FIG. 74 depicts a cross-sectional view of the placement tip of the end effector of FIG. 67, taken along line 74-74 of FIG. 70;

FIG. 75 depicts a cross-sectional view of the placement tip of the end effector of FIG. 67, taken along line 75-75 of FIG. 70;

FIG. 76 depicts a cross-sectional view of the placement tip of the end effector of FIG. 67, taken along line 76-76 of FIG. 70;

FIG. 77 depicts a cross-sectional view of the placement tip of the end effector of FIG. 67, taken along line 77-77 of FIG. 70;

FIG. 83A depicts an enlarged top view of the end effector of FIG. 82 in a first angled position;

FIG. 83B depicts an enlarged top view of the end effector of FIG. 82 in a second angled position;

FIG. 86 depicts an enlarged perspective view of a distal portion of the end effector of FIG. 85, with the upper and lower jaws in a closed configuration;

FIG. 87 depicts a front view of the end effector of FIG. 86 in the closed configuration;

FIG. 88 depicts a top view of the distal portion of the end effector of FIG. 86;

FIG. 89 depicts a side view of the distal portion of the end effector of FIG. 86 in the closed configuration;

FIG. 90A depicts a cross-sectional view of a proximal portion of the placement tip of FIG. 89, taken along line 90A-90A of FIG. 89;

FIG. 90B depicts a cross-sectional view of a central portion of the placement tip of FIG. 89, taken along line 90B-90B of FIG. 89;

FIG. 90C depicts a cross-sectional view of a distal portion of the placement tip of FIG. 89, taken along line 90C-90C of FIG. 89;

FIG. 91 depicts a perspective view of a distal portion of another exemplary end effector that includes another exemplary placement tip in a closed configuration;

FIG. 92 depicts a front view of the end effector of FIG. 91 in the closed configuration;

FIG. 93 depicts a top view of the distal portion of the end effector of FIG. 91;

FIG. 94 depicts a side view of the distal portion of the end effector of FIG. 91 in the closed configuration;

FIG. 95A depicts a cross-sectional view of a proximal portion of the placement tip of FIG. 94, taken along line 95A-95A of FIG. 94;

Figure 2:
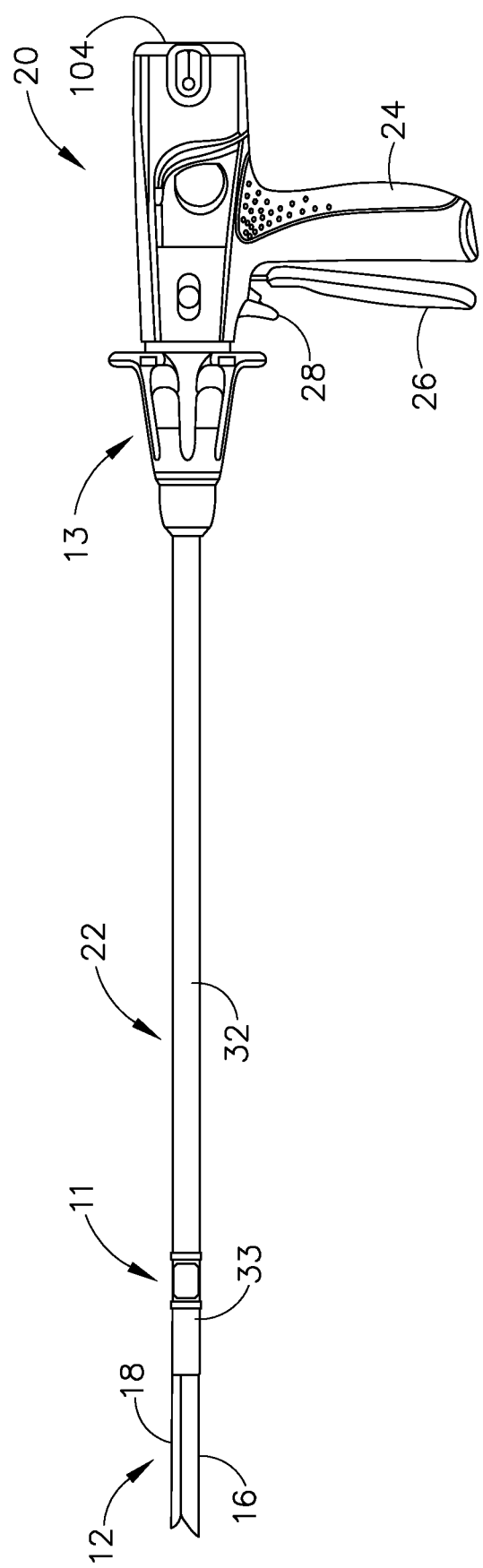
FIG. 2 depicts a side view of the instrument of FIG. 1.
Figure 8:
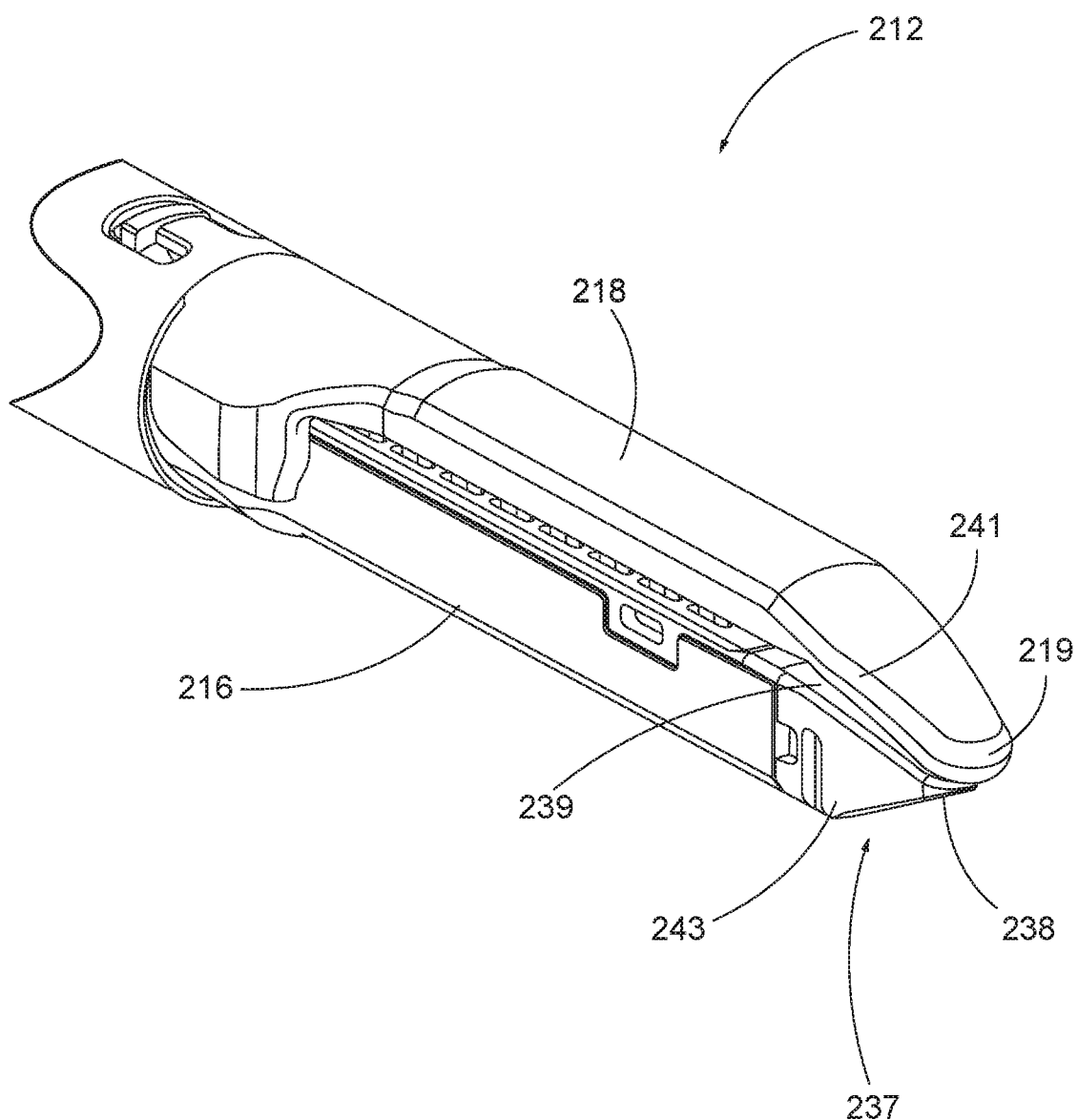
FIG. 8 depicts a perspective view of an alternative version of an end effector with an angled anvil and an angled cartridge.
Figure 94:
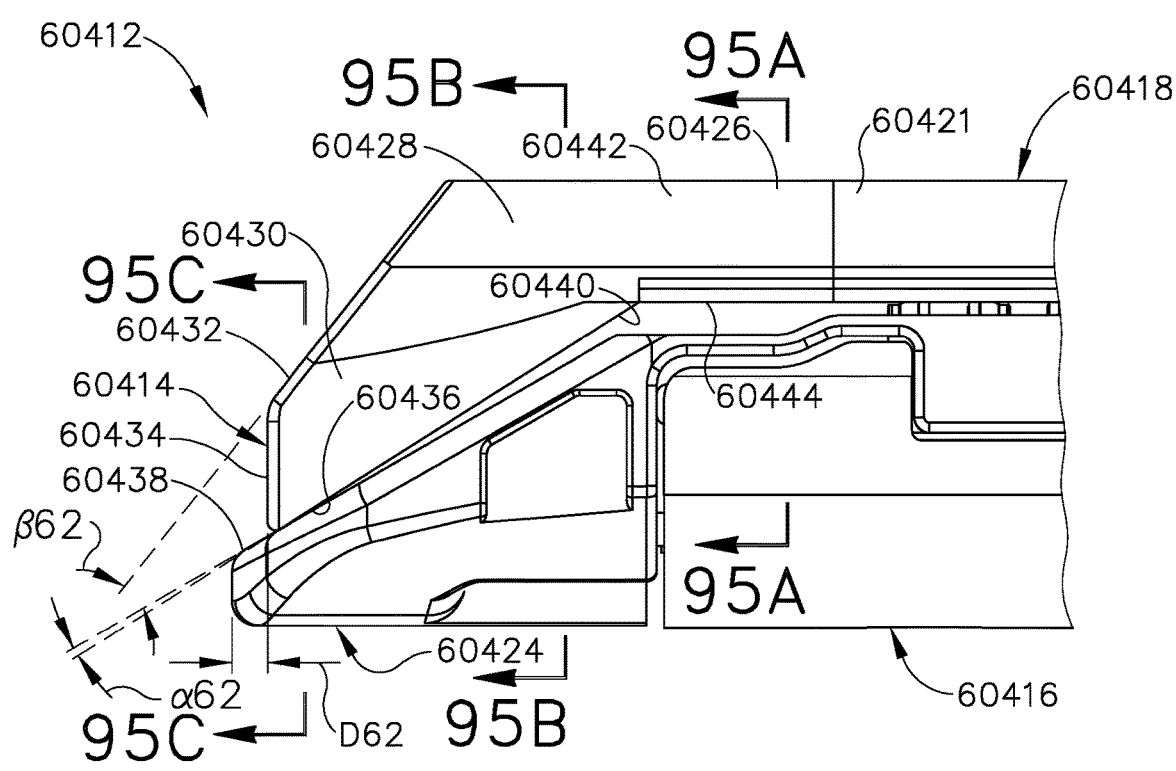
Figure 95A:
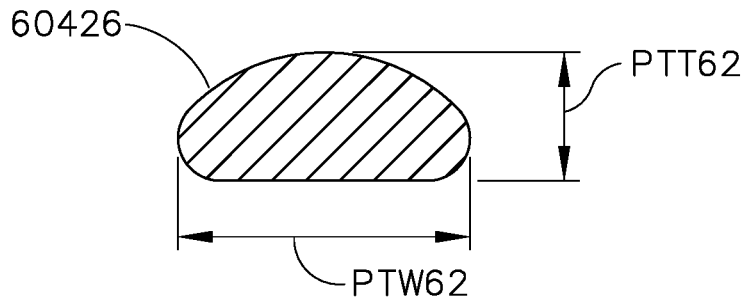
Figure 95B:
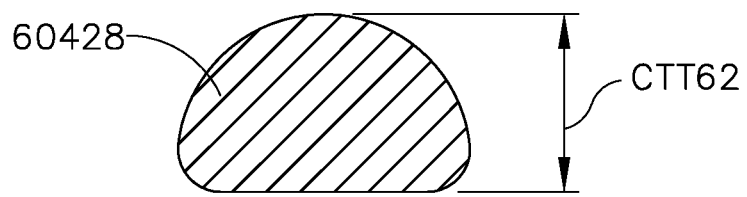
Figure 95C:
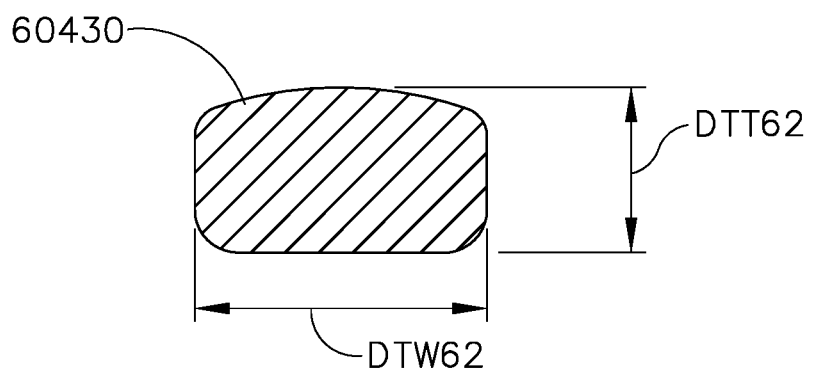
Figure 96:
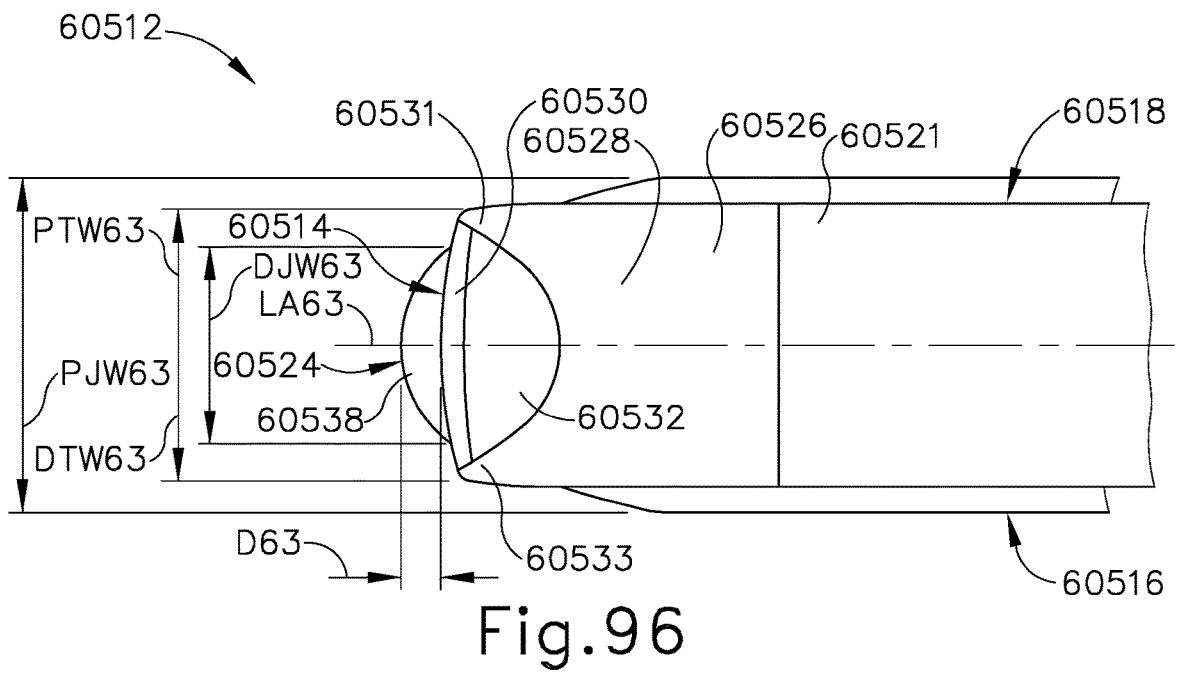
Figure 97:
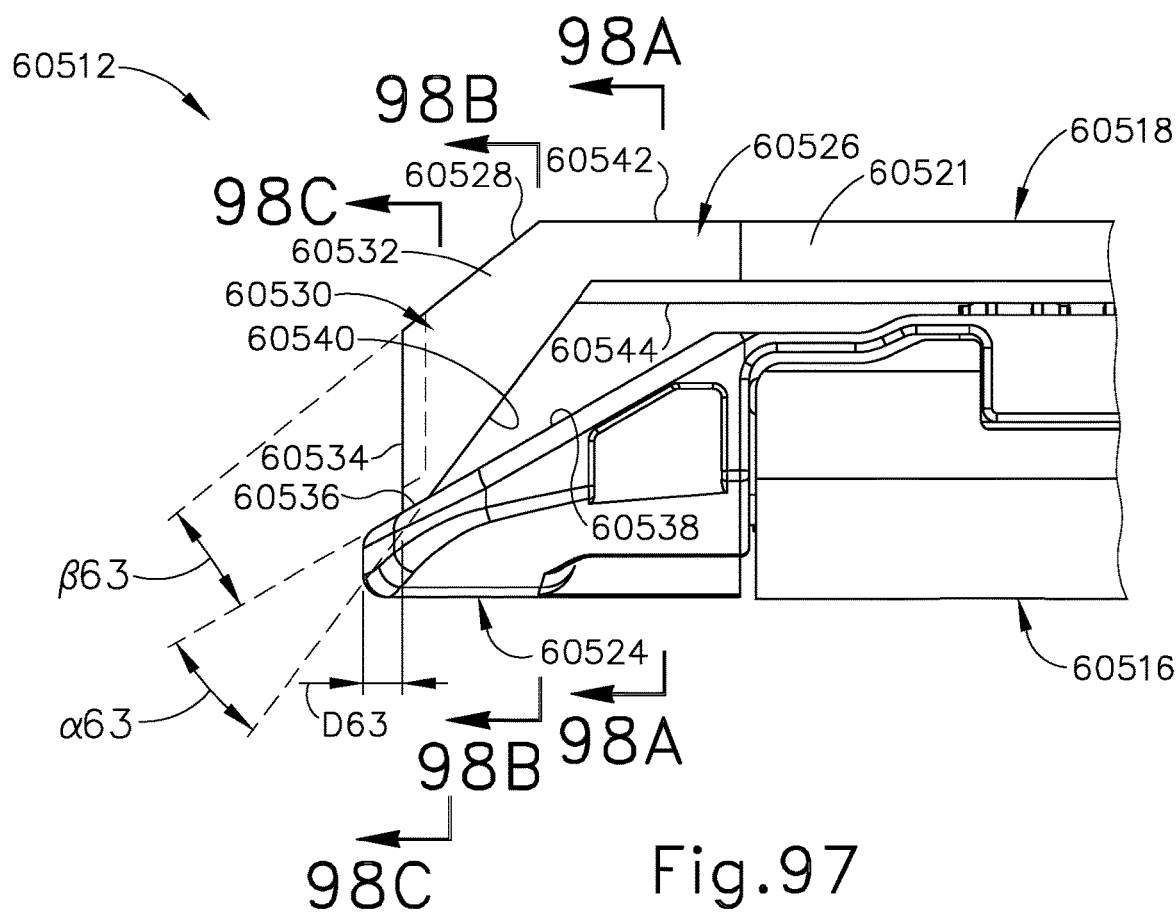
Figure 98A:
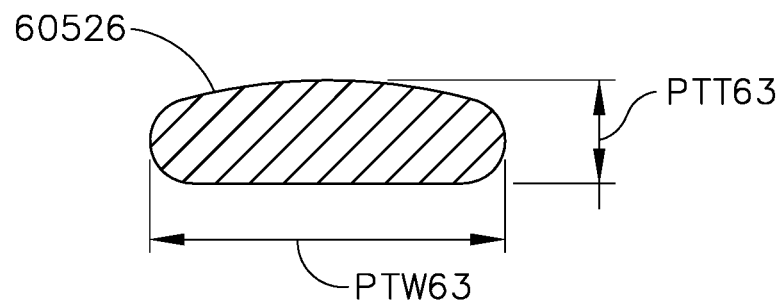
Figure 98B:
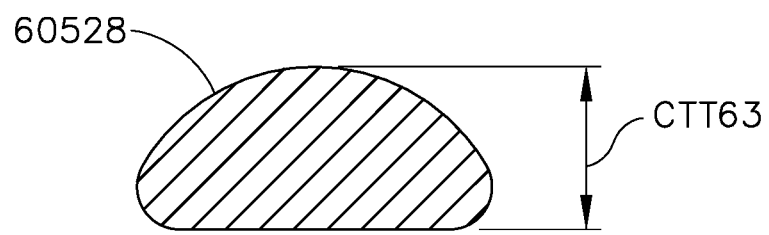
Figure 98C:
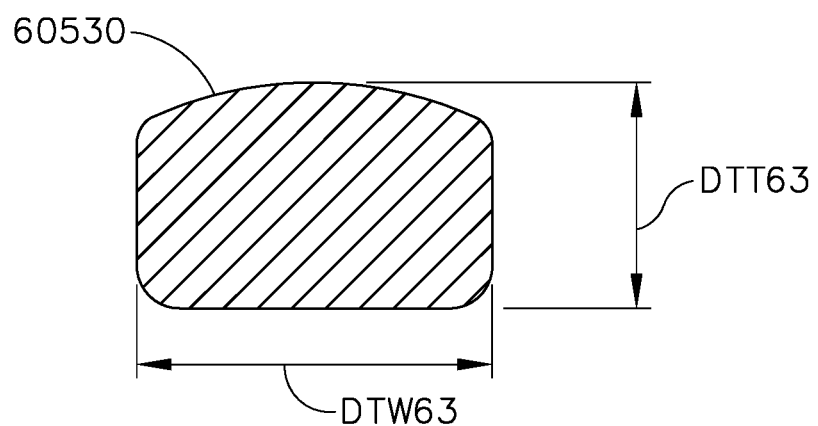
Figure 99:
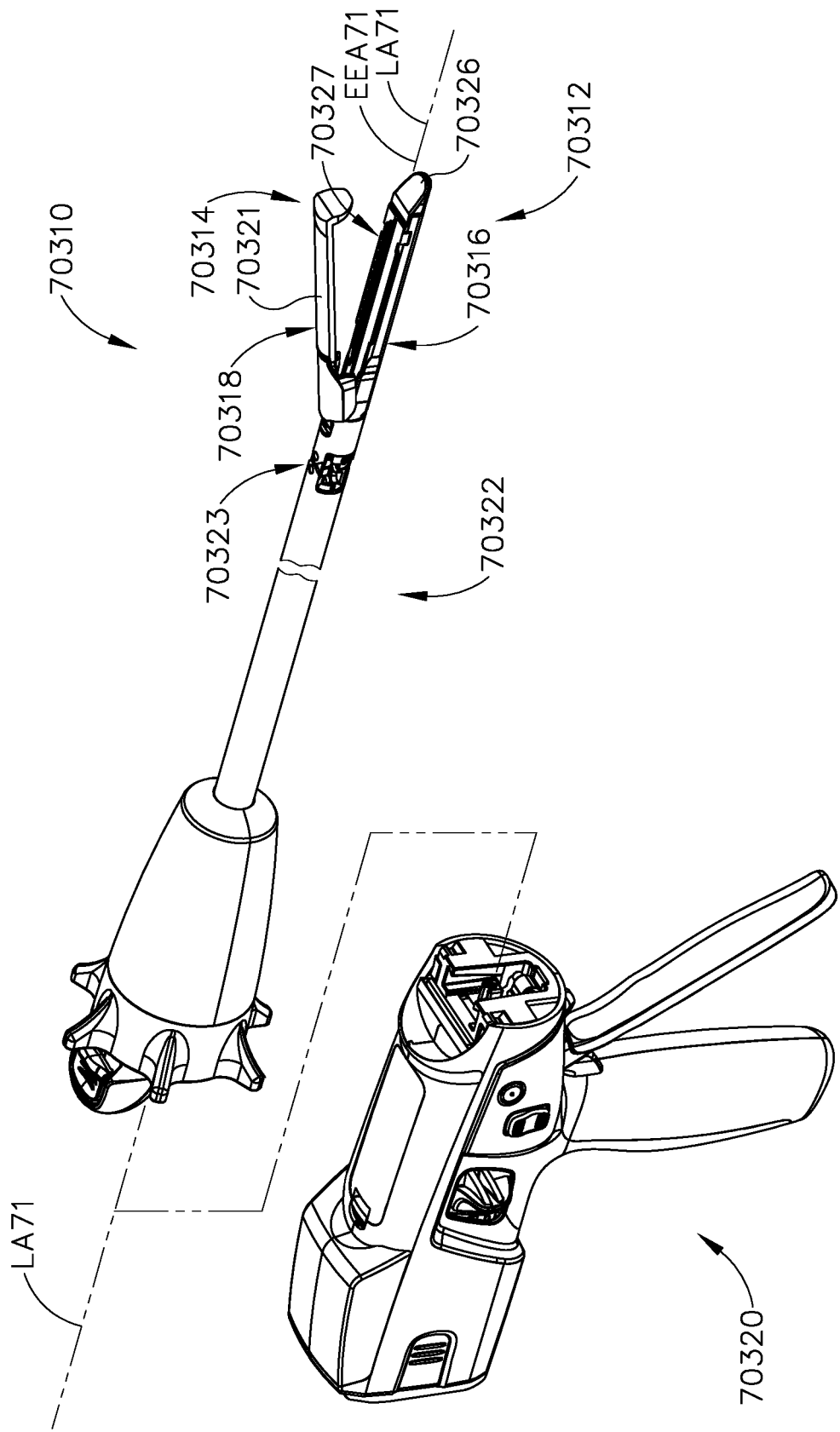
Figure 100:
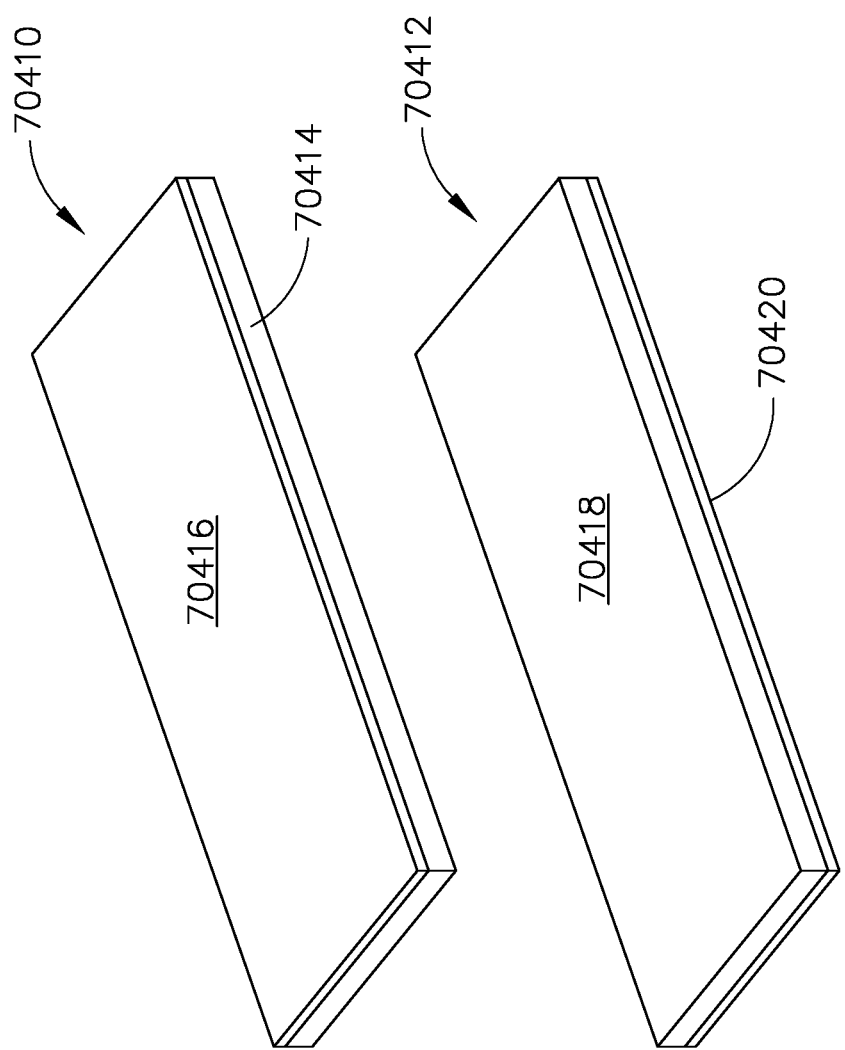
Figure 101:
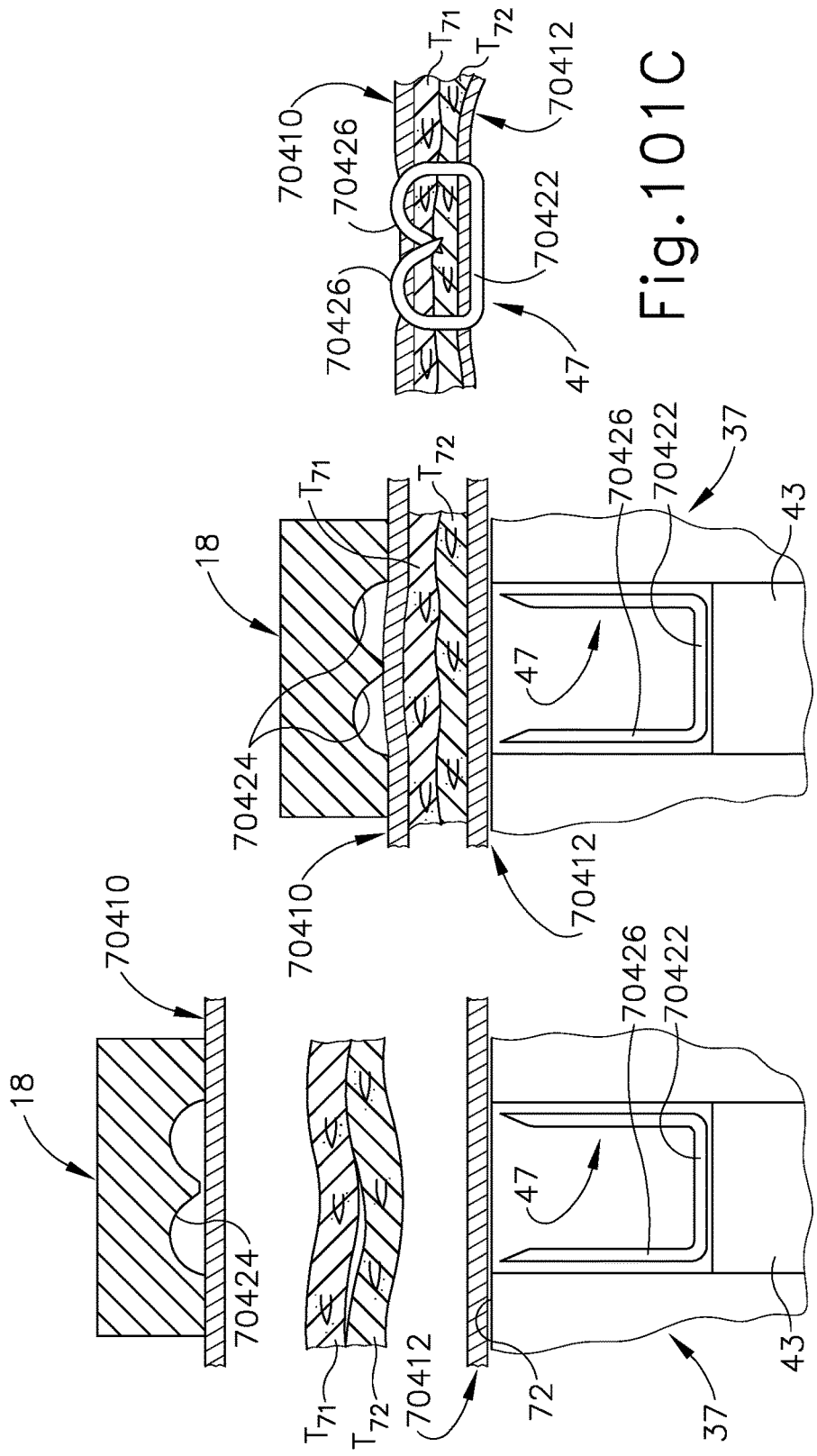
Figure 102:
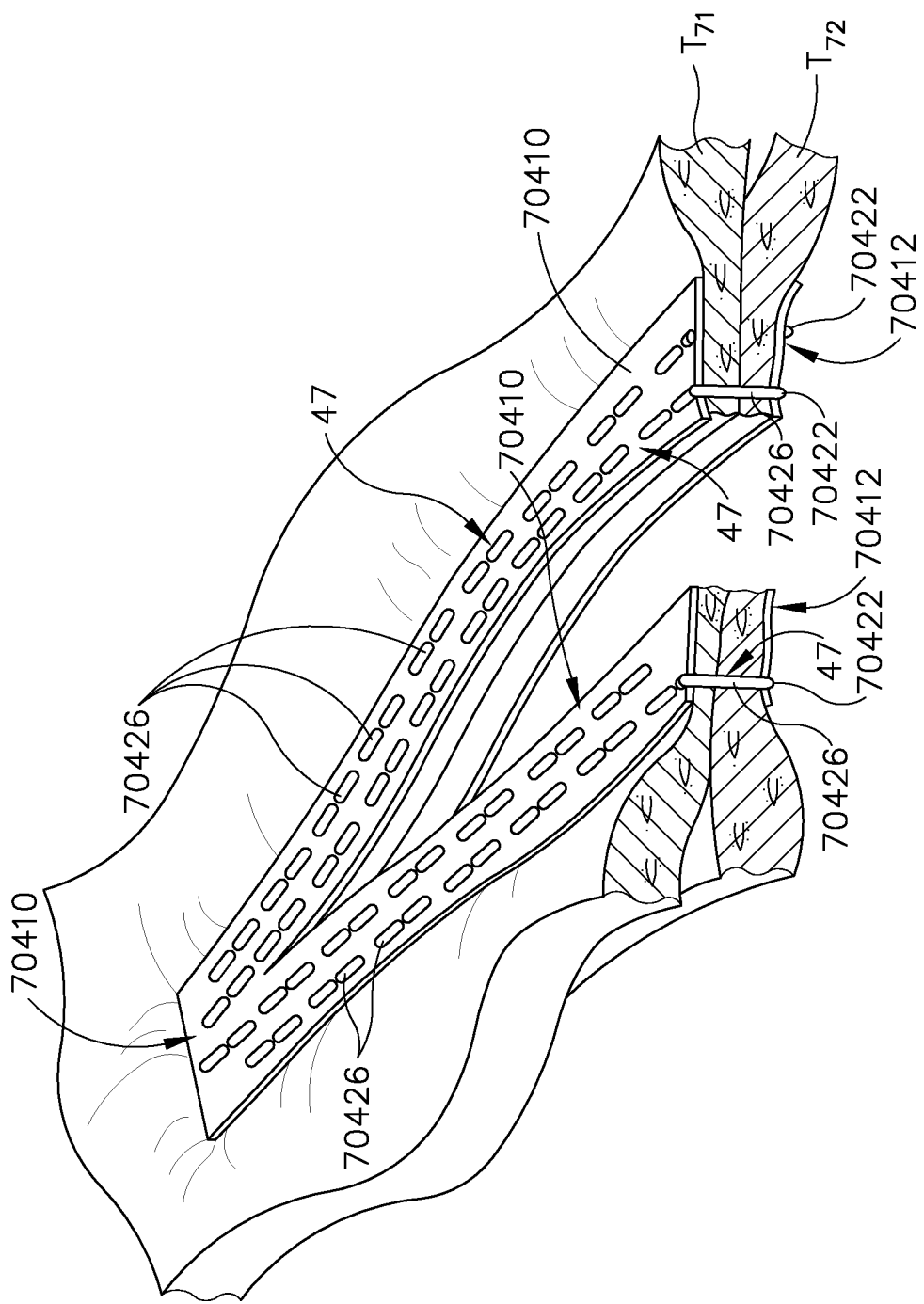
Figure 103:
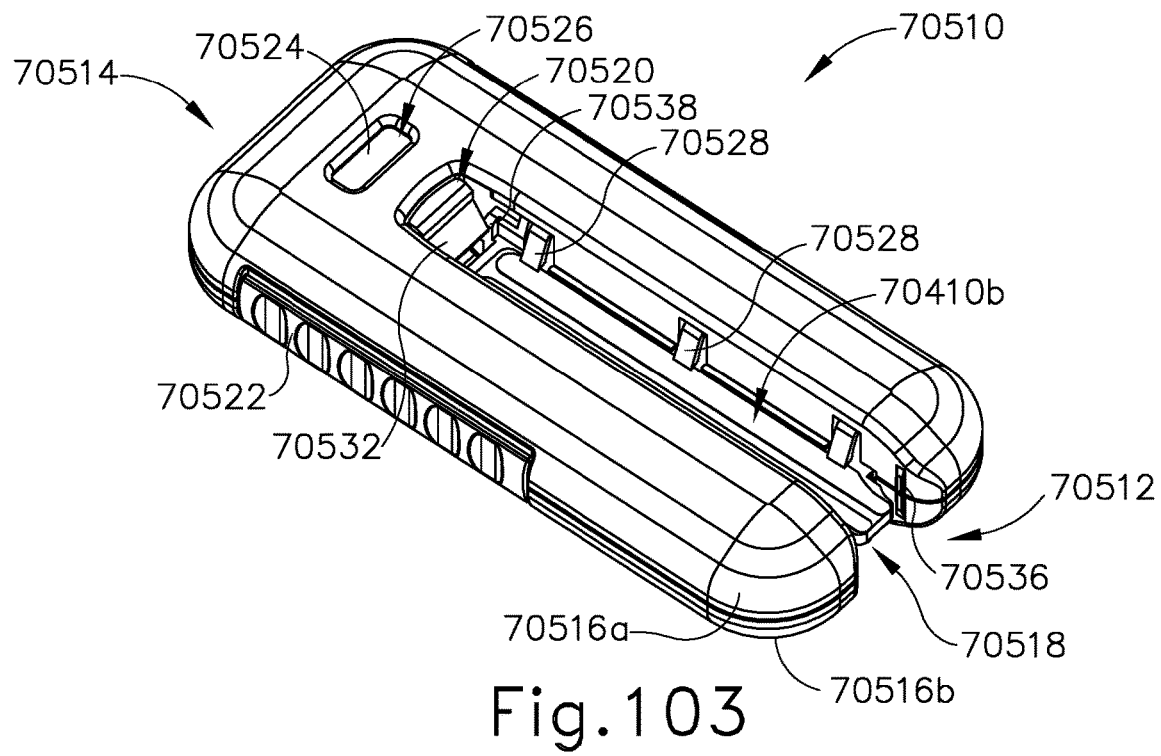
Figure 104:
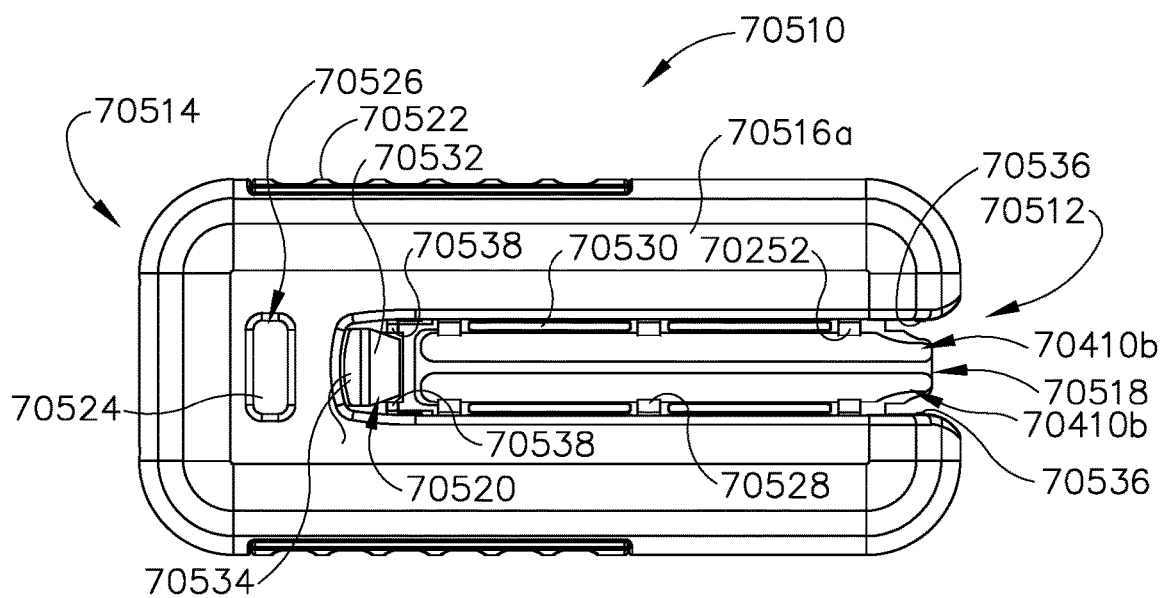
Figure 105A:
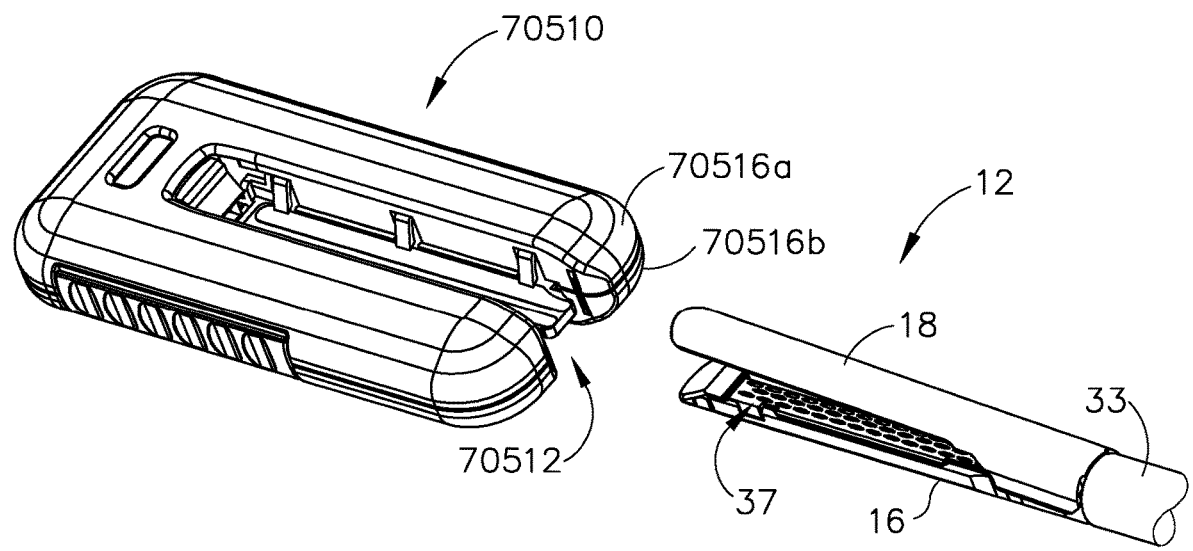
Figure 105B:
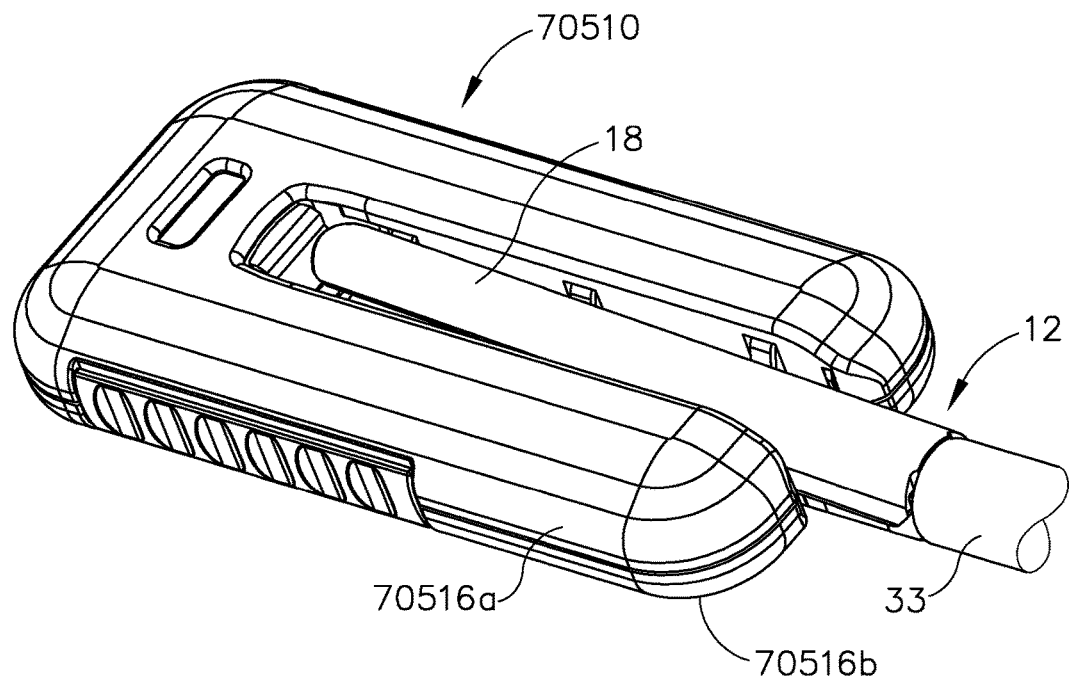
Figure 106:
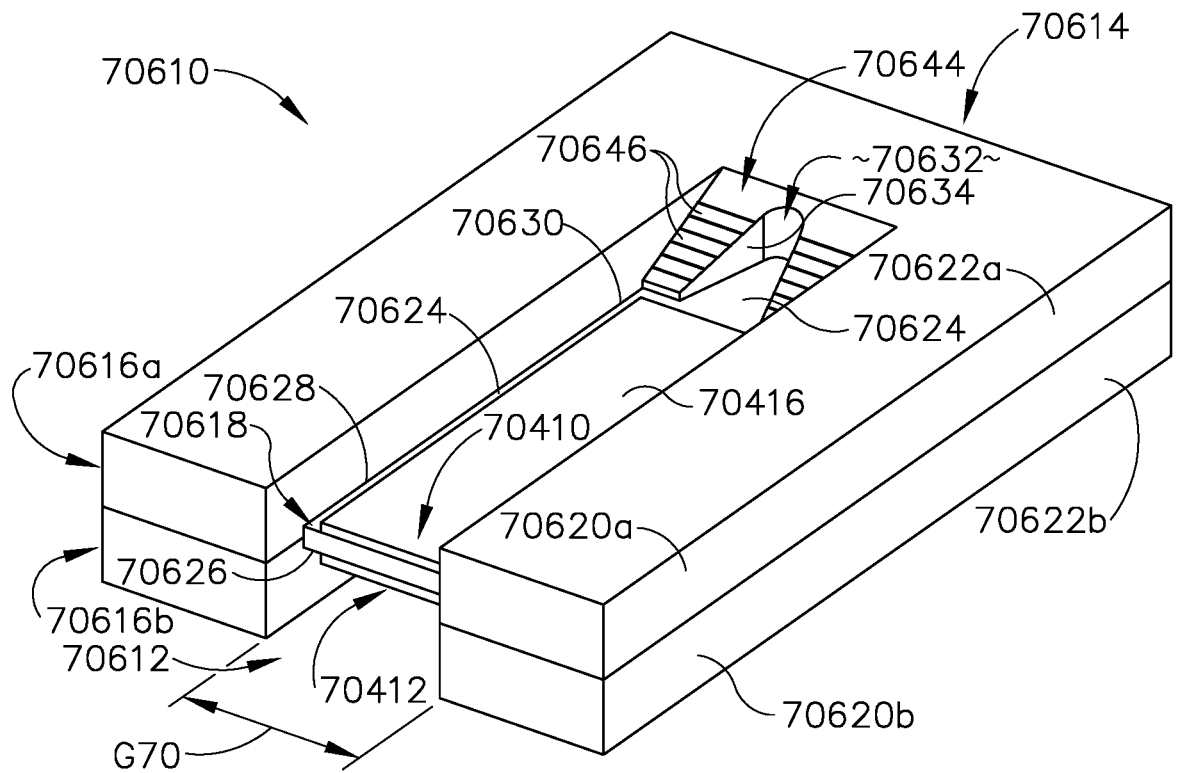
Figure 107:
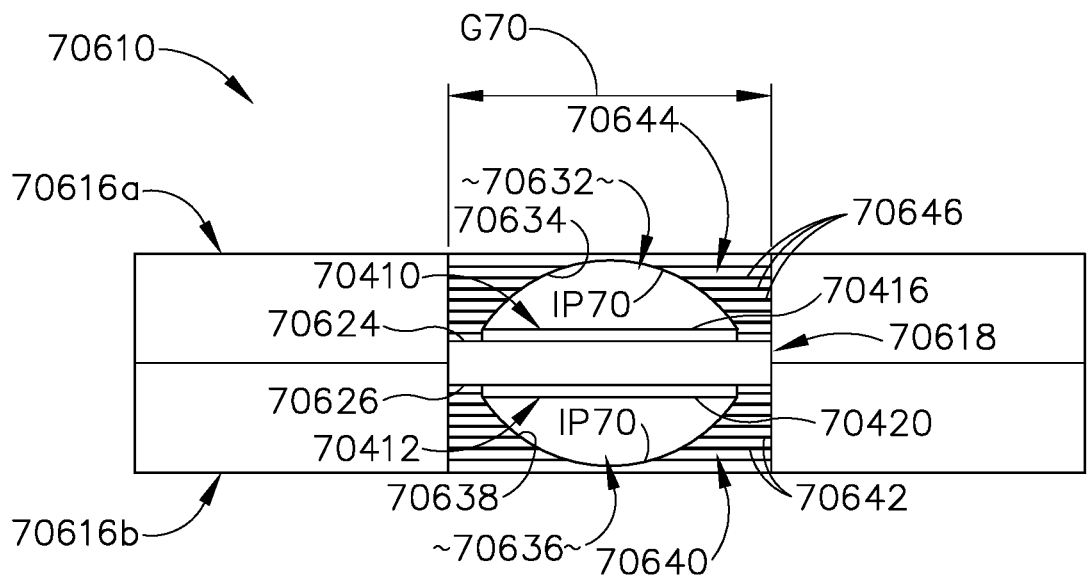
Figure 108A:
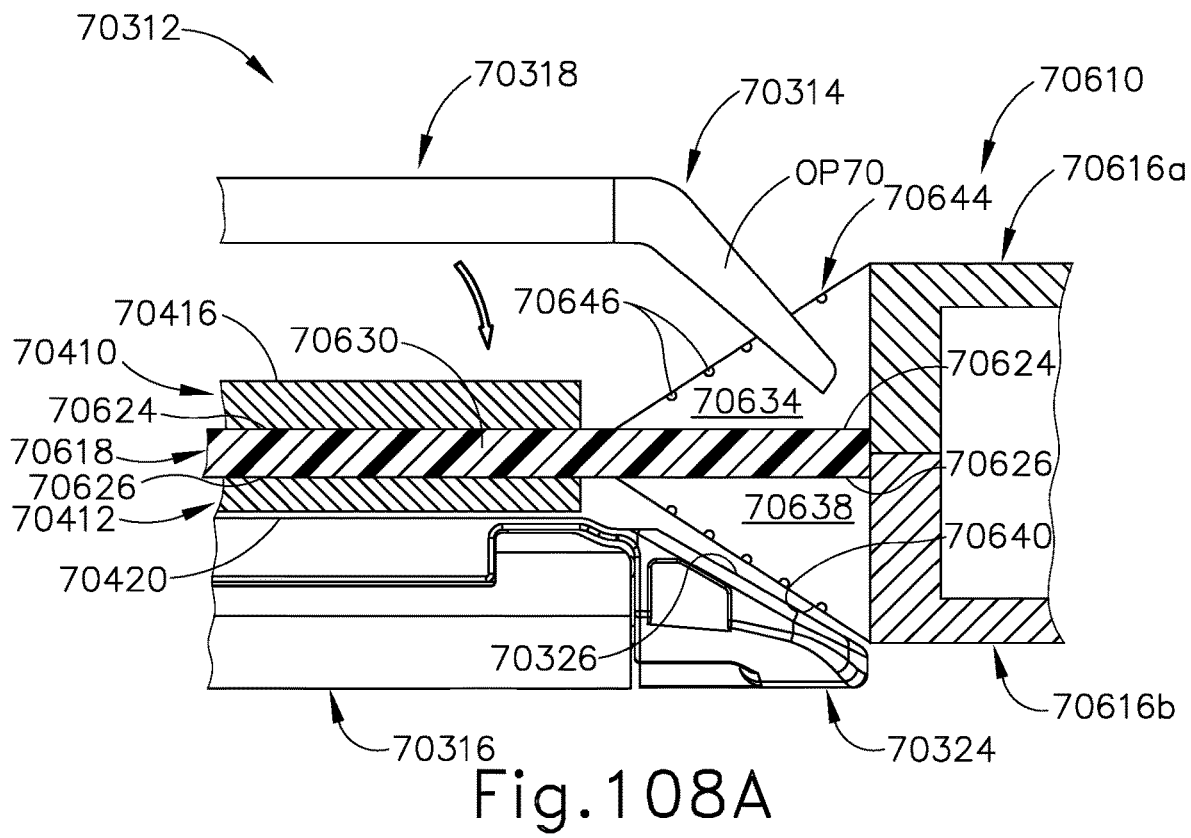
Figure 108B:
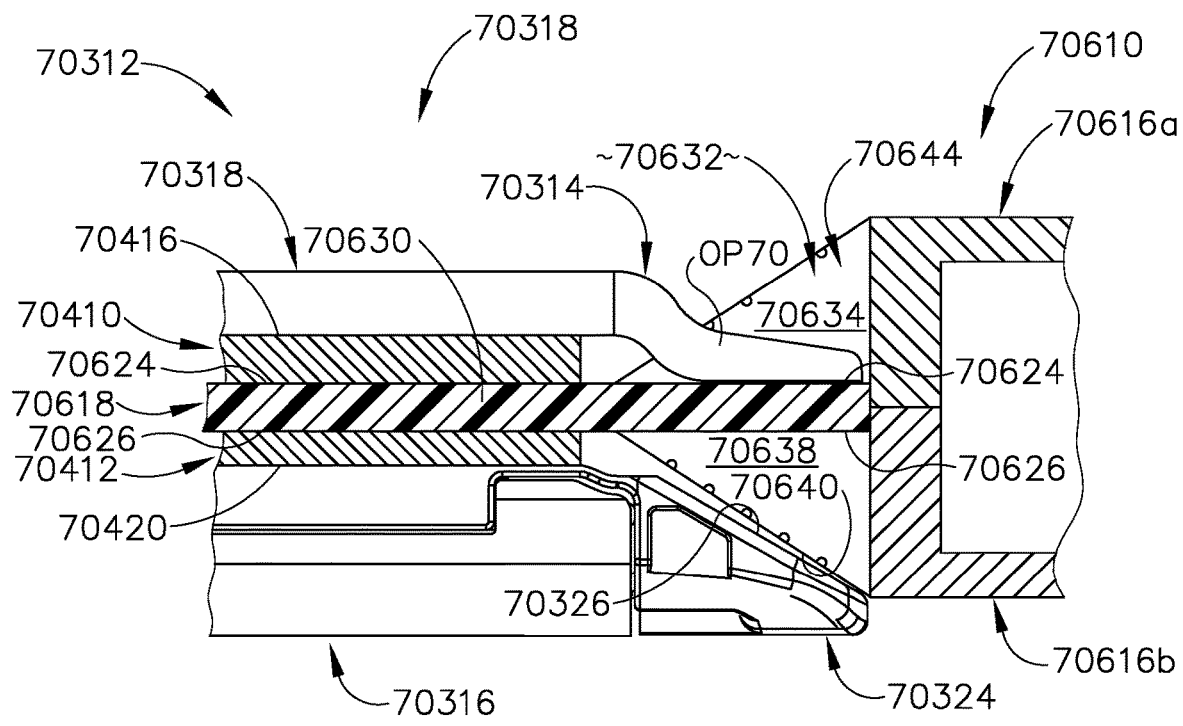
Figure 109:
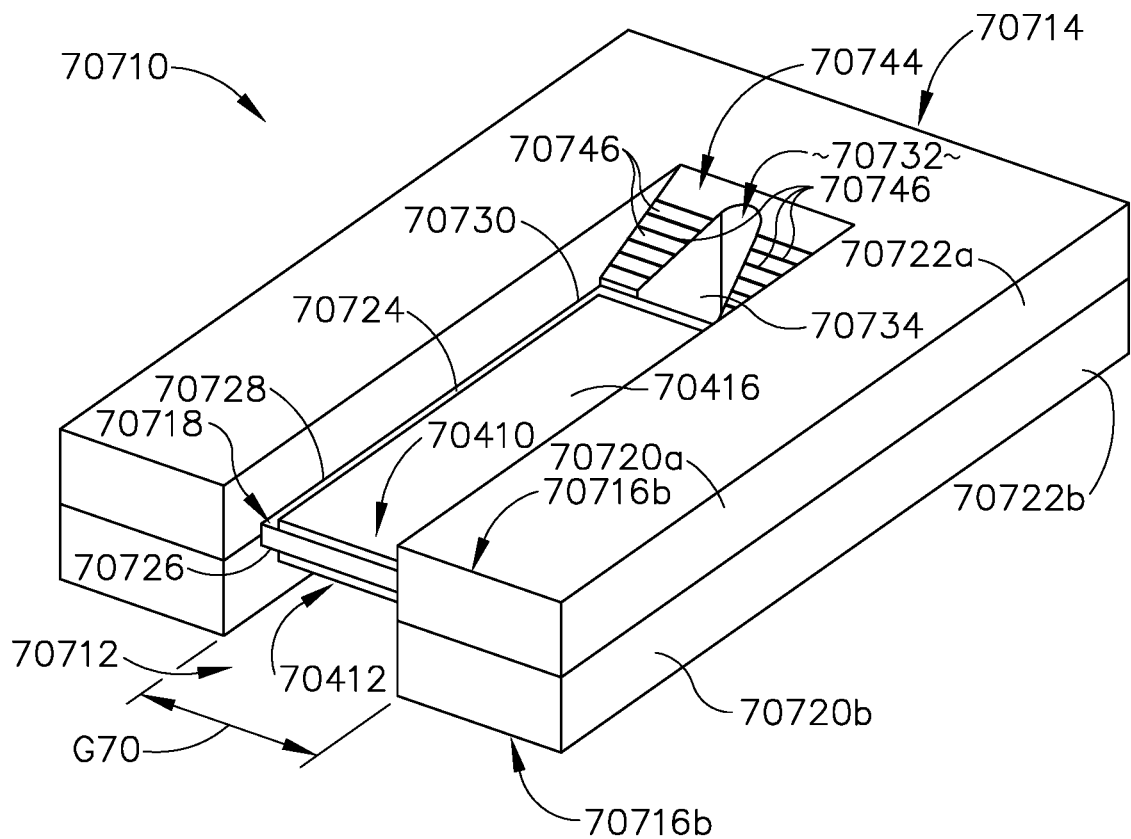
Figure 110:
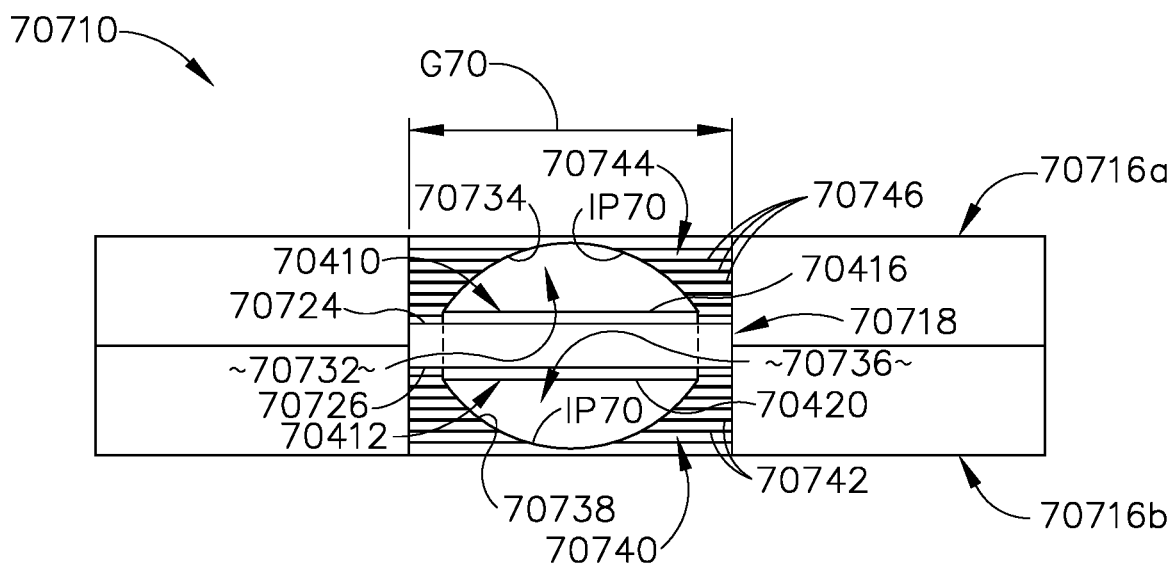
Figure 111A:
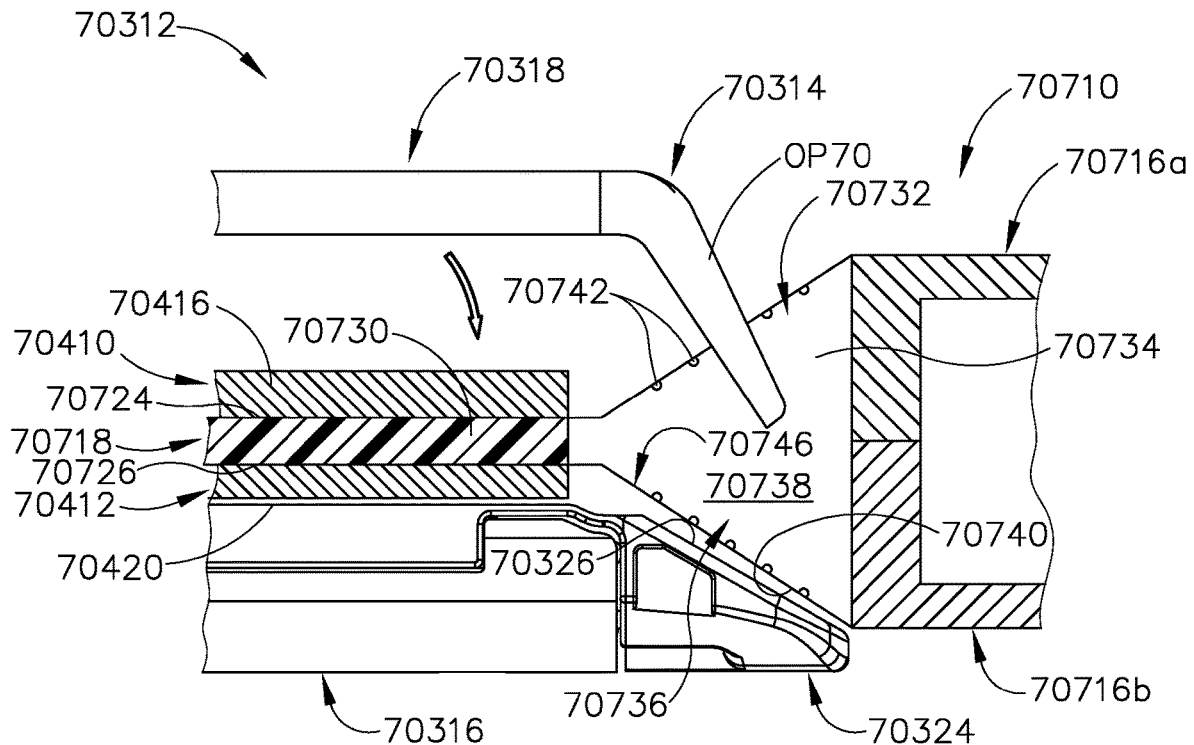
Figure 111B:
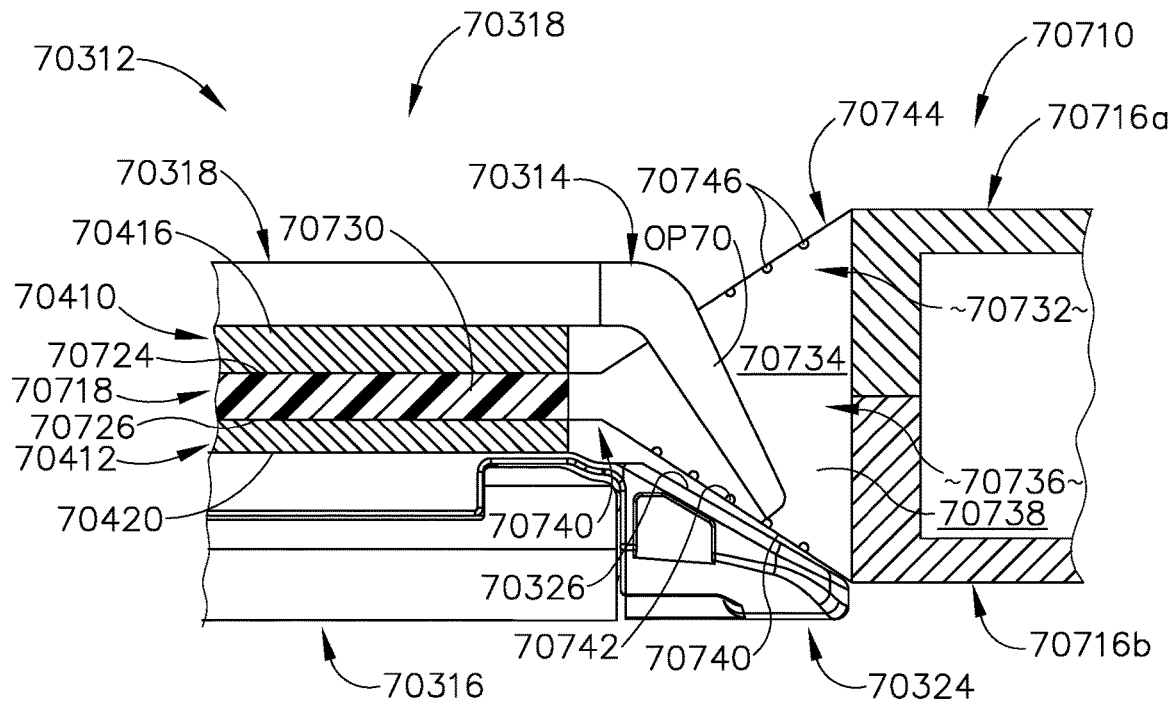

FIG. 95B depicts a cross-sectional view of a central portion of the placement tip of FIG. 94, taken along line 95B-95B of FIG. 94;

FIG. 95C depicts a cross-sectional view of a distal portion of the placement tip of FIG. 94, taken along line 95C-95C of FIG. 94;

FIG. 96 depicts a top view of a distal portion of another exemplary end effector that includes another exemplary placement tip;

FIG. 97 depicts a side view of the distal portion of the distal portion of the end effector of FIG. 96 in a closed configuration;

FIG. 98A depicts a cross-sectional view of a proximal portion of the placement tip of FIG. 2397 taken along line 98A-98A of FIG. 97;

FIG. 98B depicts a cross-sectional view of a central portion of the placement tip of FIG. 97, taken along line 98B-98B of FIG. 97;

FIG. 98C depicts a cross-sectional view of a distal portion of the placement tip of FIG. 97, taken along line 98C-98C of FIG. 97;

FIG. 99 depicts a perspective view of another surgical stapling instrument with another end effector with another placement tip, where the upper and lower jaws are in an open configuration;

FIG. 100 depicts a perspective view of an exemplary upper buttress and an exemplary lower buttress of an exemplary buttress assembly, each of which may be applied to the end effector of FIG. 2 or the end effector of FIG. 8;

FIG. 101A depicts a cross-sectional end view of a portion of the end effector of FIG. 2 with a buttress assembly formed by the buttresses of FIG. 100 applied to the end effector, with tissue positioned between the buttresses in the end effector, and with the end effector in an open configuration;

FIG. 101B depicts a cross-sectional end view of the end effector and buttress assembly of FIG. 101A, with tissue positioned between the buttresses in the end effector, and with the end effector in a closed configuration;

FIG. 101C depicts a cross-sectional view of a staple and the buttress assembly of FIG. 101A having been secured to the tissue by the end effector of FIG. 2;

FIG. 102 depicts a perspective view of staples and the buttress assembly of FIG. 13A having been secured to the tissue by the end effector of FIG. 2;

FIG. 103 depicts a perspective view of an exemplary buttress applier cartridge that may be used to carry and apply the buttress assembly of FIG. 100;

FIG. 104 depicts a top plan view of the buttress applier cartridge of FIG. 103;

FIG. 105A depicts a perspective view of the end effector of FIG. 2 and the buttress applier cartridge of FIG. 103, with the end effector approaching the buttress applier cartridge;

FIG. 105B depicts a perspective view of the end effector of FIG. 2 and the buttress applier cartridge of FIG. 103, with the buttress applier cartridge positioned in the end effector;

FIG. 106 depicts a schematic perspective view of another exemplary buttress applier cartridge that may be used to carry and apply the buttress assembly of FIG. 103;

FIG. 107 depicts a schematic front plan view of the buttress applier cartridge of FIG. 106;

FIG. 108A depicts a schematic cross-sectional side view of the end effector of FIG. 99 and the buttress applier cartridge of FIG. 106, with the buttress applier cartridge positioned in the end effector, and with the end effector in an open configuration;

FIG. 108B depicts a schematic cross-sectional side view of the end effector of FIG. 99 and the buttress applier cartridge of FIG. 106, with the buttress applier cartridge positioned in the end effector, and with the end effector in a closed configuration;

FIG. 109 depicts a schematic perspective view of another exemplary buttress applier cartridge that may be used to carry and apply the buttress assembly of FIG. 100;

FIG. 110 depicts a schematic front plan view of the buttress applier cartridge of FIG. 109;

FIG. 111A depicts a schematic cross-sectional side view of the end effector of FIG. 99 and the buttress applier cartridge of FIG. 109, with the buttress applier cartridge positioned in the end effector, and with the end effector in an open configuration; and FIG. 111B depicts a schematic cross-sectional side view of the end effector of FIG. 99 and the buttress applier cartridge of FIG. 109, with the buttress applier cartridge positioned in the end effector, and with the end effector in a closed configuration.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. EXEMPLARY SURGICAL STAPLER

Figure 1:
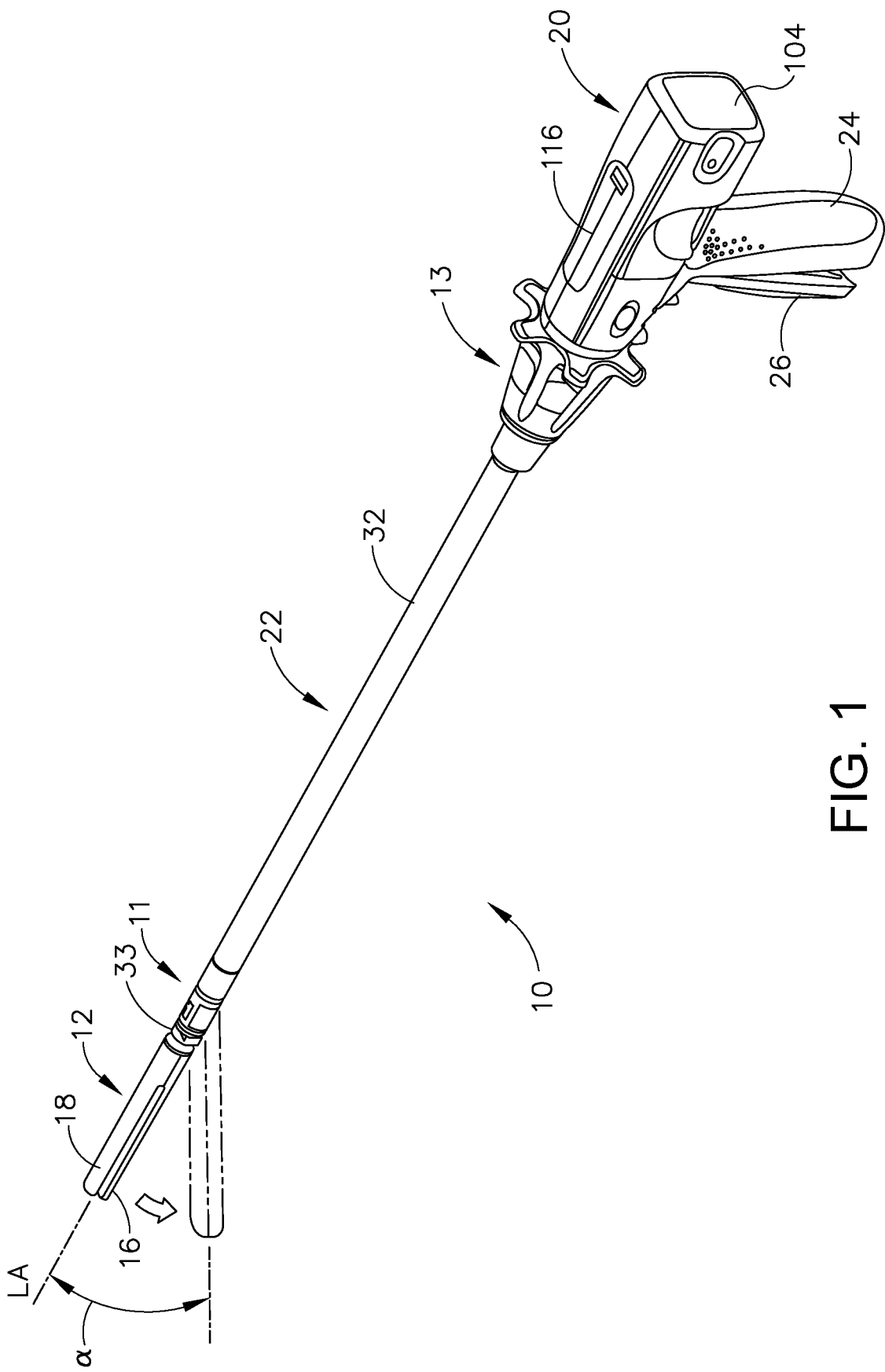
FIG. 1 depicts a perspective view of an exemplary articulating surgical stapling instrument.

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In the present example, anvil (18) can also be considered an upper jaw. Furthermore, in some versions like the present example, the upper jaw or anvil (18) pivots with respect to a stationary lower jaw (16); however, in some other versions the upper jaw or anvil (18) is stationary while the lower jaw (16) pivots. In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46), and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
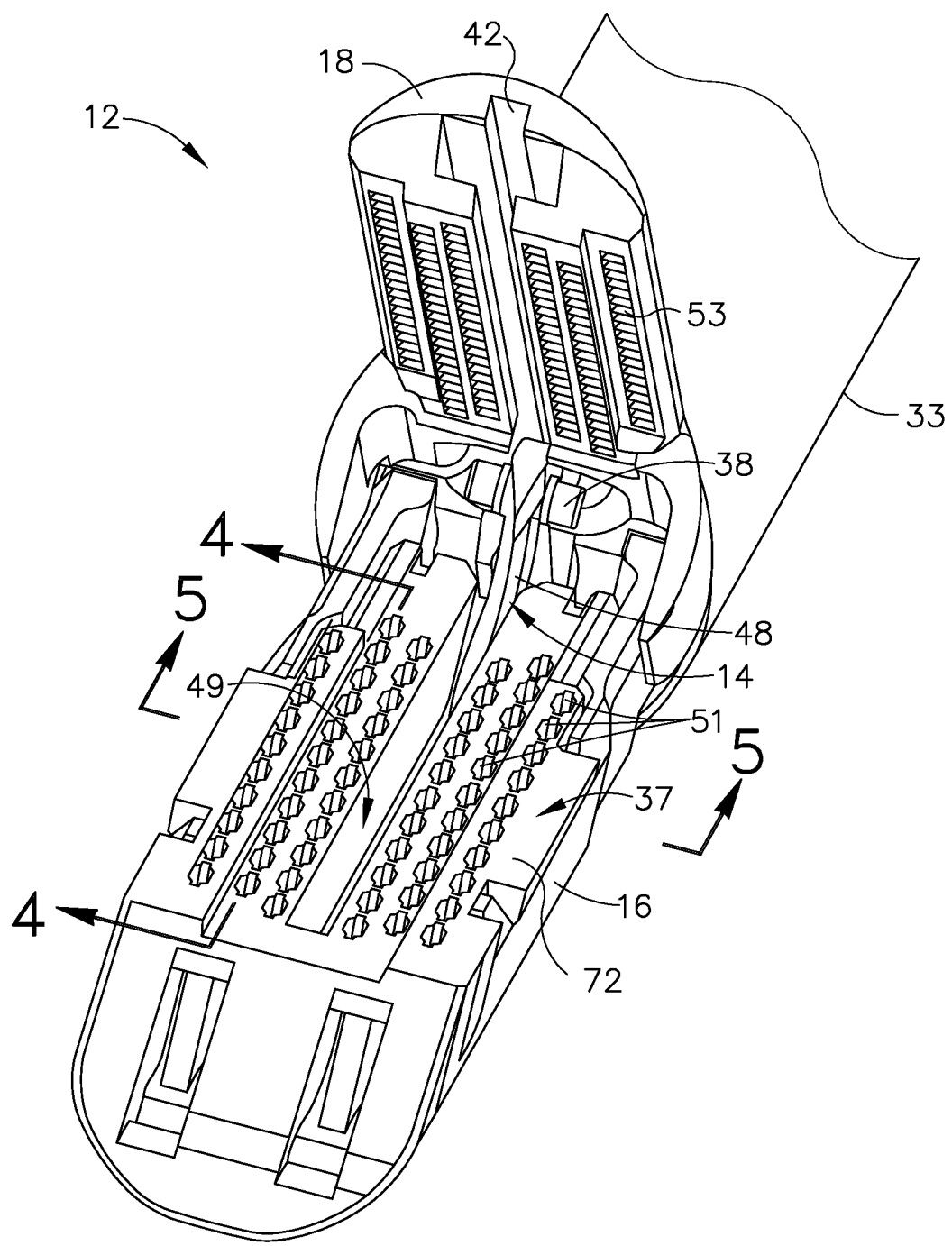
FIG. 3 depicts a perspective view of an opened end effector of the instrument of FIG. 1.
Figure 4A:
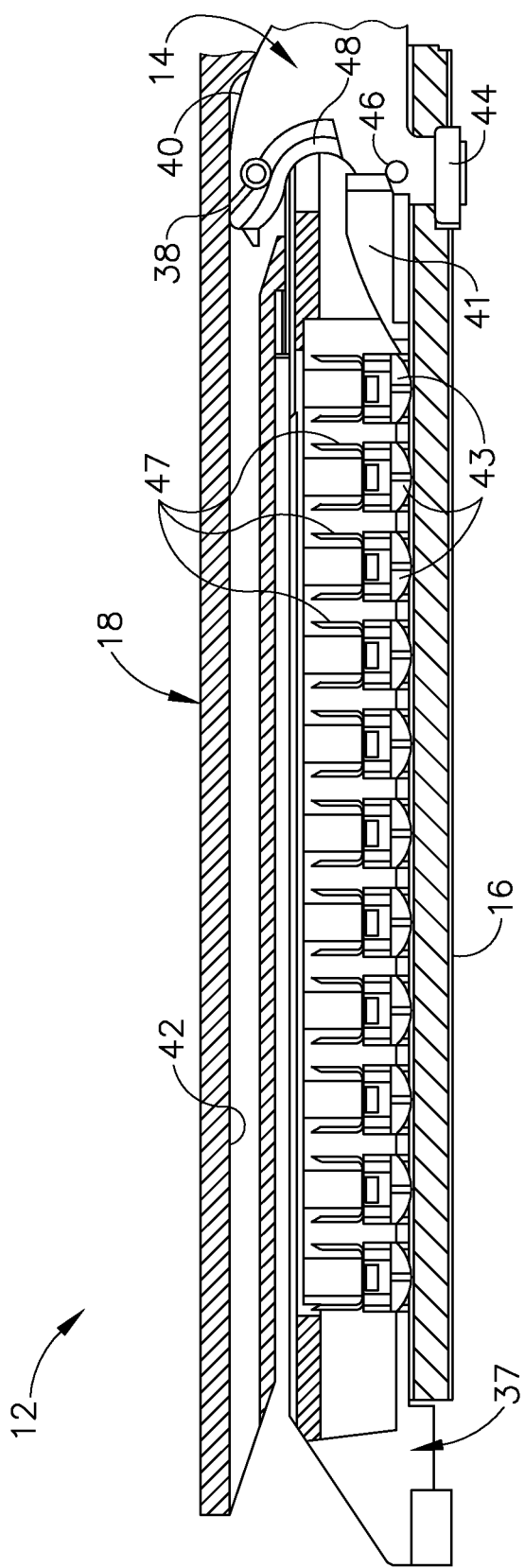
FIG. 4A depicts a side cross-sectional view of the end effector of FIG. 3, taken along line 4-4 of FIG. 3, with the firing beam in a proximal position.
Figure 4B:
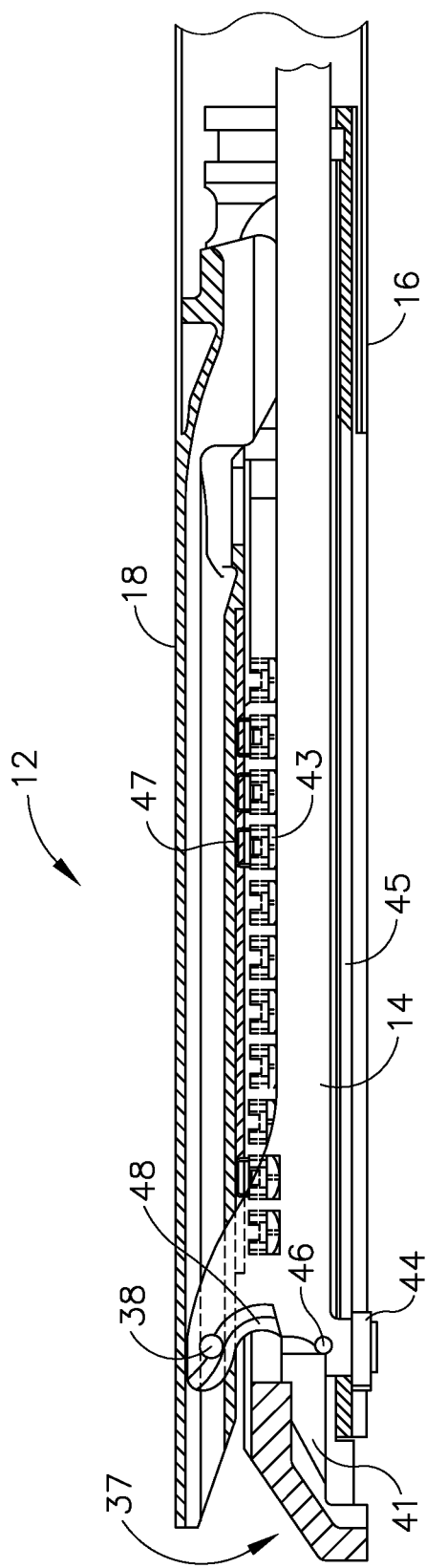
FIG. 4B depicts a side cross-sectional view of the end effector of FIG. 3, taken along line 4-4 of FIG. 3, with the firing beam in a distal position.
Figure 5:
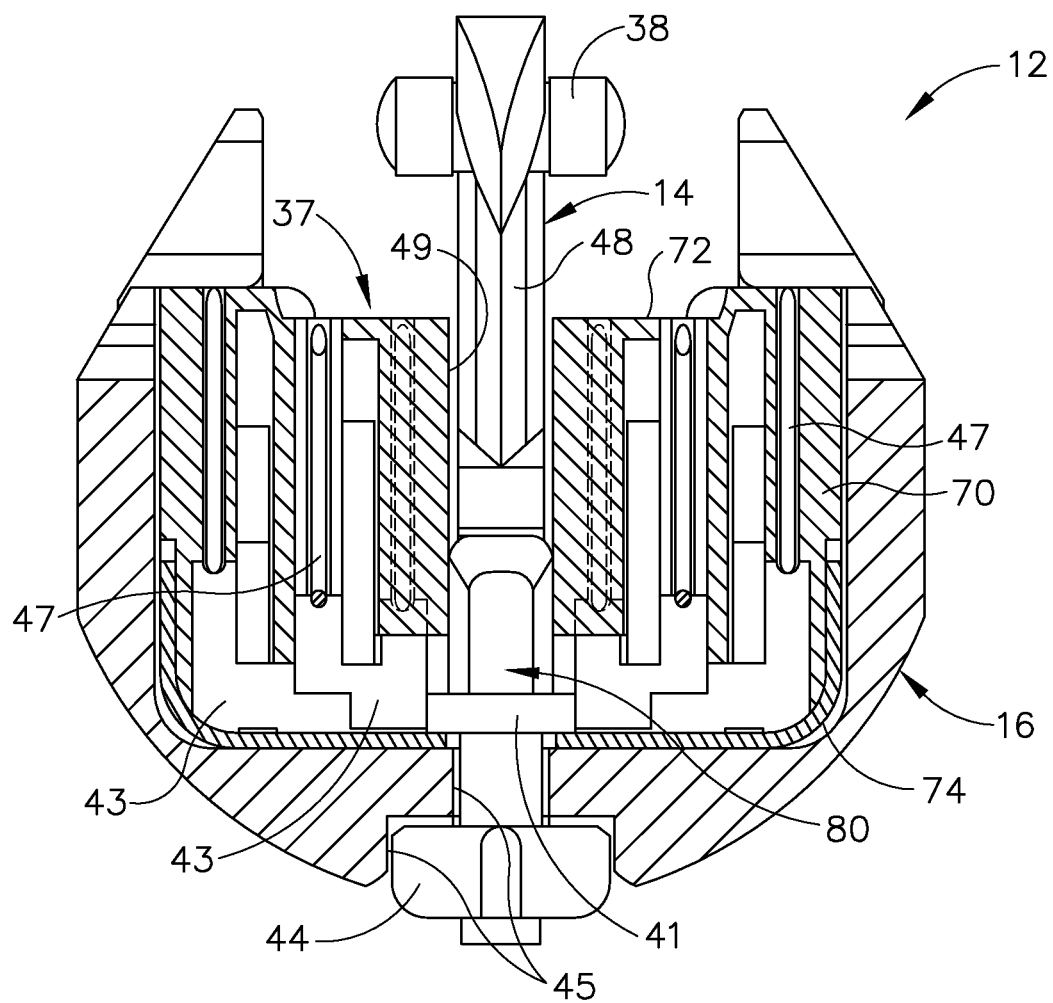
FIG. 5 depicts an end cross-sectional view of the end effector of FIG. 3, taken along line 5-5 of FIG. 3.
Figure 6:
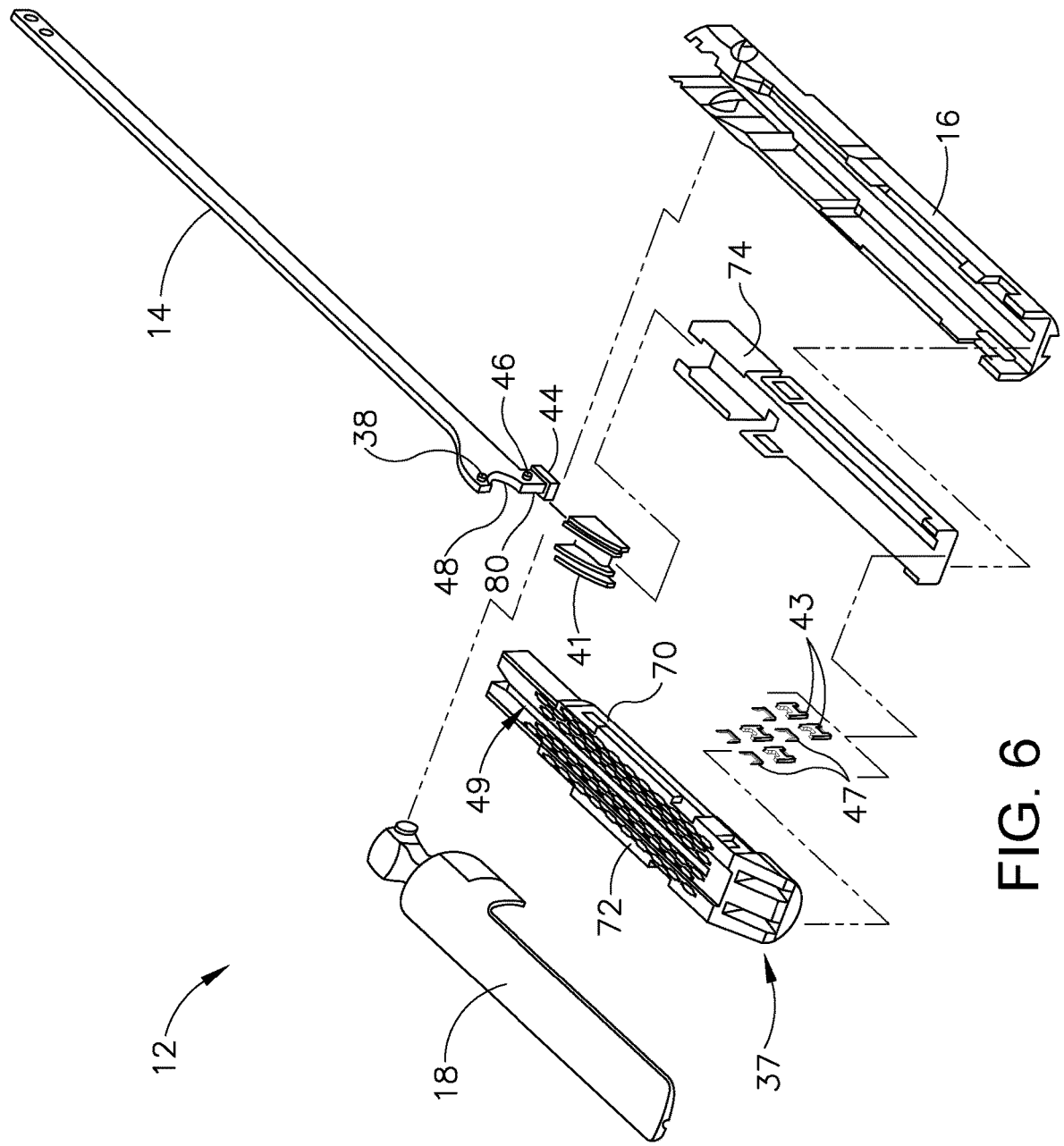
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
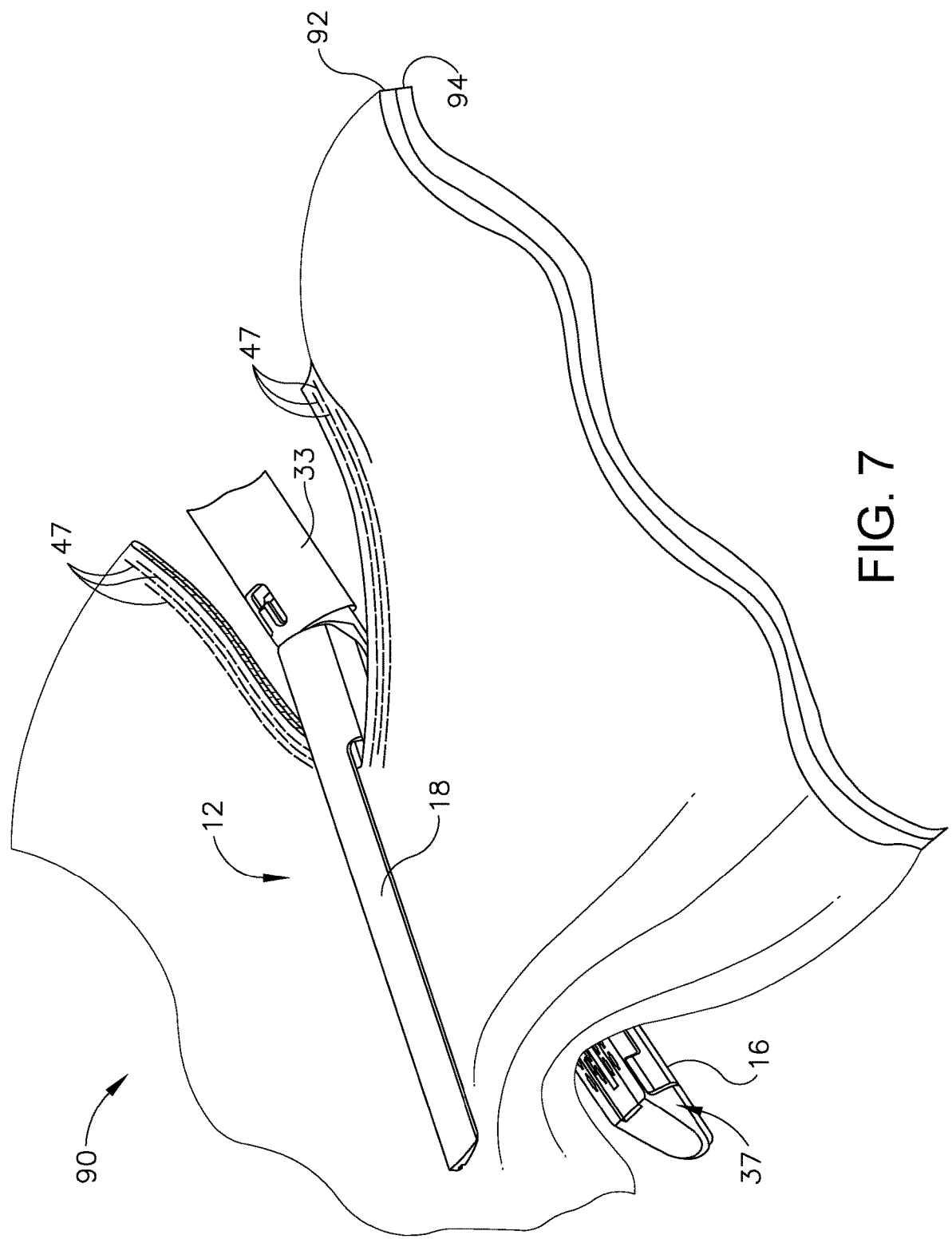
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY END EFFECTOR WITH VISUALIZATION, LEAD-IN, AND GATHERING FEATURE

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
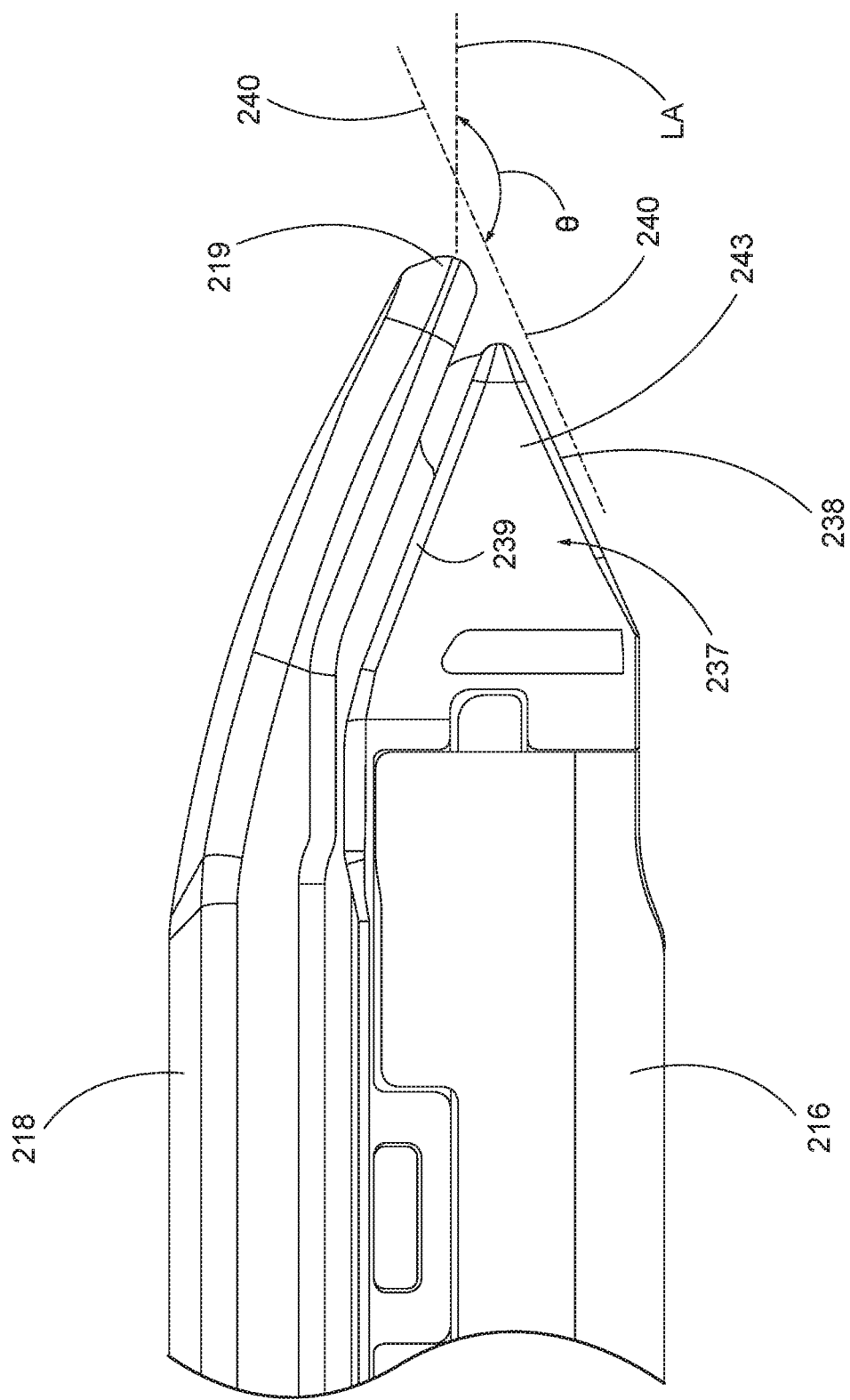
FIG. 9 depicts an enlarged, side view of the end effector of FIG. 8.
Figure 10:
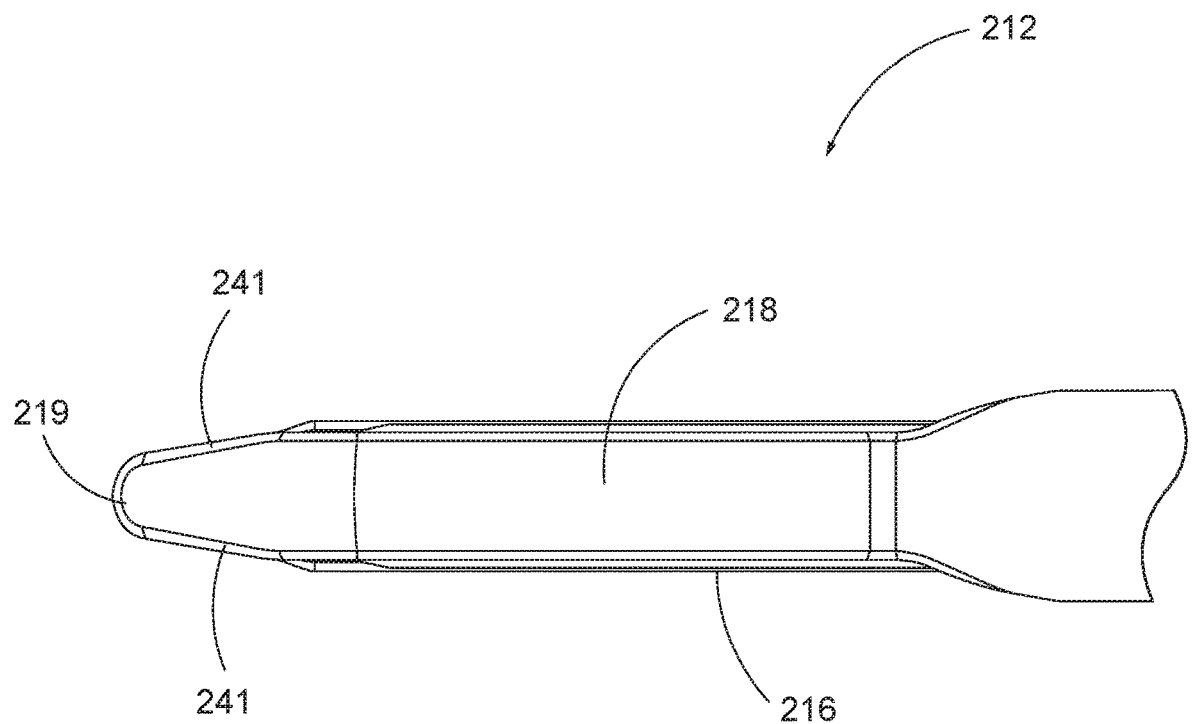
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. EXEMPLARY END EFFECTORS WITH BENT OR ANGLED ELASTICALLY DEFORMABLE ANVIL TIPS

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
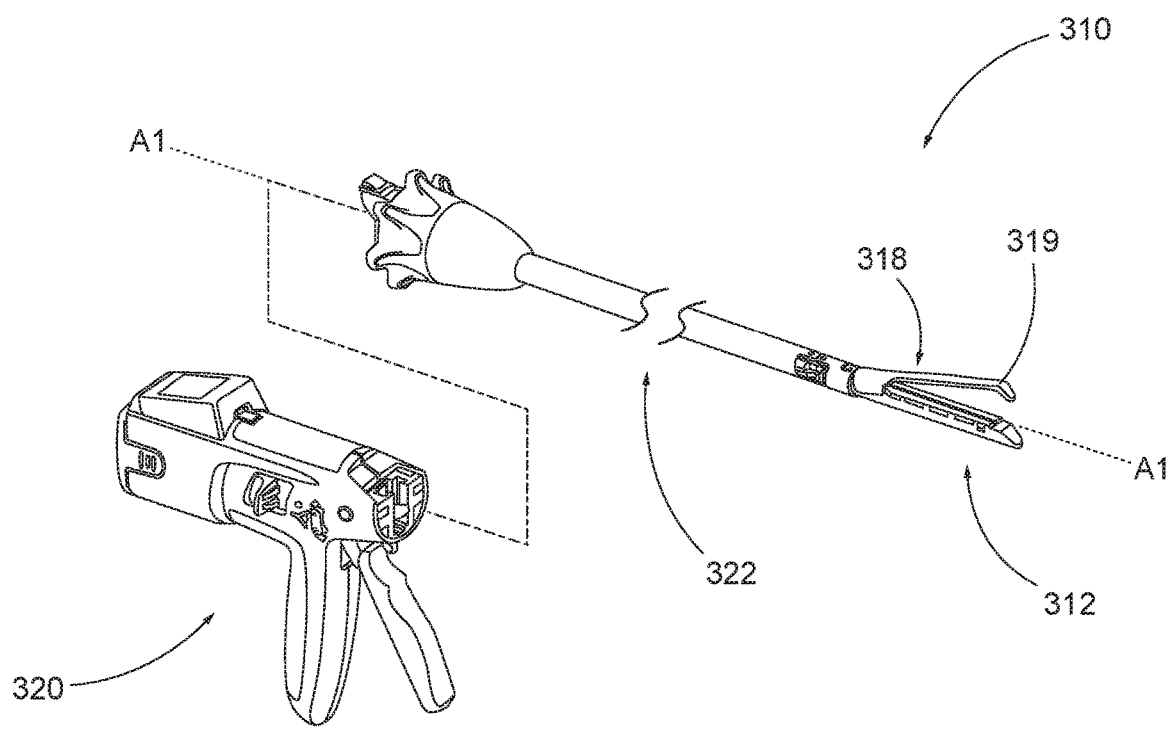
FIG. 11 depicts a perspective view of an exemplary surgical stapling instrument having an end effector with a bent or angled elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pub. No. 2017/086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
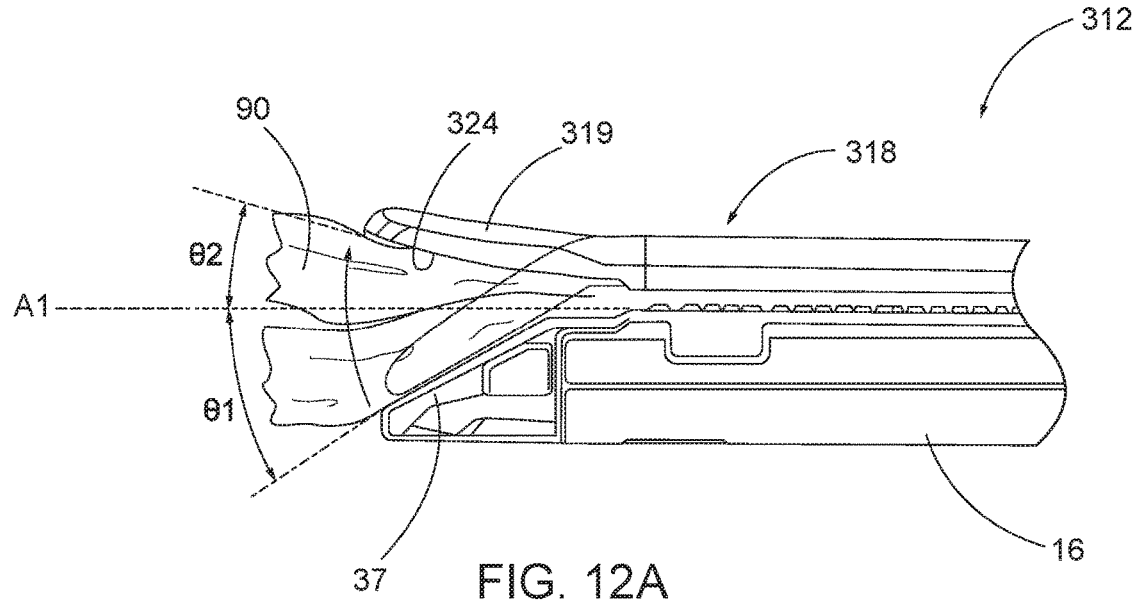
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle ($\theta1$). When closed and clamping tissue (90) between anvil (318) and lower jaw (16), underside surface (324) of tip (319) contacts tissue (90). In this position, underside surface (324) of tip (319) defines a plane that intersects longitudinal axis (A1) to form an angle ($\theta2$). In the illustrated example of FIG. 12A, angles ($\theta1$, $\theta2$) are relative to longitudinal axis (A1), and the sum of angles ($\theta1$, $\theta2$) represent the range of motion distal tip (319) undergoes. By way of example only, and not limitation, in some examples angle ($\theta1$) is between about 20 and about 70 degrees, or more particularly between about 30 degrees and about 50 degrees, in a downward direction from longitudinal axis (A1) toward cartridge (37). By way of example only, and not limitation, in some examples angle ($\theta2$) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles ($\theta1$, $\theta2$) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
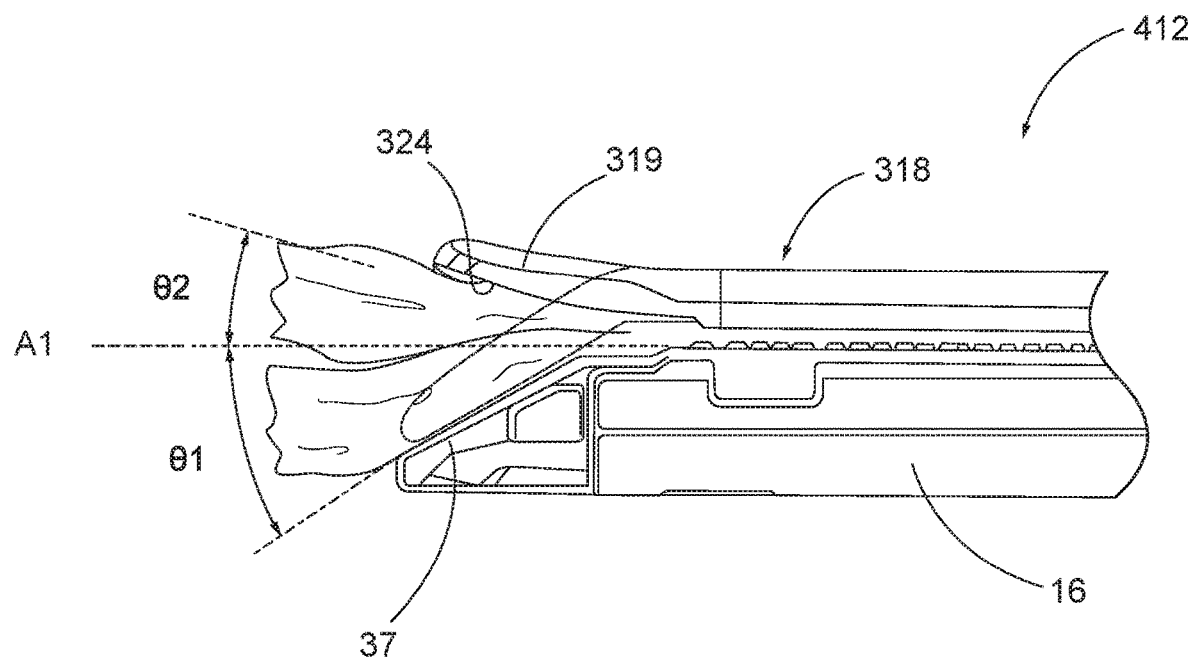
FIG. 12B depicts an enlarged side view of a distal portion of an alternate end effector similar to that of FIG. 11.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

A. Overmolded Anvil Tip

Figure 13:
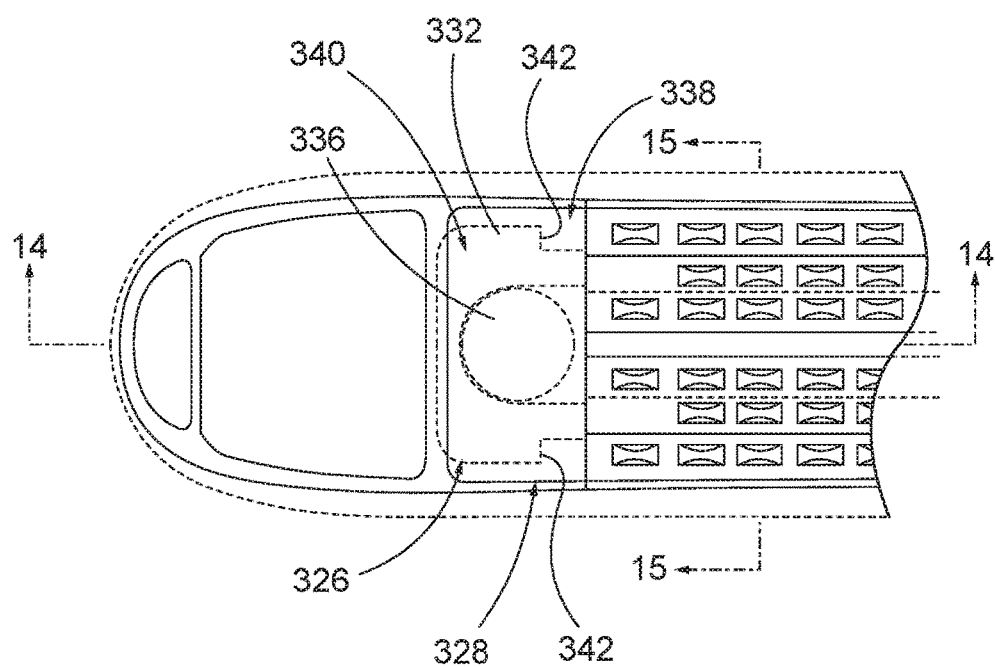
FIG. 13 depicts a bottom view of a distal portion of the end effector of FIG. 11 with the cartridge shown in phantom to reveal an underside surface of the anvil.
Figure 14:
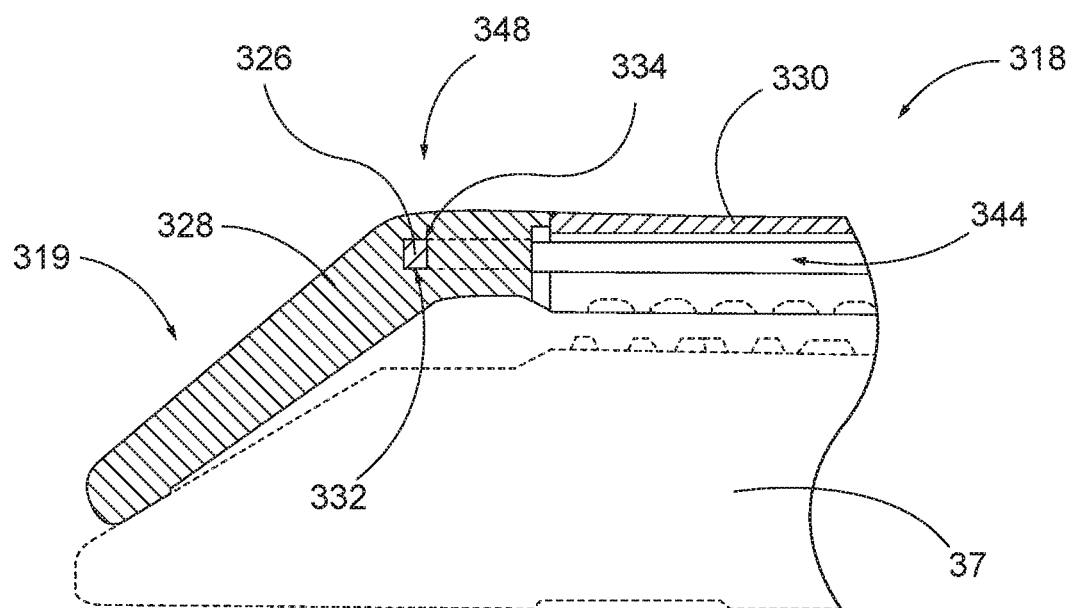
FIG. 14 depicts a side cross-sectional view of a distal portion of the end effector of FIG. 11, taken along line 14-14 of FIG. 13.
Figure 15:
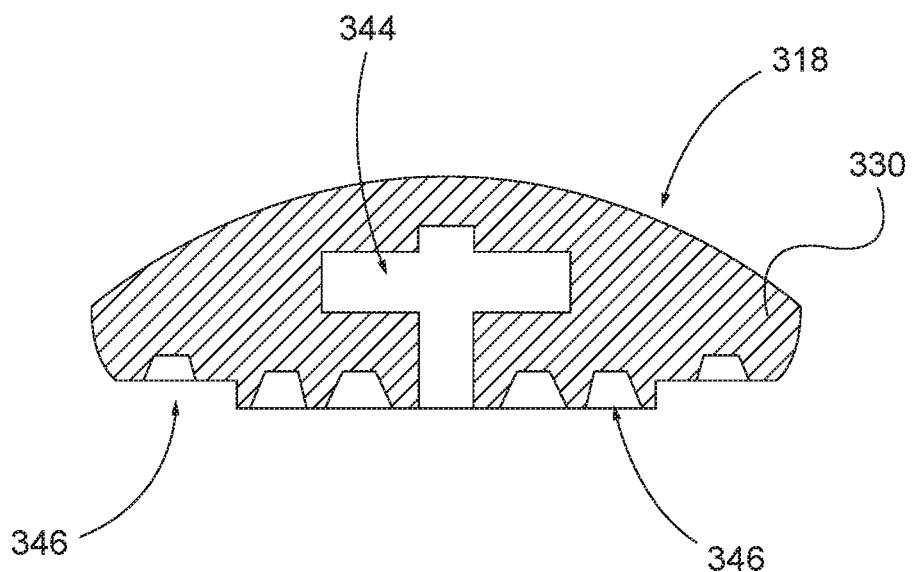
FIG. 15 depicts an end cross-sectional view of an anvil the end effector of FIG. 11, taken along line 15-15 of FIG. 13.

FIGS. 13-15 show enlarged distal views of end effector (312) to illustrate an exemplary construction. The constructions shown in FIGS. 13-15 also applies to end effector (412) shown in FIG. 12B, except for the anvil (318) length difference noted above. As shown in the top view of FIG. 13, end effector (312) comprises anvil (318) where distal tip (319) comprises a rigid portion (326) and a deflectable portion (328). In the present example, deflectable portion (328) is overmolded onto rigid portion (326) to form distal tip (319) of anvil (318). In the illustrated example as shown in FIG. 13, the outline of cartridge (37) is shown in phantom to reveal underside surface (324) of anvil (318). Rigid portion (326) of distal tip (319) extends from a body (330) of anvil (318). In the present example, body (330) is comprised of metal and rigid portion (326) is an extension of metal body (330) into distal tip (319). In other versions, body (330) and/or rigid portion (326) can be comprised of materials other than metal, including but not limited to plastic, ceramic, combinations of metal with plastic or ceramic, and other suitable materials or combinations of materials that will be apparent to those of ordinary skill in the art in view of the teachings herein. Additionally, rigid portion (326) in some versions is entirely rigid, yet in other versions rigid portion (326) can be resilient to a lesser extent than deflectable portion (328).

In the illustrated version of FIGS. 13 and 14, metal portion (326) comprises an underside surface (332) that is generally flat or planar, and a top surface (334) that is similarly generally flat or planar. Metal portion (326) further comprises an opening (336) that extends through metal portion (326) from top surface (334) to underside surface (332). Additionally, metal portion (326) comprises a neck region (338), a head region (340) that extends distally from neck region (338), and shoulders (342) at the transition between neck region (338) and head region (340). In the present example neck region (338) extends from body (330) of anvil (318). With this arrangement, metal portion (326) provides securing features or interfaces, such as opening (336) and shoulders (342), where elastomeric portion (328) can connect with metal portion (326) in a secure fashion using an overmolding process.

FIG. 15 illustrates a cross section view of anvil (318) just proximal to distal tip (319). As shown, anvil (318) comprises a longitudinal slot (344) that divides six rows of staple forming pockets (346) into two sets of three rows each. Slot (344) and staple forming pockets (346) are structurally and functionally similar to slot (42) and staple forming pockets (53) described above with respect to anvil (18). Slot (344) comprises a "t" shaped cross section as shown in FIG. 15. Referring again to FIGS. 13 and 14, opening (336) in metal portion (326) is positioned adjacent to a laterally extending portion of slot (344). In view of the teachings herein, other ways to configure metal portion (326) for suitable connection with elastomeric portion (328) using an overmolding process will be apparent to those of ordinary skill in the art.

Elastomeric portion (328) is molded onto metal portion (326) and in the molding process is imparted with an angled configuration such that elastomeric portion (328) defines a plane that intersects and is not co-planar with a plane defined by body (330) of anvil (318). In this manner, elastomeric portion (328) is formed with a bias to maintain its angled configuration unless some other force is imparted onto elastomeric portion (328) causing it to deflect from its initial angled position. During the molding process, elastomeric material flows through and fills opening (336) in metal portion (326). Elastomeric material also flows around and adjacent to shoulders (342). In this manner, elastomer portion (328) is securely connected with metal portion (326) during the overmolding process. Elastomeric portion (328) may comprise rubber, plastic, or any other suitable natural or synthetic material having the desired elastomeric properties that will allow distal tip (319) to deform when subject to force, yet resiliently return to its initial angled state when the force is no longer applied or present. During the molding process, a stop member (not shown) may be inserted into a slot (349) formed distally to slot (344), to prevent the elastomeric material from entering slot (344). In view of the teachings herein, other ways to configure elastomeric portion (328) for suitable connection with metal portion (326) using an overmolding process will be apparent to those of ordinary skill in the art.

With the configuration for distal tip (319) as described above and shown in FIGS. 13 and 14, the extension of metal portion (326) into the region of distal tip (319) defines a deflection zone (348). Deflection zone (348) coincides with a rigid portion of distal tip (319) located at a proximal end of distal tip (319). With this area of increased rigidity, distal tip (319) will deflect, for example as shown in FIG. 12A, with deflection zone (348) serving as a pivot point or location about which the remainder of distal tip (319) rotates during deflection. In view of the teachings herein, those of ordinary skill in the art will appreciate other ways in which to modify distal tip (319) to alter, modify, or control deflection zone (348) such that a desired deflection of distal tip (319) is achieved.

IV. METHOD OF SURGICAL STAPLING WITH END EFFECTOR COMPONENT HAVING A CURVED TIP

A. Exemplary Configurations for End Effectors with Elastically Deformable Placement Tips With end effectors having bent or angled elastic deformable tips, also referred to as placement tips, such as those described above with respect to end effectors (312, 412), the deformable tips can deflect during use. As described above, the elastic deformable tip can be located on the anvil, like with anvil (318). In other versions, the elastic deformable tip can be located on the cartridge. Additionally, while end effectors (12, 212, 312, 412) described above are discussed as including a lower jaw (16, 216) opposite to the anvil (18, 218, 318), in some versions the end effectors comprise an upper jaw and a lower jaw, where the anvil may be located on either jaw, and the cartridge may be located on either jaw opposite the jaw with the anvil. Furthermore, either jaw may include the elastic deformable tip, which can be part of, or associated with, the anvil or the cartridge. The following paragraphs describe several exemplary end effectors, usable with instruments (10, 310) and other instruments, that include a lower jaw, an upper jaw, and an elastic deformable tip or placement tip. These exemplary end effectors are shown and described in a variety of ways that are not intended to be mutually exclusive of each other. Instead, in many instances the features of one version applies equally to another version, as will be appreciated by those of ordinary skill in the art in view of the teachings herein.

In some versions that will be shown and described, the deflection of the deformable tip changes an angle of the deformable tip relative to a longitudinal axis defined by the jaw with which the deformable tip is located when comparing states when the end effector is in open versus closed states. In some versions that will be shown and described, the deflection of the deformable tip changes an angle of the deformable tip relative to the nose of the cartridge when the end effector is loaded or engages tissue versus when the end effector is not loaded or not engaged with tissue. In some versions that will be shown and described, the placement tip of one of the end effector jaws may adopt certain positions relative to the other of the end effector jaws when in deflected versus non-deflected states. In some versions that will be shown and described, the end effector components are configured with certain placement tip end and/or width profiles. Lastly, in some versions that will be shown and described, the end effector components are configured with certain underside surface configurations and/or gaps.

The end effectors described below can each be configured for use with instruments (10, 310) described above. For instance, it will be appreciated that each of the end effectors described below may be used in place of end effector (12) shown in FIG. 1 or in place of end effector (312) shown in FIG. 11. In some versions, each of the end effectors described below may be integrally formed with shaft (22) or alternatively may be separately formed and then combined. In some versions, each of the end effectors described below may be provided for use in robotic systems. In such robotic systems, modular shaft (322) having any of the end effectors described below may be attachable to a portion of the robotic system for use such that handle portion (320) is replaced by components of the robotic system. Still in other examples, each of the end effectors described below may be adapted for use with a robotic system in a manner where any of the end effectors described below connects with the robotic system without necessarily connecting the entire modular shaft (322). In view of the teachings herein, other ways to incorporate each of the end effectors described below into a user operated or robotic operated instrument will be apparent to those of ordinary skill in the art.

1. Exemplary Angles in Open and Closed States

Figure 16:
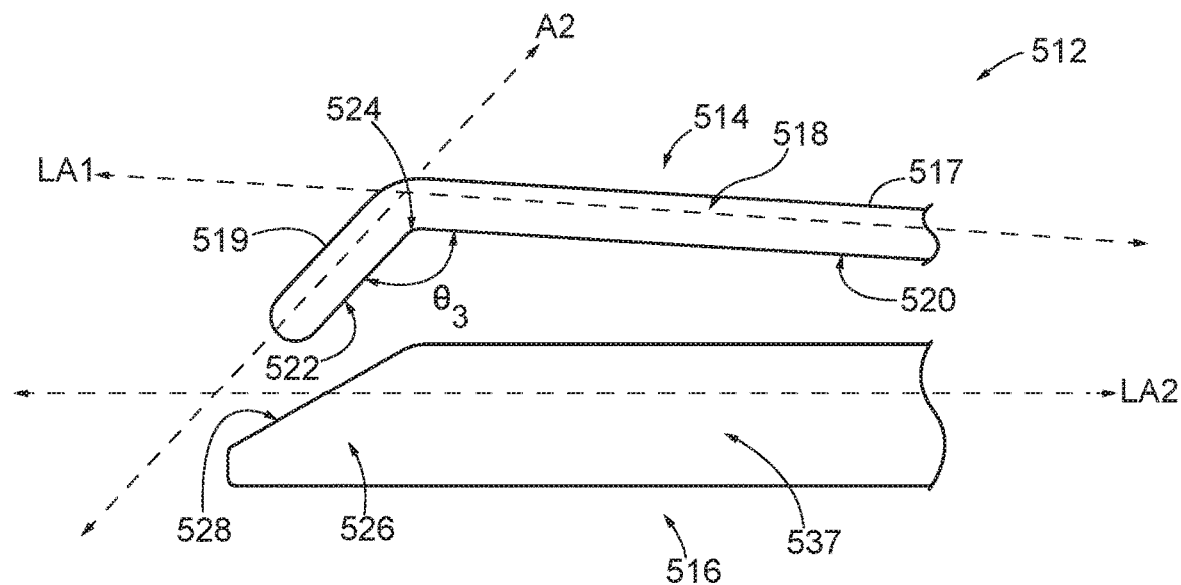
FIG. 16 depicts an enlarged side view of a distal portion of an alternative version of an end effector, shown in an open position and having an upper jaw with a placement tip that forms a first angle with a longitudinal axis of the upper jaw.
Figure 17:
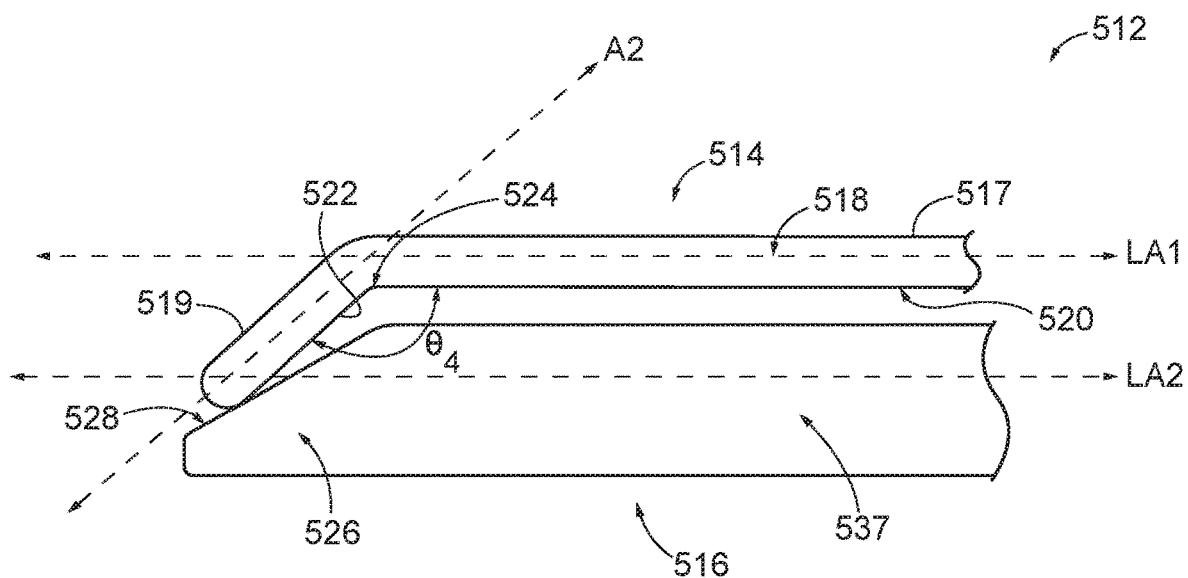
FIG. 17 depicts an enlarged side view of the distal portion of the end effector of FIG. 16, shown in a closed position and having the placement tip forming a second angle with the longitudinal axis of the upper jaw.

Referring now to FIGS. 16 and 17, an enlarged view of an end effector (512) is shown. End effector (512) is configured for use with instruments (10, 310) and/or for robotic use as described above. End effector (512) comprises an upper jaw (514) and a lower jaw (516). In the present example, upper jaw (514) comprises a body (517) having distal tip or placement tip (519) that is bent or angled and elastically deformable. Body (517), excluding placement tip (519), defines a longitudinal axis (LA1). Placement tip (519) defines another axis (A2). In the present example, longitudinal axis (LA1) extends parallel to an underside surface (520) of body (517) of upper jaw (514). Similarly, axis (A2) extends parallel to an underside surface (522) of placement tip (519).

As shown in FIG. 16, end effector (512) is in an open position or state with no tissue or other object contacting end effector (512). A first angle (θ3) is defined by the intersection of longitudinal axis (LA1) of body (517) and axis (A2) of placement tip (519). Stated another way, first angle (θ3) is defined by the intersection of a plane extending along underside surface (520) of body (517) and a plane extending along underside surface (522) of placement tip (519).

As shown in FIG. 17, end effector (512) has been moved to a closed position and still in an unloaded state without tissue contacting end effector (512). However, in the closed position, placement tip (519) of upper jaw (514) contacts lower jaw (516). With this contact and the elastically deformable nature of placement tip (519), placement tip (519) deflects from its position relative to body (517) as shown in FIG. 16. In this deflected position or state, a second angle (θ4) is defined by the intersection of longitudinal axis (LA1) of body (517) and axis (A2) of placement tip (519). Stated another way, second angle (θ4) is defined by the intersection of a plane extending along underside surface (520) of body (517) and a plane extending along underside surface (522) of placement tip (519).

With the deflection of placement tip (519), second angle (θ4) is not the same as first angle (θ3). For instance, with the illustrated deflection in FIG. 17, the lower jaw (516) contacts the underside of placement tip (519) such that placement tip (519) pivots upward away from lower jaw (516) such that the second angle (θ4) is greater than the first angle (θ3). In the present example, end effector (512) defines a pivot point (524) about which placement tip (519) pivots relative to body (517). More specifically, pivot point (524) occurs at the location where underside surface (520) of body (517) and underside surface (522) of placement tip (519) meet. With this configuration, end effector (512) comprises a placement tip (519) extending from the distal end of upper jaw (514). Placement tip (519) comprises a first angle (θ3) with respect to the axis of body (517) of upper jaw (514), or longitudinal axis (LA1), when end effector (512) is in the open position. Placement tip (519) further comprises a second angle (θ4) with respect to the axis of body (517) of upper jaw (514), when end effector (512) is in the closed position, and second angle (θ4) differs from first angle (θ3).

In view of the teachings herein, various ways to modify end effector (512) and the deflection of placement tip (519) such that other angles are achieved for second angle (θ4) when end effector (512) is in a closed position will be apparent to those of ordinary skill in the art in view of the teachings herein. By way of example only, and not limitation, one such modification would be to alter the relationship of the contact that placement tip (519) makes with lower jaw (516) when end effector (512) is closed. In the present example, lower jaw (516) comprises a nose portion (526) at a distal end of lower jaw (516). Furthermore, nose portion (526) comprises a top surface (528) that defines a plane having a slope relative to a longitudinal axis (LA2) of lower jaw (516). This slope can impact the deflection of the placement tip (519) thereby causing changes in the second angle (θ4). By way of another example only, and not limitation, another such modification would be to include features on top surface (528) that direct and/or impact the deflection of the placement tip (519) thereby causing changes in the second angle (θ4).

In some versions, upper jaw (514) comprises an anvil (518) similar to anvils (18, 218, 318) as described above. In such versions, anvil (518) comprises body (517) and placement tip (519). Also in such versions, opposite anvil (518), lower jaw (516) comprises a staple cartridge (537) with nose portion (526). With this configuration, end effector (512) comprises placement tip (519) extending from the distal end of anvil (518). Placement tip (519) comprises a first angle (θ3) with respect to anvil (518) axis or longitudinal axis (LA1) when end effector (512) is in the open position. Placement tip (519) further comprises a second angle (θ4) with respect to anvil (518) axis or longitudinal axis (LA1) when end effector (512) is in the closed position, and second angle (θ4) differs from first angle (θ3) as described above. In some other versions, the location of anvil (518) and cartridge (537) can be switched such that lower jaw (516) comprises anvil (518) while upper jaw (514) comprises staple cartridge (537).

2. Exemplary Angles with Deflection by Tissue

Figure 18:
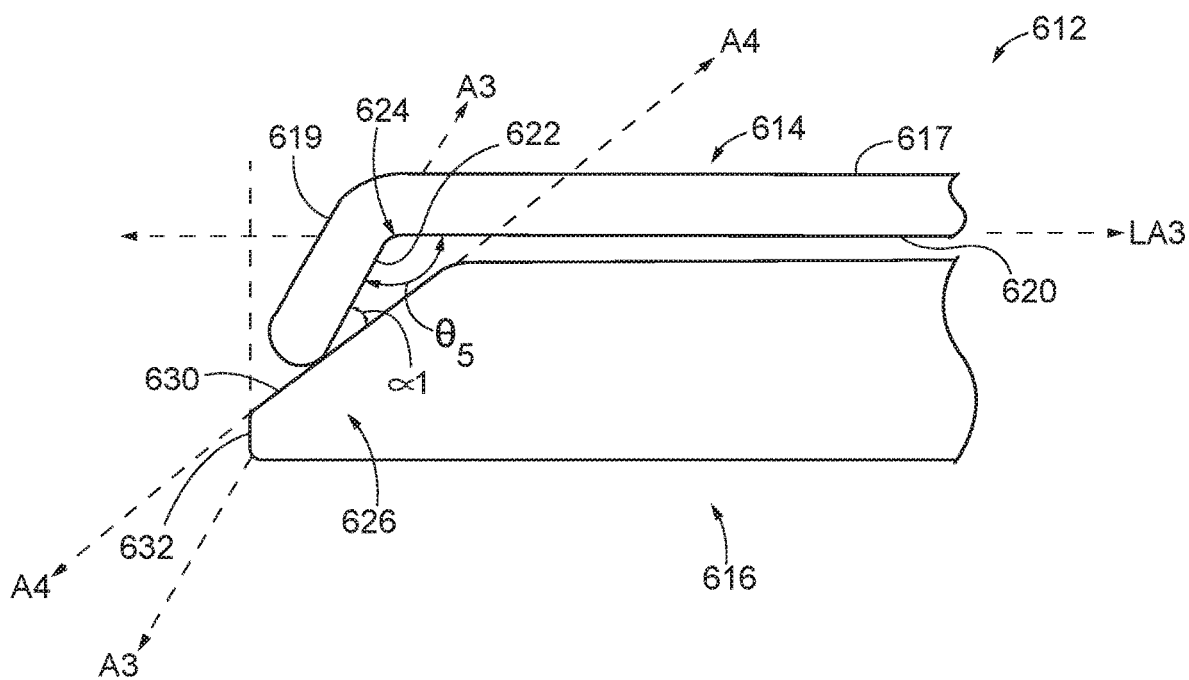
FIG. 18 depicts an enlarged side view of a distal portion of an alternative version of an end effector, shown in a closed and unloaded position and having an upper jaw with placement tip that forms a first angle with a nose portion of a lower jaw.
Figure 19:
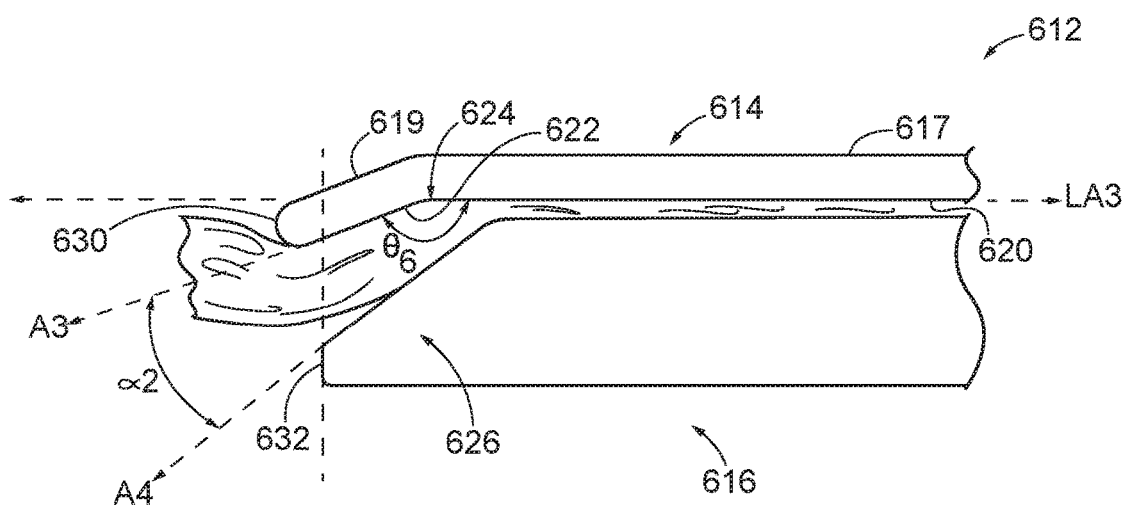
FIG. 19 depicts an enlarged side view of the distal portion of the end effector of FIG. 18, shown in a closed and loaded position and having the placement tip forming a second angle with the nose portion of the lower jaw.

Referring now to FIGS. 18 and 19, an enlarged view of an end effector (612) is shown. End effector (612) is configured for use with instruments (10, 310) and/or for robotic use as described above. End effector (612) comprises an upper jaw (614) and a lower jaw (616). In the present example, upper jaw (614) comprises a body (617) having placement tip (619) that is bent or angled and elastically deformable. Body (617), excluding the placement tip (619), defines a longitudinal axis (LA3) that extends along an underside surface (620) of body (617). Placement tip (619) defines another axis (A3) that extends along an underside surface (622) of placement tip (619). Furthermore, in the present example, lower jaw (616) comprises a tapered nose portion (626) at a distal end of lower jaw (616). Nose portion (626) defines an axis (A4) that extends along a top surface (628) of nose portion (626).

As shown in FIG. 18, end effector (612) is in an unloaded state with no tissue or other object between upper jaw (614) and lower jaw (616). A third angle (θ5) is defined by the intersection of longitudinal axis (LA3) of body (617) and axis (A3) of placement tip (619). Stated another way, third angle (θ5) is defined by the intersection of a plane extending along underside surface (620) of body (617) and a plane extending along underside surface (622) of placement tip (619) when end effector (612) is in an unloaded state. Similarly, when end effector (612) is in an unloaded state with no tissue or other object between upper jaw (614) and lower jaw (616) as shown in FIG. 18, a fifth angle (α1) is defined by the intersection of axis (A3) of placement tip (619) and axis (A4) of nose portion (626). Stated another way, fifth angle (α1) is defined by the intersection of a plane extending along underside surface (622) of placement tip (619) and a plane extending along top surface (628) of nose portion (626) when end effector (612) is in an unloaded state. As also shown in the present example of FIG. 18, with end effector (612) closed and in an unloaded state, an end (630) of placement tip (619) is located proximal to an end (632) of nose portion (626).

As shown in FIG. 19, end effector (612) has been moved to a closed position and loaded state with tissue between upper jaw (614) and lower jaw (616) of end effector (612). With tissue between jaws (614, 616) and the elastically deformable nature of placement tip (619), placement tip (619) deflects from its position relative to body (617). In this deflected position or state, a fourth angle (θ6) is defined by the intersection of longitudinal axis (LA3) of body (617) and axis (A3) of placement tip (619). Stated another way, fourth angle (θ6) is defined by the intersection of a plane extending along underside surface (620) of body (617) and a plane extending along underside surface (622) of placement tip (619) when end effector (612) is in a loaded state. Similarly, when end effector (612) is in the loaded state with tissue between upper jaw (614) and lower jaw (616) as shown in FIG. 19, a sixth angle (α2) is defined by the intersection of axis (A3) of placement tip (619) and axis (A4) of nose portion (626). Stated another way, sixth angle (α2) is defined by the intersection of a plane extending along underside surface (622) of placement tip (619) and a plane extending along top surface (628) of nose portion (626) when end effector (612) is in a loaded state. As also shown in the present example of FIG. 19, with end effector (612) closed and in a loaded state, end (630) of placement tip (619) is located distal to end (632) of nose portion (626).

With the deflection of placement tip (619) in the loaded state of FIG. 19 versus the unloaded state of FIG. 18, fourth angle (θ6) is not the same as third angle (θ5). For instance, with the illustrated deflection in FIG. 19, the tissue contacts the underside of placement tip (619) such that placement tip (619) pivots upward away from lower jaw (616) such that the fourth angle (θ6) is greater than the third angle (θ5). In the present example, end effector (612) defines a pivot point (624) about which placement tip (619) pivots relative to body (617). More specifically, pivot point (624) occurs at the location where underside surface (620) of body (617) and underside surface (622) of placement tip (619) meet. With this configuration, end effector (612) comprises a placement tip (619) extending from the distal end of upper jaw (614). Placement tip (619) comprises a third angle (θ5) with respect to the axis of body (617) of upper jaw (614), or longitudinal axis (LA3), when end effector (612) is in the closed and unloaded state. Placement tip (619) further comprises a fourth angle (θ6) with respect to the axis of body (617) of upper jaw (614), when end effector (612) is in the closed position and loaded state, and fourth angle (θ6) differs from third angle (θ5). Similarly with this configuration, end effector (612) comprises placement tip (619) having an undeflected state and a deflected state. In the undeflected state placement tip (619) and nose portion (626) define fifth angle (α1), and in the deflected state placement tip (619) and nose portion (626) define sixth angle (α2) that differs from fifth angle (α1).

In view of the teachings herein, various ways to modify end effector (612) and the deflection of placement tip (619) such that other angles are achieved for fourth angle (θ6) and sixth angle (α2) when end effector (612) is in a closed and loaded state will be apparent to those of ordinary skill in the art in view of the teachings herein. By way of example only, and not limitation, one such modification would be to alter the taper of nose portion (626) so that axis (A4) that extends along top surface (628) of nose portion (626) is steeper or shallower. By way of another example only, and not limitation, another such modification would be to include features on top surface (628) that direct the tissue held between the nose portion (626) and placement tip (619) to alter the force applied to placement tip (619) and thereby the deflection of placement tip (619) to cause changes in fourth angle (θ6) and sixth angle (α2) when end effector (612) is in a closed and loaded state.

In some versions, upper jaw (614) comprises an anvil (618) similar to anvils (18, 218, 318) as described above. In such versions, anvil (618) comprises body (617) and placement tip (619). Also in such versions, opposite anvil (618), lower jaw (616) comprises a staple cartridge (637) with nose portion (626). With this configuration, end effector (612) comprises placement tip (619) extending from the distal end of anvil (618). Placement tip (619) comprises a third angle (θ5) with respect to anvil (618) axis or longitudinal axis (LA3) when end effector (612) is in the closed and unloaded state. Placement tip (619) further comprises a fourth angle (θ6) with respect to anvil (618) axis or longitudinal axis (LA3) when end effector (612) is in the closed and loaded state, and fourth angle (θ6) differs from third angle (θ5) as described above. Similarly with this configuration, end effector (612) comprises placement tip (619) extending from the distal end of anvil (618), and nose portion (619) at a distal end of cartridge (637), where end effector (612) has an undeflected state and a deflected state. In the undeflected state placement tip (619) of anvil (618), and nose portion (626) of cartridge (637), define fifth angle (α1). In the deflected state placement tip (619) of anvil (618), and nose portion (626) of cartridge (637) define sixth angle (α2) that differs from fifth angle (α1). In some other versions, the location of anvil (618) and cartridge (637) can be switched such that lower jaw (616) comprises anvil (618) while upper jaw (614) comprises staple cartridge (637).

3. Exemplary Tip Positions in Deflected and Non-Deflected States

As described above with respect to FIGS. 18 and 19, placement tip (619) is configured to deflect when end effector (612) is loaded, and such deflection occurs in a manner where end (630) of placement tip (619) changes its relative placement or location with respect to end (632) of nose portion (626) of cartridge (637). As shown in FIGS. 18 and 19, end (630) is proximal to end (632) when end effector (612) is unloaded such that there is an absence of tissue between upper jaw (614) and lower jaw (616). And when end effector (612) is loaded with tissue between upper jaw (614) and lower jaw (616), end (630) moves distally such that end (630) is distal to end (632).

Figure 20:
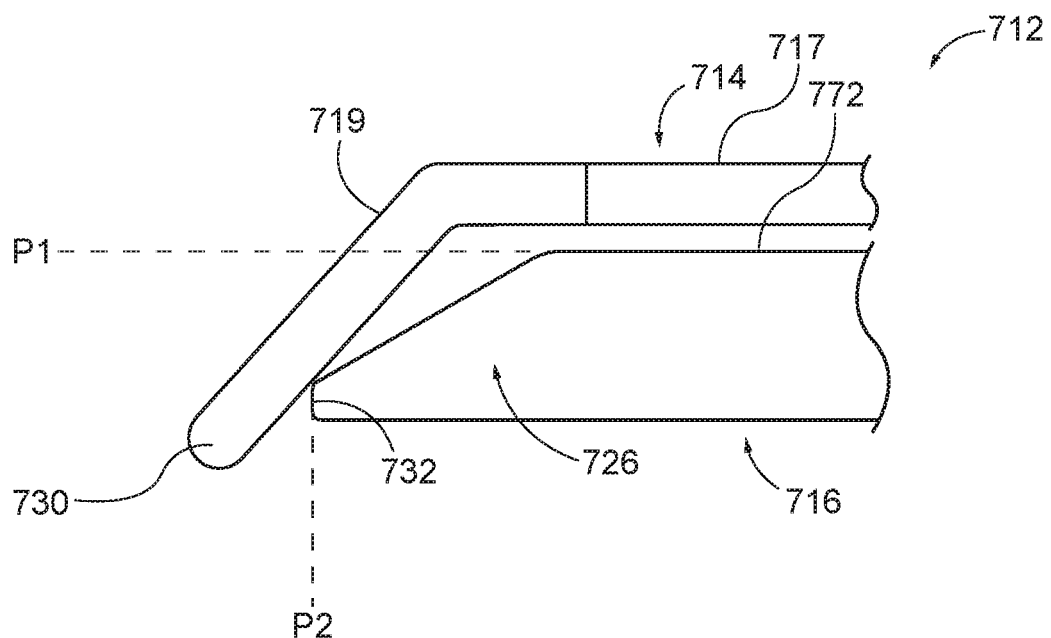
FIG. 20 depicts an enlarged side view of a distal portion of an alternative version of an end effector, shown in a closed position with a distal end of a placement tip of an upper jaw being located relative to a deck and a distal end of a lower jaw.

Referring now to FIG. 20, an enlarged view of an end effector (712) is shown. End effector (712) is configured for use with instruments (10, 310) and/or for robotic use as described above. End effector (712) comprises upper jaw (714) and lower jaw (716). Lower jaw (716) comprises nose portion (726) and end (732). Lower jaw (716) further comprises deck (772). Upper jaw (714) comprises a body (717) and a placement tip (719). Placement tip (719) has a bent or angled configuration and is elastically deformable as described above. Placement tip (719) comprises end (730) at its distal-most portion.

As shown in FIG. 20, a first reference plane (P1) is defined by deck (772), and generally extends parallel with a longitudinal axis of lower jaw (716). A second reference plane (P2) passes through end (732) of nose portion (726) such that second reference plane (P2) is orthogonal to first reference plane (P1). As shown in FIG. 20, the location or placement of end (732) of placement tip (719) can be shown and described relative to first reference plane (P1) and second reference plane (P2). In other words, the location or placement of end (730) of placement tip (719) can be described as being proximal to, even with, or distal to end (732) of nose portion (726) of lower jaw (716) as illustrated by second reference plane (P2). At the same time, the location or placement of end (730) of placement tip (719) can be described as being above, even with, or below deck (772) of lower jaw (716) as illustrated by first reference plane (P1).

Figure 21:
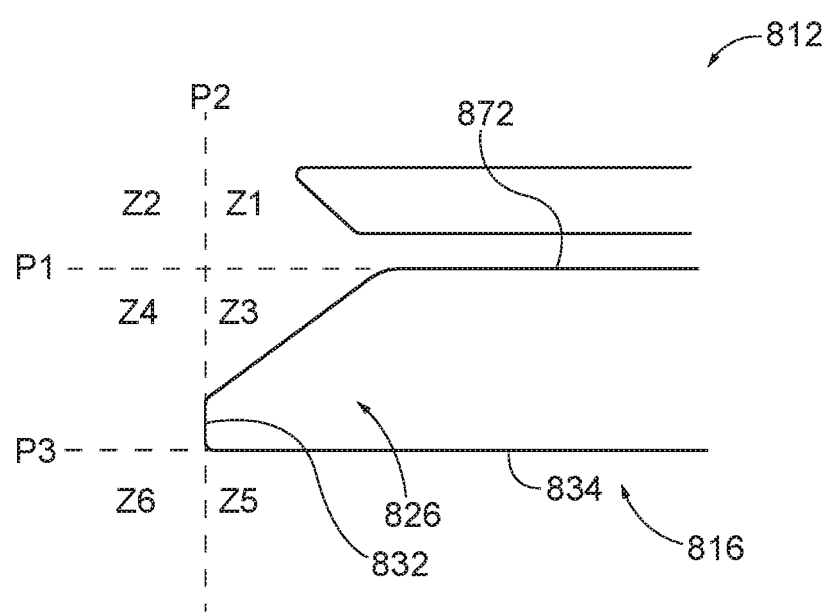
FIG. 21 depicts an enlarged side view of a distal portion of an alternative version of an end effector, shown in a closed position and with zones defined by a lower jaw with a distal end of a placement tip of an upper jaw being located in a first zone.

Referring now to FIG. 21, an enlarged view of another end effector (812) is shown with reference markings that define multiple zones that can be used to describe the location or placement of the end of the placement tip of an exemplary end effector. End effector (812) is configured for use with instruments (10, 310) and/or for robotic use as described above. As with end effector (712) and FIG. 20, end effector (812) of FIG. 21 also comprises first reference plane (P1) and second reference plane (P2). Additionally, a third reference plane (P3) is defined by and extends along a bottom surface (834) of lower jaw (816). Third reference plane (P3) in the present example is parallel with first reference plane (P1) and also orthogonal to second reference plane (P2). With this configuration, as shown in FIG. 21, six zones are defined by the intersections of first and third reference planes (P1, P3) with second reference plane (P2).

A first zone (Z1) is shown as the region above deck (872) of lower jaw (816) (corresponding with first reference plane (P1)) and proximal to end (832) of nose portion (826) (corresponding with second reference plane (P2)). A second zone (Z2) is shown as the region above deck (872) of lower jaw (816) (corresponding with first reference plane (P1)) and distal to end (832) of nose portion (826) (corresponding with second reference plane (P2)). A third zone (Z3) is shown as the region below deck (872) of lower jaw (816) (corresponding with first reference plane (P1)) yet above bottom surface (834) of lower jaw (816) (corresponding with third reference plane (P3)), and proximal to end (832) of nose portion (826) (corresponding with second reference plane (P2)). A fourth zone (Z4) is shown as the region below deck (872) of lower jaw (816) (corresponding with first reference plane (P1)) yet above bottom surface (834) of lower jaw (816) (corresponding with third reference plane (P3)), and distal to end (832) of nose portion (826) (corresponding with second reference plane (P2)). A fifth zone (Z5) is shown as the region below bottom surface (834) of lower jaw (816) (corresponding with third reference plane (P3)), and proximal to end (832) of nose portion (826) (corresponding with second reference plane (P2)). A sixth zone (Z6) is shown as the region below bottom surface (834) of lower jaw (816) (corresponding with third reference plane (P3)), and distal to end (832) of nose portion (826) (corresponding with second reference plane (P2)).

Figure 22A:
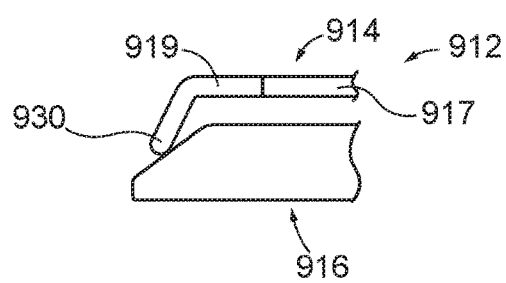
FIG. 22A depicts an enlarged side view of a distal portion of an alternative version of an end effector, shown in a closed position and with a distal end of a placement tip of an upper jaw being located in a third zone as shown in FIG. 21.

Using this reference system, several exemplary end effectors will now be described that illustrate various locations or placements for the end of the placement tip when the end effector is in a closed and unloaded state. Referring to FIG. 22A, an enlarged view of another end effector (912) is shown in a closed and unloaded state. End effector (912) is configured for use with instruments (10, 310) and/or for robotic use as described above. End effector (912) comprises an upper jaw (914) and a lower jaw (916). Upper jaw (914) comprises a body (917) and a placement tip (919). At its distal-most portion, placement tip (919) comprises an end (930). As shown, placement tip (919) has a bent or angled configuration. With the illustrated configuration, placement tip (919) extends through first zone (Z1), and the location of end (930) of placement tip (919) is in third zone (Z3). In view of the teachings herein, it will be apparent to those of ordinary skill in the art that when end effector (912) is in a closed and loaded state that the location of end (930) of placement tip (919) may deflect yet remain in third zone (Z3). However, it will also be apparent to those of ordinary skill in the art in view of the teachings herein that placement tip (919) may deflect such that end (930) of placement tip (919) changes its location in the closed and loaded state to another one of the zones.

Figure 22B:
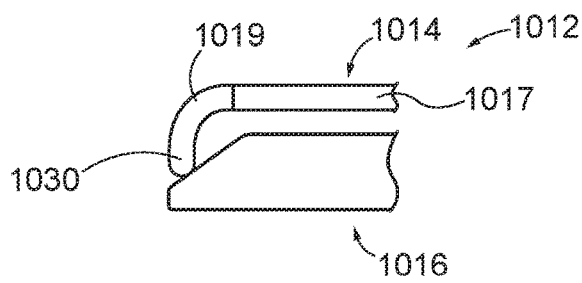
FIG. 22B depicts an enlarged side view of a distal portion of an alternative version of an end effector, shown in a closed position and with a distal end of a curved placement tip of an upper jaw being located in a third zone as shown in FIG. 21.

Referring now to FIG. 22B, an enlarged view of another end effector (1012) is shown in a closed and unloaded state. End effector (1012) is configured for use with instruments (10, 310) and/or for robotic use as described above. End effector (1012) comprises an upper jaw (1014) and a lower jaw (1016). Upper jaw (1014) comprises a body (1017) and a placement tip (1019). At its distal-most portion, placement tip (1019) comprises an end (1030). As shown, placement tip (1019) has a curved configuration. With the illustrated configuration, placement tip (1019) extends through first zone (Z1), and the location of end (1030) of placement tip (1019) is in third zone (Z3). In view of the teachings herein, it will be apparent to those of ordinary skill in the art that when end effector (1012) is in a closed and loaded state that the location of end (1030) of placement tip (1019) may deflect yet remain in third zone (Z3). However, it will also be apparent to those of ordinary skill in the art in view of the teachings herein that placement tip (1019) may deflect such that end (1030) of placement tip (1019) changes its location in the closed and loaded state to another one of the zones.

Figure 22C:
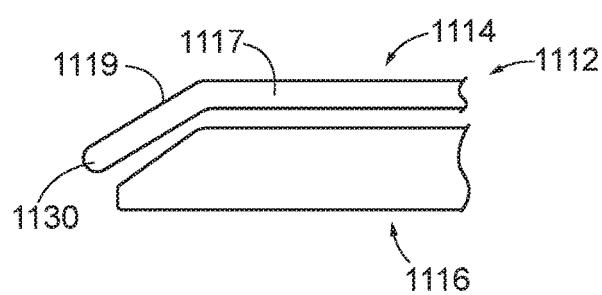
FIG. 22C depicts an enlarged side view of a distal portion of an alternative version of an end effector, shown in a closed position and with a distal end of a placement tip of an upper jaw being located in a fourth zone as shown in FIG. 21.

Referring now to FIG. 22C, an enlarged view of another end effector (1112) is shown in a closed and unloaded state. End effector (1112) is configured for use with instruments (10, 310) and/or for robotic use as described above. End effector (1112) comprises an upper jaw (1114) and a lower jaw (1116). Upper jaw (1114) comprises a body (1117) and a placement tip (1119). At its distal-most portion, placement tip (1119) comprises an end (1130). As shown, placement tip (1119) has a bent or angled configuration. With the illustrated configuration, placement tip (1119) extends through first and third zones (Z1, Z3) and the location of end (1130) of placement tip (1119) is in fourth zone (Z4). In view of the teachings herein, it will be apparent to those of ordinary skill in the art that when end effector (1112) is in a closed and loaded state that the location of end (1130) of placement tip (1119) may deflect yet remain in fourth zone (Z4). However, it will also be apparent to those of ordinary skill in the art in view of the teachings herein that placement tip (1119) may deflect such that end (1130) of placement tip (1119) changes its location in the closed and loaded state to another one of the zones.

Figure 22D:
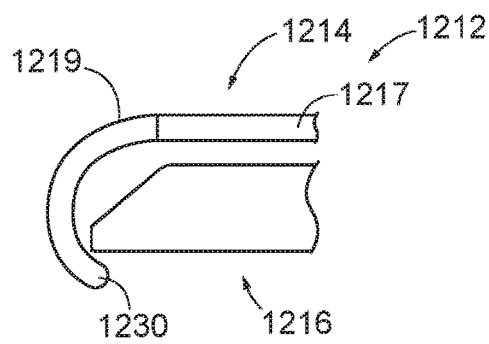
FIG. 22D depicts an enlarged side view of a distal portion of an alternative version of an end effector, shown in a closed position and with a distal end of a curved placement tip of an upper jaw being located in a fifth zone as shown in FIG. 21.

Referring now to FIG. 22D, an enlarged view of another end effector (1212) is shown in a closed and unloaded state. End effector (1212) is configured for use with instruments (10, 310) and/or for robotic use as described above. End effector (1212) comprises an upper jaw (1214) and a lower jaw (1216). Upper jaw (1214) comprises a body (1217) and a placement tip (1219). At its distal-most portion, placement tip (1219) comprises an end (1230). As shown, placement tip (1219) has a curved configuration. With the illustrated configuration, placement tip (1219) extends through first, second, third, fourth, and sixth zones (Z1, Z2, Z3, Z4, Z6) and the location of end (1230) of placement tip (1219) is in fifth zone (Z5). Out of the six total zones, placement tip (1230) passes through all of them, albeit third zone (Z3) is substantially void of placement tip (1230). In view of the teachings herein, it will be apparent to those of ordinary skill in the art that when end effector (1212) is in a closed and loaded state that the location of end (1230) of placement tip (1219) may deflect yet remain in fifth zone (Z5). However, it will also be apparent to those of ordinary skill in the art in view of the teachings herein that placement tip (1219) may deflect such that end (1230) of placement tip (1219) changes its location in the closed and loaded state to another one of the zones.

Figure 22E:
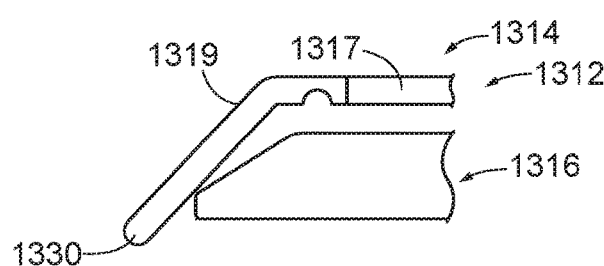
FIG. 22E depicts an enlarged side view of a distal portion of an alternative version of an end effector, shown in a closed position and with a distal end of a placement tip of an upper jaw being located in a sixth zone as shown in FIG. 21.

Referring now to FIG. 22E, an enlarged view of another end effector (1312) is shown in a closed and unloaded state. End effector (1312) is configured for use with instruments (10, 310) and/or for robotic use as described above. End effector (1312) comprises an upper jaw (1314) and a lower jaw (1316). Upper jaw (1314) comprises a body (1317) and a placement tip (1319). At its distal-most portion, placement tip (1319) comprises an end (1330). As shown, placement tip (1319) has a bent or angled configuration. With the illustrated configuration, placement tip (1319) extends through first, third, and fourth zones (Z1, Z3, Z4) and the location of end (1330) of placement tip (1319) is in sixth zone (Z6). In view of the teachings herein, it will be apparent to those of ordinary skill in the art that when end effector (1312) is in a closed and loaded state that the location of end (1330) of placement tip (1319) may deflect yet remain in sixth zone (Z6). However, it will also be apparent to those of ordinary skill in the art in view of the teachings herein that placement tip (1319) may deflect such that end (1330) of placement tip (1319) changes its location in the closed and loaded state to another one of the zones.

Figure 22F:
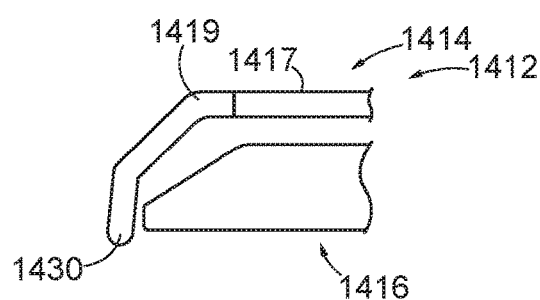
FIG. 22F depicts an enlarged side view of a distal portion of an alternative version of an end effector, shown in a closed position and with a distal end of a multi-angled placement tip of an upper jaw being located in a sixth zone as shown in FIG. 21.

Referring now to FIG. 22F, an enlarged view of another end effector (1412) is shown in a closed and unloaded state. End effector (1412) is configured for use with instruments (10, 310) and/or for robotic use as described above. End effector (1412) comprises an upper jaw (1414) and a lower jaw (1416). Upper jaw (1414) comprises a body (1417) and a placement tip (1419). At its distal-most portion, placement tip (1419) comprises an end (1430). As shown, placement tip (1419) has a multi-angled configuration. With the illustrated configuration, placement tip (1419) extends through first, third, and fourth zones (Z1, Z3, Z4) and the location of end (1430) of placement tip (1419) is in sixth zone (Z6). In view of the teachings herein, it will be apparent to those of ordinary skill in the art that when end effector (1412) is in a closed and loaded state that the location of end (1430) of placement tip (1419) may deflect yet remain in sixth zone (Z6). However, it will also be apparent to those of ordinary skill in the art in view of the teachings herein that placement tip (1419) may deflect such that end (1430) of placement tip (1419) changes its location in the closed and loaded state to another one of the zones.

Figure 22G:
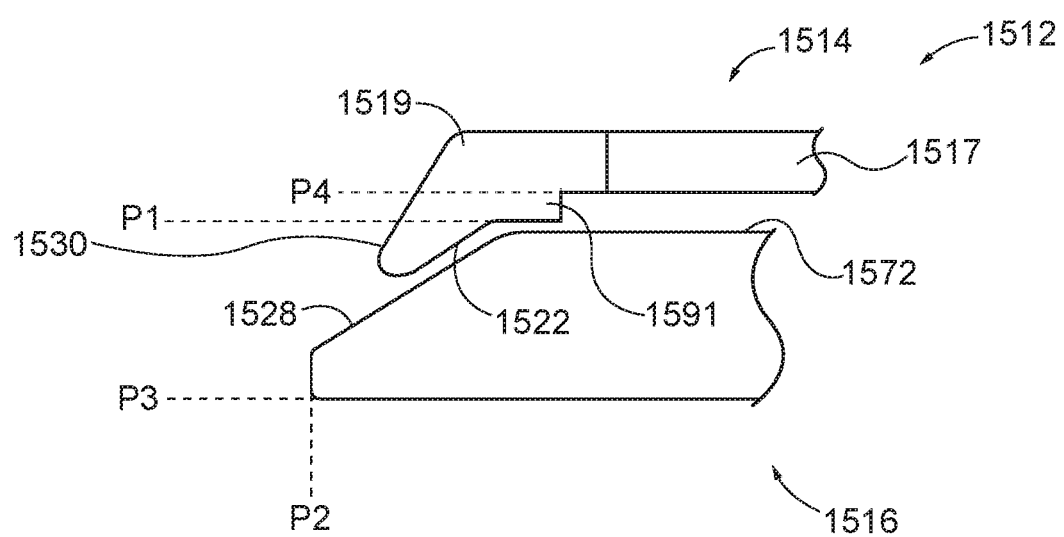
FIG. 22G depicts an enlarged side view of a distal portion of an alternative version of an end effector, shown in a closed position and with a distal end of a placement tip of an upper jaw being located in a third zone as shown in FIG. 21, and the placement tip configured with a profile of an underside surface that corresponds with a profile of a taper of the nose portion of a lower jaw.

Referring now to FIG. 22G, an enlarged view of another end effector (1512) is shown in a closed and unloaded state. End effector (1512) is configured for use with instruments (10, 310) and/or for robotic use as described above. End effector (1512) comprises an upper jaw (1514) and a lower jaw (1516). Upper jaw (1514) comprises a body (1517) and a placement tip (1519). At its distal-most portion, placement tip (1519) comprises an end (1530). As shown, placement tip (1519) has a bent or angled configuration. At its proximal end, placement tip (1519) comprises a step (1591) such that body (1517) is offset from step (1591) of placement tip (1519). With the illustrated configuration, placement tip (1519) extends through first zone (Z1) and the location of end (1530) of placement tip (1519) is in third zone (Z3). In view of the teachings herein, it will be apparent to those of ordinary skill in the art that when end effector (1512) is in a closed and loaded state that the location of end (1530) of placement tip (1519) may deflect yet remain in third zone (Z3). However, it will also be apparent to those of ordinary skill in the art in view of the teachings herein that placement tip (1519) may deflect such that end (1530) of placement tip (1519) changes its location in the closed and loaded state to another one of the zones.

As shown in FIG. 22G, end effector (1512) defines a fourth reference plane (P4) based on the offset of body (1517) from step (1591) of placement tip (1519). Also, placement tip (1519) comprises an underside surface (1522) that matches the profile of top surface (1528) and deck (1572) of lower jaw (1516). Placement tip (1519) defines pivot point (1524) where underside surface (1522) transitions from matching the profile of top surface (1528) of lower jaw (1516) to matching deck (1572) of lower jaw (1516). As shown in the illustrated version, end effector (1512) defines a first distance (D1) as extending from pivot point (1524) proximally to the proximal-most end of step (1591). First distance (D1) can be consider as representing the length of placement tip (1519) that overlaps deck (1572) of lower jaw (1516). In view of the teaching herein, various ways to modify or alter end effector (1512) and first distance (D1) to achieve greater or smaller overlaps of placement tip (1519) and deck (1572) will be apparent to those of ordinary skill in the art.

The above paragraphs describe a reference system where various reference planes are used to define zones relative to an end effector. Specifically, the various reference planes are relative to an end effector's lower jaw's deck, distal-most end, and bottom surface. This reference system is applicable to other versions of end effectors shown and described herein, other than those described above in FIGS. 22A-22G. For example, it is clear from FIG. 17 that end effector (512) comprises placement tip (519) that presents its distal-most end in third zone (Z3). Similarly, FIG. 18 illustrates that end effector (612) comprises placement tip (619) that presents its distal-most end also in third zone (Z3). With respect to end effectors (512, 612) and FIGS. 17 and 18, both end effectors (512, 612) are shown in closed and unloaded states. Referring to FIG. 19, end effector (612) is shown in a closed and loaded state. As illustrated, with end effector (612) in a closed and loaded state, placement tip (619) deflects such that the distal-most end of placement tip (619) is located mostly in second zone (Z2) with a smaller portion located in fourth zone (Z4). In view of the teachings herein, various ways to configure an end effector to locate an end of a placement tip in a desired position under various conditions, i.e. open/closed and loaded/unloaded, will be apparent to those of ordinary skill in the art.

4. Exemplary Shapes for Elastically Deformable Placement Tips

As described above, placement tips for end effectors can have a bent or angled configuration as well as a curved configuration. This is shown in the several side views of FIGS. 22A-22G for instance. In combination with these various options for placement tips of an end effector, further options for the shape of the placement tip exist. As will be described below, placement tips can be configured with various distal end profiles, width profiles, and underside surface geometries. It should be understood that the various shapes described below related to distal end profile, width profile, and underside surface geometry can be combined in a single placement tip. For instance, any of the distal end profiles shown and described can be used in a placement tip having any of the width profiles shown and described, and further such a placement tip can have any of the underside surface geometries shown and described.

a. Distal End Profiles

Figure 23A:
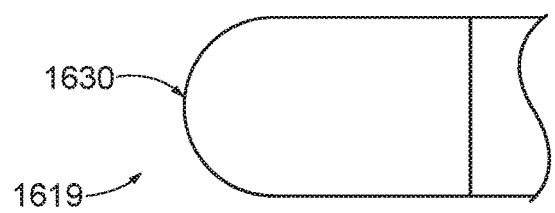
FIG. 23A depicts an enlarged top view of a placement tip of an alternative version of an end effector, with the placement tip having a distal end with a round profile.

FIGS. 23A-23F depict exemplary enlarged placement tip portions that show various distal end profiles for the placement tip. Referring to FIG. 23A, an end effector comprises a placement tip (1619). As shown in the top view of FIG. 23A, placement tip (1619) comprises a distal end (1630) having a round profile. Placement tip (1619) is configurable such that it may be positioned on either an upper jaw or lower jaw of the end effector. Furthermore, placement tip (1619) is configurable such that it may be part of an anvil or part of a staple cartridge. In view of the teachings herein, it will be apparent to those of ordinary skill in the art that this round distal end profile of placement tip (1619) can be used with any of the placement tips of the end effectors described herein.

Figure 23B:
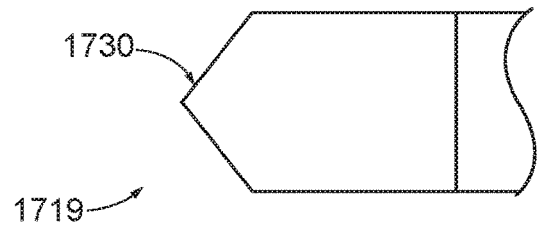
FIG. 23B depicts an enlarged top view of a placement tip of an alternative version of an end effector, with the placement tip having a distal end with an angled and pointed profile.

FIG. 23B depicts an end effector comprising a placement tip (1719). As shown in the top view of FIG. 23B, placement tip (1719) comprises a distal end (1730) having an angled and pointed profile. In this example, because placement tip (1719) is comprises of an elastomeric and deflectable material, placement tip (1719) is still configured as an atraumatic tip despite its pointed profile. Placement tip (119) is configurable such that it may be positioned on either an upper jaw or lower jaw of the end effector. Furthermore, placement tip (119) is configurable such that it may be part of an anvil or part of a staple cartridge. In view of the teachings herein, it will be apparent to those of ordinary skill in the art that this angled and pointed distal end profile of placement tip (119) can be used with any of the placement tips of the end effectors described herein.

Figure 23C:
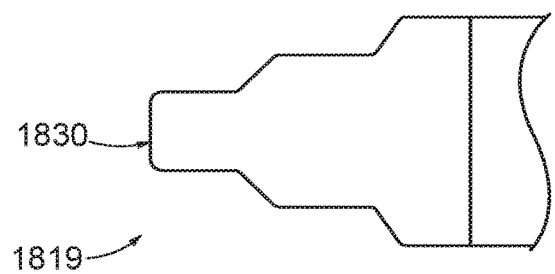
FIG. 23C depicts an enlarged top view of a placement tip of an alternative version of an end effector, with the placement tip having a distal end with a toothed profile.

FIG. 23C depicts an end effector comprising a placement tip (1819). As shown in the top view of FIG. 23C, placement tip (1819) comprises a distal end (1830) having a toothed profile. Placement tip (1819) is configurable such that it may be positioned on either an upper jaw or lower jaw of the end effector. Furthermore, placement tip (1819) is configurable such that it may be part of an anvil or part of a staple cartridge. In view of the teachings herein, it will be apparent to those of ordinary skill in the art that this toothed distal end profile of placement tip (1819) can be used with any of the placement tips of the end effectors described herein.

Figure 23D:
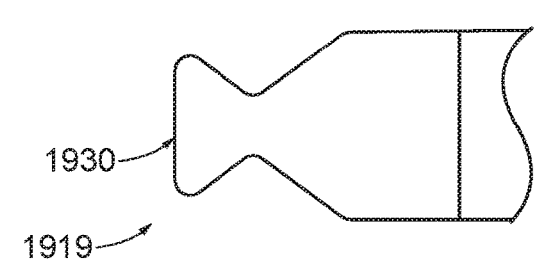
FIG. 23D depicts an enlarged top view of a placement tip of an alternative version of an end effector, with the placement tip having a distal end with a flared profile.

FIG. 23D depicts an end effector comprising a placement tip (1919). As shown in the top view of FIG. 23D, placement tip (1919) comprises a distal end (1930) having a flared profile. Placement tip (1919) is configurable such that it may be positioned on either an upper jaw or lower jaw of the end effector. Furthermore, placement tip (1919) is configurable such that it may be part of an anvil or part of a staple cartridge. In view of the teachings herein, it will be apparent to those of ordinary skill in the art that this flared distal end profile of placement tip (1919) can be used with any of the placement tips of the end effectors described herein.

Figure 23E:
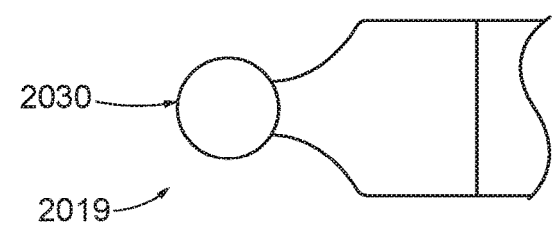
FIG. 23E depicts an enlarged top view of a placement tip of an alternative version of an end effector, with the placement tip having a distal end with an orb profile.

FIG. 23E depicts an end effector comprising a placement tip (2019). As shown in the top view of FIG. 23E, placement tip (2019) comprises a distal end (2030) having an orb profile. Placement tip (2019) is configurable such that it may be positioned on either an upper jaw or lower jaw of the end effector. Furthermore, placement tip (2019) is configurable such that it may be part of an anvil or part of a staple cartridge. In view of the teachings herein, it will be apparent to those of ordinary skill in the art that this orb distal end profile of placement tip (2019) can be used with any of the placement tips of the end effectors described herein.

Figure 23F:
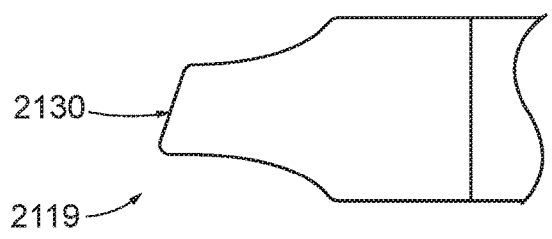
FIG. 23F depicts an enlarged top view of a placement tip of an alternative version of an end effector, with the placement tip having a distal end with an asymmetric profile.

FIG. 23F depicts an end effector comprising a placement tip (2119). As shown in the top view of FIG. 23F, placement tip (2119) comprises a distal end (2130) having an asymmetric profile. In this manner, end (2130) extends distally longer on one side than the other such that end (2130) is angled. Placement tip (2119) is configurable such that it may be positioned on either an upper jaw or lower jaw of the end effector. Furthermore, placement tip (2119) is configurable such that it may be part of an anvil or part of a staple cartridge. In view of the teachings herein, it will be apparent to those of ordinary skill in the art that this asymmetric distal end profile of placement tip (2119) can be used with any of the placement tips of the end effectors described herein. While several distal end profiles for placement tips of an end effector have been shown and described above, other distal end profiles for placement tips of an end effector will be apparent to those of ordinary skill in the art in view of the teachings herein.

b. Width Profiles

Figure 24A:
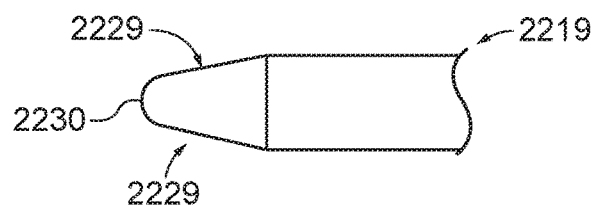
FIG. 24A depicts an enlarged top view of a placement tip of an alternative version of an end effector, with the placement tip having a width with an angled profile.

FIGS. 24A-24E depict exemplary enlarged placement tip portions that show various width profiles for the placement tip. Referring to FIG. 24A, an end effector comprises a placement tip (2219). As shown in the top view of FIG. 24A, placement tip (2219) comprises distal sides (2229) leading to distal end (2230) where distal sides (2229) define a width profile that is angled. Placement tip (2219) is configurable such that it may be positioned on either an upper jaw or lower jaw of the end effector. Furthermore, placement tip (2219) is configurable such that it may be part of an anvil or part of a staple cartridge. In view of the teachings herein, it will be apparent to those of ordinary skill in the art that this angled width profile of placement tip (2219) can be used with any of the placement tips of the end effectors described herein.

Figure 24B:
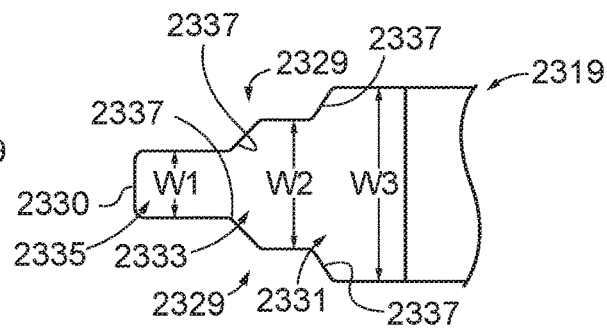
FIG. 24B depicts an enlarged top view of a placement tip of an alternative version of an end effector, with the placement tip having a width with a stepped profile.

FIG. 24B depicts an end effector comprising a placement tip (2319). As shown in the top view of FIG. 24B, placement tip (2319) comprises distal sides (2329) leading to distal end (2330) where distal sides (2329) define a width profile that is stepped. Placement tip (2319) is configurable such that it may be positioned on either an upper jaw or lower jaw of the end effector. Furthermore, placement tip (2319) is configurable such that it may be part of an anvil or part of a staple cartridge. In view of the teachings herein, it will be apparent to those of ordinary skill in the art that this stepped width profile of placement tip (2319) can be used with any of the placement tips of the end effectors described herein.

Figure 24C:
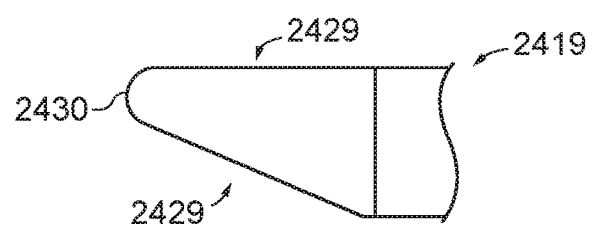
FIG. 24C depicts an enlarged top view of a placement tip of an alternative version of an end effector, with the placement tip having a width with an asymmetric profile.

FIG. 24C depicts an end effector comprising a placement tip (2419). As shown in the top view of FIG. 24C, placement tip (2419) comprises distal sides (2429) leading to distal end (2430) where distal sides (2429) define a width profile that is asymmetric such that distal sides (2429) are not symmetrically oriented, and in this instance are angled to varying degrees. Placement tip (2419) is configurable such that it may be positioned on either an upper jaw or lower jaw of the end effector. Furthermore, placement tip (2419) is configurable such that it may be part of an anvil or part of a staple cartridge. In view of the teachings herein, it will be apparent to those of ordinary skill in the art that this asymmetric width profile of placement tip (2419) can be used with any of the placement tips of the end effectors described herein.

Figure 24D:
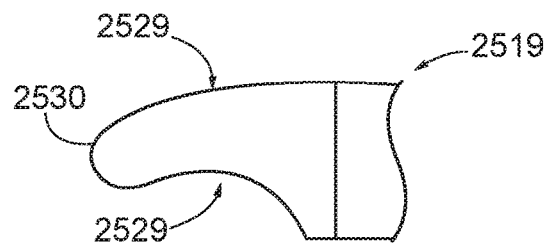
FIG. 24D depicts an enlarged top view of a placement tip of an alternative version of an end effector, with the placement tip having a width with a scallop tip-on-center profile.

FIG. 24D depicts an end effector comprising a placement tip (2519). As shown in the top view of FIG. 24D, placement tip (2519) comprises distal sides (2529) leading to distal end (2530) where distal sides (2529) define a width profile that is scalloped with distal end (2530) centered along the longitudinal axis of placement tip (2519). In this manner, one of distal sides (2529) has a curvature that is concave while the other has a curvature that is convex. Placement tip (2519) is configurable such that it may be positioned on either an upper jaw or lower jaw of the end effector. Furthermore, placement tip (2519) is configurable such that it may be part of an anvil or part of a staple cartridge. In view of the teachings herein, it will be apparent to those of ordinary skill in the art that this scalloped width profile of placement tip (2519) can be used with any of the placement tips of the end effectors described herein.

Figure 24E:
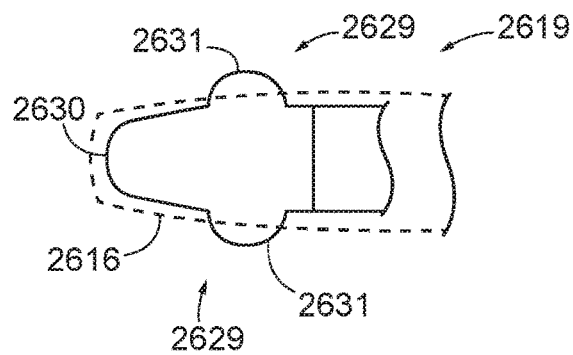
FIG. 24E depicts an enlarged top view of a placement tip of an alternative version of an end effector, with the placement tip having a width with a bump-out profile.

FIG. 24E depicts an end effector comprising a placement tip (2619). As shown in the top view of FIG. 24E, placement tip (2619) comprises distal sides (2629) leading to distal end (2630) where distal sides (2629) define a width profile having bump-outs or lateral protrusions (2631) on each side. In the illustrated version, a jaw (2616) of end effector opposite placement tip (2619) is shown in phantom. As shown in the present example, the bump-outs (2631) extend outward from jaw (2616), whereas the remaining width of placement tip (2619) is narrower than the width of jaw (2616). However, bump-outs (2631) are not required to extend out from the width of jaw (2616) in all versions. Where bump-outs (2631) do extend outward from jaw (2616), placement tip (2619) is configured to provide resistance when moving the instrument with the end effector and placement tip (2619) in and out of a site. Additionally, bump-outs (2631) are configured to dilate an aperture larger when placement tip (2619) passes therethrough. Placement tip (2619) is configurable such that it may be positioned on either an upper jaw or lower jaw of the end effector. Furthermore, placement tip (2619) is configurable such that it may be part of an anvil or part of a staple cartridge. In view of the teachings herein, it will be apparent to those of ordinary skill in the art that this width profile of placement tip (2619) having bump-outs (2631) on each side can be used with any of the placement tips of the end effectors described herein.

Figure 25:
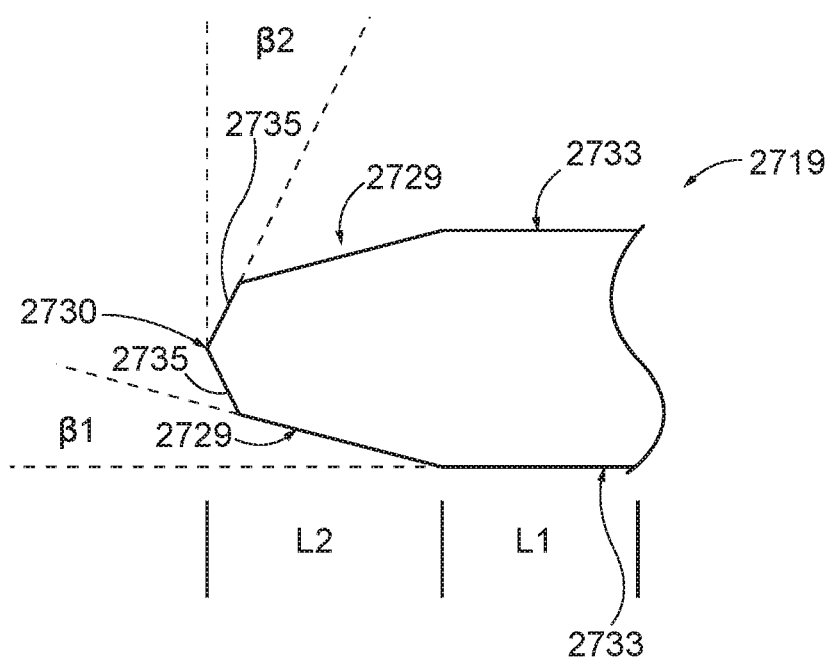
FIG. 25 depicts an enlarged top view of a placement tip of an alternative version of an end effector, with the placement tip having a distal end with an angled and pointed profile and with the placement tip having a width with an angled profile.

FIG. 25 depicts an enlarged top view of a placement tip (2719) of an end effector, with the placement tip (2719) having a distal end (2730) with an angled and pointed profile and with the placement tip (2719) having distal sides (2729) defining a width profile that angled. As described above, placement tip (2719) illustrates a combination of the angled and pointed distal end profile of placement tip (1719) of FIG. 23B, with the angled width profile of placement tip (2219) of FIG. 24A. In view of the teachings herein, and as further illustrated by this example, various combinations of distal end profiles and width profiles will be apparent to those of ordinary skill in the art.

Placement tip (2719) further illustrates the relationship between the profile at distal end (2730) compared to the width profile defined by distal sides (2729). As described above with respect to other examples, placement tips extend from a body of one of an upper jaw or lower jaw of an end effector. In the present example, placement tip (2719) is understood to have a shorter longitudinal dimension, or length, than the body of the jaw from which it extends. As shown in the illustrated version, placement tip (2719) can be understood to have a length characterized by the sum of a first length (L1) and a second length (L2). Although not shown to scale based on the wavy break line signifying that placement tip (2719) extends proximally further than shown, it should be understood that first length (L1) is substantially greater than second length (L2). When showing and describing the various distal end profiles and width profiles of placement tips above in FIGS. 23A-23F and 24A-24E, it should be understood that the distal end profiles as well as the width profiles defined by the distal sides are all included in the length of the placement tips that coincide with second length (L2).

Placement tip (2719) further illustrates an example where a plane defined by one of symmetrical distal sides (2729) in combination with another plane defined by one of proximal sides (2733), form an angle ($\beta 1$). In this example, as the width profile defined by distal sides (2729) becomes more angular or steeper, angle ($\beta 1$) increases. When the width profile defined by distal sides (2729) becomes less angular, and hence closer to parallel with proximal sides (2733), angle ($\beta 1$) decreases.

Placement tip (2719) also illustrates an example where a plane defined tangent to the distal-most portion of distal end (2730) in combination with a plane defined by one of sides (2735) of distal end (2730), forms an angle ($\beta 2$). In this example, as the sides (2735) of distal end (2730) become more angular or steeper, angle ($\beta 2$) increases. When the sides (2735) of distal end (2730) becomes less angular, and hence distal end (2730) becomes more blunt, angle ($\beta 2$) decreases.

c. Underside Surfaces

Figure 26A:
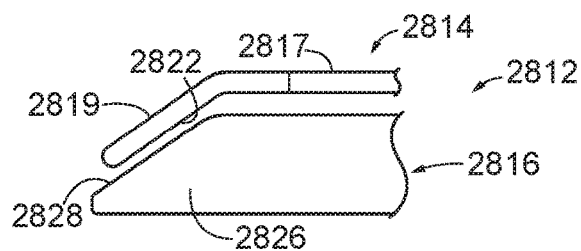
FIG. 26A depicts an enlarged side view of a distal portion of an alternative version of an end effector, with a placement tip of an upper jaw having an underside surface with a flat profile parallel with a profile of a nose portion of a lower jaw.

Now referring to the side views of FIGS. 26A-26E, various geometries for underside surfaces of placement tips are shown and described. In some instances, underside surfaces of placement tips may be referred to as inner surfaces, and these terms should be understood to be interchangeable. FIG. 26A depicts end effector (2812) comprising upper jaw (2814) and lower jaw (2816). Upper jaw (2814) comprises body (2817) and placement tip (2819) extending distally from body (2817). Placement tip (2819) has a bent or angled configuration and comprises an underside surface (2822) that is flat. In this example, underside surface (2822) is also parallel with a top surface (2828) on nose portion (2826) of lower jaw (2816). In this manner, when end effector (2812) is closed and unloaded, underside surface (2822) can contact top surface (2828).

Figure 26B:
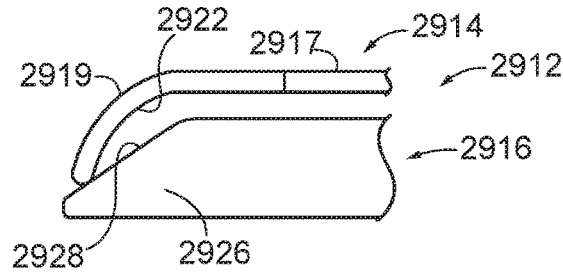
FIG. 26B depicts an enlarged side view of a distal portion of an alternative version of an end effector, with a placement tip of an upper jaw having an underside surface with a curved profile.

FIG. 26B depicts end effector (2912) comprising upper jaw (2914) and lower jaw (2916). Upper jaw (2914) comprises body (2917) and placement tip (2919) extending distally from body (2917). Placement tip (2919) has a curved configuration and comprises underside surface (2922) that is curved. Furthermore, lower jaw (2916) comprises nose portion (2926) with a tapered top surface (2928). The curvature of underside surface (2922) in combination with the tapered top surface (2928) of nose portion (2926) provides placement tip (2919) with point contact when end effector (2912) is closed and unloaded, as opposed to greater contact area as with end effector (2812) shown and described above.

Figure 26C:
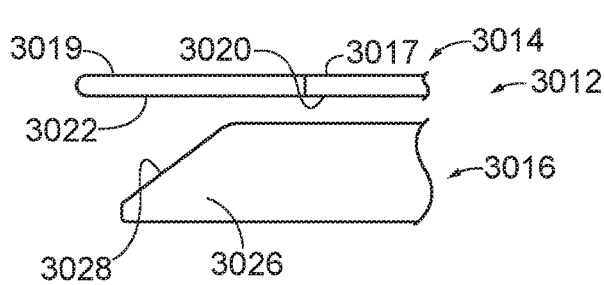
FIG. 26C depicts an enlarged side view of a distal portion of an alternative version of an end effector, with a straight placement tip of an upper jaw having an underside surface with a flat profile.

FIG. 26C depicts end effector (3012) comprising upper jaw (3014) and lower jaw (3016). Upper jaw (3014) comprises body (3017) and placement tip (3019) extending distally from body (3017). Placement tip (3019) has a straight configuration and comprises an underside surface (3022) that is straight. Placement tip (3019) is configured as elastically deformable as described above. In this manner, underside surface (3022) of placement tip (3019) extends along the same plane as an underside surface (3020) of body (3017) of upper jaw (3014). Furthermore, lower jaw (3016) comprises nose portion (3026) with a tapered top surface (3028). The straight configuration of underside surface (3022), in combination with the tapered top surface (3028) of nose portion (3026), eliminates placement tip (3019) contact with tapered top surface (3028) when end effector (3012) is closed and unloaded.

Figure 26D:
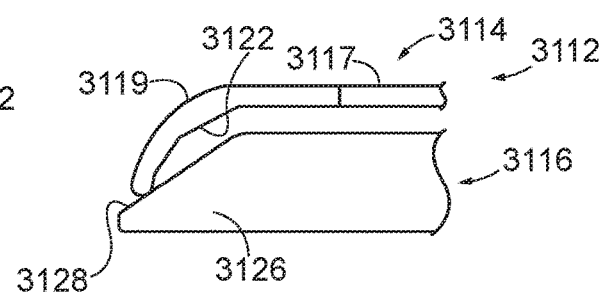
FIG. 26D depicts an enlarged side view of a distal portion of an alternative version of an end effector, with a placement tip of an upper jaw having an underside surface with a multi-angled profile.

FIG. 26D depicts end effector (3112) comprising upper jaw (3114) and lower jaw (3116). Upper jaw (3114) comprises body (3117) and placement tip (3119) extending distally from body (3117). Placement tip (3119) has a curved configuration and comprises an underside surface (3122) that is multi-angled. Placement tip (3119) is configured as elastically deformable as described above. Furthermore, lower jaw (3116) comprises nose portion (3126) with a tapered top surface (3128). The multi-angled nature of underside surface (3122) in combination with the tapered top surface (3128) of nose portion (3126) provides placement tip (3119) with point contact when end effector (3112) is closed and unloaded, as opposed to greater contact area as with end effector (3112) shown and described above.

Figure 26E:
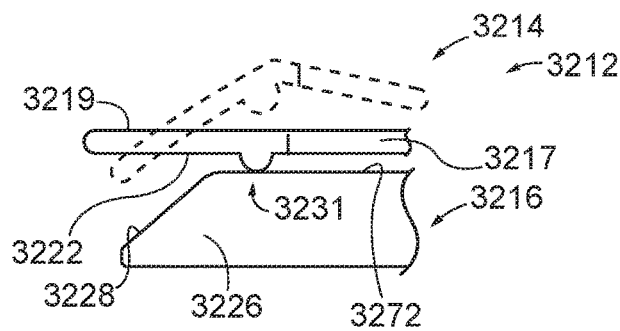
FIG. 26E depicts an enlarged side view of a distal portion of an alternative version of an end effector, with a placement tip of an upper jaw having an underside surface with a curved member and shown with the placement tip in dual positions.

FIG. 26E depicts end effector (3212) comprising upper jaw (3214) having dual positions and lower jaw (3216). Upper jaw (3214) comprises body (3217) and placement tip (3219) extending distally from body (3217). Placement tip (3219) has a bent or angled configuration when end effector (3212) is open and unloaded as shown in phantom in FIG. 26E. Placement tip (3219) comprises an underside surface (3222) that includes a curved protrusion (3231). Placement tip (3219) is configured as elastically deformable as described above. Furthermore, lower jaw (3216) comprises nose portion (3226) with a tapered top surface (3228) as well as deck (3272). The curved protrusion (3231) of underside surface (3222) of placement tip (3219) is configured to act as a pivot structure such that placement tip (3219) pivots from its bent or angled orientation shown in phantom to a straight, or at least less bent or angled, orientation in response to curved protrusion (3231) contacting a structure such as deck (3272) when end effector (3212) is closed and without tissue between jaws (3214, 3216), or tissue when end effector (3212) is closed and loaded with tissue between jaws (3214, 3216).

5. Exemplary Gaps

The various end effectors described herein provide visualization and guidance features as described above. Additionally, the ability of the placement tips to deflect or elastically deform can provide benefits in use during procedure where marching may be required or beneficial. In addition to the ability of the placement tips to elastically deform, the presence or absence of a gap between the placement tip and the opposite jaw's surface can impact visualization and marching. For instance, in some versions with little or no gap, the ability of the placement tip to elastically deform enables use of the end effector in marching procedures.

Figure 27A:
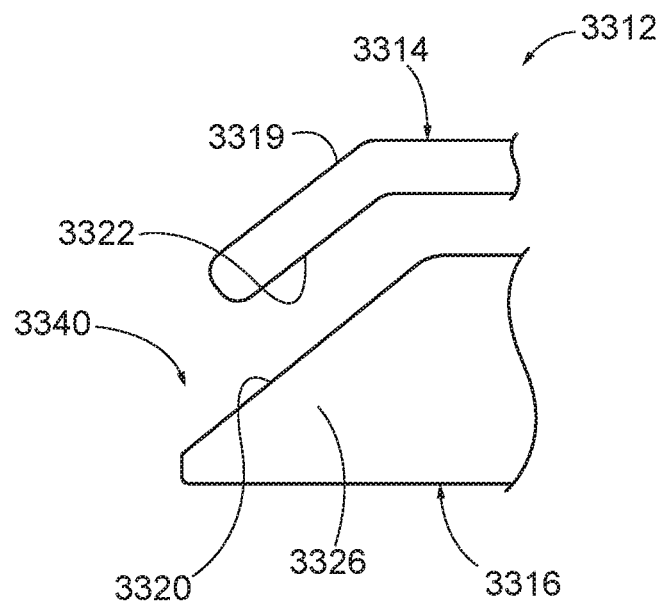
FIG. 27A depicts an enlarged side view of a distal portion of an alternative version of an end effector, showing a gap between a placement tip of an upper jaw and a nose portion of a lower jaw.
Figure 27B:
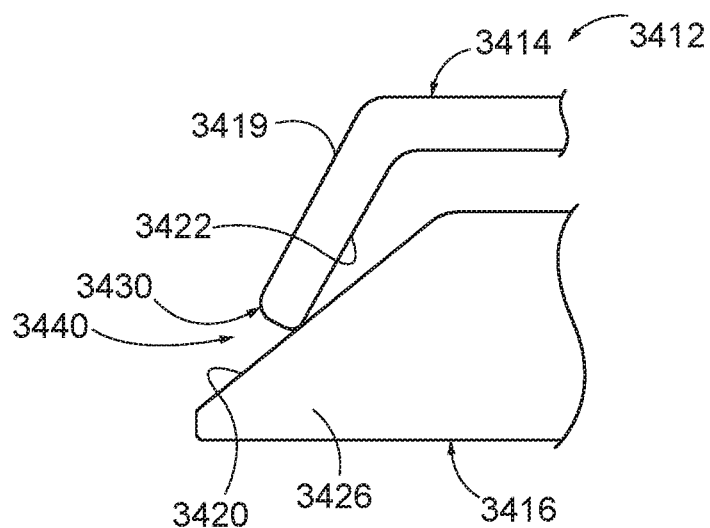
FIG. 27B depicts an enlarged side view of a distal portion of an alternative version of an end effector, showing a smaller gap between a distal end of a placement tip of an upper jaw and a nose portion of a lower jaw compared to the gap of FIG. 27A.

FIGS. 27A and 27B depict portions of end effectors that illustrate exemplary gaps and their configurations. FIG. 27A depicts an enlarged side view of a distal portion of an end effector (3312), showing a gap (3340) between a placement tip (3319) of an upper jaw (3314) and a nose portion (3326) of a lower jaw (3316). In the present example, end effector (3312) is shown in a closed and unloaded state. Placement tip (3319) comprises underside surface (3322) that is generally parallel with a top surface (3320) of nose portion (3326) of lower jaw (3316). In this manner, gap (3340) is generally of uniform size along underside surface (3322) of placement tip (3319) and top surface (3320) of nose portion (3326). With this configuration for gap (3340), and with the elastically deformable nature of placement tip (3319), end effector (3312) is configured for use in procedures where marching is desired.

FIG. 27B depicts an enlarged side view of a distal portion of an end effector (3412), showing a gap (3440) between a distal end (3430) of a placement tip (3419) of an upper jaw (3414) and a nose portion (3426) of a lower jaw (3416). Placement tip (3419) is bent or angled and with end effector (3412) closed and unloaded as shown, end (3430) contacts or nearly contacts a top surface (3420) of nose portion (3426) of lower jaw (3416). Thus in the present example, gap (3440) is either very small, or in the case where jaws (3414, 3416) touch, gap (3440) is absent altogether. In versions where gap (3440) is present, as shown gap (3440) increases in size as gap (3440) extends proximally. With this configuration, and with the elastically deformable nature of placement tip (3419), end effector (3412) is configured for use in procedures where marching is desired. In view of the teachings herein, other ways to configure end effectors with various gaps to aid in visualization, guidance, and marching will be apparent to those of ordinary skill in the art.

6. Exemplary Arcuate Side Cross Section

As described above with respect to FIGS. 26B and 26D, some exemplary end effectors are configured with a placement tip that has an arcuate side cross section. With placement tips that are elastically deformable or deflectable, the curvature or degree of curvature of the placement tip changes based on the clamping force applied to the placement tip. As described above, having an end effector with a curved placement tip can provide benefits in visualization and guidance of the end effector in use. Further, having an end effector with an elastically deformable placement tip can provide benefits in procedures where marching is used or desired. Combining curvature with deformability in a placement tip provides an end effector with desirable visualization and guidance attributes in a configuration that can be used in marching applications without needing or requiring a gap between the end effector jaws.

Referring now back to FIG. 26B, FIG. 26B depicts end effector (2912) comprising upper jaw (2914) and lower jaw (2916). Upper jaw (2914) comprises body (2917) and placement tip (2919) extending distally from body (2917). Placement tip (2919) has a curved configuration and comprises underside surface (2922) that is curved. Furthermore, lower jaw (2916) comprises nose portion (2926) with a tapered top surface (2928). The curvature of underside surface (2922) in combination with the tapered top surface (2928) of nose portion (2926) provides placement tip (2919) with point contact when end effector (2912) is closed and unloaded. In this manner, when end effector (2912) is closed and unloaded, there is no gap between upper jaw (2914) and lower jaw (2916).

In some instances, a curved placement tip can be achieved by using a multi-angled underside surface. FIG. 26D depicts such an end effector with end effector (3112), which comprises upper jaw (3114) and lower jaw (3116). Upper jaw (3114) comprises body (3117) and placement tip (3119)

extending distally from body (3117). Placement tip (3119) has a curved configuration and comprises an underside surface (3122) that is multi-angled. Placement tip (3119) is configured as elastically deformable as described above. Furthermore, lower jaw (3116) comprises nose portion (3126) with a tapered top surface (3128). The multi-angled nature of underside surface (3122) in combination with the tapered top surface (3128) of nose portion (3126) provides placement tip (3119) with point contact when end effector (3112) is closed and unloaded. In this manner, when end effector (3112) is closed and unloaded, there is no gap between upper jaw (3114) and lower jaw (3116). In view of the teachings herein, other ways to provide an end effector with a jaw having a placement tip that has an arcuate side when viewed in cross section will be apparent to those of ordinary skill in the art.

7. Exemplary Stair Step or Toothed Tip Shape

As described above, a placement tip of an end effector can be configured with various shapes, including with various width profiles. One such placement tip is shown in FIG. 24B with placement tip (2319), which has a stair step or toothed shaped. As shown in the top view of FIG. 24B, placement tip (2319) comprises distal sides (2329) leading to distal end (2330) where distal sides (2329) define a width profile that is stepped. In the present example, placement tip (2319) extends distally from an anvil of the end effector. However, placement tip (2319) is configurable such that it may be part of an anvil or part of a staple cartridge. Furthermore, placement tip (2319) is configurable such that it may be positioned on either an upper jaw or lower jaw of the end effector. In view of the teachings herein, it will be apparent to those of ordinary skill in the art that this stepped width profile of placement tip (2319) can be used with any of the placement tips of the end effectors described herein.

As shown in the illustrated version, sides (2329) of placement tip (2319) define multiple regions (2331, 2333, 2335) of placement tip (2319), and each of regions (2331, 2333, 2335) comprise a different width (W1, W2, W3) as shown. Moreover, with the stepped configuration, each width (W1, W2, W3) generally remains the same within its associated region (2331, 2333, 2335). Furthermore, when moving from a proximal end of placement tip (2319) to a distal end (2330) of placement tip (2319), the width (W1, W2, W3) of each region (2331, 2333, 2335) is less than or smaller than the width of the immediate proximally located region.

In the present example shown in FIG. 24B, placement tip (2319) comprises three distinct regions (2331, 2333, 2335). In other versions, placement tip (2319) can be configured to have greater or fewer regions, which will be apparent to those of ordinary skill in the art in view of the teachings herein. As shown in FIG. 24B, sides (2329) further comprises angled portions (2337) where one region transitions to an adjacent region. In some other versions, angled portions (2337) can be orthogonal relative to the adjacent portions of sides (2329) instead of angled. In view of the teachings herein, other ways to configure placement tip (2319) and sides (2329) to define multiple regions having different widths will be apparent to those of ordinary skill in the art.

8. Exemplary Non-Rectangular Cross Section

One of the other variety of ways various placement tips for end effectors can be configured pertains to the lateral cross-sectional profiles of the placement tips. As discussed above, surgical instruments (10, 310) described herein include an end effector at a distal end of an elongated shaft (22, 322). The end effectors include upper and lower jaws where one of the jaws includes an anvil. In at least some versions, a placement tip extends from a distal end of the anvil.

Figure 28:
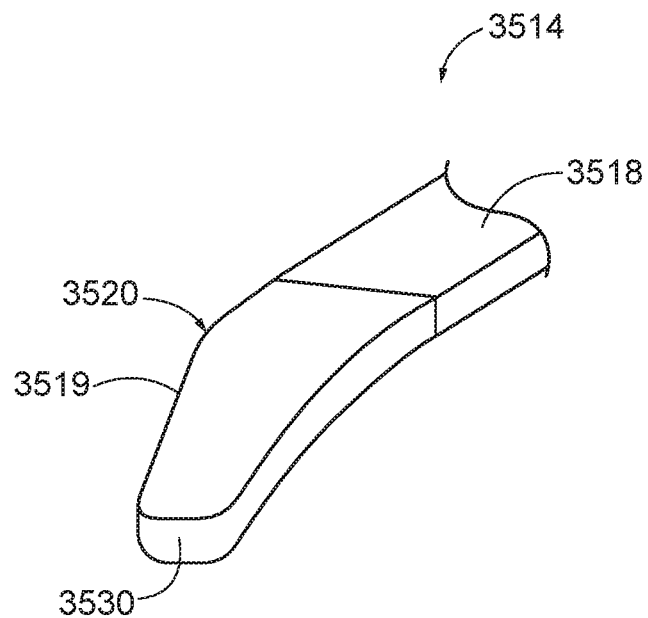
FIG. 28 depicts an enlarged perspective view of a distal portion of a jaw of an alternative version of an end effector.

FIG. 28 depicts an exemplary jaw (3514) useable with one or more of the end effectors described herein. In the illustrated example, jaw (3514) comprises an anvil (3518) and a placement tip (3519) extending from a distal end of anvil (3518). Placement tip (3519) is configured with a bend (3520) distal to the location where placement tip (3519) attaches with anvil (3518) and proximal to a distal end (3530) of placement tip (3519).

Figure 29:
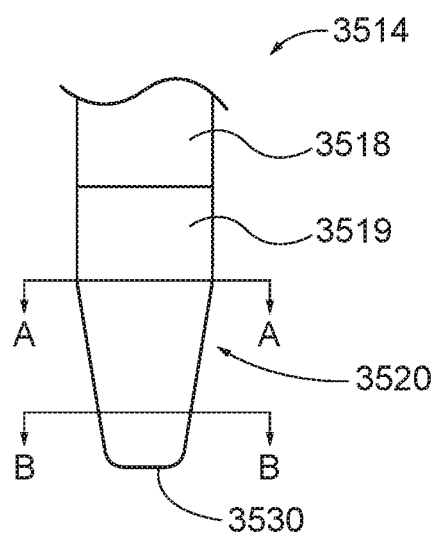
FIG. 29 depicts a top view of the jaw of FIG. 28.

Referring to FIG. 29, placement tip (3519), in the illustrated version, tapers as placement tip (3519) extends distally. Various configurations for distal end (3530) of placement tip (3519) can be used as described above. Anvil (3518) defines a longitudinal axis and placement tip (3519) defines lateral cross sections that can be taken along its length at various positions. In the illustrated example of FIG. 29, a first lateral cross section coincides with a position that is just proximal to bend (3520) and is indicated in FIG. 29 by line A-A. A second lateral cross section coincides with a position that is distal to bend (3520) and proximal to distal end (3530) and is indicated in FIG. 29 by line B-B. In view of the teachings herein, other positions for lateral cross sections of placement tip (3519) will be apparent to those of ordinary skill in the art.

Figure 30A:
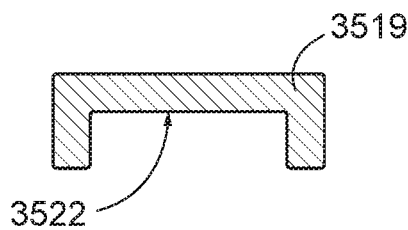
FIG. 30A depicts a front cross-sectional view of the jaw of FIG. 29, taken along line A-A.
Figure 30B:
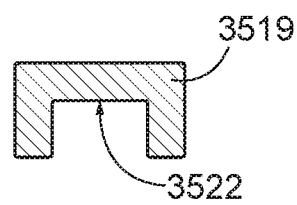
FIG. 30B depicts a front cross-sectional view of the jaw of FIG. 29, taken along line B-B.

FIGS. 30A-34B illustrate various cross-sectional profiles of placement tip (3519) or similar placement tips. Furthermore, many of the cross-sectional profiles illustrated represent non-rectangular cross-sectional profiles. For instance, FIGS. 30A and 30B illustrate exemplary inverted U-shape cross sectional profiles. FIG. 30A coincides with a location on placement tip (3519) along line A-A as shown in FIG. 29, while FIG. 30B coincides with a location on placement tip (3519) along line B-B. In this regard, the shapes of the cross-sectional profiles match, both being inverted U-shapes. However, the taper of placement tip (3519) provides for a smaller width or lateral dimension along the more distal position of placement tip (3519) compared to the more proximal position of placement tip (3519). Additionally, the inverted U-shape cross sectional profile in this version is defined by an underside surface (3522) having five connected orthogonally oriented surfaces. In this manner, the U-shape cross sectional profile defines a void or space with a rectangular shape.

Figure 31A:
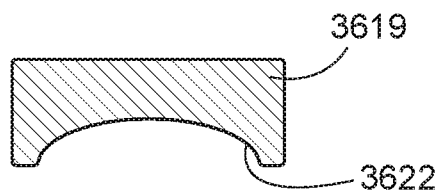
FIG. 31A depicts a front cross-sectional view of an alternate version of a jaw similar to the jaw of FIG. 29, and taken along line A-A.
Figure 31B:
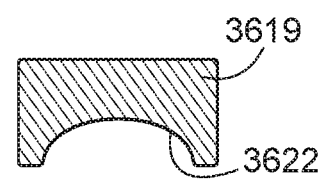
FIG. 31B depicts another front cross-sectional view of the alternate version of the jaw of FIG. 31A, taken along line B-B of FIG. 29.

FIGS. 31A and 31B illustrate various cross-sectional profiles of another placement tip (3619) that is the same as placement tip (3519) shown in FIGS. 28 and 29. Accordingly, the description of placement tip (3519) with respect to FIGS. 28 and 29 applies equally to placement tip (3619). FIGS. 31A and 31B illustrate exemplary inverted U-shape cross sectional profiles, where the U-shapes are defined by a curved underside surface (3622). FIG. 31A coincides with a location on placement tip (3619) along line A-A as shown in FIG. 29, while FIG. 31B coincides with a location on placement tip (3619) along line B-B. In this regard, the shapes of the cross-sectional profiles match, both being inverted U-shapes. However, the taper of placement tip (3619) provides for a smaller width or lateral dimension along the more distal position of placement tip (3619) compared to the more proximal position of placement tip (3619). Additionally, the inverted U-shape cross sectional profile in this version is defined by an underside surface (3622) having a curved surface as mentioned. In this manner, the U-shape cross sectional profile defines a void or space with a half-circle shape.

Figure 32A:
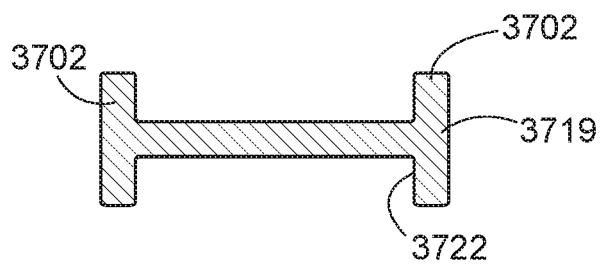
FIG. 32A depicts a front cross-sectional view of an alternate version of a jaw similar to the jaw of FIG. 29, taken along line A-A.
Figure 32B:
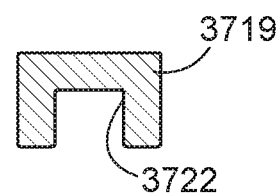
FIG. 32B depicts another front cross-sectional view of the alternate version of the jaw of FIG. 32A, taken along line B-B of FIG. 29.

FIGS. 32A and 32B illustrate various cross-sectional profiles of another placement tip (3719) that is the same as placement tip (3519) shown in FIGS. 28 and 29, except for the region proximal to bend (3520). With placement tip (3719), as will be shown by the cross sections, the region proximal to the bend includes raised sides (3702) such that the cross-sectional profile is not flat or straight across the top surface as will be shown and described relative to FIG. 32A. Besides this difference between placement tip (3519) and placement tip (3719), the description of placement tip (3519) with respect to FIGS. 28 and 29 applies equally to placement tip (3719). FIG. 32A illustrates an exemplary H-shape cross sectional profile, while FIG. 32B illustrates an exemplary U-shape cross sectional profile. FIG. 32A coincides with a location on placement tip (3719) along line A-A as shown in FIG. 29, while FIG. 32B coincides with a location on placement tip (3719) along line B-B. In this regard, the shapes of the cross-sectional profiles are different unlike the examples discussed above. Also, the taper of placement tip (3719) provides for a smaller width or lateral dimension along the more distal position of placement tip (3719) compared to the more proximal position of placement tip (3719). Additionally, the inverted U-shape the bottom part of the H-shape cross sectional profiles in this version are defined by an underside surface (3722) having five connected orthogonally oriented surfaces. In this manner, these portions of the cross-sectional profiles define a void or space with a rectangular shape.

Figure 33A:
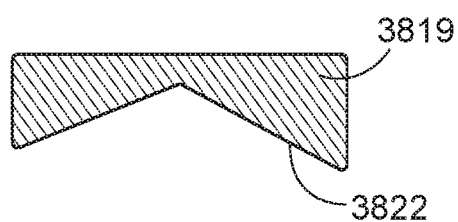
FIG. 33A depicts a front cross-sectional view of an alternate version of a jaw similar to the jaw of FIG. 29, taken along line A-A.
Figure 33B:
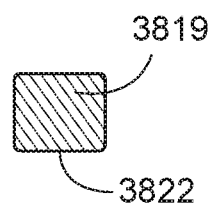
FIG. 33B depicts another front cross-sectional view of the alternate version of the jaw of FIG. 33A, taken along line B-B of FIG. 29.

FIGS. 33A and 33B illustrate various cross-sectional profiles of another placement tip (3819) that is the same as placement tip (3519) shown in FIGS. 28 and 29. Accordingly, the description of placement tip (3519) with respect to FIGS. 28 and 29 applies equally to placement tip (3819). FIG. 33A illustrates an exemplary inverted V-shape cross sectional profile, while FIG. 33B illustrates an exemplary rectangular shape profile. FIG. 33A coincides with a location on placement tip (3819) along line A-A as shown in FIG. 29, while FIG. 33B coincides with a location on placement tip (3819) along line B-B. In this regard, the shapes of the cross-sectional profiles are different. Also, the taper of placement tip (3819) provides for a smaller width or lateral dimension along the more distal position of placement tip (3819) compared to the more proximal position of placement tip (3819). Additionally, at the more proximal region of placement tip (3819), the inverted V-shape cross sectional profile is defined by an underside surface (3822) having two connected angled surfaces. At the more distal region of placement tip (3819), the rectangular shape cross sectional profile is defined by underside surface (3822) that is flat or straight. In this manner, the V-shape cross sectional profile defines a void or space with a triangle shape, whereas the rectangular shape cross sectional profile does not define any such void or space.

Figure 34A:
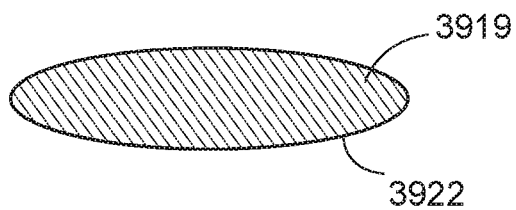
FIG. 34A depicts a front cross-sectional view of an alternate version of a jaw similar to the jaw of FIG. 29, taken along line A-A.
Figure 34B:
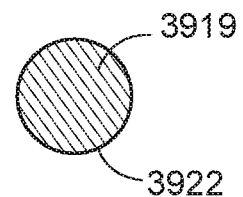
FIG. 34B depicts another front cross-sectional view of the alternate version of the jaw of FIG. 34A, taken along line B-B of FIG. 29.

FIGS. 34A and 34B illustrate various cross-sectional profiles of another placement tip (3919) that is the same as placement tip (3519) shown in FIGS. 28 and 29, except for the sides of placement tip (3919) are rounded. This impacts the cross-sectional profiles as will be shown and described. Besides this difference between placement tip (3519) and placement tip (3919), the description of placement tip (3519) with respect to FIGS. 28 and 29 applies equally to placement tip (3919). FIGS. 34A and 34B illustrate exemplary oval cross-sectional profiles. FIG. 34A coincides with a location on placement tip (3919) along line A-A as shown in FIG. 29, while FIG. 34B coincides with a location on placement tip (3919) along line B-B. In this regard, the shapes of the cross-sectional profiles are of the same broad category, i.e. both oval, but the shapes differ in that the appearance of the oval shapes at each profile is not the same. The taper of placement tip (3919) provides for a smaller width, diameter, or lateral dimension along the more distal position of placement tip (3919) compared to the more proximal position of placement tip (3919). Additionally, the oval cross-sectional profiles in this version are defined by an underside surface (3922) having a curved surface as mentioned. In this manner, the oval cross-sectional profile does not define a void or space because the curvature of the underside surface (3922) is convex unlike the curvature of underside surface (3622) shown in FIGS. 31A-31B. With respect to FIG. 34B, in some other versions, the shape of the cross-sectional profile along line B-B of FIG. 29 is circular instead of oval. In view of the teachings herein, various modifications to the oval and circular configurations of the cross-sectional profiles of placement tip (3919) will be apparent to those of ordinary skill in the art.

In the present examples, placement tips (3519, 3619, 3719, 3819, 3919) are configured as elastically deformable or deflectable. As discussed above, this allows placement tips (3519, 3619, 3719, 3819, 3919) to deflect when subject to a force such as a clamping force. The various lateral cross-sectional profiles shown and described above can be used to manipulate or control the nature and degree of deflection that placement tips (3519, 3619, 3719, 3819, 3919) may undergo when subject to a clamping force. Still in other versions, placement tips (3519, 3619, 3719, 3819, 3919) are not required to be configured as elastically deformable or deflectable. In view of the teachings herein, various ways to configure and modify a placement tip for an end effector as described herein, including ways to modify construction and lateral cross-sectional profiles, will be apparent to those of ordinary skill in the art.

9. Exemplary Durometer Ranges and Visual Contrast

Figure 35:
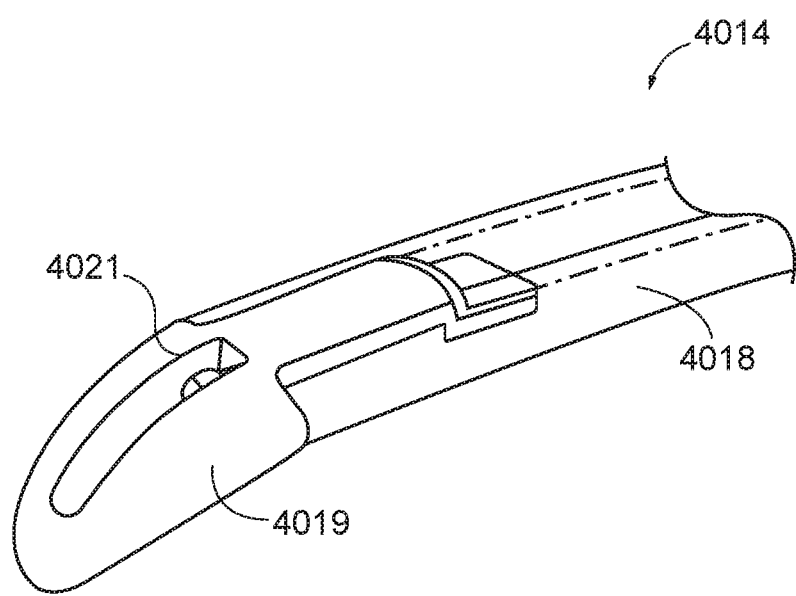
FIG. 35 depicts an enlarged perspective view of a distal portion of a jaw of an alternative version of an end effector, showing a high contrast placement tip.

FIG. 35 depicts another exemplary jaw (4014) useable with one or more of the end effectors described herein. In the illustrated example, jaw (4014) comprises an anvil (4018) and a placement tip (4019) extending from a distal end of anvil (4018). Placement tip (4019) is configured with a curved or bent configuration in the illustrated version. However, this curved or bent configuration is not required in all cases, and in other versions, placement tip (4019) can have a straight configuration. Returning to the illustrated version, placement tip (4019) is further configured as elastically deformable or deflectable. This allows placement tip (4019) to deflect when subject to a force such as a clamping force.

Placement tip (4019) is constructed from a material having a particular durometer range. For instance, in the present example, placement tip (4019) is constructed from a material having a durometer between about Shore 40A and about Shore 40D. However, this range should not be considered limiting or required in all versions, and in view of the teachings herein other suitable durometer ranges will be apparent to those of ordinary skill in the art.

Additionally, placement tip (4019) is constructed from a material having a high contrast color. By having a high contrast color compared to other materials of the surgical instrument, and compared to the environment where the surgical instruments are being used, placement tip (4019) can provided enhanced visualization for placement during use. In the present example, placement tip (4019) is constructed of a material having a neon green color. In some instances, this color may be described as iridescent green or fluorescent green or highlighter green. In the present example, placement tip (4019) is further configured with slot (4021), which can provide a further color contrast relative to the material of placement tip (4019). Slot (4021) is not required in all versions, however. And further, in some versions, slot (4021) is omitted entirely or replaced as a region or area having another contrasting color to the remainder of placement tip (4019). In view of the teachings herein, other high contrast colors and/or patterns of colors for use with placement tip (4019) will be apparent to those of ordinary skill in the art.

10. Exemplary Deflectable Straight Tip Extending Beyond Cartridge

While many of the elastically deformable placement tips shown and described above are curved or bent, in other versions an end effector may incorporate a placement tip that extends distally from one of the jaws in a straight manner. FIGS. 36-39 illustrate views of exemplary end effectors (4112, 4212) that each comprises an elastically deformable or deflectable straight placement tip (4119, 4219). Beginning with FIG. 36, end effector (4112) comprises an upper jaw (4114) and a lower jaw (4116). One or both of jaws (4114, 4116) are operable to move relative to the other so as to open and close end effector (4112). End effector (4112) further comprises an anvil (4118) and a cartridge (4137), which is the same or similar to cartridge (37) described above. Cartridge (4137) includes staples that are configured to strike or contact anvil (4118) in use as described and shown above with respect to instruments (10, 310). In the present example, upper jaw (4114) comprises anvil (4118), while lower jaw (4116) comprises cartridge (4137). Furthermore, in the present example, placement tip (4119) extends distally from anvil (4118) and does not angle toward lower jaw (4116) with cartridge (4137); but instead remains flat. Additionally, placement tip (4119) extends distally beyond cartridge (4137) of lower jaw (4116).

Figure 37:
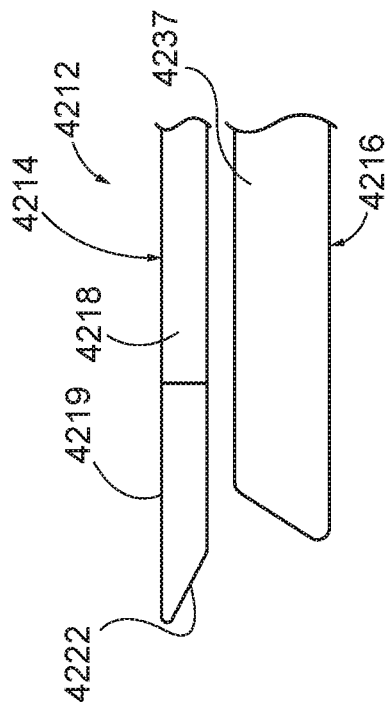
FIG. 37 depicts an enlarged side view of a distal portion of an alternate version of an end effector having a straight placement tip with a taper.

FIG. 37 illustrates end effector (4212), which comprises an upper jaw (4214) and a lower jaw (4216). One or both of jaws (4214, 4216) are operable to move relative to the other so as to open and close end effector (4212). End effector (4212) further comprises an anvil (4218) and a cartridge (4237), which is the same or similar to cartridge (37) described above. Cartridge (4237) includes staples that are configured to strike or contact anvil (4218) in use as described and shown above with respect to instruments (10, 310). In the present example, upper jaw (4214) comprises anvil (4218), while lower jaw (4216) comprises cartridge (4237). Furthermore, in the present example, placement tip (4219) extends distally from anvil (4218) and does not angle toward lower jaw (4216) with cartridge (4237); but instead angles away from lower jaw (4216) with cartridge (4237). In this manner, placement tip (4219) comprises upward angled surface (4222) near its distal end. Additionally, placement tip (4219) extends distally beyond cartridge (4237) of lower jaw (4216).

Figure 39:
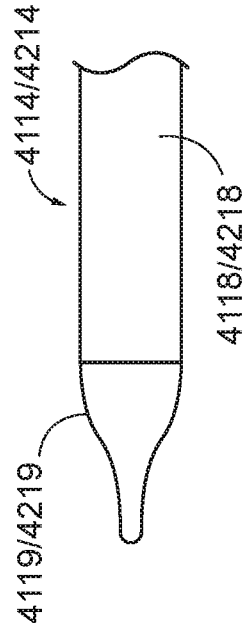
FIG. 39 depicts an enlarged top view of a distal portion of another exemplary anvil and placement tip usable with the end effectors of FIGS. 36 and 37.
Figure 38:
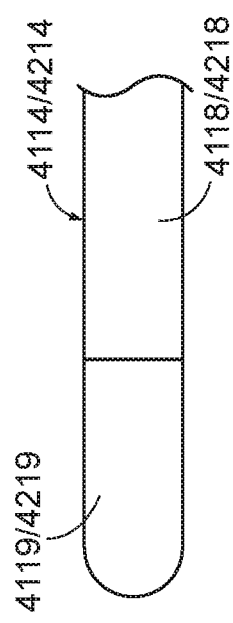
FIG. 38 depicts an enlarged top view of a distal portion of an anvil and placement tip usable with the end effectors of FIGS. 36 and 37.

FIGS. 38 and 39 illustrate top views of the upper jaws (4114,4214) of end effectors (4112, 4212). It should be understood that the top view of FIG. 38 applies to both upper jaws (4114, 4214) of end effectors (4112, 4212) in slightly different versions. Similarly, the top view of FIG. 39 applies to both upper jaws (4114, 4214) of end effectors (4112, 4212) in slightly different versions.

Figure 36:
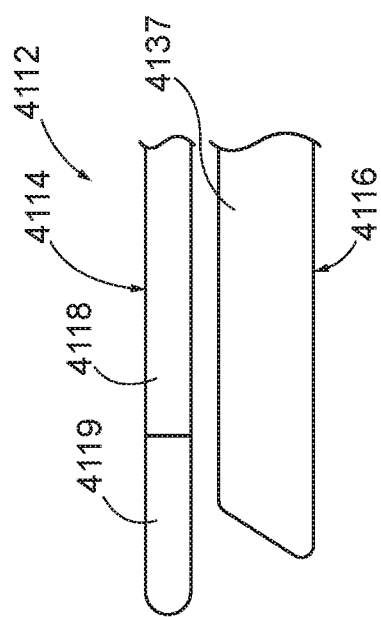
FIG. 36 depicts an enlarged side view of a distal portion of an alternate version of an end effector having a straight placement tip.

With end effector (4112) of FIG. 36, in one version upper jaw (4114) with anvil (4118) and placement tip (4119) has placement tip (4119) that is flat and rounded at its distal end as shown in FIG. 38. Additionally, as shown in FIG. 38, placement tip (4119) comprises the same width as anvil (4118). In another version of end effector (4112), upper jaw (4114) with anvil (4118) and placement tip (4119) has placement tip (4119) that is tapered with more of a pointed, yet slightly rounded, distal end as shown in FIG. 39. Additionally, as shown in FIG. 39, while placement tip (4119) tapers as it extends distally, at its proximal attachment point with anvil (4118) it has the same width as anvil (4118).

With end effector (4212) of FIG. 37, in one version upper jaw (4214) with anvil (4218) and placement tip (4219) has placement tip (4219) that is flat and rounded its distal end as shown in FIG. 38. Additionally, as shown in FIG. 38, placement tip (4219) comprises the same width as anvil (4218). In another version of end effector (4212), upper jaw (4214) with anvil (4218) and placement tip (4219) has placement tip (4219) that is tapered with more of a pointed, yet slightly rounded, distal end as shown in FIG. 39. Additionally, as shown in FIG. 39, while placement tip (4219) tapers as it extends distally, at its proximal attachment location with anvil (4218) it has the same width as anvil (4218).

Regarding end effectors (4112, 4212), upper jaws (4114, 4214) with anvils (4118, 4218) and placement tips (4119, 4219) have been described above as being straight relative to a longitudinal axis of respective anvils (4118, 4218), yet deflectable when subject to a force such as a clamping force. Furthermore, placement tips (4119, 4219) have been described as having various configurations that include flat and rounded, angled away and rounded, flat and tapered, and angled away and tapered. In view of the teachings herein, various modifications to a deflectable and straight placement tip of an end effector that extends beyond a cartridge will be apparent to those of ordinary skill in the art. By way of example only, and not limitation, some such modifications may be directed to the shape of the distal end or other regions of the placement tip, including cross sectional profiles both laterally and longitudinally.

V. SURGICAL STAPLING END EFFECTOR JAW WITH TIP DEFLECTING TOWARD OTHER JAW

A. End Effectors with Elastically Deformable Cartridge Tips

In some instances when a straight and rigid anvil is desired, another approach to modify an end effector for enhanced visualization, maneuverability, and tissue gathering with an atraumatic tip includes the addition of an elastomeric curved tip to the distal end of a cartridge. In this manner, when end effector is closed and maneuvering to a procedure site, the added elastomeric curved tip on the distal end of cartridge fills the space that would otherwise exist at the distal end of the end effector. This configuration can reduce the drag at the distal end when maneuvering the end effector by helping to deflect tissue away from the distal end of end effector when moving the end effector through and along tissue.

Figure 40:
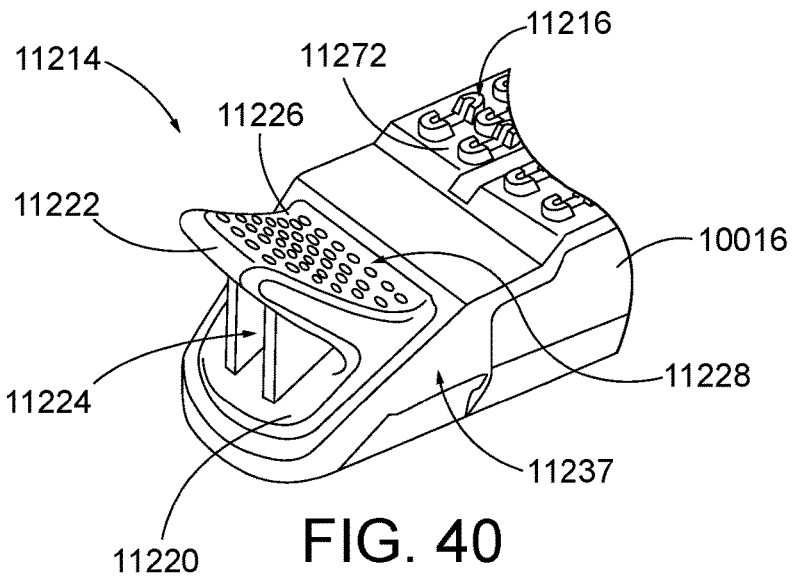
FIG. 40 depicts an enlarged perspective view of a distal portion of an exemplary alternative cartridge for an end effector for use with the surgical stapling instruments described herein.
Figure 41:
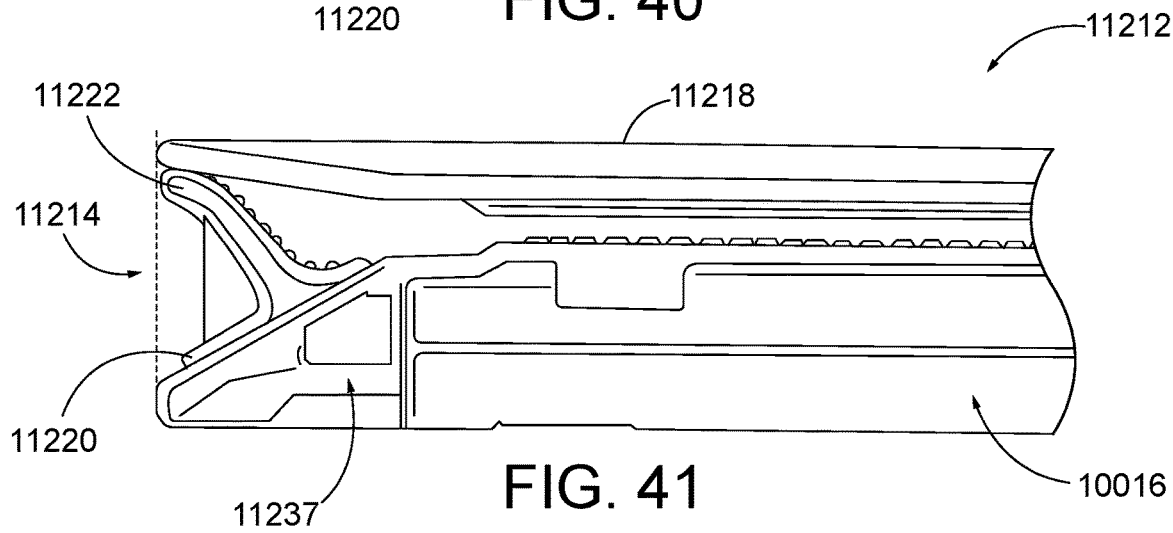
FIG. 41 depicts a side view of a distal portion of an exemplary alternative end effector having the cartridge of FIG. 40, shown without tissue capture.
Figure 42:
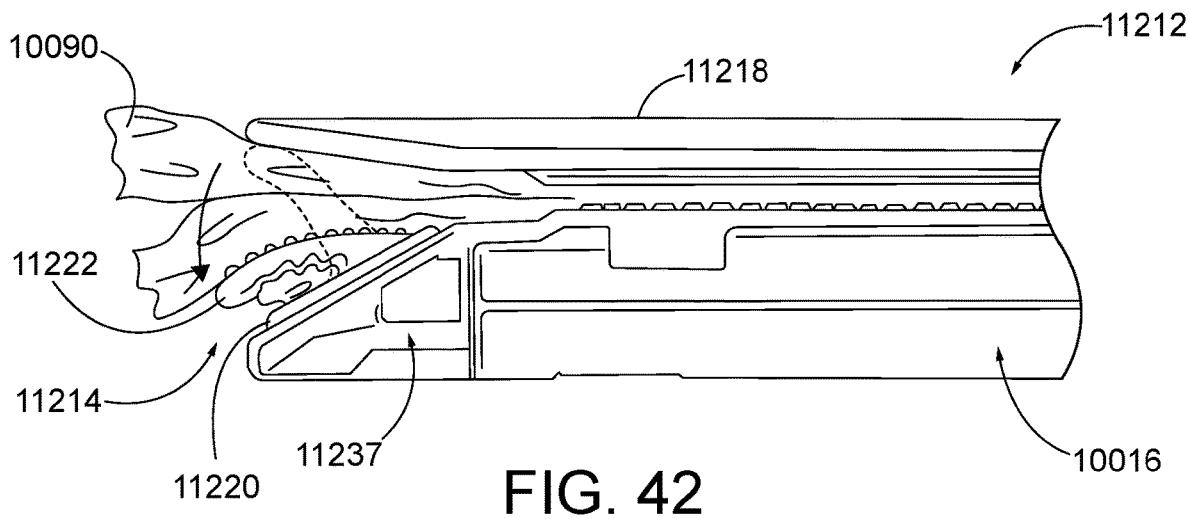
FIG. 42 depicts a side view of a distal portion of the end effector of FIG. 41, shown with tissue captured between the anvil and the cartridge.

FIGS. 40-42 show another exemplary end effector (11212) or components thereof incorporating an elastomeric curved tip (11214) attached to a distal end of a cartridge (11237). In addition to curved tip (11214) and cartridge (11237), end effector (11212) further comprises lower jaw (10016) and anvil (11218). Lower jaw (10016) is configured to receive cartridge (11237) in the same or similar manner as lower jaw (16) receives cartridge (37) as described above. Anvil (11218) is similar to anvil (18) described above, but with a more pointed distal end but being straight instead of curved. Cartridge (11237) is similar to cartridge (37) as described above with a difference being the incorporation of elastomeric curved tip (11214). As shown in FIG. 40, cartridge (11237) further comprises tissue gripping features (11216) located on an upper deck (11272) of cartridge (11237). Such tissue gripping features (11216) are optional features and they may be omitted in other versions.

As mentioned above, elastomeric curved tip (11214) is attached with the angled distal end of cartridge (11237). The connection of curved tip (11214) to cartridge (11237) may be achieved using a chemical or mechanical fastening. In view of the teachings herein those of ordinary skill in the art will appreciate the various ways to connect curved tip (11214) with distal end of cartridge (11237). In some versions, curved tip (11214) is bonded to cartridge (11237) using a molding process. In such examples, distal end of cartridge (11237) may comprise various structural features configured to engage with elastomeric material of curved tip (11214) during molding to thereby secure curved tip (11214) to distal end of cartridge (11237). In the present example, curved tip (11214) is resiliently biased to extend substantially perpendicularly from the angled distal face of cartridge (11237), though it should be understood that curved tip (11214) may have any other suitable angular relationship with the angled distal face of cartridge (11237). In addition, curved tip (11214) is resiliently biased to extend along a plane that is oriented obliquely relative to the longitudinal axis of end effector (11212) in the present example.

Curved tip (11214) comprises lower lip (11220), upper lip (11222), and dividers (11224). Lower lip (11220) attaches with the angled distal end of cartridge (11237) as described above. Upper lip (11222) extends from and connects with a proximal portion of lower lip (11220). Dividers (11224) extend vertically from lower lip (11220) and connect lower lip (11220) and upper lip (11222). In the present example, upper lip (11222) comprises top surface (11226) that includes gripping features (11228) configured to improve gripping tissue clamped between anvil (11218) and cartridge (11237), for example as shown in FIG. 42.

Referring to FIGS. 41 and 42, end effector (11212) is shown in the closed position both when not clamping tissue and when clamping tissue. As shown, in the closed position in either scenario, the distal end of anvil (11218) aligns with the longitudinal position of the distal end of cartridge (11237). In other versions, end effector (11212) may be configured such that the distal end of anvil (11218) extends past cartridge (11237) when end effector (11212) is closed. Still in other versions, end effector (11212) may be configured such that the distal end of anvil (11218) terminates proximal to the distal end of cartridge (11237) when end effector (11212) is closed.

As shown in FIG. 42, when tissue (10090) is captured between anvil (11218) and cartridge (11237), elastomeric curved tip (11214) deforms from its open state in FIG. 41 to a closed state as shown in FIG. 42. In this deformed state, upper lip (11222) deflects downwardly toward lower lip (11220). Furthermore, dividers (11224) are compressed and deflect laterally. As shown in FIG. 42, in its deformed state, upper lip (11222) of curved tip (11214) extends distally of anvil (11218) and cartridge (11237). With tissue clamped between end effector (11212) a cutting and stapling sequence can now occur with end effector (11212) in a similar manner to that described above with respect to end effector (12). When the clamping force is released, curved tip (11214) may resiliently return to the configuration and orientation shown in FIGS. 40-41.

In view of the teachings herein, it will be appreciated that end effector (11212) may be used in place of any of the other end effectors described herein. For instance, end effector (11212) may be used in place of end effector (12) shown in FIG. 1, or in place of end effector (312) shown in FIG. 11. In some versions, end effector (11212) may be integrally formed with either shaft (22, 322) or alternatively may be separately formed and then combined. In some versions, end effector (11212) may be provided for use in robotic systems as described above.

B. End Effectors with Elastically Deformable Tips on Thicker Jaw

In some instances when a straight and rigid jaw is desired, another approach to modify an end effector for enhanced visualization, maneuverability, and tissue gathering includes the addition of a placement tip on the distal end of the opposing jaw. In this manner, when end effector is closed and maneuvering to a procedure site, the placement tip fills at least some of the space that would otherwise exist at the distal end of the end effector. This configuration can reduce the drag at the distal end when maneuvering the end effector by helping to deflect tissue away from the distal end of end effector when moving the end effector through and along tissue. In some cases as will be described, the placement tip is made of an elastically deformable material such that the placement tip is responsive or deflects when subject to force associated with clamping tissue between the jaws.

Figure 43:
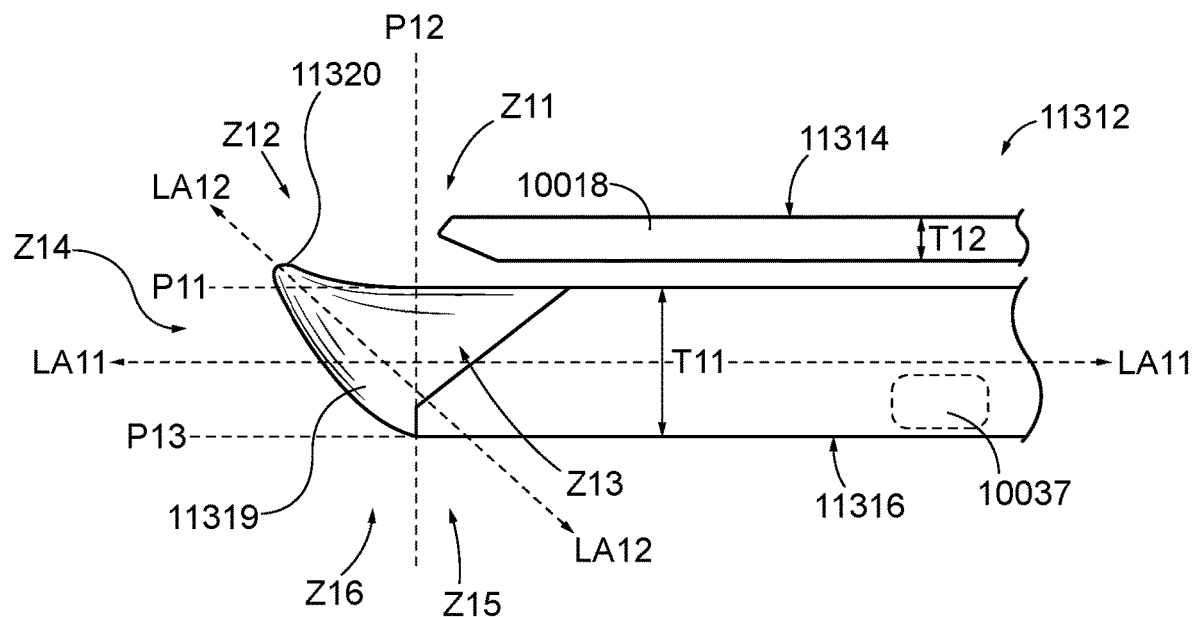
FIG. 43 depicts an enlarged side view of a distal portion of another exemplary end effector for use with the surgical stapling instruments described herein, showing a deformable tip extending from a thicker jaw.

FIG. 43 shows an enlarged view of end effector (11312), which is configured for use with instruments (10, 310) and/or for robotic use as described above. End effector (11312) comprises jaw (11314) and jaw (11316) that are configured in an opposing manner. Furthermore, jaws (11314, 11316) are operably configured such that one or both of the jaws (11314, 11316) are movable relative to the other to change the state of end effector (11312) from an open position or state to a closed position or state. For instance, this opening and closing of end effector (11312) provides for the ability to grasp, clamp, or release tissue. In the present example, FIG. 43 shows jaw (11314) as an upper jaw and jaw (11316) as a lower jaw. As mentioned above, the terms "upper" and "lower" are used as relative spatial references to help clarify the description of end effector (11312) and should not be interpreted in a limiting manner.

In the present example, a distal tip or placement tip (11319) extends distally from jaw (11316). Jaw (11316), excluding placement tip (11319), defines a longitudinal axis (LA11) that generally extends along the length of jaw (11316) from the proximal end to the distal end. Placement tip (11319) defines another longitudinal axis (LA12). In the present example, axis (LA12) defined by placement tip (11319) extends in a non-parallel manner with respect to longitudinal axis (LA11) defined by jaw (11316) from which placement tip (11319) extends. With this configuration, placement tip (11319) extends from jaw (11316) toward opposing jaw (11314). In other words, longitudinal axis (LA12) extends away from longitudinal axis (LA11) toward jaw (11314).

As shown in FIG. 43, jaw (11316) comprises a thickness (T11), while jaw (11314) comprises a thickness (T12). In the illustrated examples, jaw (11316) has a greater thickness than jaw (11314). Furthermore, placement tip (11319) connects with and extends from thicker jaw (11316) in the present example. As mentioned above in the present example placement tip (11316) extends from thicker jaw (11316) toward opposing thinner jaw (11314). As also shown in the illustrated version of FIG. 43, but not required in all versions, placement tip (11319) comprises about the same thickness as jaw (11316) to which it connects, at its thickest point. Furthermore, placement tip (11319) bends or curves toward jaw (11314) such that placement tip (11319) comprises a taper. In the present example placement tip (11319) tapers longitudinally. In some versions, placement tip (11319) tapers laterally. Still in some other versions, placement tip (11319) tapers both longitudinally and laterally. In view of the teachings herein, other configurations for the taper of placement tip (11319), or lack thereof, will be apparent to those of ordinary skill in the art.

In some versions of end effector (11312), placement tip (11319) is constructed of an elastically deformable material. In this manner placement tip (11319) is biased to an initial orientation or position when not subjected to force, and placement tip (11319) deflects to another orientation or position when subject to force, i.e. the force exerted on placement tip (11319) when clamping tissue. When the force is removed, placement tip (11319) is resilient and thus returns to its initial orientation or position. Additionally, in the present example, placement tip (11319) is constructed of a resilient material as mentioned, where that material and placement tip (11319) has a lower stiffness than jaw (11316) to which placement tip (11319) connects. In other words, the material of placement tip (11319) has a lower stiffness than the material of jaw (11316) from which placement tip (11319) extends. In some instances, placement tip (11319) tapers such that placement tip (11319) comprises a distal end (11320) that is pointed. In such instances, where placement tip (11319) is comprised of an elastomeric and deflectable material, placement tip (11319) is still configured as an atraumatic tip despite its pointed shape.

As described further above, end effector (11312) like end effectors (11212, 212), is configured such that one of jaws (11314, 11316) comprise anvil (10018), while the other of jaws (11314, 11316) comprise cartridge (10037). Although not required in all versions, in the present example jaw (11316) is configured to selectively retain cartridge (10037) or a similar cartridge, and jaw (11314) comprises anvil (10018) or a similar anvil. With this configuration, the thicker jaw (11316) comprises cartridge (10037) as well as placement tip (11319). In some other versions, the thicker jaw with placement tip (11319) may be configured as anvil (10018), while the thinner jaw may be configured to selectively retain the cartridge (10037). Thus, it is not required in all versions that the thicker jaw necessarily is the jaw that also selectively retains the cartridge. Furthermore, while the present example illustrates jaw (11316), to which placement tip (11319) connects, as a lower jaw relative to jaw (11314), in other versions the thicker jaw having placement tip (11319) is an upper jaw that may or may not also include cartridge (10037) as mentioned above. In view of the teachings herein, other ways to configure end effector (11312) with placement tip (11319) on the thicker jaw will be apparent to those of ordinary skill in the art.

Figure 44:
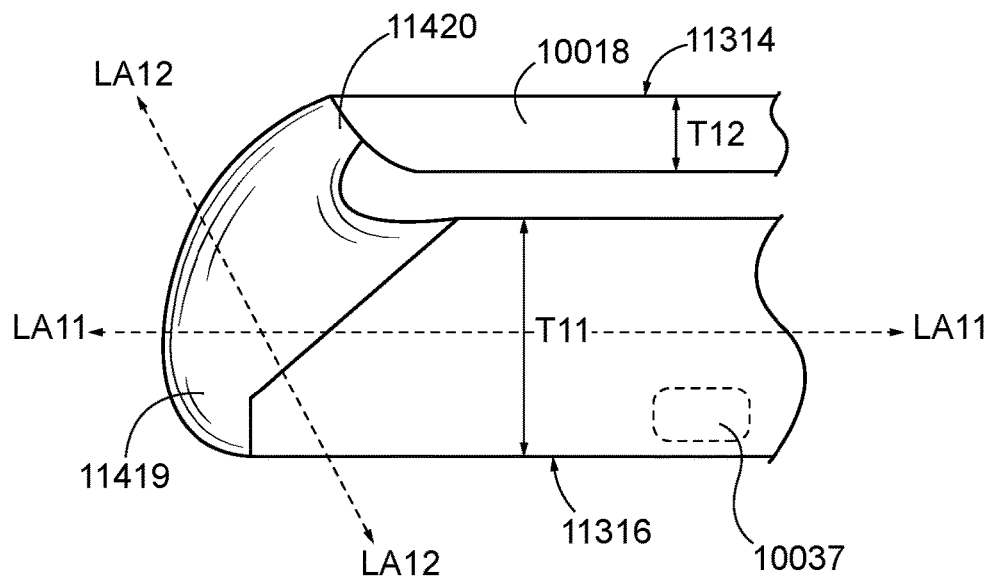
FIG. 44 depicts an enlarged side view of a distal portion of another exemplary end effector for use with the surgical stapling instruments described herein, showing a deformable tip extending from a thicker jaw in a touching or contacting configuration with the opposite jaw.
Figure 45:
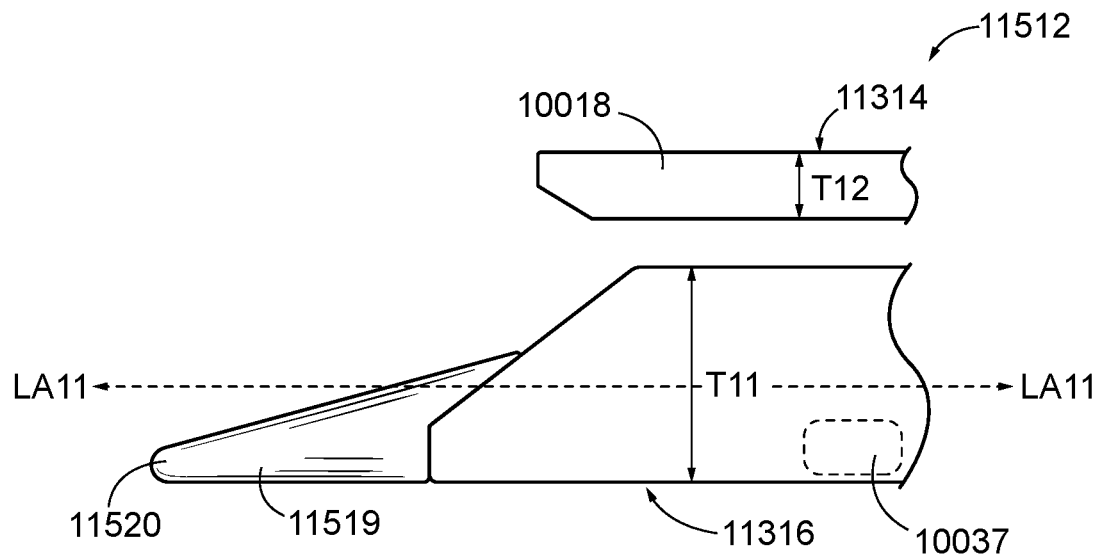
FIG. 45 depicts an enlarged side view of a distal portion of another exemplary end effector for use with the surgical stapling instruments described herein, showing a deformable tip extending from a thicker jaw in a straight configuration.
Figure 46:
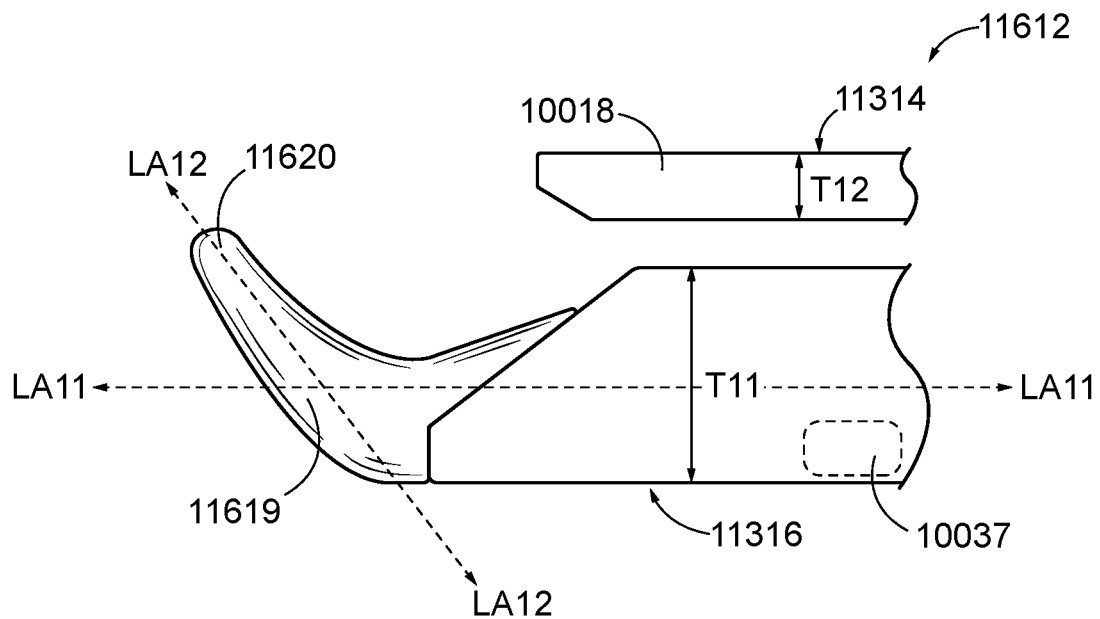
FIG. 46 depicts an enlarged side view of a distal portion of another exemplary end effector for use with the surgical stapling instruments described herein, showing a deformable tip extending from a thicker jaw in a curved non-touching or non-contacting configuration with the opposite jaw.

FIGS. 44-46 illustrate other enlarged views of exemplary end effectors suitable for use with instruments (10, 310) and/or for robotic use as described above. Other than the placement tips, the other components of the end effectors of FIGS. 44-46 are the same as those of end effector (11312) of FIG. 43. Therefore, the discussion that follows focuses on the placement tips rather than repeating the description of those features that are the same as with end effector (11312) and already described above.

FIG. 44 shows an enlarged view of an end effector (11412). End effector (11412) is the same as end effector (11312) with the exception that placement tip (11319) is replaced with placement tip (11419). Placement tip (11419) extends from jaw (11316), which is the thicker jaw compared to jaw (11314) as described above. In the version shown in FIG. 44, placement tip (11419) curves or bends away from jaw (11316) and longitudinal axis (LA11) and toward jaw (11314). In the present example, placement tip (11419) comprises an end (11420) that touches or contacts the distal-most end of jaw (11314) when end effector is in a closed an unloaded state where tissue is not between jaws (11314, 11316). With this configuration, placement tip (1419) fills the gap or space between jaws (11314, 11316) when end effector (11412) is closed. Such a configuration can improve maneuverability when moving end effector (11412) through tissue to a desired site.

As also shown in the illustrated version of FIG. 44, but not required in all versions, placement tip (11419) comprises about the same thickness as jaw (11316) to which it connects, at its thickest point. Furthermore, placement tip (11419) comprises a taper such that placement tip (11419) tapers as it extends away from jaw (11316) and toward jaw (11314). In the present example placement tip (11419) tapers longitudinally. In some versions, placement tip (11419) tapers laterally. Still in some other versions, placement tip (11419) tapers both longitudinally and laterally. In view of the teachings herein, other configurations for the taper of placement tip (11419), or lack thereof, will be apparent to those of ordinary skill in the art.

In the present example, but not required in all examples, placement tip (11419) is constructed of an elastically deformable material. In this manner placement tip (11419) is biased to an initial orientation or position when not subjected to force, and placement tip (11419) deflects to another orientation or position when subject to force, i.e. the force exerted on placement tip (11419) when clamping tissue. When the force is removed, placement tip (11419) is resilient and thus returns to its initial orientation or position. Additionally, in the present example, placement tip (11419) is constructed of a resilient material as mentioned, where that material and placement tip (11419) has a lower stiffness than jaw (11316) to which placement tip (11419) connects. In other words, the material of placement tip (11419) has a lower stiffness than the material of jaw (11316) from which placement tip (11419) extends. In some instances, placement tip (11419) tapers such that placement tip (11419) comprises a distal end (11420) that is pointed. In such instances, where placement tip (11419) is comprised of an elastomeric and deflectable material, placement tip (11419) is still configured as an atraumatic tip despite its pointed shape.

End effector (11412), like end effector (11312) and others described above, is configured such that one of jaws (11314, 11316) comprise anvil (10018), while the other of jaws (11314, 11316) comprise cartridge (10037). Although not required in all versions, in the present example jaw (11316) is configured to selectively retain cartridge (10037) or a similar cartridge, and jaw (11314) comprises anvil (10018) or a similar anvil. With this configuration, the thicker jaw (11316) comprises cartridge (10037) as well as placement tip (11419). In some other versions, the thicker jaw with placement tip (11419) may be configured as anvil (10018), while the thinner jaw may be configured to selectively retain the cartridge (10037). Thus, it is not required in all versions that the thicker jaw necessarily is the jaw that also selectively retains the cartridge. Furthermore, while the present example illustrates jaw (11316), to which placement tip (11419) connects, as a lower jaw relative to jaw (11314), in other versions the thicker jaw having placement tip (11419) is an upper jaw that may or may not also include cartridge (10037) as mentioned above. In view of the teachings herein, other ways to configure end effector (11412) with placement tip (11419) on the thicker jaw will be apparent to those of ordinary skill in the art.

FIG. 45 shows an enlarged view of an end effector (11512). End effector (11512) is the same as end effector (11312) with the exception that placement tip (11319) is replaced with placement tip (11519). Placement tip (11519) extends from jaw (11316), which is the thicker jaw compared to jaw (11314) as described above. In the version shown in FIG. 45, placement tip (11519) comprises a straight geometry where placement tip (11519) extends distally from jaw (11316) in a straight fashion without bending or curving toward opposing jaw (11314). This configuration provides a large gap or space between jaws (11314, 11316) when end effector (11512) is in a closed and unloaded state as shown in FIG. 45. Such a configuration can improve tissue capture and visibility when clamping, cutting, and stapling tissue.

As also shown in the illustrated version of FIG. 45, but not required in all versions, placement tip (11519) is less thick compared to thickness (T11) of jaw (11316) to which placement tip (11519) connects. Furthermore, placement tip (11519) comprises a taper such that placement tip (11519) tapers as it extends away from jaw (11316). In the present example placement tip (11519) tapers longitudinally. In some versions, placement tip (11519) tapers laterally. Still in some other versions, placement tip (11519) tapers both longitudinally and laterally. In view of the teachings herein, other configurations for the taper of placement tip (11519), or lack thereof, will be apparent to those of ordinary skill in the art.

In the present example, but not required in all examples, placement tip (11519) is constructed of an elastically deformable material. In this manner placement tip (11519) is biased to an initial orientation or position when not subjected to force, and placement tip (11519) deflects to another orientation or position when subject to force, i.e. the force exerted on placement tip (11519) when clamping tissue. When the force is removed, placement tip (11519) is resilient and thus returns to its initial orientation or position. Additionally, in the present example, placement tip (11519) is constructed of a resilient material as mentioned, where that material and placement tip (11519) has a lower stiffness than jaw (11316) to which placement tip (11519) connects. In other words, the material of placement tip (11519) has a lower stiffness than the material of jaw (11316) from which placement tip (11519) extends. In some instances, placement tip (11519) tapers such that placement tip (11519) comprises a distal end (11520) that is pointed. In such instances, where placement tip (11519) is comprised of an elastomeric and deflectable material, placement tip (11519) is still configured as an atraumatic tip despite its pointed shape.

End effector (11512), like end effector (11312) and others described above, is configured such that one of jaws (11314, 11316) comprise anvil (10018), while the other of jaws (11314, 11316) comprise cartridge (10037). Although not required in all versions, in the present example jaw (11316) is configured to selectively retain cartridge (10037) or a similar cartridge, and jaw (11314) comprises anvil (10018) or a similar anvil. With this configuration, the thicker jaw (11316) comprises cartridge (10037) as well as placement tip (11519). In some other versions, the thicker jaw with placement tip (11519) may be configured as anvil (10018), while the thinner jaw may be configured to selectively retain the cartridge (10037). Thus, it is not required in all versions that the thicker jaw necessarily is the jaw that also selectively retains the cartridge. Furthermore, while the present example illustrates jaw (11316), to which placement tip (11519) connects, as a lower jaw relative to jaw (11314), in other versions the thicker jaw having placement tip (11519) is an upper jaw that may or may not also include cartridge (10037) as mentioned above. In view of the teachings herein, other ways to configure end effector (11512) with placement tip (11519) on the thicker jaw will be apparent to those of ordinary skill in the art.

FIG. 46 shows an enlarged view of an end effector (11612). End effector (11612) is the same as end effector (11312) with the exception that placement tip (11319) is replaced with placement tip (11619). Placement tip (11619) extends from jaw (11316), which is the thicker jaw compared to jaw (11314) as described above. In the version shown in FIG. 46, placement tip (11619) curves or bends away from jaw (11316) and longitudinal axis (LA11) and toward jaw (11314). In the present example, placement tip (11619) comprises an end (11620) that does not touch or contact the distal-most end of jaw (11314) when end effector is in a closed an unloaded state where tissue is not between jaws (11314, 11316). With this configuration, there remains a gap or space between jaws (11314, 11316) when end effector (11612) is closed and in an unloaded state as shown in FIG. 46. Such a configuration can improve tissue capture and visibility when clamping, cutting, and stapling tissue.

As also shown in the illustrated version of FIG. 46, but not required in all versions, placement tip (11619) is less thick compared to thickness (T11) of jaw (11316) to which placement tip (11619) connects. Furthermore, placement tip (11619) comprises a taper such that placement tip (11619) tapers as it extends away from jaw (11316). In the present example placement tip (11619) tapers longitudinally. In some versions, placement tip (11619) tapers laterally. Still in some other versions, placement tip (11619) tapers both longitudinally and laterally. In view of the teachings herein, other configurations for the taper of placement tip (11619), or lack thereof, will be apparent to those of ordinary skill in the art.

In the present example, but not required in all examples, placement tip (11619) is constructed of an elastically deformable material. In this manner placement tip (11619) is biased to an initial orientation or position when not subjected to force, and placement tip (11619) deflects to another orientation or position when subject to force, i.e. the force exerted on placement tip (11619) when clamping tissue. When the force is removed, placement tip (11619) is resilient and thus returns to its initial orientation or position. Additionally, in the present example, placement tip (11619) is constructed of a resilient material as mentioned, where that material and placement tip (11619) has a lower stiffness than jaw (11316) to which placement tip (11619) connects. In other words, the material of placement tip (11619) has a lower stiffness than the material of jaw (11316) from which placement tip (11619) extends. In some instances, placement tip (11619) tapers such that placement tip (11619) comprises a distal end (11620) that is pointed. In such instances, where placement tip (11619) is comprised of an elastomeric and deflectable material, placement tip (11619) is still configured as an atraumatic tip despite its pointed shape.

End effector (11612), like end effector (11312) and others described above, is configured such that one of jaws (11314, 11316) comprise anvil (10018), while the other of jaws (11314, 11316) comprise cartridge (10037). Although not required in all versions, in the present example jaw (11316) is configured to selectively retain cartridge (10037) or a similar cartridge, and jaw (11314) comprises anvil (10018) or a similar anvil. With this configuration, the thicker jaw (11316) comprises cartridge (10037) as well as placement tip (11619). In some other versions, the thicker jaw with placement tip (11619) may be configured as anvil (10018), while the thinner jaw may be configured to selectively retain the cartridge (10037). Thus, it is not required in all versions that the thicker jaw necessarily is the jaw that also selectively retains the cartridge. Furthermore, while the present example illustrates jaw (11316), to which placement tip (11619) connects, as a lower jaw relative to jaw (11314), in other versions the thicker jaw having placement tip (11619) is an upper jaw that may or may not also include cartridge (10037) as mentioned above. In view of the teachings herein, other ways to configure end effector (11612) with placement tip (11619) on the thicker jaw will be apparent to those of ordinary skill in the art.

Referring again to FIG. 43, FIG. 43 illustrates reference markings that define multiple zones that can be used to describe the location or placement of the end of the placement tip of an exemplary end effector. For instance, a first reference plane (P11) is defined by a top surface of jaw (11316), and second reference plane (P12) is defined by a distal end of jaw (11316). Additionally, a third reference plane (P13) is defined by a bottom surface of jaw (11316). Third reference plane (P13) in the present example is parallel with first reference plane (P11) and also orthogonal to second reference plane (P12). With this configuration, six zones are defined by the intersections of first and third reference planes (P11, P13) with second reference plane (P12).

A first zone (Z11) is the region above the top surface of jaw (11316) (corresponding with first reference plane (P11)) and proximal to the distal end of jaw (11316) (corresponding with second reference plane (P12)). A second zone (Z12) is shown as the region above the top surface of jaw (11316) (corresponding with first reference plane (P11)) and distal to the distal end of jaw (11316) (corresponding with second reference plane (P12)). A third zone (Z13) is shown as the region below the top surface of jaw (11316) (corresponding with first reference plane (P11)) yet above the bottom surface of jaw (11316) (corresponding with third reference plane (P13)), and proximal to the distal end of jaw (11316) (corresponding with second reference plane (P12)). A fourth zone (Z14) is shown as the region below the top surface of jaw (11316) (corresponding with first reference plane (P11)) yet above the bottom surface of jaw (11316) (corresponding with third reference plane (P13)), and distal to the distal end of jaw (11316) (corresponding with second reference plane (P12)). A fifth zone (Z15) is shown as the region below the bottom surface of jaw (11316) (corresponding with third reference plane (P13)), and proximal to the distal end of jaw (11316) (corresponding with second reference plane (P12)). A sixth zone (Z16) is shown as the region below the bottom surface of jaw (11316) (corresponding with third reference plane (P13)), and distal to the distal end of jaw (11316) (corresponding with second reference plane (P12)).

Using this reference system, exemplary end effectors (11312, 11412, 11512, 11612) can be described in a way that illustrates various locations or placements for the end of the various placement tips when the end effector is in a closed and unloaded state. Referring to FIG. 43, the illustrated configuration shows placement tip (11319) extends through third zone (Z13) and fourth zone (Z14), and the location of an end (11320) of placement tip (11319) is in second zone (Z12). In view of the teachings herein, it will be apparent to those of ordinary skill in the art that when placement tip (11319) is deformable and end effector (11312) is in a closed and loaded state that the location of end (11320) of placement tip (11319) may deflect yet remain in second zone (Z12), or placement tip (11319) may deflect such that end (11320) changes its location in the closed and loaded state to another one of the zones.

With respect to FIG. 44 and placement tip (11419), the illustrated configuration shows placement tip (11419) extends through third zone (Z13), fourth zone (Z14), second zone (Z12), and the location of an end (11420) of placement tip (1419) is in first zone (Z11). In view of the teachings herein, it will be apparent to those of ordinary skill in the art that when placement tip (11419) is deformable and end effector (11412) is in a closed and loaded state that the location of end (11420) of placement tip (11419) may deflect yet remain in first zone (Z11), or placement tip (11419) may deflect such that end (11420) changes its location in the closed and loaded state to another one of the zones.

With respect to FIG. 45 and placement tip (11519), the illustrated configuration shows placement tip (11519) extends through third zone (Z13), and the location of an end (11520) of placement tip (11519) is in fourth zone (Z14). In view of the teachings herein, it will be apparent to those of ordinary skill in the art that when placement tip (11519) is deformable and end effector (15112) is in a closed and loaded state that the location of end (11520) of placement tip (11519) may deflect yet remain in fourth zone (Z14), or placement tip (11519) may deflect such that end (11520) changes its location in the closed and loaded state to another one of the zones.

With respect to FIG. 46 and placement tip (11619), the illustrated configuration shows placement tip (11619) extends through third zone (Z13), fourth zone (Z14), and the location of an end (11620) of placement tip (11619) is in second zone (Z12). In view of the teachings herein, it will be apparent to those of ordinary skill in the art that when placement tip (11619) is deformable and end effector (11612) is in a closed and loaded state that the location of end (11620) of placement tip (11619) may deflect yet remain in second zone (Z12), or placement tip (11619) may deflect such that end (11620) changes its location in the closed and loaded state to another one of the zones.

VI. PERMANENT ATTACHMENT MEANS FOR CURVED TIP OF COMPONENT OF SURGICAL STAPLING INSTRUMENT

A. Exemplary Attachment for End Effector Deflectable Tip

In some instance where a surgical instrument incorporates a deflectable tip the same or similar to those described above, the deflectable tip can be a structure that is attached with the distal end of an end effector of the surgical instrument. In some cases, this attachment may be configured to create a permanent attachment between the deflectable tip and the end effector, but in other instances the attachment may be selective such that permanent attachment is not required. Regardless of the nature of the attachment, the deflectable tip is attached with the end effector such that it remains secured with the end effector during use of the instrument.

1. Mechanical Fastening

FIGS. 47-49 depicts views of an enlarged portion of a jaw (20418) of an end effector, which is configured for use with instruments (10, 310) and/or for robotic use as described above. Jaw (20418), is positionable opposite to another jaw, such as jaw (16) or jaw (216) as described above in forming the end effector. Jaw (20418) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (20418) may be used with a variety of end effectors, at least some of which are described herein or incorporated by reference.

In the illustrated example, jaw (20418) comprises a base (20420), a cap (20422), a placement tip (20424), and a retention feature (20426). Placement tip (20424) is elastically deformable and extends distally from the base (20420) when assembled. As shown in the illustrated version, placement tip (20424) is bent or angled such that a proximal portion (20428) of placement tip (20424) and a distal portion (20430) define an angle that is less than 180 degrees. Still in other versions, placement tip (20424) is not required to be bent or angled, and instead placement tip (20424) is straight such that proximal portion (20428) and distal portion (20430) are co-planar and define an angle that is 180 degrees or thereabout. Still in other versions, placement tip (20424) may be curved, wherein as placement tip (20424) extends distally, placement tip (20424) curves toward the opposing jaw. In view of the teachings herein, other shapes and ways to configure placement tip (20424) will be apparent to those of ordinary skill in the art.

A connection member (20432) extends proximally from proximal portion (20428) of placement tip (20424). Connection member (20432) is configured with an opening (20434) as well as first lateral projecting wing (20436) and second lateral projecting wing (20438). In the present example, opening (20434) is located between first and second lateral projecting wings (20436, 20438). Furthermore, opening (20434) is configured to receive retention feature (20426) when attaching placement tip (20424) with base (20420). When retention feature (20426) is inserted within opening (20434), first and second lateral projecting wings (20436, 20438) deflect laterally away from opening (20434). This deflection of first and second lateral projecting wings (20436, 20438) increases the contact or engagement between placement tip (20424) and base (20420), which aids in securing placement tip (20424) with base (20420).

As mentioned, retention feature (20426) is configured to secure placement tip (20424) with jaw (20418), and in the present example with base (20420) of jaw (20418). Retention feature (20426) is further configured to prevent removal of placement tip (20424) from jaw (20418). In the present example, retention feature (20426) comprises gripping features (20440) in the form of ribs or threads that are configured to bite into or engage the surface of first and second lateral projecting wings (20436, 20438) that defines opening (20434). In this manner, retention feature (20426) securely attaches with connection member (20432), and as mentioned, imparts an outward force on first and second lateral projecting wings (20436, 20438) causing wings (20436, 20438) to deflect outward and engage with base (20420). In view of the teachings herein, other ways to modify or configure retention member (20426) to provide for secure attachment with placement tip (20424) will be apparent to those of ordinary skill in the art.

As shown in FIG. 47, in the present version retention feature (20426) comprises a fastener, such as a tack or similar fastener, having a body (20442) and post (20444) extending from body (20442). Post (20444) includes gripping features (20440) described above. In the illustrated example of FIGS. 47-49, jaw (20418) is configured such that retention feature (20426) connects or attaches placement tip (20424) with base (20420) by locating retention feature (20426) above placement tip (20424) and advancing retention feature (20426) downward such that post (20444) extends through opening (20434) of connection member (20432). In this manner, retention feature (20426) is insertable from the side of base (20420) that faces away from or is farthest from the opposing jaw used with jaw (20418) in forming the end effector.

Base (20420) comprises central channel (20446) defined between and by inner elongated portions (20448). Base (20420) further comprises outer elongated portions (20450) that extend parallel to inner elongated portions (20448). Although not required in all versions, elongated portions (20448, 450) may be formed together as a unitary structure. At a distal end of base (20420), a space (20452) is defined between inner elongated portions (20448 and outer elongated portions (20450). Space (20452) is configured with a complementary shape to connection member (20432), such that connection member (20432) is able to fit within space (20452). In this manner, space (20452) can also be considered a notch or cut-out configured to receive connection member (20432). Base (20420) further includes a bottom surface beneath space (20452) such that connection member (20432) cannot pass through space (20452). As shown, outer elongated portions (20450) each comprise distal flange (20454). Distal flanges (20454) are configured to abut or contact shoulder portions (20456) of connection member (20432) when connection member (20432) is within space (20452). In this manner, this interference fitting prevents placement tip (20424) from distal separation from base (20420).

Jaw (20418) further comprises cap (20422) as mentioned above. Cap (20422) is configured to attach with base (20420) and with part of proximal portion (20428) of placement tip (20426). Furthermore, cap (20422) installs from above placement tip (20424), retention feature (20426), and base (20420). In this manner, cap (20422) covers retention feature (20426) such that retention feature (20426) is concealed within jaw (20418). Furthermore, in the present example, an underside surface of cap (20422) contacts body (20442) of retention feature (20426) to further secure retention feature (20426) in place. As will be described below, cap (20422) is not required in all versions, nor is it required in all versions that retention feature (20426) is entirely concealed within jaw (20418). In the present example, cap (20422) is configured to permanently attach with base (20420) and the part of placement tip (20424) as shown. This permanent attachment of cap (20422) is achieved by welding cap (20422) in place, but can be permanently attached other ways like adhesives, mechanical fasteners, etc. In other versions, cap (20422) is configured to securely but selectively connect with or attach with base (20420) and the part of placement tip (20424). In view of the teachings herein, other ways to configure cap (20422) to connect with other components of jaw (20418) to secure placement tip (20424) with jaw (20418) will be apparent to those of ordinary skill in the art in view of the teachings herein.

FIGS. 43 and 44 depicts views of an enlarged portion of a jaw (20518) of an end effector, which is configured for use with instruments (10, 310) and/or for robotic use as described above. Jaw (20518), is positionable opposite to another jaw, such as jaw (16) or jaw (216) as described above in forming the end effector. Jaw (20518) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (20518) may be used with a variety of end effectors, at least some of which are described herein or incorporated by reference.

In the illustrated version, jaw (20518) comprises a base (20520), a cap (20522), a placement tip (20524), and a retention feature (20526). Placement tip (20524) is elastically deformable and extends distally from the base (20520) when assembled. As shown in the illustrated version, placement tip (20524) is bent or angled such that a proximal portion (20528) of placement tip (20524) and a distal portion (20530) define an angle that is less than 180 degrees. Still in other versions, placement tip (20524) is not required to be bent or angled, and instead placement tip (20524) is straight such that proximal portion (20528) and distal portion (20530) are co-planar and define an angle that is 180 degrees or thereabout. Still in other versions, placement tip (20524) may be curved, wherein as placement tip (20524) extends distally, placement tip (20524) curves toward the opposing jaw. In view of the teachings herein, other shapes and ways to configure placement tip (20524) will be apparent to those of ordinary skill in the art.

A connection member (20532) extends proximally from proximal portion (20528) of placement tip (20524). Connection member (20532) is configured with an opening (20534) as well as first lateral projecting wing (20536) and second lateral projecting wing (20538). In the present example, opening (20534) is located between first and second lateral projecting wings (20536, 20538). Furthermore, opening (20534) is configured to receive retention feature (20526) when attaching placement tip (20524) with base (20520). When retention feature (20526) is inserted within opening (20534), first and second lateral projecting wings (20536, 538) deflect laterally away from opening (20534). This deflection of first and second lateral projecting wings (20536, 20538) increases the contact or engagement between placement tip (20524) and base (20520), which aids in securing placement tip (20524) with base (20520).

As mentioned, retention feature (20526) is configured to secure placement tip (20524) with jaw (20518), and in the present example with base (20520) of jaw (20518). Retention feature (20526) is further configured to prevent removal of placement tip (20524) from jaw (20518). In the present example, retention feature (20526) comprises gripping features (20540) in the form of ribs or threads that are configured to bite into or engage the surface of first and second lateral projecting wings (20536, 20538) that defines opening (20534). In this manner, retention feature (20526) securely attaches with connection member (20532), and as mentioned, imparts an outward force on first and second lateral projecting wings (20536, 20538) causing wings (20536, 20538) to deflect outward and engage with base (20520). In view of the teachings herein, other ways to modify or configure retention member (20526) to provide for secure attachment with placement tip (20524) will be apparent to those of ordinary skill in the art.

As best shown in FIG. 44, in the present version retention feature (20526) comprises a fastener, such as a tack or similar fastener, having a body (20542) and post (20544) extending from body (20442). Post (20444) includes gripping features (20440) described above. Body (20442) comprises gripping features (20545), which are configured to assist in gripping tissue grasped between jaw (20518) and the opposing jaw of the end effector using jaw (20518). In the illustrated example of FIGS. 43 and 44, jaw (20518) is configured such that retention feature (20526) connects or attaches placement tip (20524) with base (20520) by locating retention feature (20526) below placement tip (20524) and advancing retention feature (20526) upward such that post (20544) extends through opening (20534) of connection member (20532). In this manner, retention feature (20526) is insertable from the side of base (20520) facing or closest to the opposing jaw used with jaw (20518) in forming the end effector.

Base (20520) comprises central channel (20546) defined between and by inner elongated portions (20548). Base (20520) further comprises outer elongated portions (20550) that extend parallel to inner elongated portions (20548). Although not required in all versions, elongated portions (20548, 20550) may be formed together as a unitary structure. At a distal end of base (20520), a space (20552) is defined between inner elongated portions (20548 and outer elongated portions (20550). Space (20552) is configured with a complementary shape to connection member (20532), such that connection member (20532) is able to fit within space (20552). In this manner, space (20552) can also be considered a notch or cut-out configured to receive connection member (20532). Base (20520) further includes a top surface above space (20552) such that connection member (20532) cannot pass through space (20552). As shown, outer elongated portions (20550) join at the distal end of base (20520) and comprise distal flange (20554). Distal flange (20554) is configured to abut or contact shoulder portions (20556) of connection member (20532) when connection member (20532) is within space (20552). In this manner, this interference fitting prevents placement tip (20524) from distal separation from base (20520).

Jaw (20518) further comprises cap (20522) as mentioned above. Cap (20522) is configured to attach with base (20520), and in particular with an upper surface of base (20520). As shown in FIG. 43, with jaw (20518) assembled, the only portion of retention feature (20526) that is exposed or revealed is the surface facing the opposing jaw that includes gripping features (20545). While FIG. 44 illustrates cap (20522) as part of jaw (20518), in some other versions, cap (20522) is omitted entirely. In the illustrated version of FIG. 44 where cap (20522) is present, cap (20522) is configured to permanently attach with base (20520). This permanent attachment of cap (20522) is achieved by welding cap (20522) in place, but can be permanently attached other ways like adhesives, mechanical fasteners, etc. Still, in other versions, cap (20522) is configured to securely but selectively connect with or attach with base (20520). In view of the teachings herein, other ways to configure cap (20522) to connect with other components of jaw (20518) to secure placement tip (20524) with jaw (20518) will be apparent to those of ordinary skill in the art in view of the teachings herein.

In the above described versions of jaws (20418, 20518), each of jaw (20418, 20518) is configured as an anvil, where each base (20420, 20520) comprises a plurality of staple forming pockets on an underside surface. For instance, FIG. 44 illustrates staple forming pockets (20558). With this configuration, the opposing jaw to jaws (20418, 20518) comprise a jaw that is configured to retain a stapling cartridge. By way of example, and not limitation, as mentioned above, jaws (16, 216) described above may be used in conjunction with either of jaws (20418, 20518) when configuring the end effector for use with surgical instruments (10, 310). In some other versions, jaws (20418, 20518) are not required to comprise an anvil, and instead may be configured or modified such that jaws (20418, 20518) may comprise a cartridge, with the opposing jaw configured with an anvil. In view of the teachings herein, other ways to configure jaws (20418, 20518) for use with an end effector for a surgical instrument (10, 310) will be apparent to those of ordinary skill in the art.

2. Surface Treatment and Features with Overmolding

While the above section describes and illustrates ways of attaching a deflectable placement tip with a jaw of an end effector using a retention feature such as a fastener or tack, other ways to attach a deflectable placement tip with a jaw of an end effector include overmolding the placement tip onto a part of the jaw of the end effector. With the description of the jaws that follow, surface treatments and/or features are added to the jaws to provide for improved overmolding attachment of the deformable or deflectable placement tip, and to prevent detachment and edge peeling.

FIG. 45 depicts a perspective view of a portion of an exemplary jaw (20618) of an end effector, which is configured for use with instruments (10, 310) and/or for robotic use as described above. Jaw (20618), is positionable opposite to another jaw, such as jaw (16) or jaw (216) as described above in forming the end effector. Jaw (20618) and/or the other opposing jaw of the end effector are operable to move relative to one another between an open position and a closed position. In this manner, the end effector is operable to receive tissue between the jaws and subsequently release, clamp, cut, and/or staple the tissue. In view of the teachings herein, it will be apparent to those of ordinary skill in the art that jaw (20618) may be used with a variety of end effectors, at least some of which are described herein or incorporated by reference.

Referring to FIGS. 45 and 46, jaw (20618) comprises a body (20620) and a placement tip (20624). With respect to FIG. 46, placement tip (20624) is shown in phantom to reveal further features of body (20620) as will be described further below. In the present example, body (20620) comprises an anvil that includes staple forming pockets and a channel for a cutting blade as described above. In other versions, body (20620) is not required to be configured as the anvil, and instead the anvil may be the opposite jaw to jaw (20620). In such other versions, body (20620) can be configured to retain a staple cartridge as described above.

Returning now to the present illustrated example, body or anvil (20620) comprises a distal portion (20626). Distal portion (20626) comprises connection features that are configured to improve the overmolding attachment of placement tip (20624) with body (20620). One such connection feature comprises a protrusion (20628). Protrusion (20628) has a similar shape with the majority of body (20620) but is sized slightly smaller. Protrusion (20628) extends distally from the remainder of body (20620) and defines a bonding surface (20630) that extends around the circumference of protrusion (20628) and that is oriented orthogonally to a bonding surface (20632) defined by body (20620). Protrusion (20628) further defines another bonding surface (20634), which is generally orthogonal to bonding surface (20630) and parallel with bonding surface (20632).

Another connection feature of distal portion (20626) is protrusion (20636), which extends distally from protrusion (20628). Protrusion (20636) comprises a rectangular prism having a bore (20638) extending therethrough. Bore (20638) acts as a connection feature by providing space where material of the overmolded placement tip (20624) can flow and bond to. Furthermore, protrusion (20636) also defines another connection feature with a bonding surface (20640) on the four sides of protrusion. Bonding surface (20640) is oriented orthogonally to bonding surface (20634) of protrusion (20628).

Another connection feature of distal portion (20626) is protrusion (20642), which is at the distal end of distal portion (20626). Protrusion (20642) is oriented orthogonally relative to protrusion (20636) from which it is attached. Protrusion (20642) further comprises a plurality of notches (20644) that act as additional connection features by providing space where material of the overmolded placement tip (20624) can flow and bond to. In this manner, notches (20644) provide increased surface area for material bonding during the overmolding process. In the illustrated version, but not required in all versions, protrusion (20642) comprises six notches. Furthermore, each of the six notches are generally shaped the same, as square cut-outs. In some other versions, greater or fewer notches, and/or notches having other shapes or varying shapes can be used. In view of the teachings herein, other ways to configure protrusion (20642) and notches (20644) will be apparent to those of ordinary skill in the art. In addition to the bonding surfaces provided by notches (20644), protrusion (20642) further defines a bonding surface (20646) on proximal and distal surfaces of protrusion (20642). Bonding surface (20646) is oriented orthogonally relative to bonding surface (20640) of protrusion (20636).

With the above described configuration of body (20620) and in particular distal portion (20626), improved overmolding is achieved by incorporating a plurality of connection features. Moreover, these connection features can have the form of a series of protrusions (20628, 20636, 20642) where each protrusion extends distally from the preceding protrusion. Still yet, these protrusions (20628, 20636, 20642) are configured to present alternating orthogonally oriented bonding surfaces (20630, 20640, 20646). Another noteworthy connection feature of distal portion (20626) comprises the relative sizes of protrusions (20628, 636, 642). In particular, the middle protrusion, protrusion (20636), has a smaller lateral dimension or width than the other protrusions (20628, 20642). With this configuration, distal portion (20626) defines voids (20648) on each side of protrusion (20636) where material for overmolding placement tip (20624) can flow. While a variety of connection features have been shown and described above, other ways to configure or modify distal portion (20626) to define various connection features to improve overmolding will be apparent to those of ordinary skill in the art in view of the teachings herein. Furthermore, some such modifications can include using the various connection features presented independently from one another or in other combinations other than those depicted in FIGS. 45 and 46.

Sometimes with surgical instruments such as instruments (10, 310) that use end effectors as described herein for surgical cutting and stapling, lubricants are applied to the anvil portions of the end effector jaws. Added lubricant can help promote better sliding of the staples along the forming pockets as well as better sliding of the blade or knife through the anvil longitudinal channel. In some instances, it may be desirable to remove lubricant from distal portion (20626) where the overmolding occurs, or to prevent lubricant from being applied to distal portion (20626) in the first instance. Such removal or prevention of lubrication can provide for improved overmolding attachment of placement tip (20624) with body or anvil (20620).

In one example, lubricant is applied to body (20620), including distal portion (20626), and then before overmolding, the lubricant is removed from distal portion (20626) by an etching application. Etching distal portion (20626) can provided additional benefit in roughening the surface of distal portion (20626) to promote better bonding of the material used for overmolding with distal portion (20626). In another example, distal portion (20626) is masked or covered prior to lubricating body (20620) such that distal portion (20626) remains free of lubricant. In this way, better overmolding success can be achieved where distal portion (20626) remains free of lubricant. Still in another example, combinations of masking and etching can be used. In view of the teachings herein, other ways to lubricate portions of jaw (20618) in a targeted manner such that improved overmolding can be achieved will be apparent to those of ordinary skill in the art.

VII. SURGICAL STAPLING END EFFECTOR COMPONENT WITH DEFORMABLE TIP HAVING VOID

A. Another Exemplary Surgical Instrument Having Various End

Effectors and Placement Tips

Figure 54:
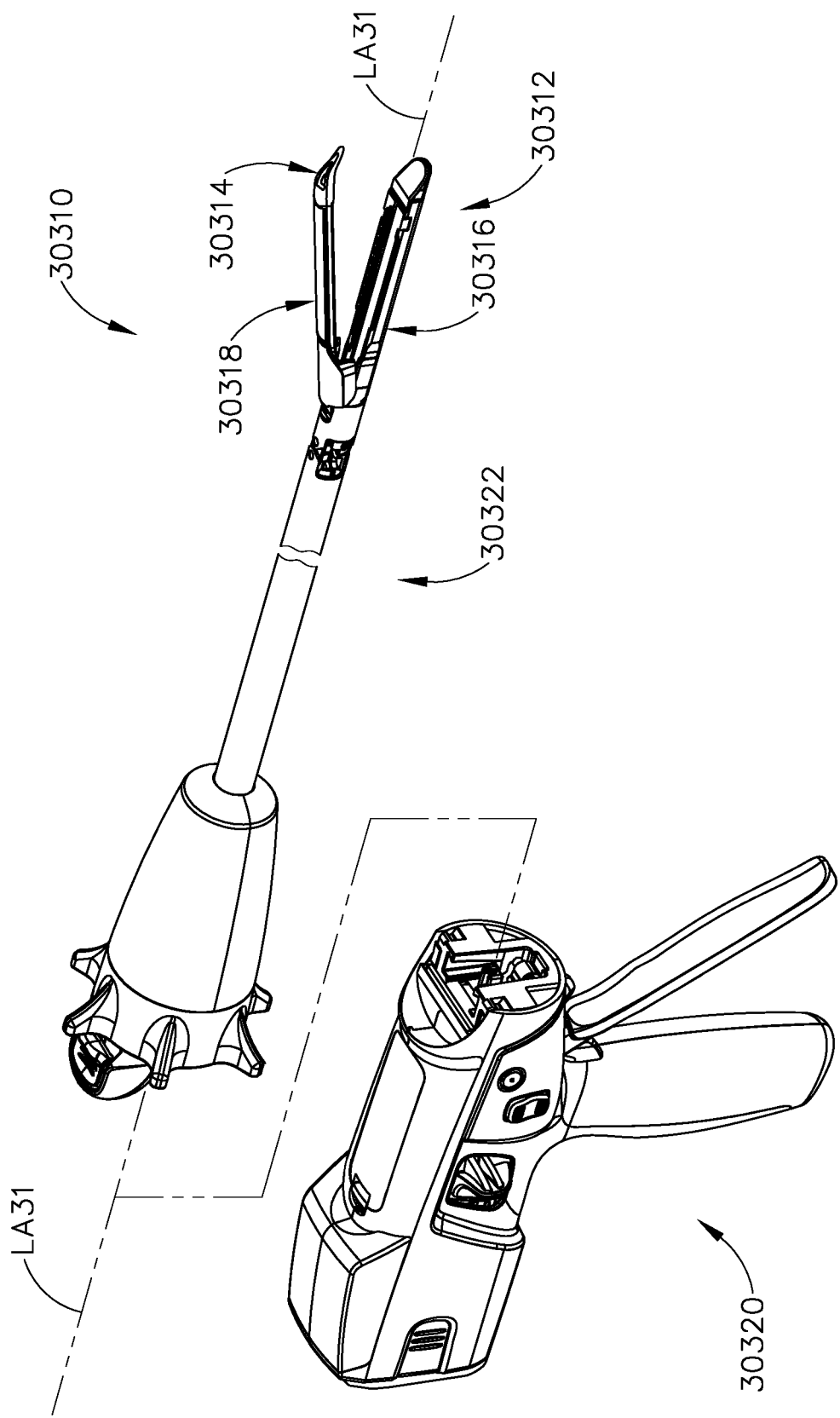
FIG. 54 depicts a perspective view of another exemplary surgical stapling instrument with another exemplary end effector with another exemplary placement tip, where the upper and lower jaws are in an open configuration.

FIG. 54 shows another exemplary surgical instrument (30310) configured as a surgical stapler. Instrument (30310) comprises a handle portion (30320) and a shaft (30322). Shaft (30322) defines a longitudinal axis (LA31) that extends from handle portion (30320). Instrument (30310) has a modular configuration such that shaft (30322) is selectively removable from, and attachable to, handle portion (30320). Instrument (30310) is configured similarly to instrument (10), such that the operability and use of instrument (30310) is the same as described above for instrument (10) with the added feature of instrument (30310) being a modular configuration. With its modular configuration, instrument (30310) provides a way to change the desired end effector. Features operable for providing the modular configuration of instrument (30310) may be configured in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (30322) is not detachable from handle portion (30320).

As will be discussed in greater detail below, exemplary end effectors (30312, 30412, 30512) are provided on shaft (30322) that is detachable from handle portion (30320). End effectors (30312, 30412, 30512) are operable to compress, staple, and cut tissue. End effectors (30312, 30412, 30512) may be used in place of end effector (12) shown in FIG. 1. In some versions, end effectors (30312, 30412, 30512) may be integrally formed with shaft (30322) or, alternatively, may be separately formed and then combined. In some versions, end effectors (30312, 30412, 30512) may be provided for use in robotic systems. In such robotic systems, modular shaft (30322) having any of the following end effectors (30312, 30412, 30512) may be attachable to a portion of the robotic system for use such that handle portion (30320) is replaced by components of the robotic system, including a body. Other ways to incorporate an end effector (30312, 30412, 30512) having any of the following placement tips (30314, 30414, 30514) into a user operated or robotic operated instrument will be apparent to those of ordinary skill in the art.

As will be described in greater detail below, placement tips (30314, 30414, 30514) are configured to be coupled with an upper jaw (such as anvil 30318, 30418, 30518) or a lower jaw (30316, 30416, 30516). Placement tips (30314, 30414, 30514) may be positioned on the same jaw as staple cartridge (37) or on the same jaw as anvil (30318, 30418, 30518). Placement tips (30314, 30414, 30514) are operable to elastically deform from a first angled position to a second angled position. The second angled position for placement tips (30314, 30414, 30514) may be substantially straight in some versions, but may be angled to a degree (e.g., slightly above or slightly below the longitudinal axis (LA31, LA32, LA33)) in other versions. The second angled position for placement tips (30314, 30414, 30514) may be defined by the characteristics (e.g., thickness, density, etc.) of the tissue that is being captured between anvils (30318, 30418, 30518) and lower jaws (30316, 30416, 30516) and/or central voids (30332, 30436, 30536) that are located at least partially within placement tips (30314, 30414, 30514) as will be discussed in greater detail below. Central voids (30332, 30436, 30536) allow placement tips (30314, 30414, 30514) to be formed from stiffer, more rigid, materials. Central voids (30332, 30436, 30536) enable placement tips (30314, 30414, 30514) to deflect in part due to their spatial geometries. While shown as central voids (30332, 30436, 30536), voids may not necessarily be in the geometric center and may be offset a distance from the geometric center.

The exemplary placement tips (30314, 30414, 30514) described below may be used with any surgical instrument (10, 310) described above and below and in any of the various procedures described in the various patent references cited herein. As will be described in greater detailed below, placement tips (30314, 30414, 30514) may be used singularly or in combination with other placement tips, such as placement tips (30314, 30414, 30514). To this end, like numbers below indicate like features described above. Except as otherwise described below, instrument (30310) described below may be constructed and operable like instrument (10) described above. Certain details of instrument (30310) will therefore be omitted from the following description, it being understood that such details are already provided above in the description of instrument (10). Other suitable ways in which various surgical instruments may be used will be apparent to those of ordinary skill in the art in view of the teachings herein.

Figure 55:
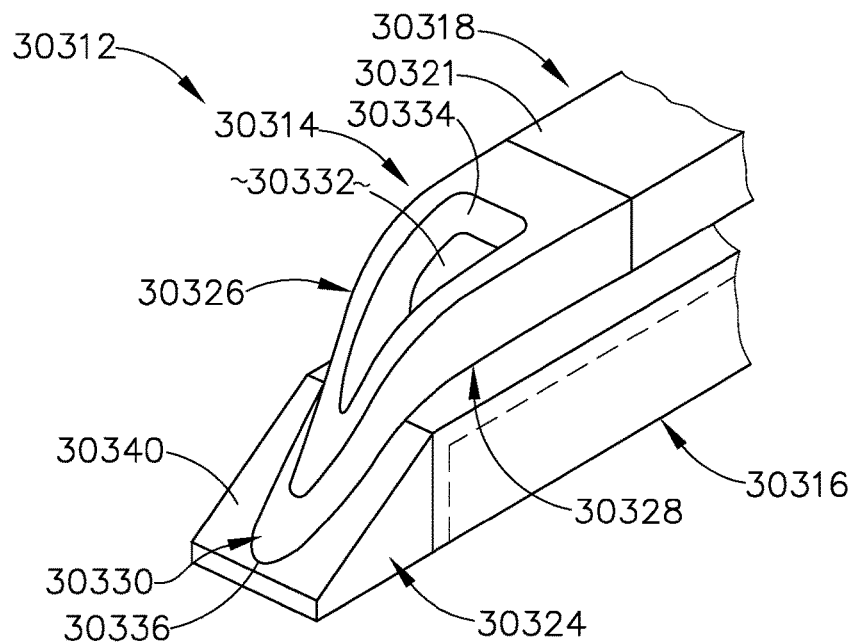
FIG. 55 depicts an enlarged schematic perspective view of the end effector of FIG. 54 with the placement tip and the lower jaw in a closed configuration.
Figure 56:
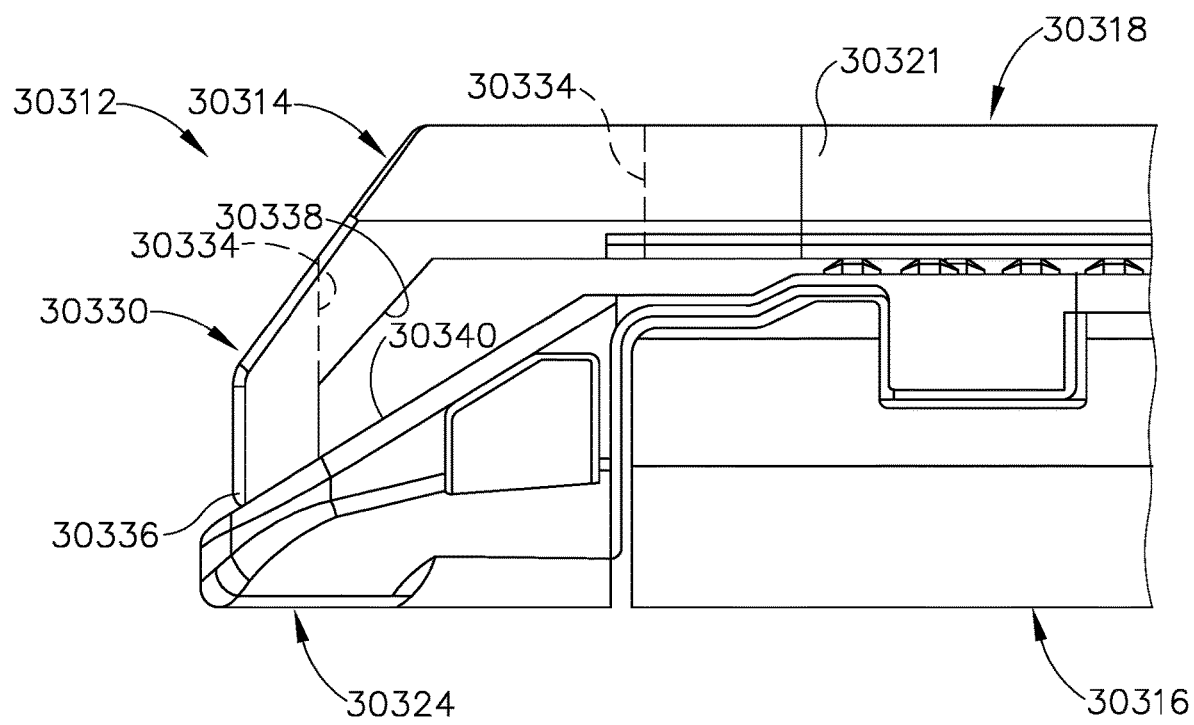
FIG. 56 depicts a schematic side view of the end effector of FIG. 55 in the closed configuration.
Figure 57:
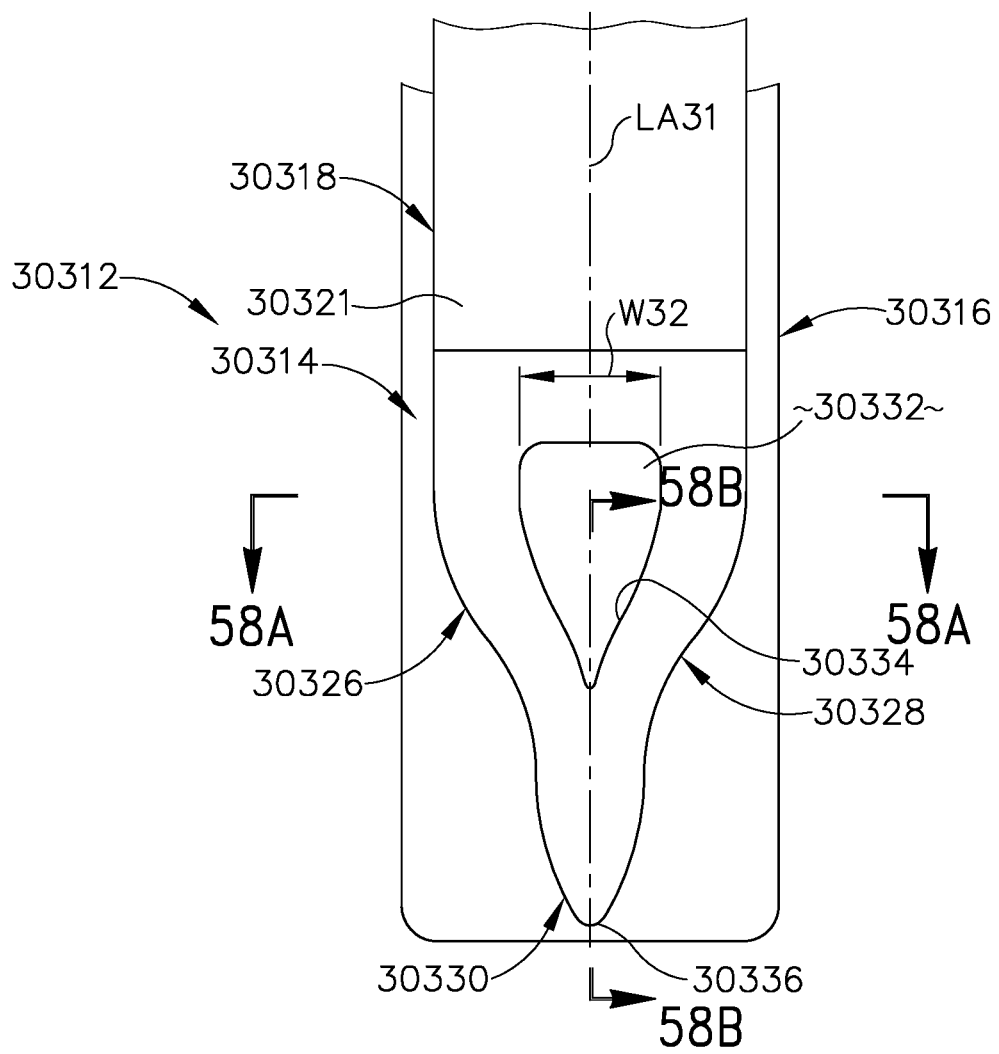
FIG. 57 depicts a schematic top view of the placement tip and anvil of FIG. 55.

1. Another Exemplary Surgical Instrument Having Another Exemplary End Effector and Another Example of a Placement Tip FIGS. 54-58B show another exemplary surgical instrument (30310) that comprises another exemplary end effector (30312) and another exemplary placement tip (30314). FIGS. 55-57 show enlarged views of a distal end of end effector (30312) shown in FIG. 54. As shown, end effector (30312) includes an upper jaw (shown as including an anvil (30318)), and a lower jaw (30316). While anvil (30318) is included in an upper jaw, and cartridge (30324) is received in lower jaw (30316), this relationship may be reversed. Lower jaw (30316) is shown schematically in FIG. 55, and in greater detail in FIG. 56. Staple cartridge (30324) is removably coupled with lower jaw (30316). As described above with respect to staple cartridge (37), staple cartridge (30324) is configured to hold one or more staples.

At least one of anvil (30318) or lower jaw (30316) is movable relative to other of anvil (30318) or lower jaw (30316) between an open configuration and a closed configuration. As shown, anvil (30318) pivotably rotates toward lower jaw (16) in the same manner as anvil (18) as described above with respect to instrument (10). In this manner, end effector (30312) is similar to end effector (12), however, placement tip (30314) is elastically deformable. Placement tip (30314) obtains a first angled position, shown in FIGS. 55 and 56, when end effector (30312) is not clamping tissue. In this first angled position, end effector (30312) may be in an open configuration as shown in FIG. 54, or a closed configuration as shown in FIGS. 55 and 56. Specifically regarding the closed configuration, FIG. 56 shows distal tip (30336) is in contact with angled surface (30340). In instances when end effector (30312) is in this angled configuration, end effector (30312) may be considered in a non-loaded state or non-loaded position. Conversely, in a second angled position when end effector (30312) is clamping tissue, end effector (30312) may be considered in a loaded state or a loaded position. In the second angled position, at least a portion of placement tip (30314) deflects upwardly.

Placement tip (30314) is located adjacent at least one of distal end (30321) of the anvil (30318) or a distal end of lower jaw (30316). As shown in FIGS. 55-57, placement tip (30314) is coupled with a distal end (30321) of anvil (30318). As shown in FIG. 13, lower jaw (30316) is thicker (i.e. vertically taller) than anvil (30318) or placement tip (30314). As shown in the top view of FIG. 57, lower jaw (30316) is longer and wider than anvil (30318) and placement tip (30314). Additionally, as shown in FIG. 57, placement tip (30314) is symmetric about a longitudinal axis (LA31). However, placement tip (30314) may be non-symmetric, if desired. Placement tip (30314) may be integrally formed together as unitary piece.

Figure 58A:
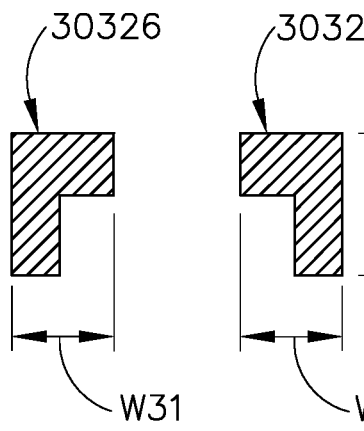
FIG. 58A depicts a transverse cross-sectional view of first and second legs of the placement tip of FIG. 57, taken along line 58A-58A of FIG. 57.

Placement tip (30314) includes first and second legs (30326, 30328) and a distal portion (30330). As shown, first and second legs (30326, 30328) extend distally from anvil (30318). First and second legs (30326, 30328) are separated by central void (30332), which is shown as extending completely through placement tip (30314). With reference to FIG. 58A, first and second legs (30326, 30328) have a generally L-shaped cross-section. Additionally, first and second legs (30326, 30328) each have a first width (W31) shown in FIG. 58A that is less than a second width (W32) of a central void (30332) shown in FIG. 57. Central void (30332) is defined by an inner wall (30334) extending through placement tip (30314). While FIG. 57 shows central void (30332) being generally pentagon shaped when viewed from above, central void (30332) may have a variety of different shapes and/or sizes depending on the desired degree of upward flexibility according to the specific orientation shown. Additionally, while inner wall (30334) forming central void (30332) is shown as extending generally perpendicular to longitudinal axis (LA31) of placement tip (30314), inner wall (30334) may alternatively be angled, if desired.

Figure 58B:
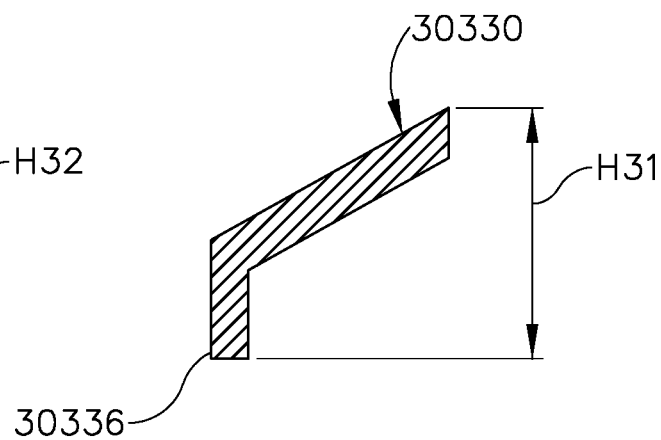
FIG. 58B depicts a longitudinal cross-sectional view of a distal portion of the placement tip of FIG. 57, taken along line 58B-58B of FIG. 57.

Distal portion (30330) of placement tip (30314) connects first and second legs (30326, 30328). As shown in FIGS. 58A-58B, distal portion (30330) has a first cross-sectional height (H31) that is greater than second cross-sectional height (H32) of first and second legs (30326, 30328). Since H31 is greater than H32, placement tip (30314) is elastically deformable. More specifically, since distal portion (30330) has a first cross-sectional height (H31) that is greater than second cross-sectional height (H32) of first and second legs (30326, 30328), the first and second legs (30326, 30328) deflect before distal portion (30330) deflects, allowing distal portion (30330) to remain generally rigid. Additionally, central void (30332) allows first and second legs (30326, 30328) of placement tip (30314) to deflect upwardly when in contact with tissue. This spatial geometry of placement tip (30314) allows placement tip (30314) to be formed from a rigid material, while still retaining the desired degree of flexibility.

Additionally, distal portion (30330) of placement tip (30312) terminates at distal most point (30336), which may be blunt or sharp. When distal tip (30336) is rigid, such as when a portion of or the entire placement tip (30314) is formed from a rigid material, distal tip (30336) allows for jabbing at small areas of tissue and subsequent dilatation of the area of tissue as placement tip (30314) is advanced distally. Additionally, in the closed configuration, since distal portion (30330) maybe in contact with lower jaw (30316), distal tip (30336) may be sharp because distal tip (30336) is shielded from damaging tissue by lower jaw (30316). In other versions, placement tip (30312) is deformable. Such deformability may be elastic or malleable.

2. Another Exemplary Surgical Instrument Having Another Exemplary End Effector and Another Example of a Placement Tip FIGS. 59-63B show another exemplary end effector (30412) and another exemplary placement tip (30414). As shown, end effector (30412) comprises upper and lower opposing jaws, a staple cartridge (30437) similar to staple cartridge (37, 30324), and placement tip (30414). While the upper jaw includes anvil (30418) and lower jaw (30416) accepts staple cartridge (30437), this relationship may be reversed. Placement tip (30414) may be permanently coupled with or removably coupled with an anvil (30418). Lower jaw (30416) is similar to lower jaw (16). Staple cartridge (30437) is removably coupled with lower jaw (30416) in a similar manner to staple cartridge (37) and lower jaw (16) and is configured to hold one or more staples.

Figure 63A:
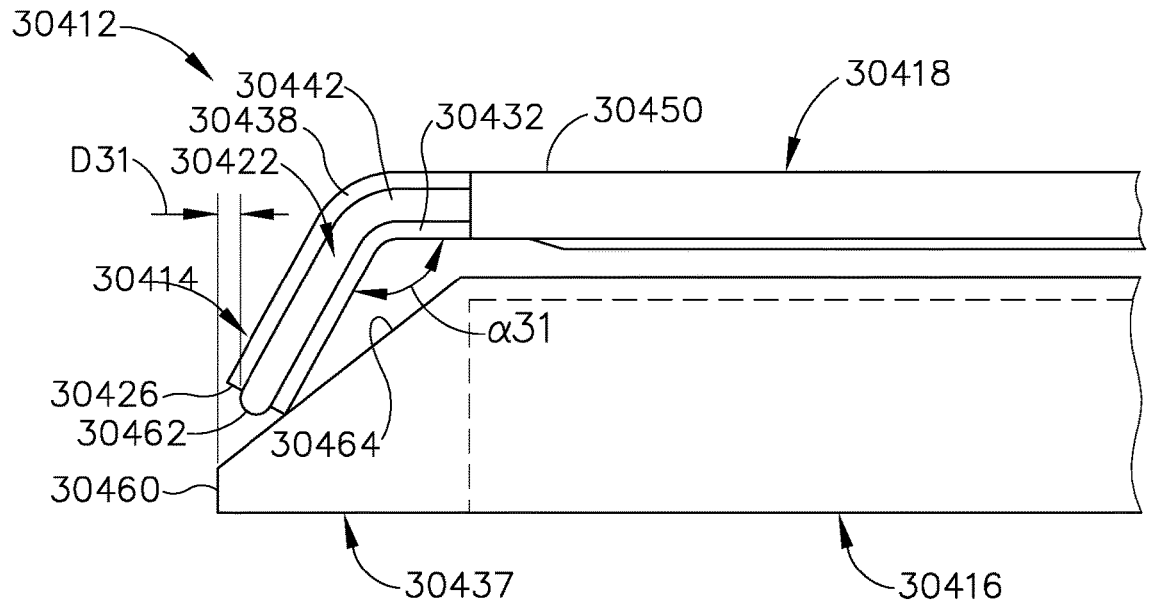
FIG. 63A depicts a side view of the placement tip of FIG. 61 in a first bent configuration.

At least one of anvil (30418) or lower jaw (30416) is movable relative to other of anvil (30418) or lower jaw (30416) between an open configuration and a closed configuration. As shown, anvil (30418) pivotably rotates toward lower jaw (30416) in the same manner as anvil (18) as described above with respect to instrument (10). In this manner, end effector (30412) is like end effector (12). However, placement tip (30414) is elastically deformable. Placement tip (30414) assumes a first angled position, shown in FIG. 63A, when end effector (30412) is not clamping tissue. In this first angled position, end effector (30412) may be in an open configuration like what is shown in FIG. 54; or a closed configuration as shown in FIG. 63A where placement tip (30414) is in contact with staple cartridge (30437) of lower jaw (30416). In instances when end effector (30412) is in the first angled configuration, end effector (30412) may be considered in a non-loaded state or non-loaded position. Conversely, while not shown, in a second angled position when end effector (30412) is clamping tissue, end effector (30412) may be considered in a loaded state or a loaded position. In the second angled position, at least a portion of placement tip (30414) deflects upwardly.

Figure 61:
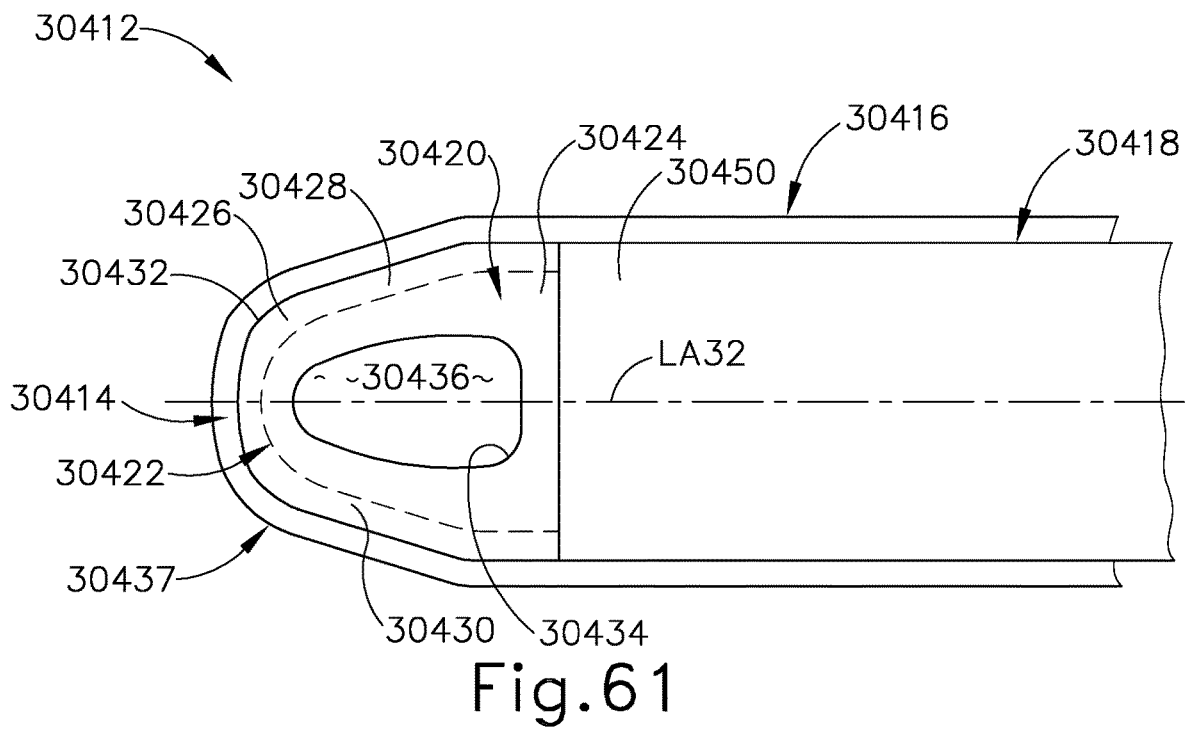
FIG. 61 depicts a top view of another exemplary end effector that includes a lower jaw as well as the anvil and the placement tip of FIG. 59.

Placement tip (30414) is located adjacent at least one of distal end (30450) of the anvil (30418) or a distal end of lower jaw (30416). As shown in FIGS. 61-63B, placement tip (30414) is coupled with a distal end (30421) of anvil (30418). As shown in FIGS. 63A-63B, lower jaw (30416) is thicker (i.e. vertically taller) than anvil (30418) or placement tip (30414). Additionally, as shown in the top view of FIG. 61, lower jaw (30416) is longer and wider than anvil (30418) and placement tip (30414). As shown in FIG. 61, placement tip (30414) is symmetric about a longitudinal axis (LA32). However, placement tip (30414) may be non-symmetric, if desired.

FIGS. 59-63B show placement tip (30414) as including a body portion (30420) and a malleable member (30422). Body portion (30420) includes proximal and distal portions (30424, 30426) separated by first and second legs (30428, 30430). Body portion (30420) is formed between an outer perimeter (30432) and an inner perimeter (30434) of placement tip (30414). Inner perimeter (30434) is defined by a central void (30436) extending through placement tip (30412). At least a portion of distal portion (30426) of body portion (30420) is bent towards the opposing jaw, shown as lower jaw (30416). At least body portion (30420) of placement tip (30314) may be integrally formed together as unitary piece.

Figure 62:
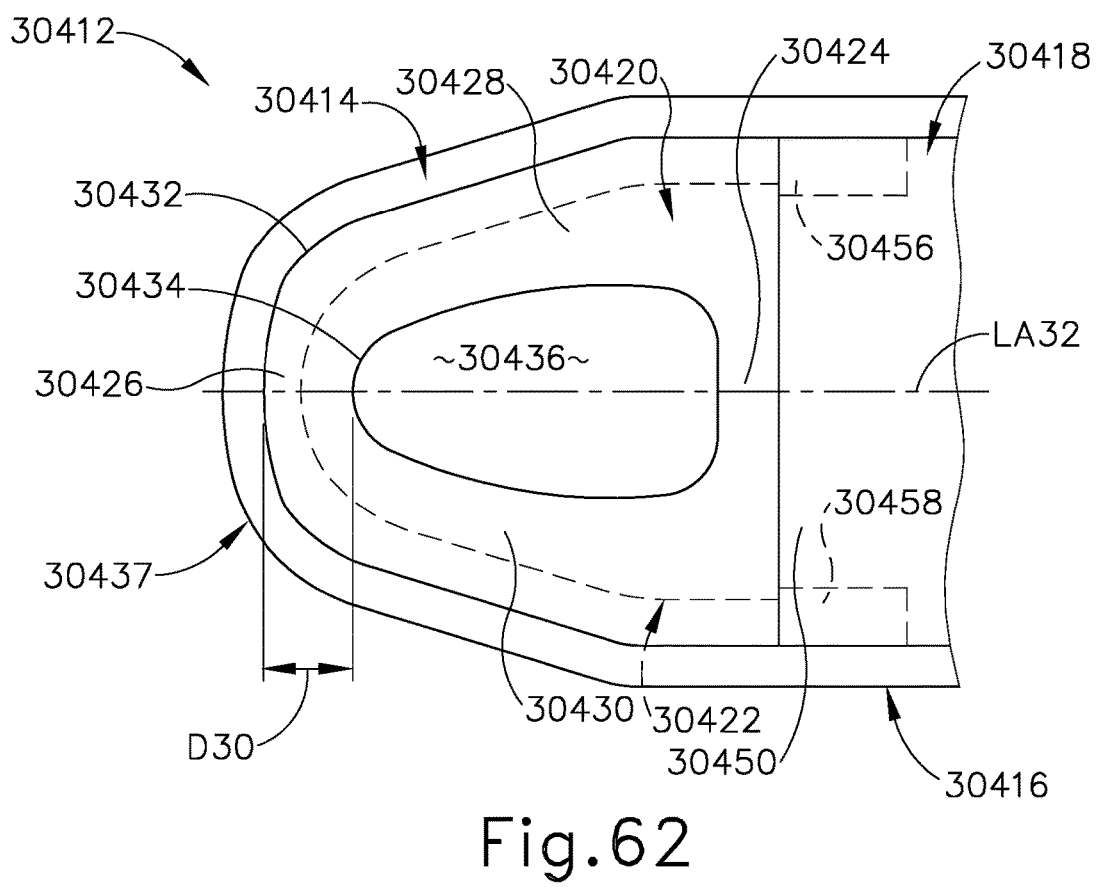
FIG. 62 depicts an enlarged top view of the placement tip of FIG. 61.
Figure 63B:
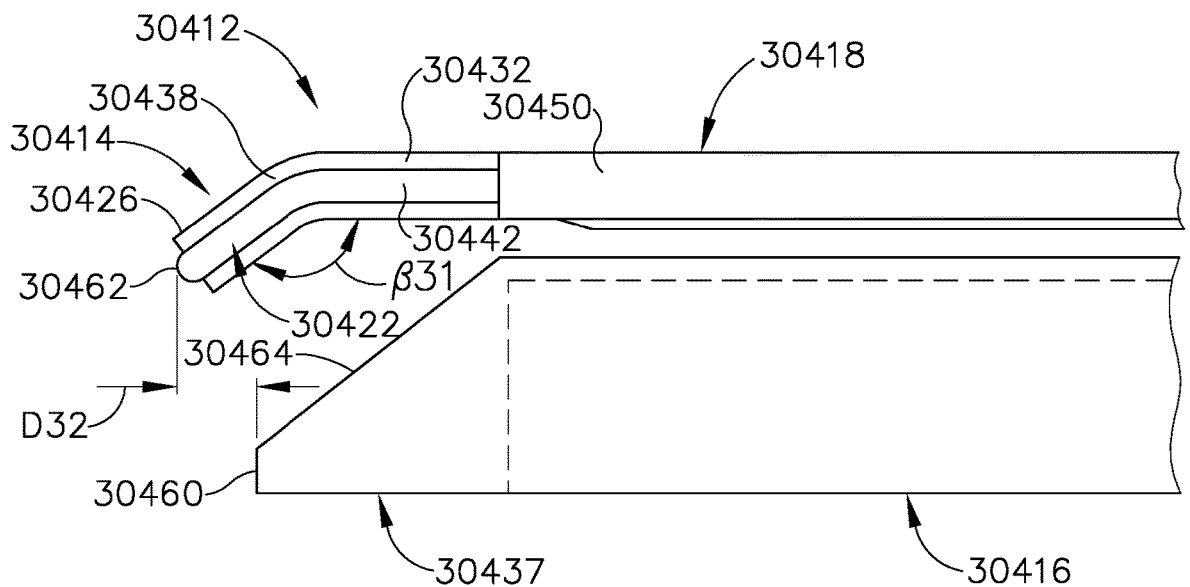
FIG. 63B depicts a side view of the placement tip of FIG. 61 in a second bent configuration.
Figure 64:
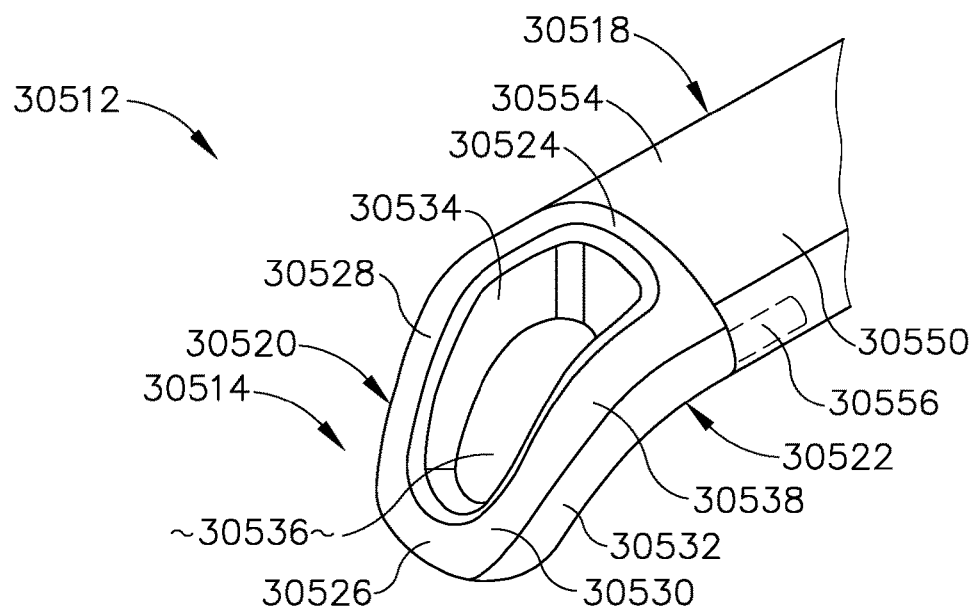
FIG. 64 depicts a perspective view of another exemplary placement tip with a malleable member embedded within the placement tip.

Additionally, as shown in FIGS. 59-62, and more clearly in the top views of FIGS. 61-62, each of body portion (30420) and central void (30436) have a generally oval shape when viewed from the top. In the example shown, central void (30436) is egg-shaped and is wider adjacent proximal portion (30424) than adjacent distal portion (30426). Additionally, central void (30436) formed by inner perimeter (30434) forms a full oval (i.e. a 360-degree oval). Body portion (30420) is oval shaped and forms about half oval (i.e. a 180-degree oval). As shown in FIG. 62, the distance (D30) between outer perimeter (30432) and inner perimeter (30434) is generally uniform. Placement tip (30414) includes a bend (30438) disposed along longitudinal axis (LA32) producing a bent oval placement tip shape at least in the first angled state shown in FIGS. 59-60 and 63A-63B. As shown in FIGS. 63A-63B, bend (30438) directs placement tip (30414) toward staple cartridge (30437) of lower jaw (30416).

Figure 59:
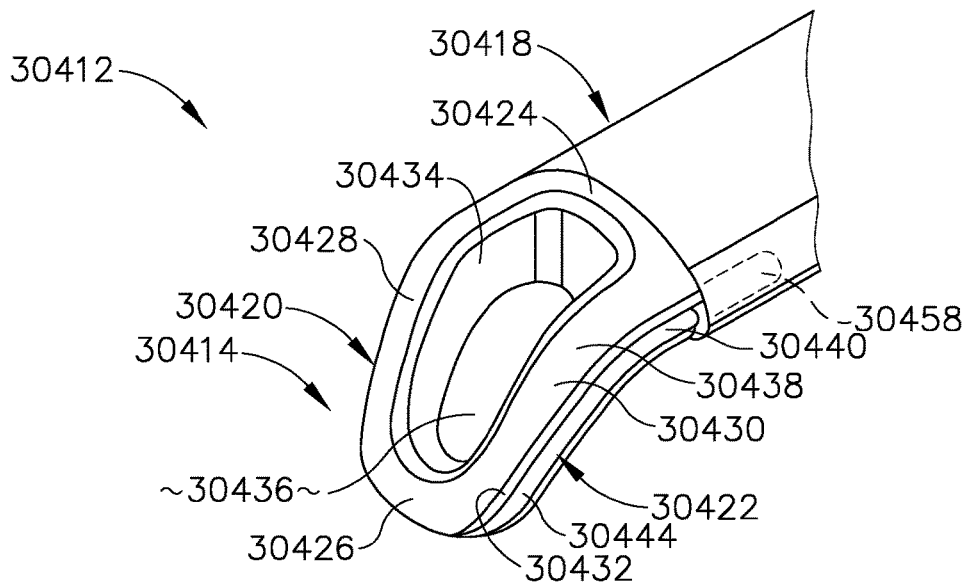
FIG. 59 depicts a perspective view of an anvil and another exemplary placement tip with a malleable member.
Figure 60:
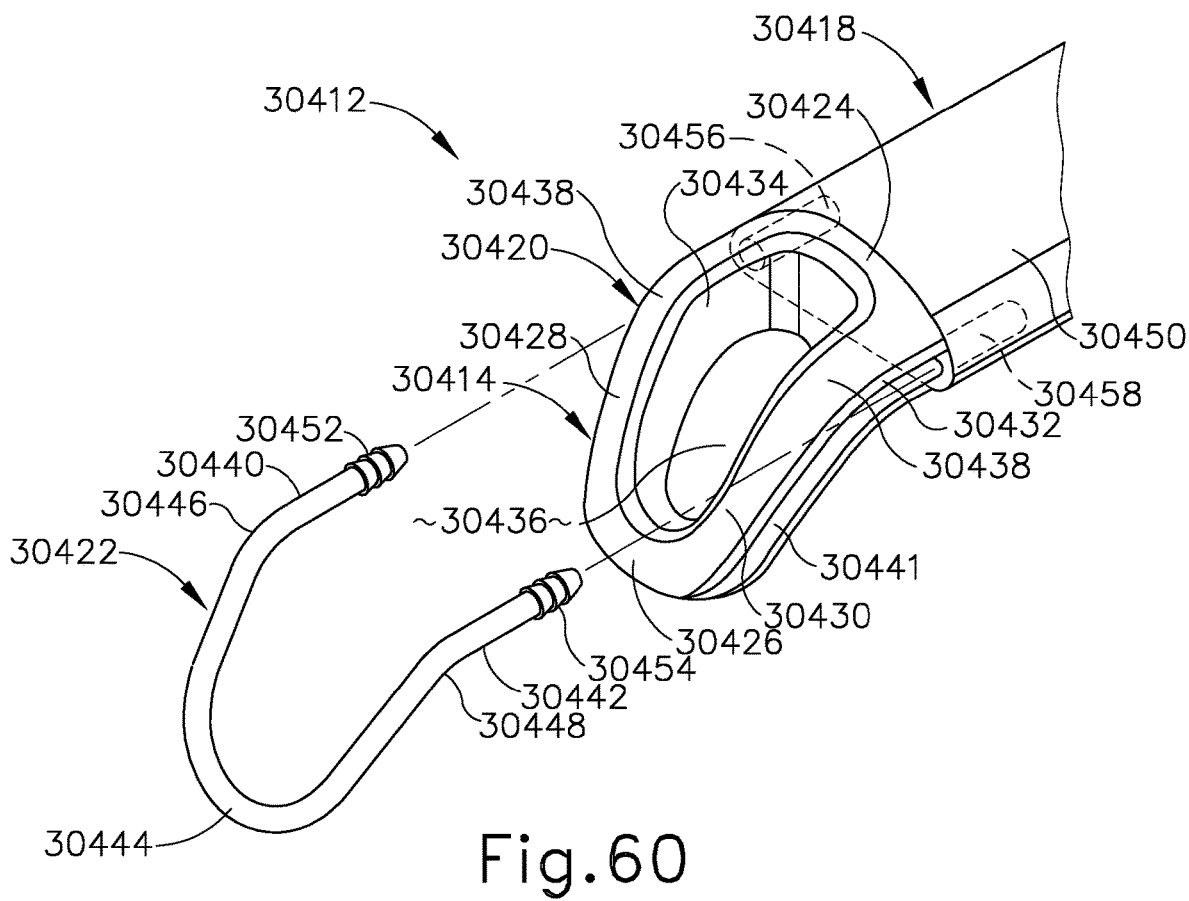
FIG. 60 depicts an exploded perspective view of the anvil and the placement tip of FIG. 59, but with the malleable member separated from the placement tip.

As shown in FIGS. 59-60, malleable member (30422) fits in a generally U-shaped channel (30440) disposed in outer perimeter (30432) of body portion (30420). Channel (30440) may take the form of a variety of shapes and sizes and may even be entirely omitted. As shown in FIG. 60, malleable member (30422) includes first and second legs (30440, 30442) and generally U-shaped portion (30446) configured to contact outer perimeter (30432) of body portion (30420). Malleable member (30422) also includes first and second bent portions (30446, 30448). Malleable member (30422) allows for ad hoc customization of the bend angle.

As previously described, malleable member (30422) may be removably coupled with at least one of placement tip (30414) or the jaw that includes placement tip (30414), which is shown as such as anvil (30418). Alternatively, while not shown, if placement tip (30414) is desired to be coupled with lower jaw (30416), malleable member (30422) may be removably coupled with at least one of placement tip (30414) or lower jaw (30416). Distal end (30450) of anvil (30418) includes at least one coupling feature that is configured to mate with at least one coupling feature of malleable member (30422). As shown, the coupling features of malleable member (30422) include first and second barbed fittings (30452, 30454). The coupling features disposed at distal end (30450) of anvil (30418) are configured to be in locking engagement with first and second corresponding receptacles (30456, 30458) configured to securably couple with first and second barbed fittings (30452, 30454). For this reason, the interior of first and second receptacles (30456, 30458) may include a non-smooth surface.

As shown in FIGS. 63A-63B, malleable member (30422) is configured to increase the rigidity of placement tip (30414) and allow an operator to customize the shape of placement tip (30414) by producing different angles of placement tip (30414). For example, FIG. 63A may refer to a pre-customized standard angle alpha (α31), while FIG. 63B may refer to a post-customized angle beta (β31). As shown, angle alpha (α32) is less than angle beta (β32). As shown in the pre-customized configuration of FIG. 63A, a distal end (30460) of cartridge (30437) extends a first distance (D31) beyond distal portion (30426) of placement tip (30414). Angled surface (30464) of cartridge (30437) is in contact with a distal portion (30426) of placement tip (30414). However, in the post-customized configuration of FIG. 63B, distal portion (30426) of placement tip (30414) extends a second distance (D32) beyond distal end (30460) of cartridge (30437). Distal tip (30462) of malleable member (30422) may extend beyond distal portion (30426) of body portion (30420). Additionally, it is envisioned that the operator may use different malleable members (30422) having various different stiffnesses to obtain the desired amount of rigidity of placement tip (30414).

3. Another Exemplary Surgical Instrument Having Another Exemplary End Effector and Another Example of a Placement Tip FIGS. 64-66B show another exemplary end effector (30512) that comprises an upper jaw, a lower jaw (30516), a staple cartridge (30537) (like staple cartridge (37)), and another exemplary placement tip (30514). As shown, the upper jaw includes anvil (30518). Lower jaw (30516) is like lower jaw (16). Staple cartridge (30537) is removably coupled with lower jaw (30516) in a similar manner and function as lower jaw (16) and staple cartridge (37) described above. Staple cartridge (30537) is configured to hold one or more staples. At least one of anvil (30518) or lower jaw (30516) is movable relative to other of anvil (30518) or lower jaw (30516) between an open configuration (shown in FIG. 54 with respect to end effector (30312)) and a closed configuration shown in FIGS. 66A-66B. Anvil (30518) pivotably rotates toward lower jaw (30516) in a similar manner as anvil (18) as described above with respect to instrument (10). End effector (30512) is thus like effector (12), but with anvil (30518) comprising placement tip (30514) that is elastically deformable. While not shown, placement tip (30514) may be located adjacent one or both of a distal end (30550) of the anvil (30518) or a distal end of lower jaw (30516).

Figure 65:
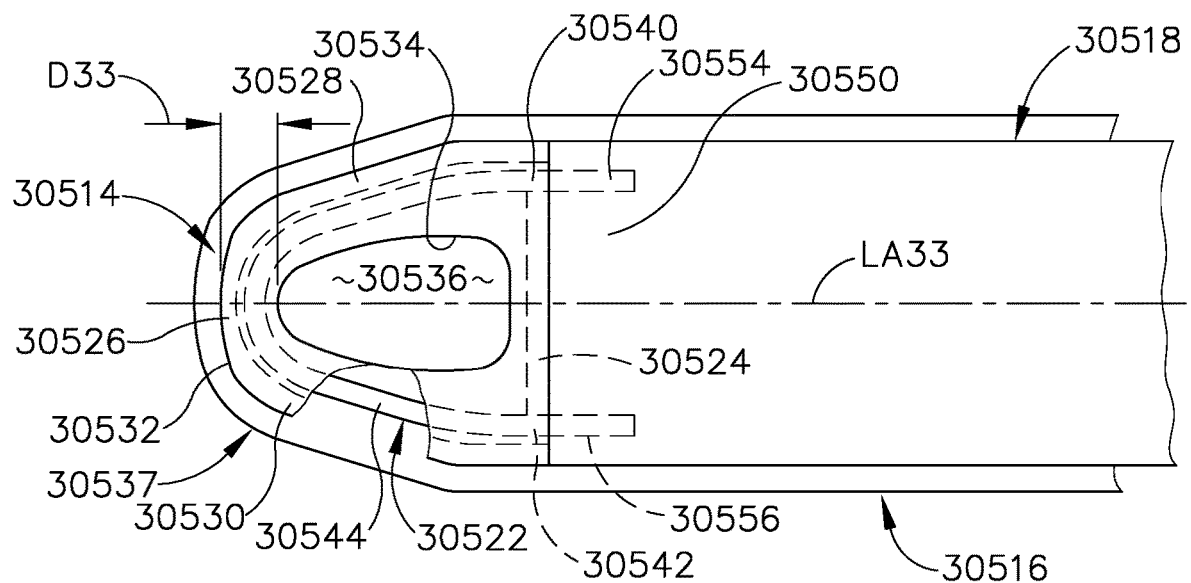
FIG. 65 depicts a top view another exemplary end effector that includes a lower jaw as well as the anvil and the placement tip of FIG. 64.

As shown in 64-66B, placement tip (30514) includes a body portion (30520) and a malleable member (30522). Placement tip (30514) is like placement tip (30414) described above, but malleable member (30522) is permanently coupled with body portion (30520). Body portion (30520) includes proximal and distal portions (30524, 526) separated by first and second legs (30528, 30530). Body portion (30520) is formed between an outer perimeter (30532) and an inner perimeter (30534) of placement tip (30514). Inner perimeter (30534) is defined by a central void (30536) extending through placement tip (30512). At least a portion of distal portion (30526) of body portion (30520) is bent toward the opposing jaw, shown as lower jaw (30516). As shown in FIG. 65, the distance between inner perimeter (30534) and outer perimeter (30532) is generally uniform.

As shown in the top view of FIG. 65, each of body portion (30520) and central void (30536) have a generally oval shape when viewed from the top. Central void (30536) is egg shaped and is wider adjacent proximal portion (30524) than adjacent distal portion (30526). Additionally, central void (30536), which is formed by inner perimeter (30534), forms a full oval (i.e. a 360-degree oval). Body portion (30520) is oval shaped and forms about half oval (i.e. a 180-degree oval). Like FIG. 62 regarding distance (D33), the distance between outer perimeter (30532) and inner perimeter (30534) is generally uniform. Placement tip (30514) includes a bend (30538) disposed along a longitudinal axis (LA33) producing a bent oval shape for placement tip (30514). As shown, placement tip (30514) is generally formed from a rigid material. As shown in FIG. 65, placement tip (30514) is symmetric about longitudinal axis (LA33). Alternatively, placement tip may be non-symmetric if desired. As shown in FIGS. 63A-63B, lower jaw (30516) is thicker than anvil (30518) that includes placement tip (30514). Additionally, as shown in FIG. 65, lower jaw (30516) is longer and wider than anvil (30518) and placement tip (30514).

In the present example, body portion (30520) of placement tip (30514) is integrally formed together with malleable member (30522). As shown in FIG. 60, malleable member (30522) includes first and second legs (30540, 30542) and a generally U-shaped portion (30544) disposed within body portion (30520). Malleable member (30522) also includes a bent portion (30548) shown in FIG. 66B. Malleable member (30522) allows for ad hoc customization of the bend angle. As previously described, placement tip (30514) may be removably coupled with or integrally formed with the anvil (30518). As shown, distal end (30552) of anvil (30518) includes first and second coupling features (30554, 30556) that are configured to mate with first and second legs (30540, 542) of malleable member (30522).

In the present example, malleable member (30522) is comprised of a malleable metal. Body portion (30520) may be comprised of various metals, plastic, ceramic, combinations of metal with plastic or ceramic, and other suitable materials or combinations of materials that will be apparent to those of ordinary skill in the art in view of the teachings herein. Additionally, body portion (30520) in some versions is entirely rigid, yet in other versions body portion (30520) may be resilient to a lesser extent than malleable member (30522). During the molding process, material flows through and fills mold surrounding malleable member (30522). In this manner, malleable member (30522) is securely connected with body portion (30520) during the overmolding process. Alternatively, if less rigidity is desired, body portion (30520), may comprise rubber, plastic, or any other suitable natural or synthetic material having the desired elastomeric properties.

Figure 66A:
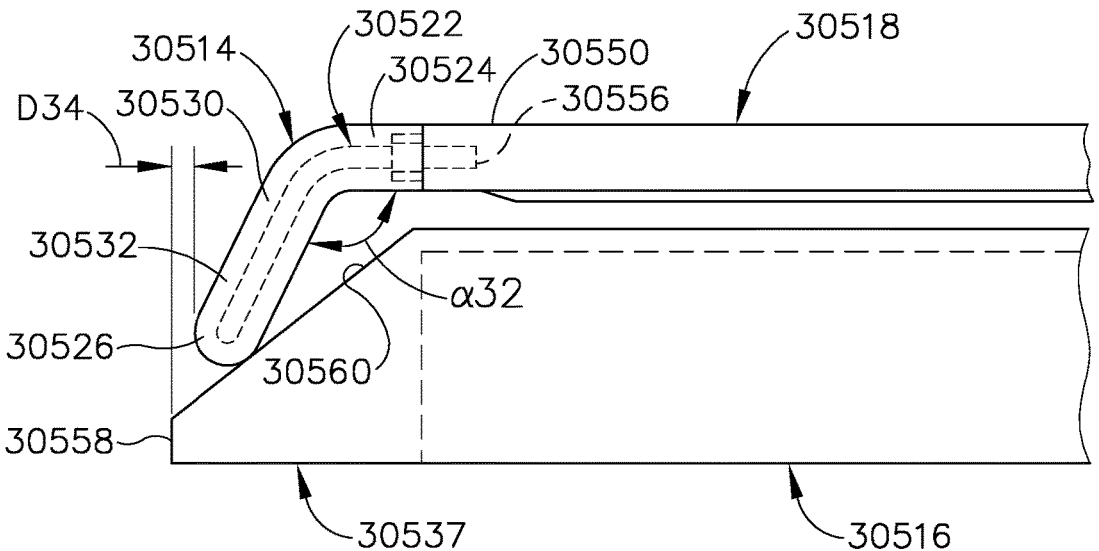
FIG. 66A depicts a side view of the end effector of FIG. 65 in a first bent configuration.
Figure 66B:
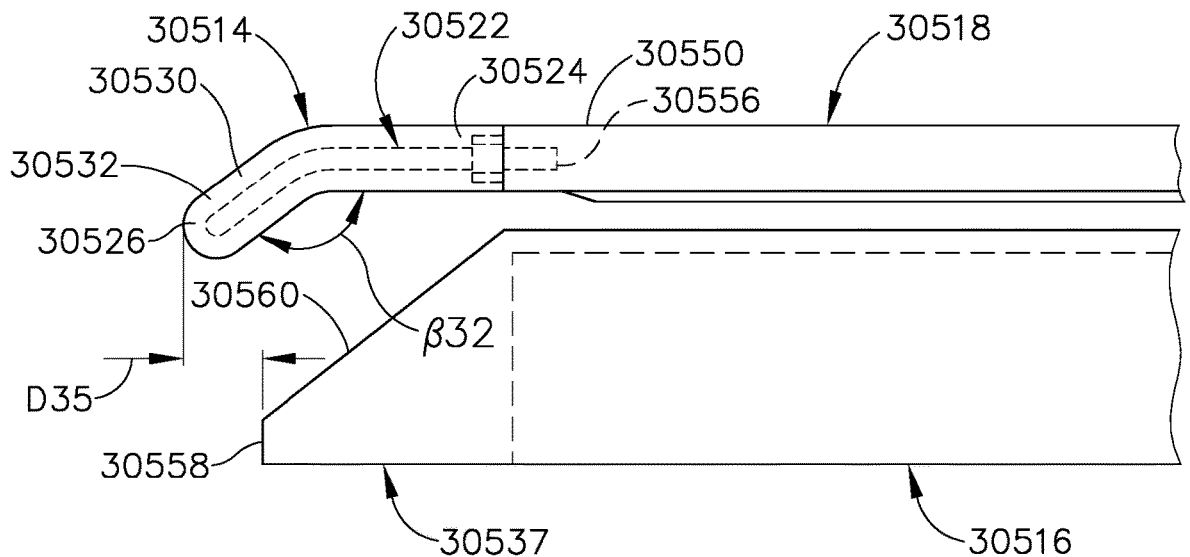
FIG. 66B depicts a side view of the end effector of FIG. 65 in a second bent configuration.

As shown in FIGS. 66A-66B, malleable member (30522) is configured to increase the rigidity of placement tip (30514) and allow an operator to customize the shape of placement tip (30514) by producing different angles of placement tip (30414). For example, FIG. 66A may refer to a pre-customized standard angle alpha (α32), while FIG. 66B may refer to a post-customized angle beta (β32). As shown, angle alpha (α32), is less than angle beta (β32). As shown in FIG. 66A in the pre-customized configuration, a distal end (30558) of cartridge (30537) extends a third distance (D34) beyond distal portion (30526) of placement tip (30514). Angled surface (30560) of cartridge (30537) is in contact with a distal portion (30526) of placement tip (30514). However, as shown in FIG. 66B in the post-customized configuration, distal portion (30526) of placement tip (30514) extends a fourth distance (D35) beyond distal end (30558) of cartridge (30537).

VIII. SURGICAL STAPLING END EFFECTOR COMPONENT WITH DEFORMABLE TIP SKEWING IN MULTIPLE PLANES

A. Another Exemplary Surgical Instrument Including End Effector with Placement Tip FIGS. 67-81 show another exemplary instrument (40310) with exemplary end effectors (40312, 40412, 40512) and exemplary placement tips (40314, 40414, 40514). Instrument (40310) may have a modular configuration such that shaft (40322) is selectively removable from, and selectively attachable to, handle portion (40320). Instrument (40310) is configured similarly to instrument (10), such that the operability and use of instrument (40310) is the same as described above for instrument (10) with the added feature of instrument (40310) having a modular configuration. With its modular configuration, instrument (40310) provides a way to change the desired end effector. Features operable for providing the modular configuration of instrument (40310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (40322) is not detachable from handle portion (40320).

As will be discussed in greater detail below, end effectors (40312, 40412, 40512) are provided on shaft (40322) that is detachable from handle portion (40320). End effectors (40312, 40412, 40512) are operable to compress, staple, and cut tissue. End effectors (40312, 40412, 40512) may be used in place of end effector (12) shown in FIG. 1. In some versions, end effectors (40312, 40412, 40512) may be integrally formed with shaft (40322) or, alternatively, may be separately formed and subsequently combined. In some versions, end effectors (40312, 40412, 40512) may be provided for use in robotic systems. In such robotic systems, modular shaft (40322) having any of the following end effectors (40312, 40412, 40512) may be attachable to a portion of the robotic system for use such that handle portion (40320) is replaced by components of the robotic system, including a body. Other ways to incorporate end effectors (40312, 40412, 40512) having any of the following placement tips (40314, 40414, 40514) into a user operated or robotic operated instrument will be apparent to those of ordinary skill in the art.

Figure 67:
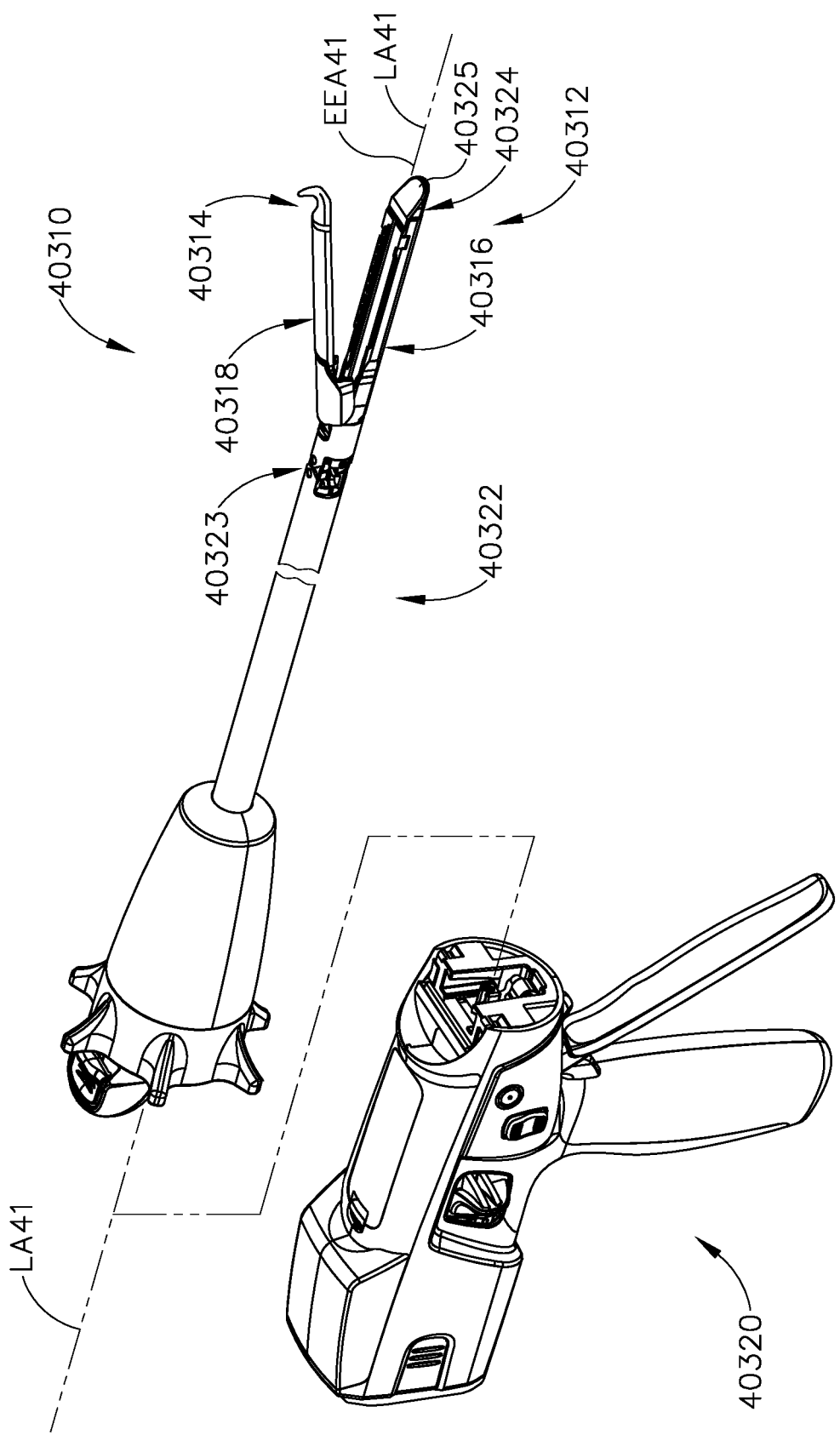
FIG. 67 depicts a perspective view of another exemplary surgical stapling instrument with another exemplary end effector with another exemplary placement tip, where the upper and lower jaws are in an open configuration.

Placement tips (40314, 40414, 40514) are operable to elastically deform from a non-deflected position to a deflected position. Placement tips (40314, 40414, 40514) obtain the non-deflected position when end effectors (40312, 40412, 40512) are not clamping tissue. More specifically, in this non-deflected position, end effectors (40312, 40412, 40512) may be in the open configuration as shown in FIG. 67, or in the closed configuration as shown in FIGS. 8 and 9 with respect to end effector (212). In instances when end effectors (40312, 40412, 40512) are in this non-deflected position, end effectors (40312, 40412, 40512) may be considered in a non-loaded state or non-loaded position. Conversely, in the deflected position (not shown) when end effectors (40312, 40412, 40512) are clamping tissue, end effectors (40312, 40412, 40512) may be considered in a loaded state or a loaded position. In the deflected position, at least a portion of placement tips (40314, 40414, 40514) deflect upwardly. The deflected position for placement tips (40314, 40414, 40514) may be substantially straight in some versions, but may be deflected to a degree (e.g., slightly above or slightly below end effector axis (EEA41, EEA42, EEA43)) in other versions. It should be understood that the deflected position for placement tips (40314, 40414, 40514)

may be defined by the characteristics (e.g., thickness, density, etc.) of the tissue that is being captured between respective lower jaws (40316, 40416, 40516) and anvils (40318, 40418, 40518), thereby causing the deflection of placement tips (40314, 40414, 40514). In some variations, placement tips (40314, 40414, 40514) do not deflect in response to a load.

The placement tips (40314, 40414, 40514) described below may be used with any surgical instrument (10, 40310) described above and below and in any of the various procedures described in the various patent references cited herein. As will be described in greater detailed below, placement tips (40314, 40414, 40514) may be used singularly or in combination with other placement tips, such as placement tips (40314, 40414, 40514). To this end, like numbers below indicate like features described above. Except as otherwise described below, instrument (40310) described below may be constructed and operable like instrument (10) described above. Certain details of instrument (40310) will therefore be omitted from the following description, it being understood that such details are already provided above in the description of instrument (10). Other suitable ways in which various surgical instruments may be used will be apparent to those of ordinary skill in the art in view of the teachings herein.

1. Another Exemplary Surgical Instrument Including Another End Effector with Another Example of a Placement Tip FIGS. 67-70 show surgical instrument (40310), configured as a surgical stapler, that comprises another exemplary end effector (40312) and another exemplary placement tip (40314). End effector (40312) includes an upper jaw and a lower jaw (40316), with the upper jaw including an anvil (40318). Instrument (40310) additionally includes a body, shown as a handle portion (40320), and a shaft (40322) that extends from handle portion (40320). As shown in FIG. 67, shaft (40322) defines a longitudinal axis (LA41) that is colinear with an end effector axis (EEA41) of end effector (40312), but which may non-colinear, and instead angled, when end effector (40312) is articulated relative to shaft (40322) using articulation joint (40323).

Figure 68:
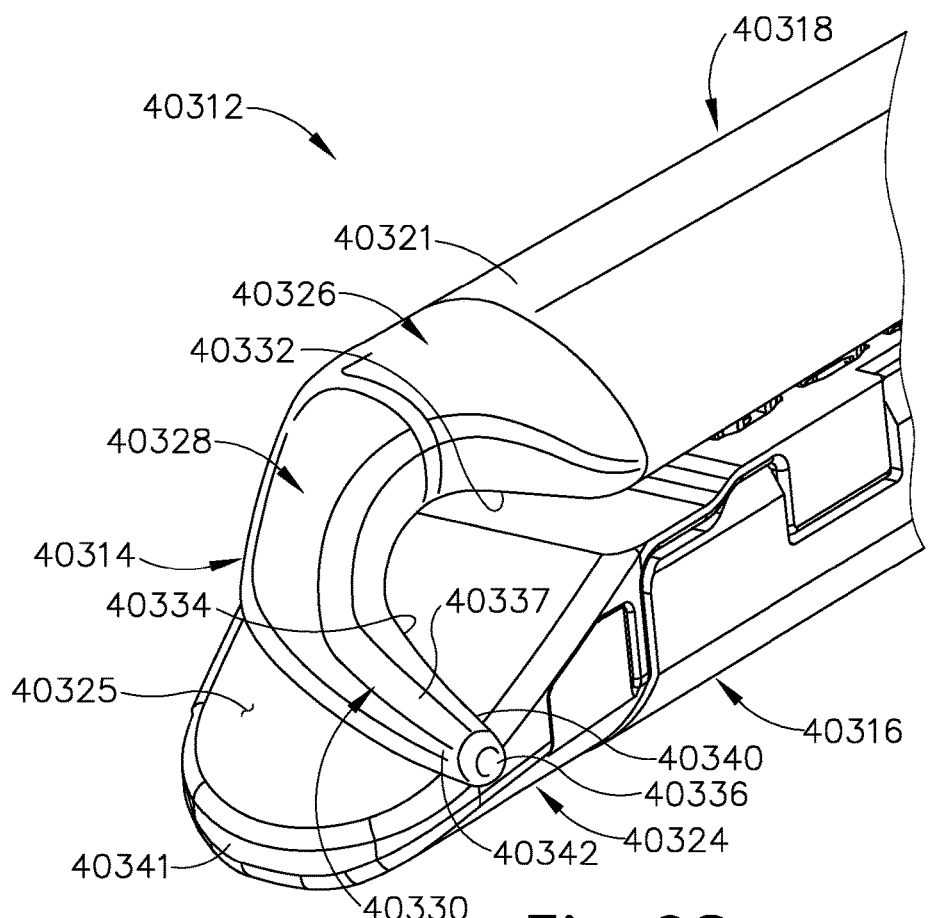
FIG. 68 depicts an enlarged perspective view of a distal portion of the end effector of FIG. 67, with the upper and lower jaws in a closed configuration.
Figure 69:
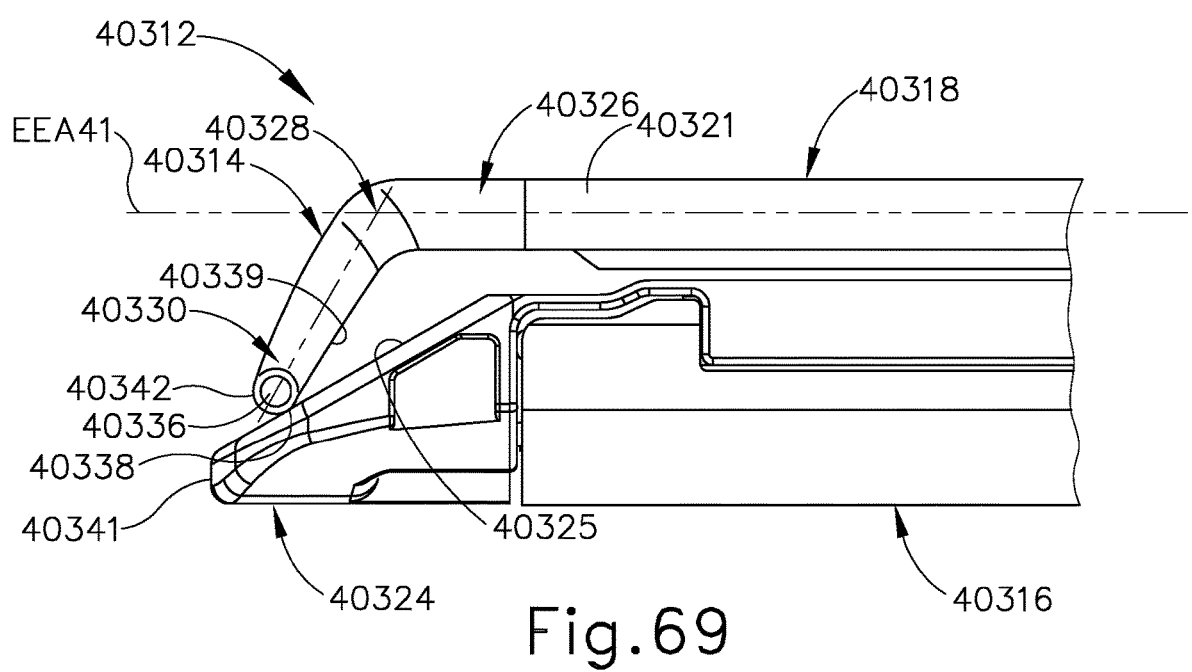
FIG. 69 depicts a side view of the distal portion of the end effector of FIG. 67 in the closed configuration.
Figure 70:
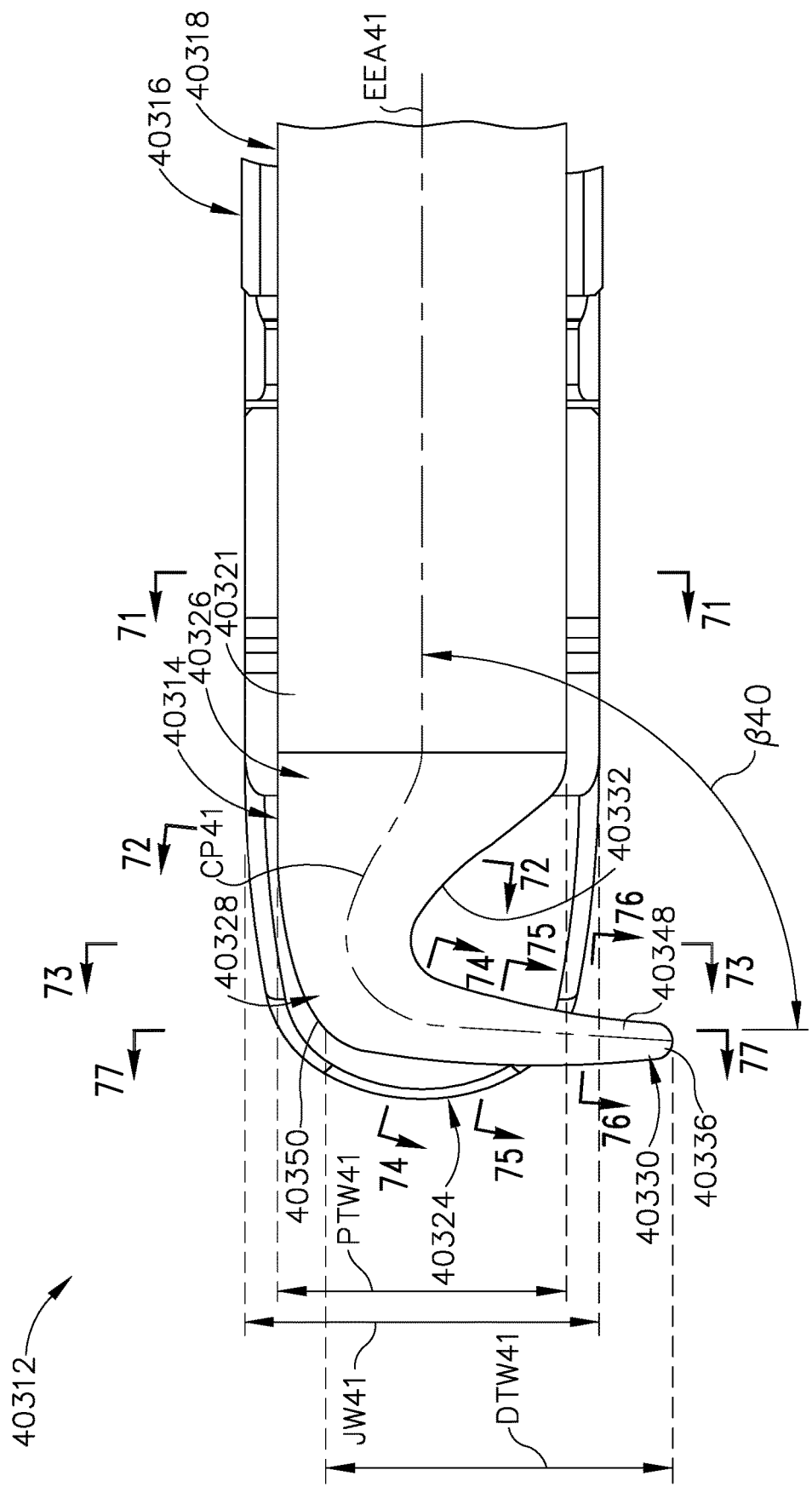
FIG. 70 depicts a top view of the end distal portion of the effector of FIG. 67.

FIGS. 68-70 show enlarged views of a distal end of end effector (40312). Placement tip (40314) is located adjacent at least one of a distal end (40321) of anvil (40318) or a distal end of lower jaw (40316). As shown in FIGS. 67-70, placement tip (40314) is coupled with distal end (40321) of anvil (40318). Placement tip (40314) may be permanently coupled with anvil (40318), or alternatively, placement tip (40314) may be removably coupled with anvil (40318). Placement tip (40314) may be integrally formed together with anvil (40318) as unitary piece or consist of separately formed components. Placement tip (40314) may be positioned on the same jaw as staple cartridge (40324) or on the same jaw as anvil (40318). As shown in FIG. 67, upper jaw includes anvil (40318), while lower jaw (40316) is removably coupled with staple cartridge (40324). However, this relationship may be reversed if desired. Staple cartridge (40324) is configured to hold one or more staples in a manner similar to staple cartridge (37). As previously described, at least one of anvil (40318) or lower jaw (40316) is movable relative to other of anvil (40318) or lower jaw (40316) between the open configuration and the closed configuration. As shown, anvil (40318) pivotably rotates toward lower jaw (40316) in the same manner as anvil (18) as described above with respect to instrument (10). In this manner, end effector (40312) is like end effector (12), except for the laterally deflected configuration and deformability of placement tip (40314).

FIGS. 68-69 show placement tip (40314) as including a proximal portion (40326), a central portion (40328), and a distal portion (40330). Proximal portion (40326) extends distally from distal end (40321) of anvil (40318) and is disposed opposite from lower jaw (40316). Central portion (40328) is disposed longitudinally between proximal and distal portions (40326, 40330). Central portion (40328) and distal portion (40330) of placement tip (40314) each include an asymmetric profile along longitudinal axis of end effector (40312), i.e. end effector axis (EEA41). FIGS. 68 and 70 show central portion (40328) tapering inwardly along an inwardly tapering portion (40332) on the left side (when viewed from above), then tapering outwardly along an outwardly tapering portion (40334). The radius of curvature of the inwardly and outwardly tapering portions (40332, 40334) may be constant or changing. Additionally, as shown in FIG. 68, the opposite right side (when viewed from above) extends arcuately toward distal portion (40330). As shown, placement tip (40314) terminates at a tip end (40336). Placement tip (40314) is thus generally C-shaped in this example. As shown in FIG. 69, in the closed configuration, a contacting portion (40338) of distal portion (40330) is in abutting contact with a distal angled surface (40325) of staple cartridge (40324). Alternatively, a gap may exist between placement tip (40314) and distal angled surface (40325) of staple cartridge (40324). Also, an underside surface (40339) of placement tip (40314) is disposed at an angle relative to distal angled surface (40325) of staple cartridge (40324). In other words, underside surface (40339) is not parallel to distal angled surface (40325); but may be parallel if desired.

Placement tip (40314) generally follows a curvilinear path (CP41) along proximal, central, and distal portions (40326, 40328, 40330) toward tip end (40336). FIG. 70 and the cross-sections of FIGS. 71-76 show successive perimeters of anvil (40318) or placement tip (40314) taken perpendicular to curvilinear path (CP41). More specifically, FIG. 71 shows a cross-section of anvil (40318), while FIGS. 72-76 show cross-sections of placement tip (40314) taken at various locations along proximal, central, and distal portions (40326, 40328, 40330). The perimeters of the successive cross-sections of FIGS. 71-76 decrease moving along curvilinear path (CP41) toward tip end (40336). For example, the perimeter of the cross-section shown in FIG. 71 is greater than the perimeter of the cross-section shown in FIG. 72, which is greater than the perimeter of the cross-section shown in FIG. 73, which is greater than the perimeter of the cross-section shown in FIG. 74. Likewise, the perimeter of the cross-section shown in FIG. 74 is greater than the perimeter of the cross-section shown in FIG. 75, which is greater than the perimeter of the cross-section shown in FIG. 76.

Regarding the lateral widths shown in FIG. 70, distal portion (40330) of placement tip (40314) has a lateral width that is greater than the lateral width of the opposing jaw, shown as lower jaw (40316). As used herein, the lateral width is measured perpendicular to end effector axis (EEA41). More specifically, as shown in FIG. 70, proximal portion (40326) has a proximal tip width (PTW41) that is less than a jaw width (JW41) of lower jaw (40316) disposed opposite placement tip (40314). For example, proximal tip width (PTW41) may be measured where placement tip (40314) couples with distal end (40321) of anvil (40318). As shown in FIGS. 70-71, proximal tip width (PTW41) has the same lateral width as anvil (40318). Central portion (40328) has a lateral width that is less than the lateral width of proximal portion (40326).

Distal portion (40330) has a distal tip width (DTW41) depicted in the cross-section of FIG. 77 that is greater than jaw width (JW41) of lower jaw (40316) disposed opposite placement tip (40314). Unlike the cross-sections of FIG. 72 and FIGS. 74-76 that are taken perpendicular to curvilinear path (CP41) but are not perpendicular to end effector axis (EEA41), FIG. 77 is taken perpendicular to end effector axis (EEA41), similar to FIGS. 71 and 73. As shown in FIG. 70, distal portion (40330) includes an overhang portion (40348) that extends beyond the opposite jaw only on a single lateral side. However, an angled portion (40350) may extend laterally beyond the width of lower jaw (40316) or the width of staple cartridge (40324), such that placement tip (40314) extends beyond both lateral sides (i.e. left and right sides) of lower jaw (40316) or staple cartridge (40324). Tip end (40336) includes a proximal surface (40340) and a distal surface (40342), with proximal surface (40340) extending adjacent outwardly tapering portion (40334). Additionally, as shown in FIGS. 69 and 70, a distal tip (40341) of staple cartridge (40324) extends distally beyond distal surface (40342) of tip end (40336). In other words, lower jaw (40316) extends distally beyond tip end (40336) of placement tip (40314). However, lower jaw (40316) may be shorter and/or and narrower than anvil (40318) and placement tip (40314) if desired.

Distal portion (40330) includes a tip axis (TA41) defined by the direction that tip end (40336) of distal portion (40330) extends. In the example shown, tip axis (TA41) is measured using proximal surface (40340) of placement tip (40314). Alternatively, other surfaces (e.g. distal surface (40342)) may also be used. As shown in FIG. 70, tip axis (TA41) is generally perpendicular to end effector axis (EEA41) and longitudinal axis (LA41) of shaft (40322). In other words, the angle beta (β40) formed between tip end (40336) and end effector axis (EEA41) is about 90 degrees. However, this non-zero angle may vary. As shown in FIGS. 68 and 70, given the geometry of placement tip (40314), distal portion (40330) of placement tip (40314) is configured to deflect proximally as placement tip (40314) is advanced distally through the trocar of a patient.

Figure 78:
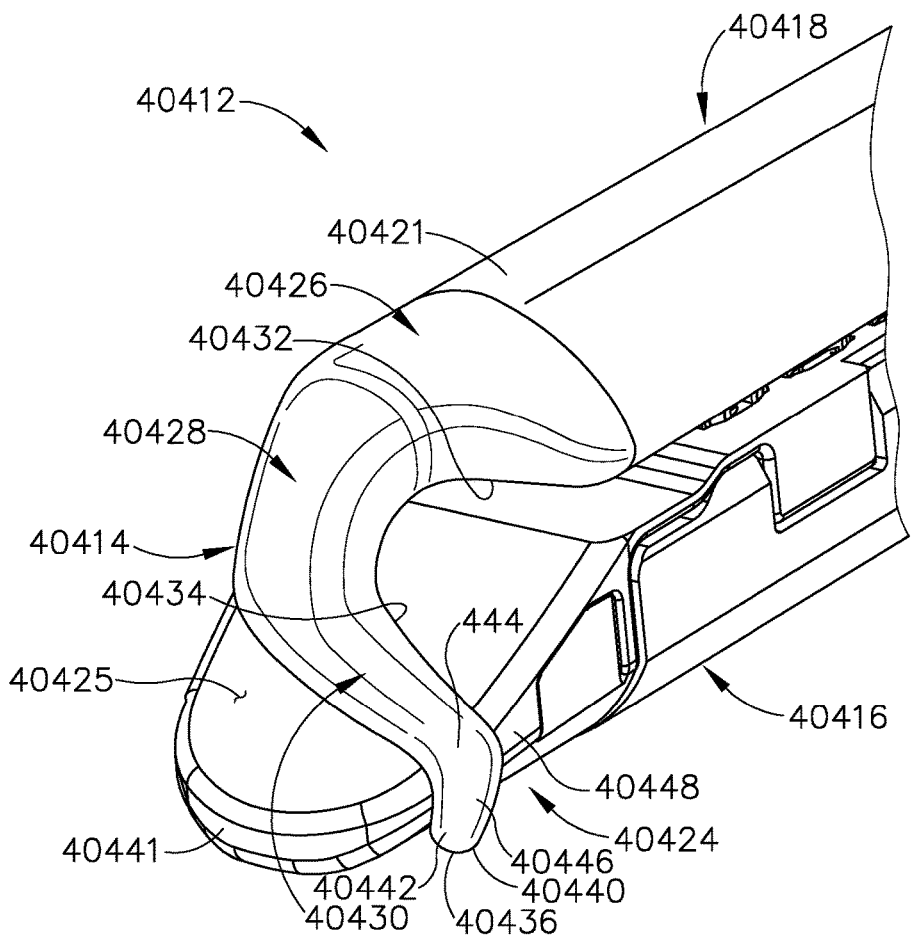
FIG. 78 depicts a perspective view of a distal portion of another exemplary end effector with another exemplary placement tip in a closed configuration.
Figure 79:
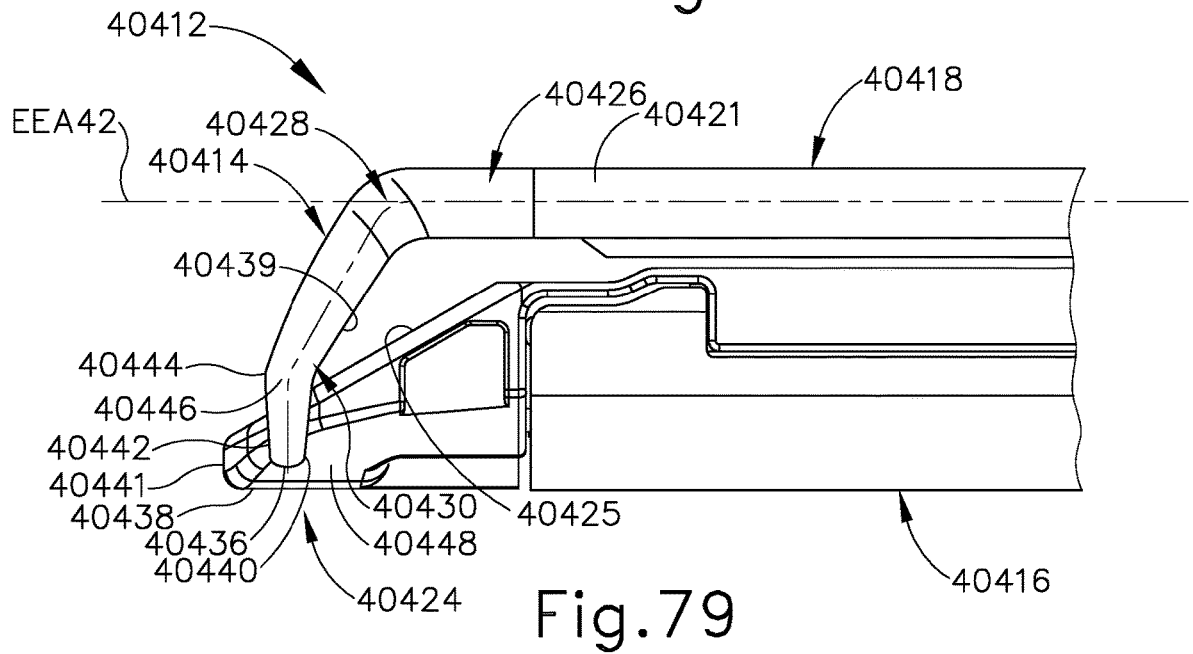
FIG. 79 depicts a side view of the distal portion of the end effector of FIG. 78.
Figure 80:
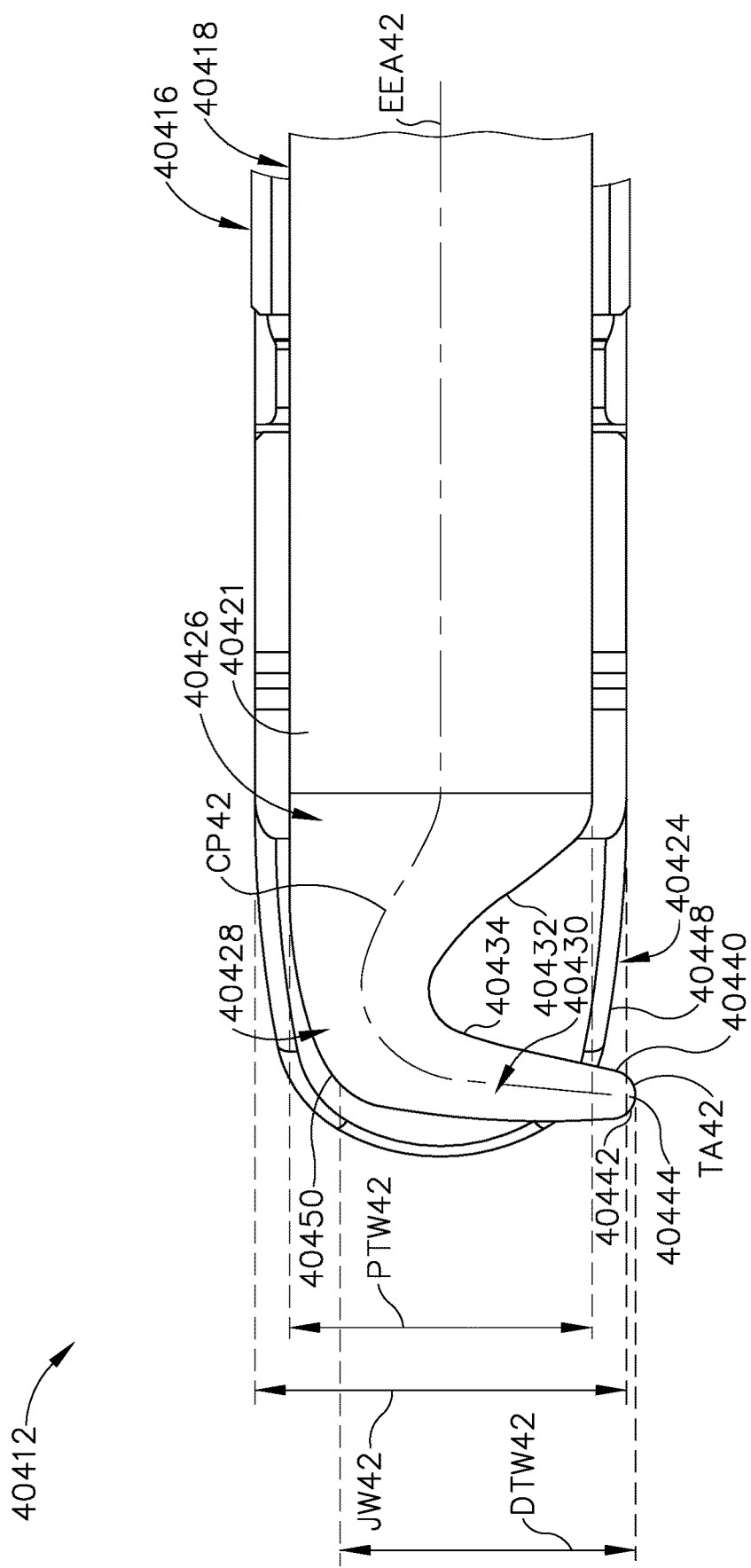
FIG. 80 depicts a top view of the distal portion of the end effector of FIG. 78 in the closed configuration.

2. Another Exemplary Surgical Instrument Including Another End Effector with Another Example of a Placement Tip FIGS. 78-80 show another exemplary end effector (40412) and another exemplary placement tip (40414). End effector (40412) and placement tip (40414) are similar to end effector (40312) and placement tip (40314) described in connection to FIGS. 67-77 with notable differences indicated below. End effector (40412) includes placement tip (40414), a lower jaw (40416), an anvil (40418), a distal end (40421), a staple cartridge (40424), a distal angled surface (40425), a proximal portion (40426), a central portion (40428), a distal portion (40430), an inwardly tapering portion (40432), an outwardly tapering portion (40434), a tip end (40436), an underside surface (40439), a proximal surface (40440), a distal surface (40442), and an angled portion (40450).

As shown in FIG. 78, the upper jaw includes anvil (40418), and lower jaw (40416) is like lower jaw (16, 40316). Staple cartridge (40424) is removably coupled with lower jaw (40416) in a similar manner and function as lower jaws (16, 40316) and staple cartridges (37, 40324) described above. At least one of lower jaw (40416) or anvil (40418) is movable relative to the other of lower jaw (40416) or anvil (40418) between an open configuration (shown in FIG. 67 with respect to end effector (40312)) and a closed configuration (shown in FIGS. 78-79). Anvil (40418) pivotably rotates toward lower jaw (40416) in a similar manner to anvils (18, 40318) as described above with respect to instruments (10, 40310). End effector (40412) is thus like effector (12), but with anvil (40418) comprising placement tip (40414) that is elastically deformable. While not shown, placement tip (40414) may be located adjacent one or both of distal end (40421) of anvil (40418) or a distal end of lower jaw (40416).

FIGS. 78-80 show placement tip (40414) as including proximal, central, and distal portions (40426, 40428, 40430). Proximal portion (40426) extends distally from distal end (40421) of anvil (40418) and is disposed opposite from lower jaw (40416). Central portion (40428) is disposed longitudinally between proximal and distal portions (40426, 430). Central portion (40428) and distal portion (40430) of placement tip (40414) each include an asymmetric profile along an end effector axis (EEA42). As shown in FIGS. 78 and 80, central portion (40428) tapers inwardly along inwardly tapering portion (40432), then tapers outwardly along outwardly tapering portion (40434). The radius of curvature of inwardly and outwardly tapering portions (40432, 40434) may be constant or changing. Additionally, as shown in FIG. 80, the opposite side extends arcuately toward distal portion (40430). Placement tip (40414) terminates at tip end (40436). Similar to placement tip (40314) described relative to FIGS. 70-76, successive perimeters of placement tip (40414) taken perpendicular to curvilinear path (CP2) decrease moving toward tip end (40436).

As shown in FIG. 78, distal portion (40430) extends downwardly at an overhang portion (40444) toward lower jaw (40416) and staple cartridge (40424), in a manner that differs from placement tip (40314). Moreover, as shown in FIG. 79, a projection (40446) of distal portion (40430) extends below distal angled surface (40425) of staple cartridge (40424) and approaches a bottom surface (40438) of staple cartridge (40424). As shown, tip end (40436) extends parallel to and is separated a distance from a tapered side surface (40448) of staple cartridge (40424) in the closed configuration. Alternatively, tip end (40436) may extend parallel to and be in contact with tapered side surface (40448) of staple cartridge (40424) in the closed configuration.

Regarding the lateral widths shown in FIG. 80, distal portion (40430) of placement tip (40414) has a lateral width that is less than the lateral width of the opposing jaw, shown as lower jaw (40416). As used herein, the lateral width is measured perpendicular to end effector axis (EEA42). More specifically, as shown in FIG. 80, proximal portion (40426) has a proximal tip width (PTW42) that is less than a jaw width (JW42) of lower jaw (40416) disposed opposite placement tip (40414). Proximal tip width may be measured where placement tip (40414) couples with distal end (40421) of anvil (40418). Additionally, distal portion (40430) has a distal tip width (DTW42) that is less than jaw width (JW42) of lower jaw (40416) disposed opposite placement tip (40414).

Additionally, distal portion (40430) includes overhang portion (40444) that extends beyond the opposite jaw only on one lateral side. However, an angled portion (40435) may extend laterally beyond the width of lower jaw (40416) or the width of staple cartridge (40424), such that placement tip (40414) extends beyond both lateral sides of lower jaw (40416) or staple cartridge (40424). Central portion (40428) has a lateral width that is less than the lateral width of proximal portion (40426). Additionally, lower jaw (40416) extends distally beyond tip end (40436) of placement tip (40414). More specifically, as shown in FIG. 79, a distal tip (40441) of staple cartridge (40424) extends distally beyond distal surface (40442) of tip end (40436). However, lower jaw (40416) may be shorter and/or and narrower than anvil (40418) and placement tip (40414) if desired.

Figure 81:
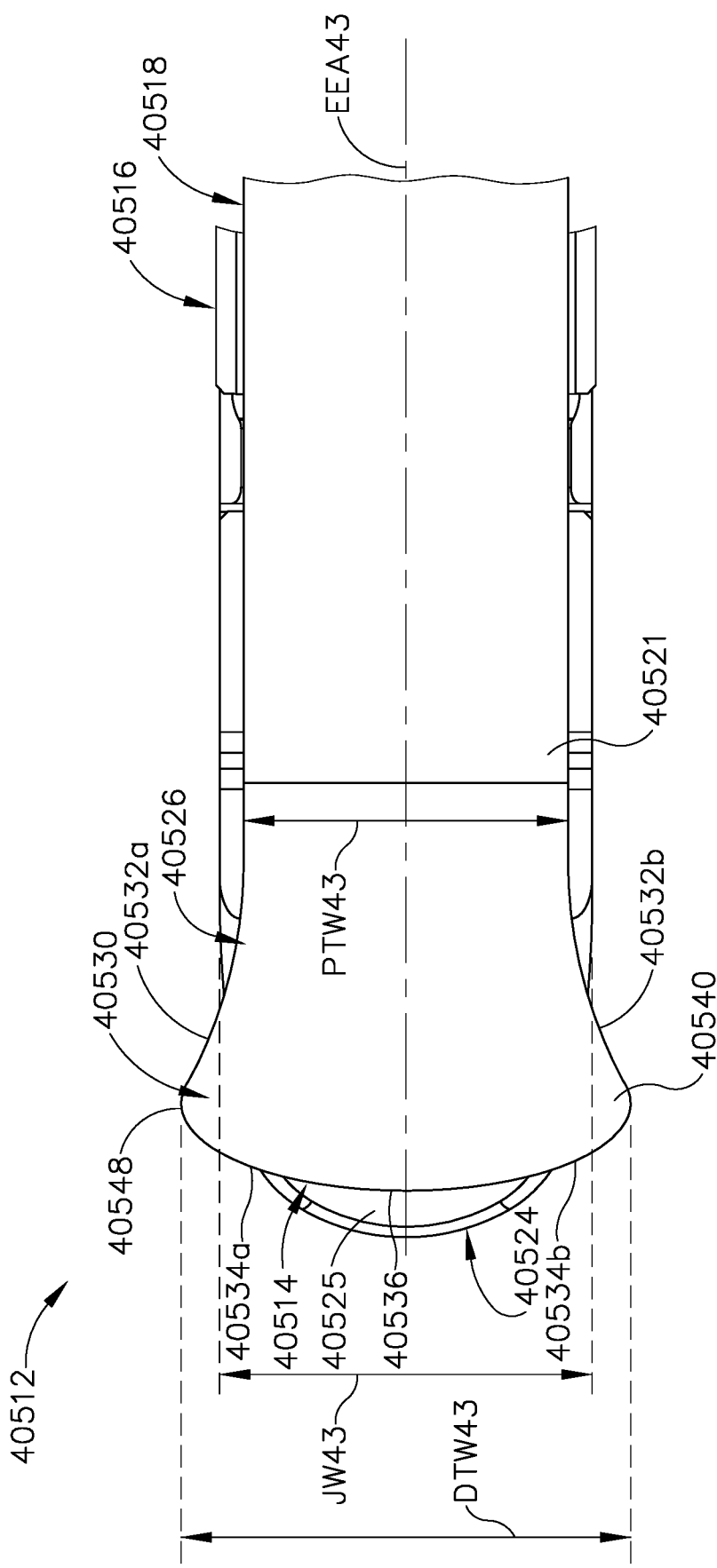
FIG. 81 depicts a perspective view of a distal portion of another exemplary end effector with another exemplary placement tip in a closed configuration.

3. Another Exemplary Surgical Instrument Including Another End Effector with Another Example of a Placement Tip FIG. 81 shows another exemplary end effector (40512) and another exemplary placement tip (40514). End effector (40512) and placement tip (40514) are similar to end effector (40312) and placement tip (40314) described in connection to FIGS. 67-77 with notable differences indicated below. End effector (40512) includes placement tip (40514), a lower jaw (40516), an anvil (40518), a distal end (40521), a staple cartridge (40524), a distal angled surface (40525), a proximal portion (40526), and a distal portion (40530).

As shown in FIG. 81, the upper jaw includes anvil (40518), and lower jaw (40516) is like lower jaws (16, 40316). Staple cartridge (40524) is removably coupled with lower jaw (40516) in a similar manner and function as lower jaws (16, 40316) and staple cartridges (37, 40324) described above. At least one of lower jaw (40516) or anvil (40518) is movable relative to the other of lower jaw (40516) or anvil (40518) between an open configuration (shown in FIG. 67 with respect to end effector (40312)) and a closed configuration (shown generally in FIG. 81). Anvil (40518) pivotably rotates toward lower jaw (40516) in a similar manner to anvils (18, 40318) as described above with respect to instruments (10, 40310). End effector (40512) is thus like effector (12), but with anvil (40518) comprising placement tip (40514) that is elastically deformable. While not shown, placement tip (40514) may be located adjacent one or both of distal end (40521) of anvil (40518) or a distal end of lower jaw (40516).

FIG. 81 shows placement tip (40514) as including proximal and distal portions (40526, 40530) that are each symmetric along an end effector axis (EEA43). Proximal portion (40526) extends distally from distal end (40521) of anvil (40518) and is disposed opposite from lower jaw (40516). Distal portion (40530) tapers outwardly along outwardly tapering portions (40532*a-b*), then tapers inwardly along inwardly tapering portions (40534*a-b*). The radius of curvature of inwardly and outwardly tapering portions (40532*a-b*, 40534*a-b*) may be constant or changing. Placement tip (40514) terminates at a tip end that is along end effector axis (EEA43).

Regarding the lateral widths shown in FIG. 81, distal portion (40530) of placement tip (40514) has a lateral width that is greater than the lateral width of the opposing jaw, shown as lower jaw (40516). As used herein, the lateral width is measured perpendicular to end effector axis (EEA43). More specifically, proximal portion (40526) has a proximal tip width (PTW43) that is less than a jaw width (JW43) of lower jaw (40516) disposed opposite placement tip (40514). Proximal tip width (PTW43) may be measured where placement tip (40514) couples with distal end (40521) of anvil (40518) is shown as the same as an anvil tip width.

Additionally, distal portion (40530) has a distal tip width (DTW43) depicted in the cross-section of FIG. 81 that is greater than jaw width (JW43) of lower jaw (40516) disposed opposite placement tip (40514). Additionally, distal portion (40530) includes first and second overhang portions (40538, 40540) that each extend beyond the lateral width of the opposing jaw on both lateral sides. As shown, placement tip (40514) extends beyond both lateral sides (left and right sides) of both lower jaw (40516) and staple cartridge (40524). First and second overhang portions (40538, 40540) are symmetric about end effector axis (EEA43). As shown, lower jaw (40516) extends distally beyond tip end (40536) of placement tip (40514). However, lower jaw (40516) may be shorter and/or and narrower than anvil (40518) and placement tip (40514) if desired.

IV. SURGICAL STAPLING END EFFECTOR COMPONENT WITH ARTICULATION AND ASYMMETRIC DEFORMABLE TIP

A. Another Exemplary Surgical Instrument Including End Effector with Placement Tip FIGS. 82, 83A-83E, and 84A-84D show another exemplary surgical instrument (50310), configured as a surgical stapler, that comprises another exemplary end effector (50312) and another exemplary placement tip (50314). End effector (50312) includes an upper jaw and a lower jaw (50316), with the upper jaw including an anvil (50318). Instrument (50310) additionally includes a body, shown as a handle portion (50320), and a shaft (50322) that extends from handle portion (50320). As shown in FIGS. 82 and 83A-83E, shaft (50322) defines a longitudinal axis that is commonly referred to below as a shaft axis (SA50). Except as otherwise described below, instrument (50310) described below may be constructed and operable like instrument (10) described above. Certain details of instrument (50310) will therefore be omitted from the following description, it being understood that such details are already provided above in the description of instrument (10).

Instrument (50310) may have a modular configuration such that shaft (50322) is selectively removable from, and selectively attachable to, handle portion (50320). Instrument (50310) is configured similarly to instrument (10), such that the operability and use of instrument (50310) is the same as described above for instrument (10) with the added feature of instrument (50310) having a modular configuration. With its modular configuration, instrument (50310) provides a way to change the desired end effector. In addition to or in lieu of the foregoing, features operable for providing the modular configuration of instrument (50310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (50322) is not detachable from handle portion (50320).

As discussed in greater detail below, end effector (50312) is provided on shaft (50322) and is operable to compress, staple, and cut tissue. End effector (50312) may be used in place of end effector (12) shown in FIG. 1. In some versions, end effector (50312) may be integrally formed with shaft (50322) or, alternatively, may be separately formed and subsequently combined. In some versions, end effector (50312) may be provided for use in robotic systems. In such robotic systems, modular shaft (50322) having end effector (50312) may be attachable to a portion of the robotic system for use such that handle portion (50320) is replaced by components of the robotic system, including a body. Other ways to incorporate an end effector (50312) having placement tip (50314) into a user operated or robotic operated instrument will be apparent to those of ordinary skill in the art.

Placement tip (50314) is operable to elastically deform from a non-deflected position to a deflected position. Placement tip (50314) obtains the non-deflected position when end effector (50312) is not clamping tissue. More specifically, in this non-deflected position, end effector (50312) may be in the open configuration as shown in FIG. 83, or in the closed configuration as shown in FIGS. 8 and 9 with respect to end effector (212). In instances when end effector (50312) is in this non-deflected position, end effector (50312) may be considered in a non-loaded state or non-loaded position. Conversely, in the deflected position (not shown) when end effector (50312) is clamping tissue, end effector (50312) may be considered in a loaded state or a loaded position. In the deflected position, at least a portion of placement tip (50314) deflects upwardly. The deflected position for placement tip (50314) may be substantially straight in some versions, but may be deflected to a degree (e.g., slightly above or slightly below shaft axis (SA50)) in other versions. It should be understood that the deflected position for placement tip (50314) may be defined by the characteristics (e.g., thickness, density, etc.) of the tissue that is being captured between anvil (50318) and lower jaw (50316), thereby causing the deflection of placement tip (50314). In some variations, placement tip (50314) does not deflect in response to a load.

1. Another Exemplary Surgical Instrument Including Another End Effector with Another Example of Placement Tip FIGS. 83A-83E show enlarged views of a distal end of end effector (50312). Placement tip (50314) is located adjacent at least one of distal end (50321) of anvil (50318) or a distal end of lower jaw (50316). As shown in FIGS. 82 and 83A-83E, placement tip (50314) is coupled with a distal end (50321) of anvil (50318). Placement tip (50314) may be permanently secured to anvil (50318), or alternatively, placement tip (50314) may be removable coupled with anvil (50318). Placement tip (50314) may be integrally formed together with anvil (50318) as unitary piece or consist of separately formed components. Placement tip (50314) may be positioned on the same jaw as staple cartridge (50324) or on the same jaw as anvil (50318). As shown in FIGS. 82 and 83A-83E, upper jaw includes anvil (50318), while lower jaw (50316) is removably coupled with staple cartridge (50324). However, this relationship may be reversed if desired. Staple cartridge (50324) is configured to hold one or more staples in a manner similar to staple cartridge (37).

As previously described, at least one of anvil (50318) or lower jaw (50316) is movable relative to other of anvil (50318) or lower jaw (50316) between the open configuration and the closed configuration. As shown, anvil (50318) pivotably rotates toward lower jaw (50316) in the same manner as anvil (18) as described above with respect to instrument (10). In this manner, end effector (50312) is like end effector (12), except for the laterally deflected configuration and deformability of placement tip (50314). In the closed configuration, a portion of placement tip (50314) may in abutting contact with an angled surface (50338) of staple cartridge (50324); or alternatively, a lateral gap may exist between placement tip (50314) and staple cartridge (50324). Additionally, as shown in the top view of FIGS. 83A-83E, lower jaw (50316) is generally longer and wider than anvil (50318) and placement tip (50314). However, lower jaw (50316) may be shorter and/or and narrower than anvil (50318) and placement tip (50314) if desired.

FIGS. 82 and 83A-83E show placement tip (50314) as including a proximal portion (50326), a central portion (50328), and a distal portion (50330). Proximal portion (50326) extends distally from distal end (50321) of anvil (50318) and is disposed opposite from lower jaw (50316). Central portion (50328) is disposed longitudinally between proximal and distal portions (50326, 50330). Central portion (50328) and distal portion (50330) of placement tip (50314) each include an asymmetric profile along the longitudinal axis of shaft (50322), i.e. shaft axis (SA50). As shown in the top views of FIGS. 83A-83E, central portion (50328) tapers inwardly along an inwardly tapering portion (50329) on the left side (when viewed from above), while the opposite right side extends arcuately toward distal portion (50330).

Distal portion (50330) includes a tip axis (TA50) defined by the direction to which a tip (50314) of distal portion (50330) extends. Tip (50314) includes a proximal surface (50340) and a distal surface (50342), with proximal surface (50340) extending outwardly from inwardly tapering portion (50329). In the example shown, tip axis (TA50) is measured using proximal surface (50340) of tip (50314). Alternatively, other surfaces (e.g. distal surface (50342) may also be used. Moreover, shaft axis (SA50) and tip axis (TA50) define an angle that is selectively adjustable. For improved clarity, a modified shaft axis (SA50') is respectively shown in FIGS. 83A-83E to better visualize angle theta ($\theta$51-$\theta$55) generally formed between shaft axis (SA50) and tip axis (TA50). A modified shaft axis (SA50') is offset from and extends parallel to shaft axis (SA50). Additionally, as shown in FIGS. 83A-83E, tip axis (TA50) is generally perpendicular to the longitudinal axis of end effector (50312), which is referred herein as end effector axis (EEA50).

As previously described with respect to instrument (10), instrument (50310) is shown as including an articulation joint (50332) that pivotably couples shaft (50322) with end effector (50312). Articulation joint (50332) may be the same or similar to articulation joint (11) described above, with details pertaining to articulation joint (50332) being omitted for the sake of brevity. Articulation joint (50332) is configured to enable end effector (50312) to pivot laterally relative to shaft (50322). As shown in FIGS. 83A-83E, modified shaft axis (SA50') and tip axis (TA50) collectively define various angle thetas ($\theta$51-$\theta$55), with angle theta being selectively adjustable using articulation joint (50332). Articulation joint (50332) may be selectively adjustable by a user using powered articulation. Alternatively, articulation joint (50332) may be manually powered using articulation control (50344) shown in FIG. 82. Articulation joint (50332) moves end effector axis (EEA50) relative to shaft axis (SA50), resulting in a different angle theta ($\theta$51-$\theta$55).

Figure 83C:
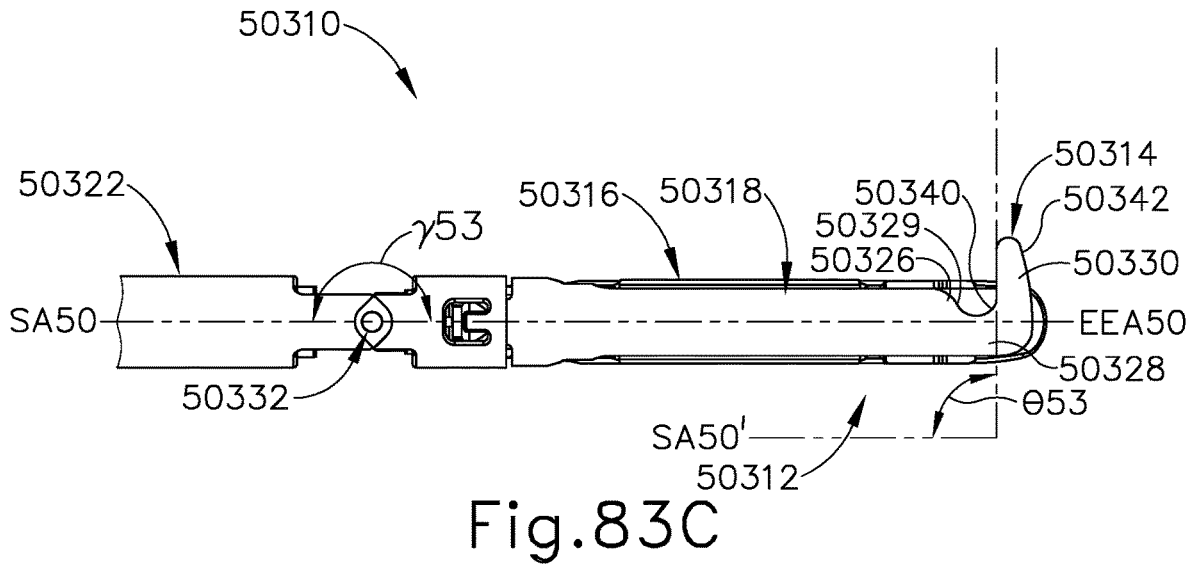
FIG. 83C depicts an enlarged top view of the end effector of FIG. 82 in a third angled position.

As described below in greater detail, FIGS. 83A-83E show various angle thetas ($\theta$51-$\theta$55) that are selectively adjustable between about 0 degrees to about 180 degrees. While FIGS. 83A-83E show angle theta ($\theta$51-$\theta$55) as five distinct angles, it is to be understood that angle theta may be any angle in between about 0 degrees to about 180 degrees as well. For example, FIG. 83A shows angle theta ($\theta$51) defined by modified shaft axis (SA50') and tip axis (TA50) being about 0 degrees, such that shaft axis (SA50) and tip axis (TA50) extend generally parallel to one another. End effector axis (EEA50) extends approximately perpendicular to both shaft axis (SA51) and tip axis (TA50), such that angle gamma ($\gamma$51) is 90 degrees. When angle theta ($\theta$51) is 0 degrees, tip (50314) of distal portion (50330) is directed parallel to the shaft axis (SA50). Tip (50314) is also oriented proximally relative to shaft (50322) in the state shown in FIG. 83A.

FIG. 83B shows angle theta (θ52) being about 45 degrees and measured between modified shaft axis (SA50') and tip axis (TA50). Angle gamma (γ52) is about 135 degrees and is measured between shaft axis (SA50) and end effector axis (EEA50).

FIG. 83C shows angle theta (θ53) being about 90 degrees and measured between modified shaft axis (SA50') and tip axis (TA50). Additionally, angle gamma (γ53) is about 180 degrees measured between shaft axis (SA50) and end effector axis (EEA50).

Figure 83D:
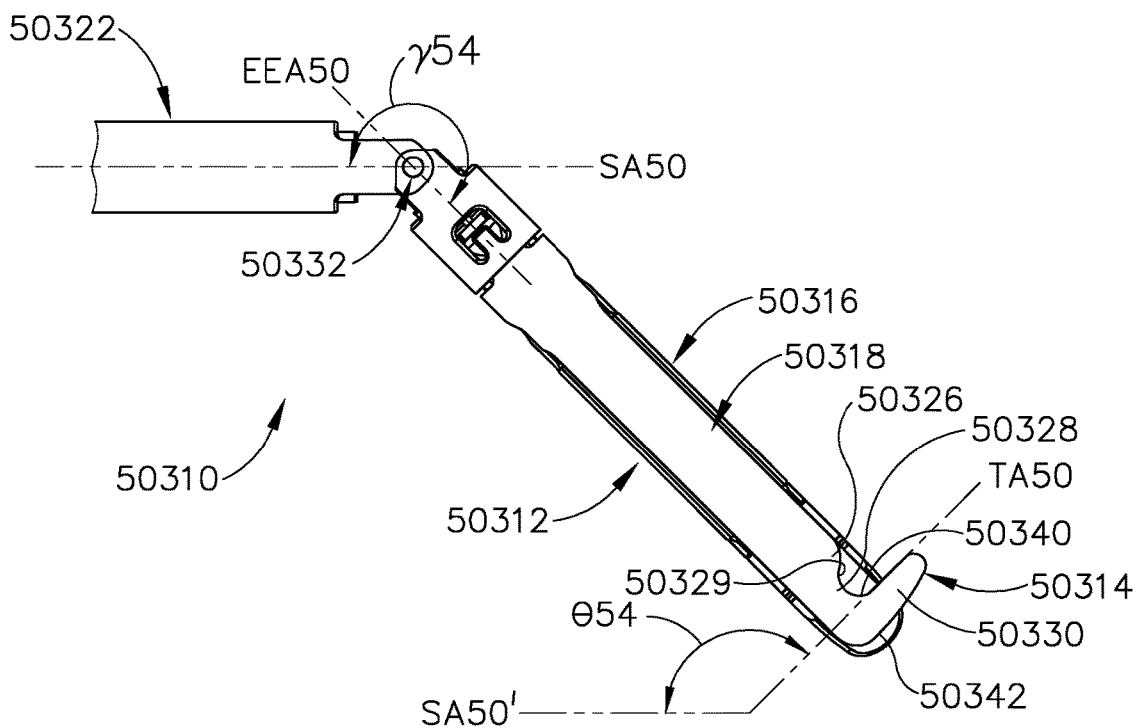
FIG. 83D depicts an enlarged top view of the end effector of FIG. 82 in a fourth angled position.

FIG. 83D shows angle theta (θ54) being about 135 degrees and measured between modified shaft axis (SA50') and tip axis (TA50). Additionally, angle gamma (γ54) is about 225 degrees measured between shaft axis (SA50) and end effector axis (EEA50).

Figure 83E:
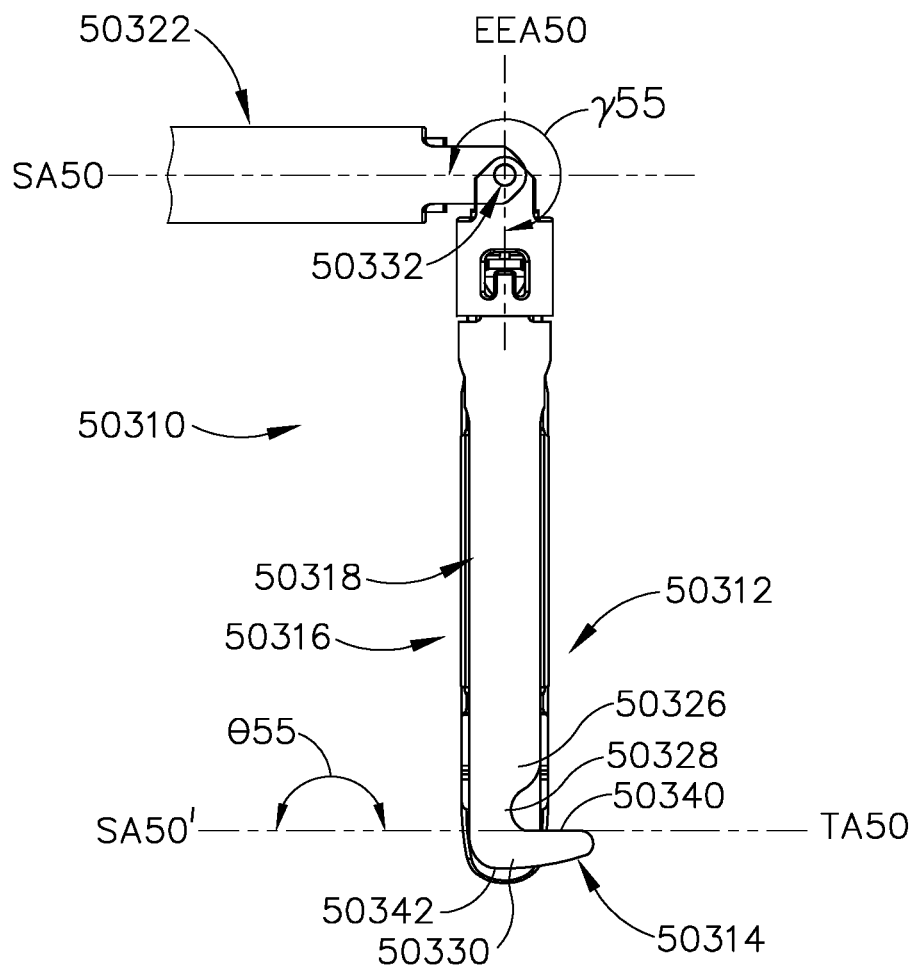
FIG. 83E depicts an enlarged top view of the end effector of FIG. 82 in a fifth angled position.

FIG. 83E shows angle theta (θ55) being about 180 degrees and measured between modified shaft axis (SA50') and tip axis (TA50). Additionally, angle gamma (γ5) is about 270 degrees measured between shaft axis (SA50) and end effector axis (EEA50). When the angle theta (θ55) is 180 degrees, tip (50314) of distal portion (50330) is directed parallel to shaft axis (SA50). Tip (50314) is also oriented distally relative to shaft (50322) in the state shown in FIG. 83E.

Figure 82:
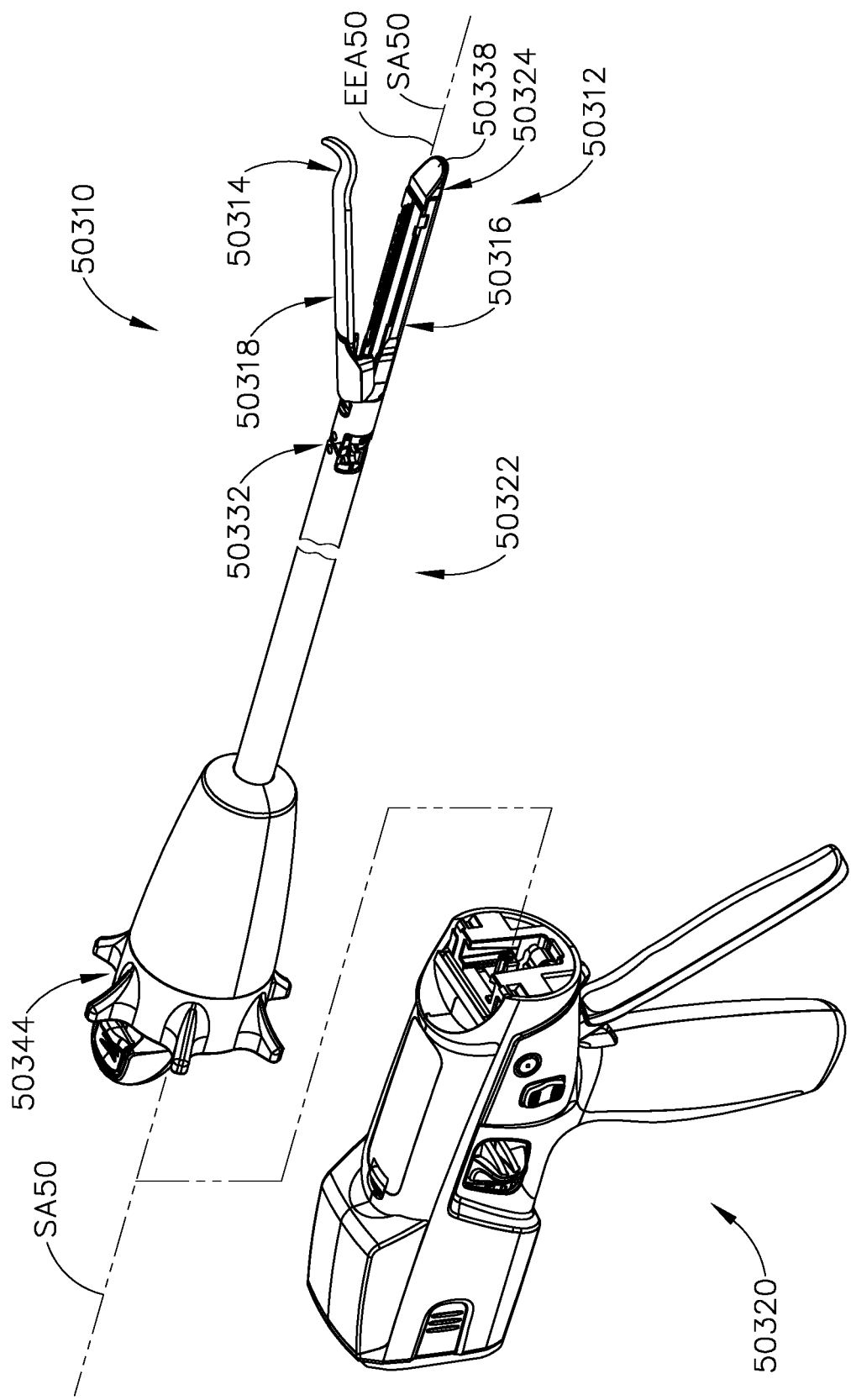
FIG. 82 depicts a perspective view of another exemplary surgical stapling instrument including another exemplary end effector and another exemplary placement tip, where the upper and lower jaws are in an open configuration.

Assuming the position of FIG. 83C of end effector (50312) is a baseline position, like FIG. 82, when tip angle (θ53) is 90 degrees, shaft axis (SA50) is parallel to end effector axis (EEA50). Moreover, assuming FIG. 83C is the baseline position, angle theta (θ51-θ52) as shown in FIGS. 83A and 83B, forms an acute angle along a first direction of articulation (shown as a counter clockwise rotation). Conversely, angle theta (θ54-θ55) as shown in FIGS. 83D and 83E forms an obtuse angle along a second direction of articulation, that is opposite the first direction of articulation (shown as a clockwise rotation).

2. Exemplary Method of Operating Instrument

Figure 84A:
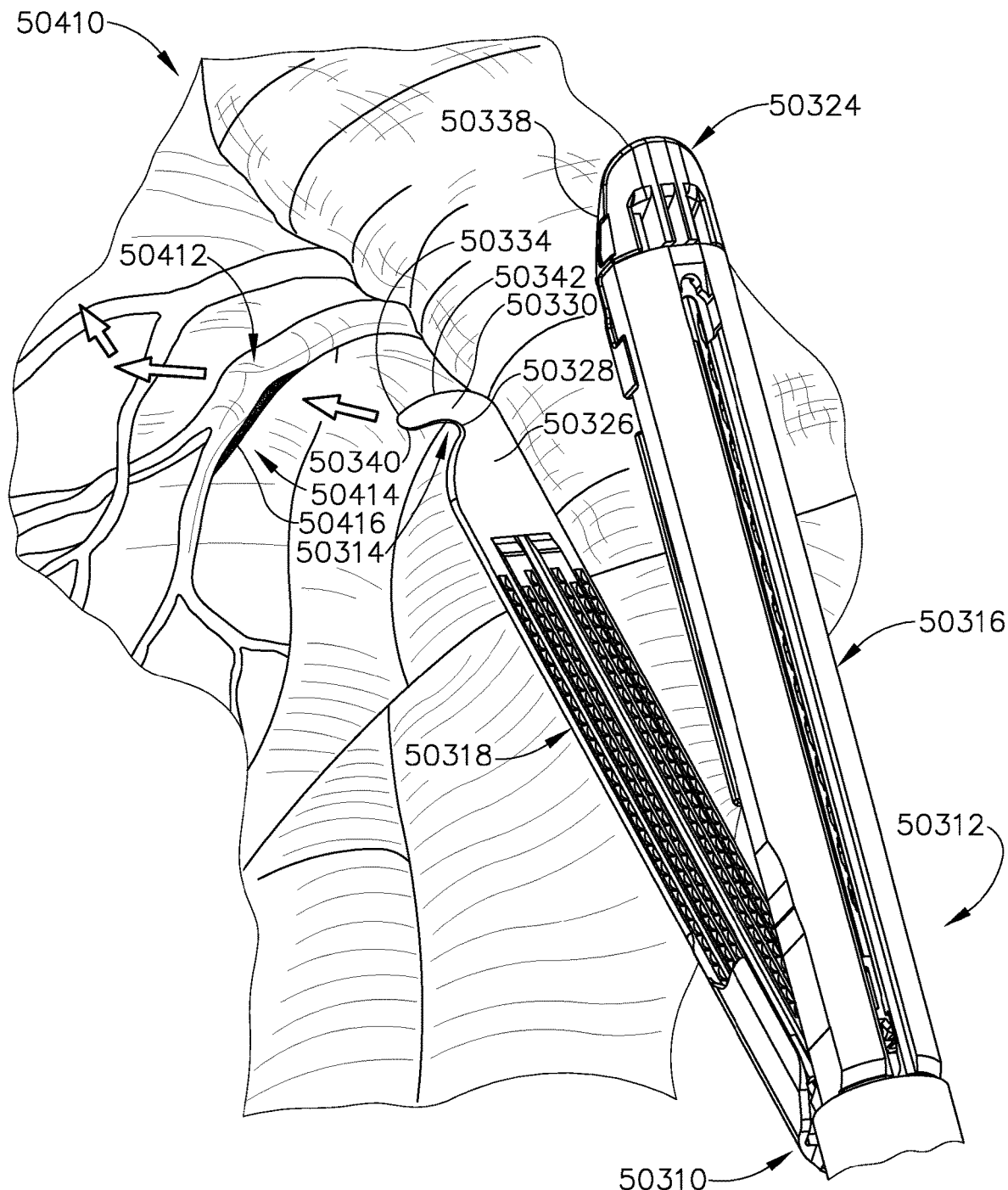
FIG. 84A depicts an enlarged perspective view of the end effector of FIG. 82 prior to entering a tissue opening.

FIGS. 84A-84D show an exemplary method of operating instrument (50310) for contacting tissue (50410). As shown, instrument (50310) again includes end effector (50312), placement tip (50314), lower jaw (50316), anvil (50318), shaft (50322), staple cartridge (50324), proximal portion (50326), central portion (50328), distal portion (50330), tip (50314), angled surface (50338), proximal surface (50340), and distal surface (50342). FIG. 84A shows instrument (50310) being introduced toward already separated first and second layers (50412, 50414) of tissue (50410). First and second layers (50412, 50414) collectively define a tissue opening (50416). As shown, instrument (50310) is in the open configuration. While not shown, it is also envisioned that upper jaw and lower jaw (50316) may be in the closed configuration. Additionally, the shape of placement tip (50314) may vary if desired.

Figure 84B:
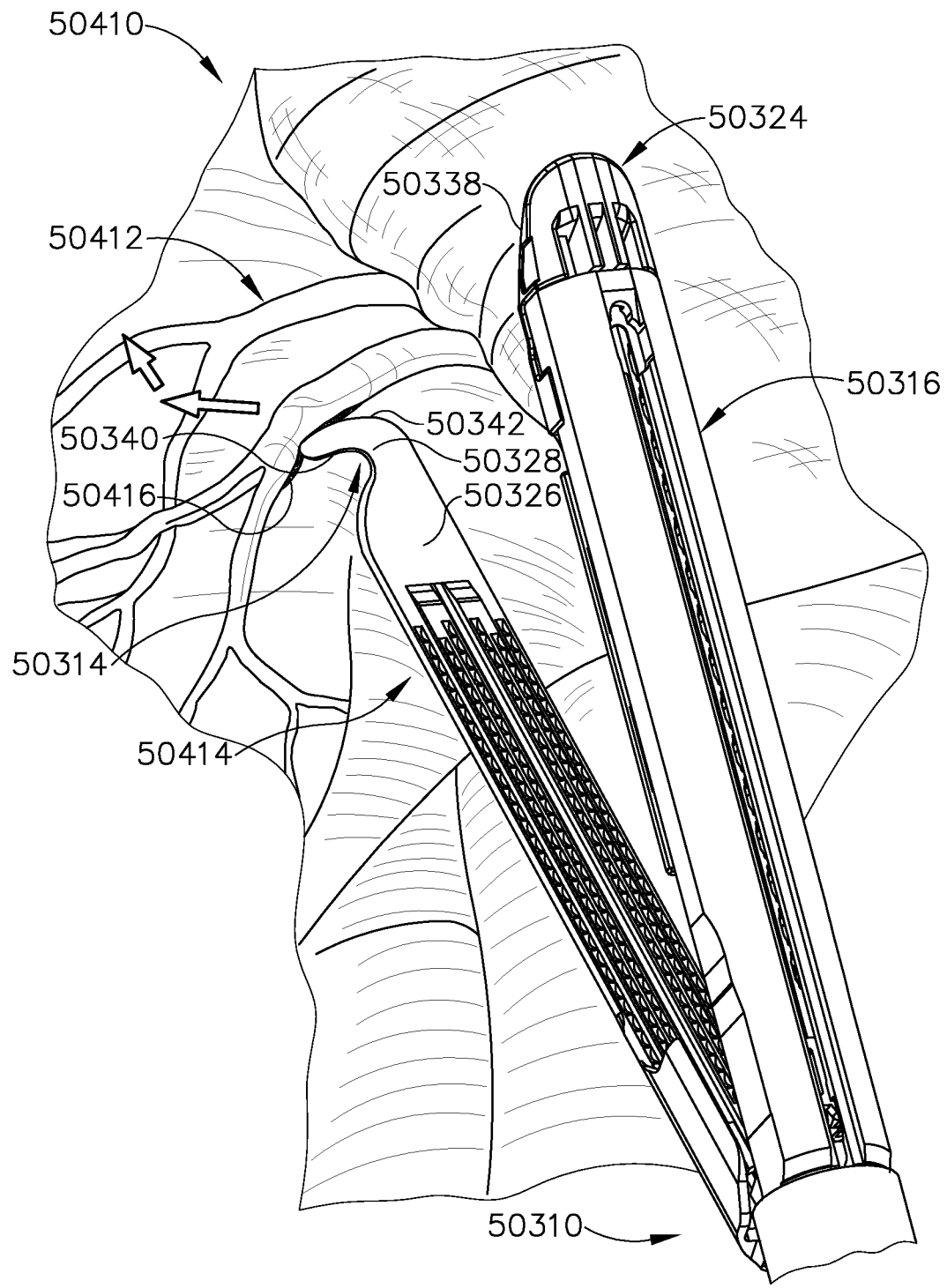
FIG. 84B depicts a perspective view of the end effector of FIG. 82 moving laterally to a second position entering the tissue opening of FIG. 84A.

FIG. 84B shows instrument (50310) being moved laterally toward already separated first and second layers (50412, 50414) of tissue (50410) that collectively define tissue opening (50416). As shown, tip (50314) of placement tip (50314) enters an already formed tissue opening (50416). Placement tip (50314) does not perform dissection of tissue (50410), which includes separation of first and second layers (50412, 50414) to form tissue opening (50416). Instead, first and second layers (50412, 50414) of tissue (50410) are already separated using any one of a variety of known methods and devices. In some other variations, placement tip (50314) provides at least some blunt dissection of tissue (e.g., separating different anatomical structures apart from each other) as end effector (50312) is moved in the patient.

Figure 84C:
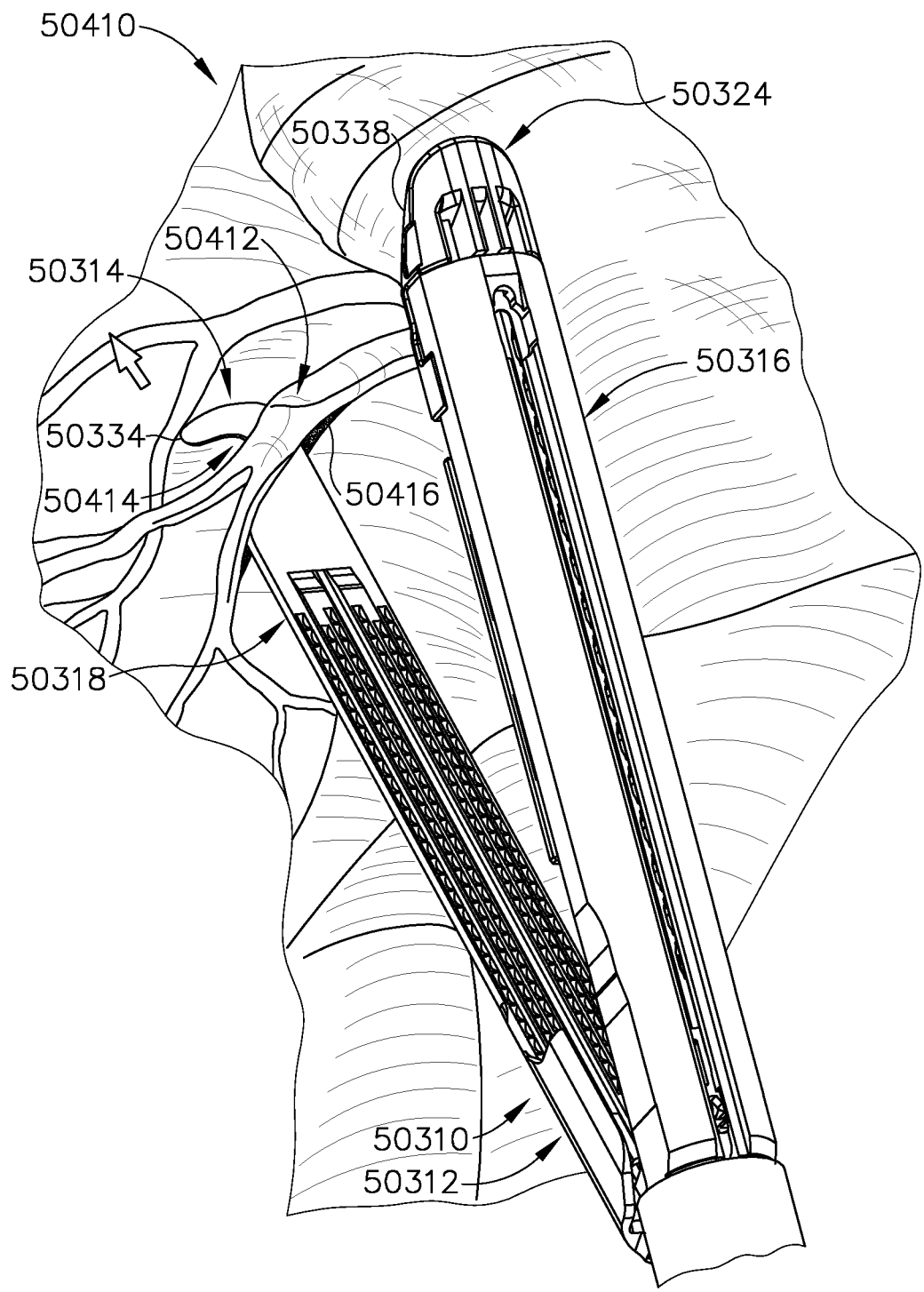
FIG. 84C depicts a perspective view of the end effector of FIG. 82 moving laterally to a third position already through the tissue opening of FIG. 84A.

FIG. 84C shows placement tip (50314) of instrument (50310) moving laterally through tissue opening (50416). Placing placement tip (50314) through tissue opening (50416) may be obtained using only a lateral motion in this example. As previously indicated, central portion (50328) and distal portion (50330) have an asymmetric profile along tip axis (TA50) of placement tip (50314). As shown, distal portion (50330) is now through already separated first and second layers of tissue (50412, 50414).

Figure 84D:
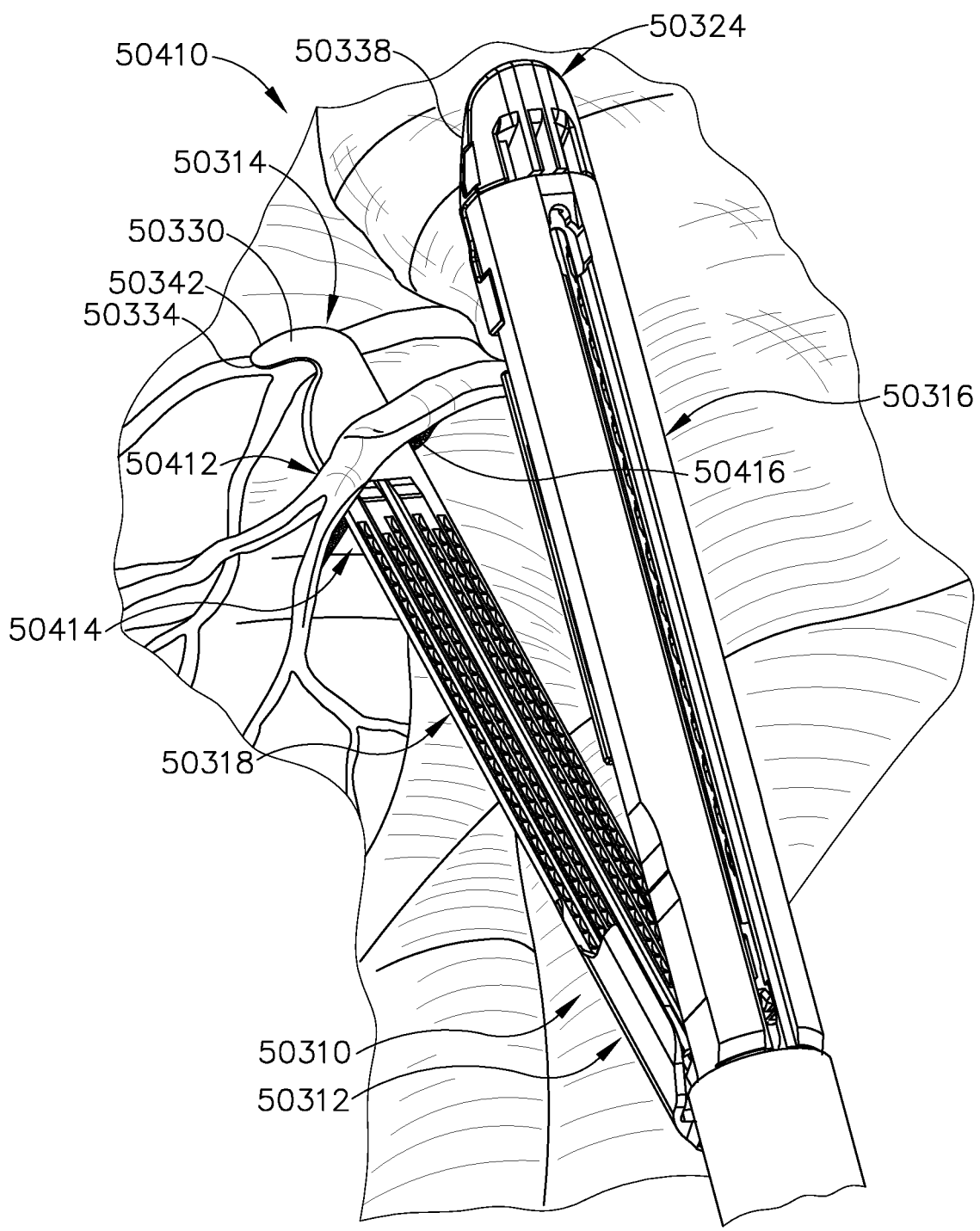
FIG. 84D depicts a perspective view of the end effector of FIG. 82 moved distally to a fourth position after moving laterally through the tissue opening of FIG. 84A.

FIG. 84D shows placement tip (50314) subsequently advancing (50314) distally once already through tissue opening (50416). According to the perspective view of FIG. 84D, distally is shown as being upwards and to the left. This of course may vary given the position of tissue (50410). After reaching the state shown in FIG. 84D, the operator may further position end effector (50312) such that tissue (50412) (e.g., a vessel targeted for transection) is positioned between staple forming pockets of anvil (50318) and corresponding staple apertures of the staple cartridge. The operator may then actuate end effector (50312) to transect and staple the tissue (50412).

Instrument (50310) according to this example may include articulation joint (50332) to rotate end effector (50312) to the desired angle, in a manner similar or different to that described above with respect to FIGS. 83A-83E. Laterally moving open jaw of instrument (50310) through tissue opening (50416) may include the user selectively adjusting articulation joint (50332) manually or using powered articulation as described previously with respect to instrument (10, 50310).

Figure 85:
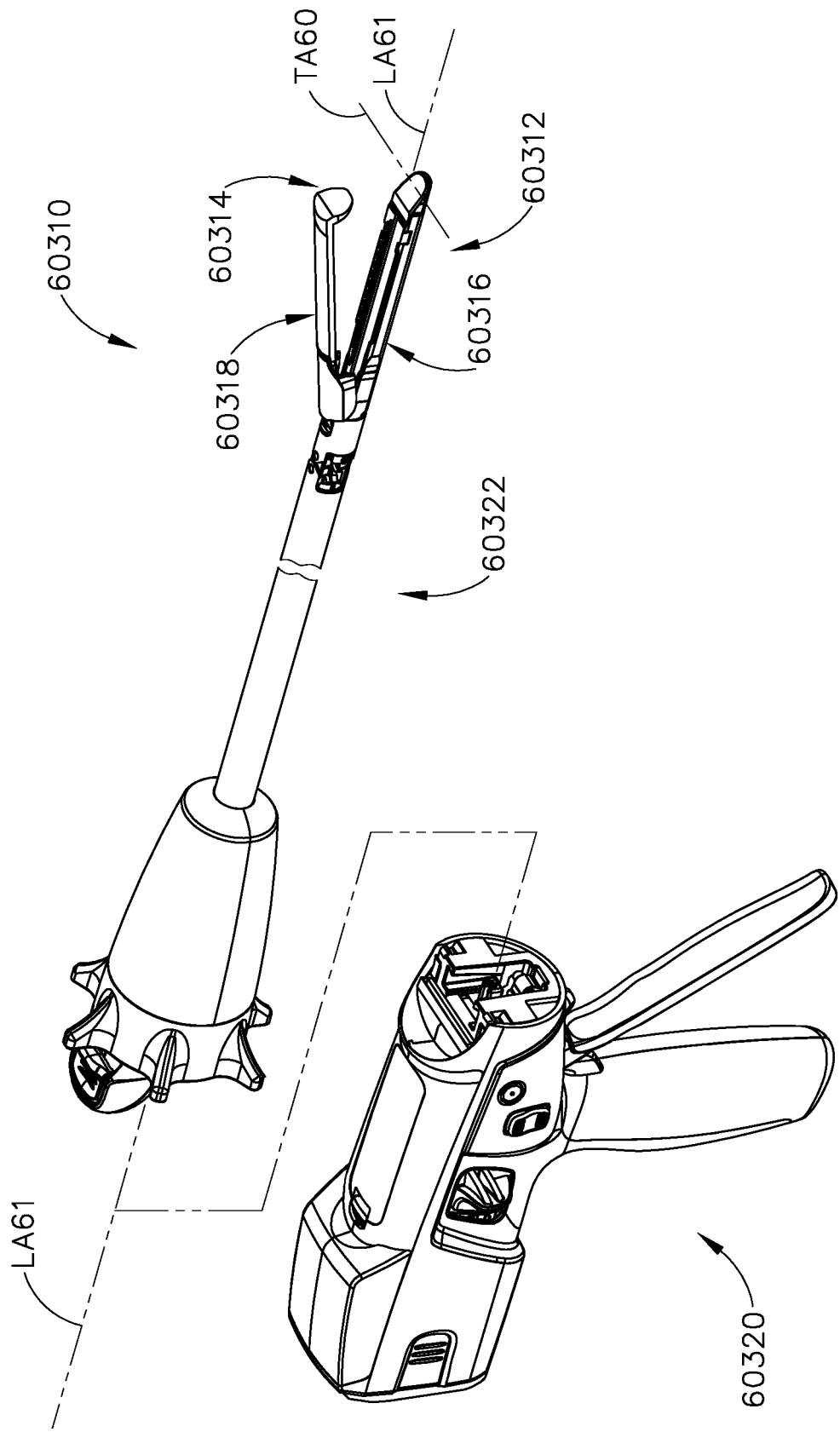
FIG. 85 depicts a perspective view of another exemplary surgical stapling instrument with another exemplary end effector with another exemplary placement tip, where the upper and lower jaws are in an open configuration.

X. SURGICAL STAPLING END EFFECTOR COMPONENT WITH DEFORMABLE TIP HAVING Thick Distal End A. Another Exemplary Surgical Instrument Having Various End Effectors and Placement Tips FIG. 85 shows another exemplary surgical instrument (60310) configured as a surgical stapler. Instrument (60310) comprises a body, shown as a handle portion (60320), and a shaft (60322). Shaft (60322) defines a longitudinal axis (LA61) that extends from handle portion (60320). Instrument (60310) has a modular configuration such that shaft (60322) is selectively removable from, and selectively attachable to, handle portion (60320). Instrument (60310) is configured similarly to instrument (10), such that the operability and use of instrument (60310) is the same as described above for instrument (10) with the added feature of instrument (60310) being a modular configuration. With its modular configuration, instrument (60310) provides a way to change the desired end effector. Features operable for providing the modular configuration of instrument (60310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (60322) is not detachable from handle portion (60320).

As will be discussed in greater detail below, exemplary end effectors (60312, 60412, 60512) are provided on shaft (60322) that is detachable from handle portion (60320). End effectors (60312, 60412, 60512) are operable to compress, staple, and cut tissue. End effectors (60312, 60412, 60512) may be used in place of end effector (12) shown in FIG. 1. In some versions, end effectors (60312, 60412, 60512) may be integrally formed with shaft (60322) or, alternatively, may be separately formed and then combined. In some versions, end effectors (60312, 60412, 60512) may be provided for use in robotic systems. In such robotic systems, modular shaft (60322) having any of the following end effectors (60312, 60412, 60512) may be attachable to a portion of the robotic system for use such that handle portion (60320) is replaced by components of the robotic system, including a body. Other ways to incorporate an end effector (60312, 60412, 60512) having any of the following placement tips (60314, 60414, 60514) into a user operated or robotic operated instrument will be apparent to those of ordinary skill in the art.

As will be described in greater detail below, placement tips (60314, 60414, 60514) are configured to be coupled with at least one of an upper jaw (such as anvil 60318, 60418, 60518) or a lower jaw (60316, 416, 516). Placement tips (60314, 60414, 60514) may be positioned on the same jaw as staple cartridge (37) or on the same jaw as anvil (60318, 60418, 60518). Placement tips (60314, 60414, 60514) are operable to elastically deform from a first angled position to a second angled position. The first angled position will be discussed below with respect to each placement tip (60314, 60414, 60514). The second angled position for placement tips (60314, 60414, 60514) may be substantially straight in some versions, but may be angled to a degree (e.g., slightly above or slightly below a longitudinal axis (LA61, LA62, LA63)) in other versions. The second angled position for placement tips (60314, 60414, 60514) may be defined by the characteristics (e.g., thickness, density, etc.) of the tissue that is being captured between anvils (60318, 60418, 60518) and lower jaws (60316, 416, 516).

Placement tips (60314, 60414, 60514) described below may be used with any surgical instrument (10, 60310) described above and below and in any of the various procedures described in the various patent references cited herein. As will be described in greater detailed below, placement tips (60314, 60414, 60514) may be used singularly or in combination with other placement tips, such as placement tips (60314, 60414, 60514). To this end, like numbers below indicate like features described above. Except as otherwise described below, instrument (60310) described below may be constructed and operable like instrument (10) described above. Certain details of instrument (60310) will therefore be omitted from the following description, it being understood that such details are already provided above in the description of instrument (10). Other suitable ways in which various surgical instruments may be used will be apparent to those of ordinary skill in the art in view of the teachings herein.

1. Another Exemplary Surgical Instrument Having Another Exemplary End Effector and Another Example of a Placement Tip FIGS. 85-90C show end effector (60312) and another exemplary placement tip (60314) of surgical instrument (60310). FIGS. 86-89 show enlarged views of a distal end of end effector (60312) shown in FIG. 85. As shown, end effector (60312) includes an upper jaw and a lower jaw (60316). While anvil (60318) is included in an upper jaw, and cartridge (60324) is received in lower jaw (60316), this relationship may be reversed. Staple cartridge (60324) is configured to hold one or more staples in a manner similar to staple cartridge (37).

At least one of anvil (60318) or lower jaw (60316) is movable relative to other of anvil (60318) or lower jaw (60316) between an open configuration and a closed configuration. As shown, anvil (60318) pivotably rotates toward lower jaw (16) in the same manner as anvil (18) as described above with respect to instrument (10). In this manner, end effector (60312) is similar to end effector (12), though placement tip (60314) is elastically deformable in this example. Placement tip (60314) obtains a first angled position, shown in FIGS. 86-89, when end effector (60312) is not clamping tissue. More specifically, in this first angled configuration, end effector (60312) may be in an open position as shown in FIG. 85, or in a closed position as shown in FIGS. 86-89. In instances when end effector (60312) is in this first angled configuration, end effector (60312) may be considered in a non-loaded state or non-loaded position. Conversely, in a second angled position (not shown) when end effector (60312) is clamping tissue, end effector (60312) may be considered in a loaded state or a loaded position. In the second angled position, at least a portion of placement tip (60314) deflects upwardly.

Placement tip (60314) is located adjacent at least one of distal end (60321) of anvil (60318) or a distal end of lower jaw (60316). As shown in FIGS. 86-89, placement tip (60314) is coupled with a distal end (60321) of anvil (60318). Additionally, as shown in the top view of FIG. 88, lower jaw (60316) is longer and wider than anvil (60318) and placement tip (60314). However, lower jaw (60316) may be shorter and/or and narrower than anvil (60318) and placement tip (60314), if desired.

Figure 86:
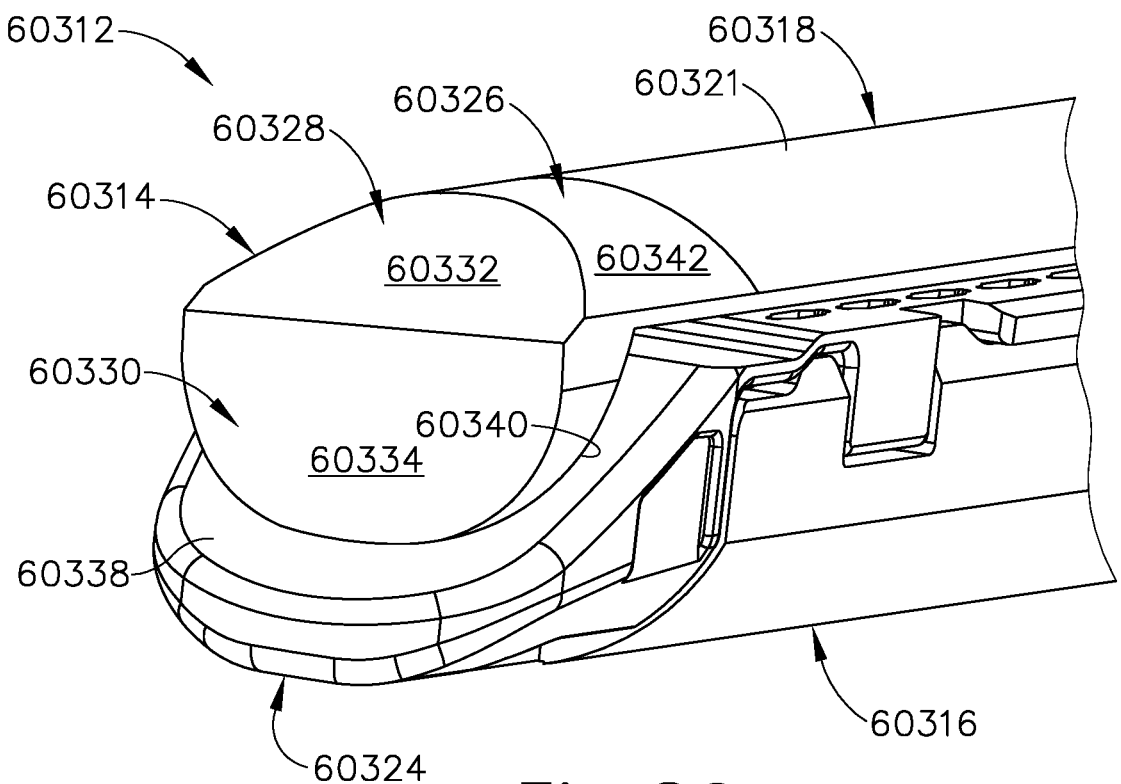
Figure 87:
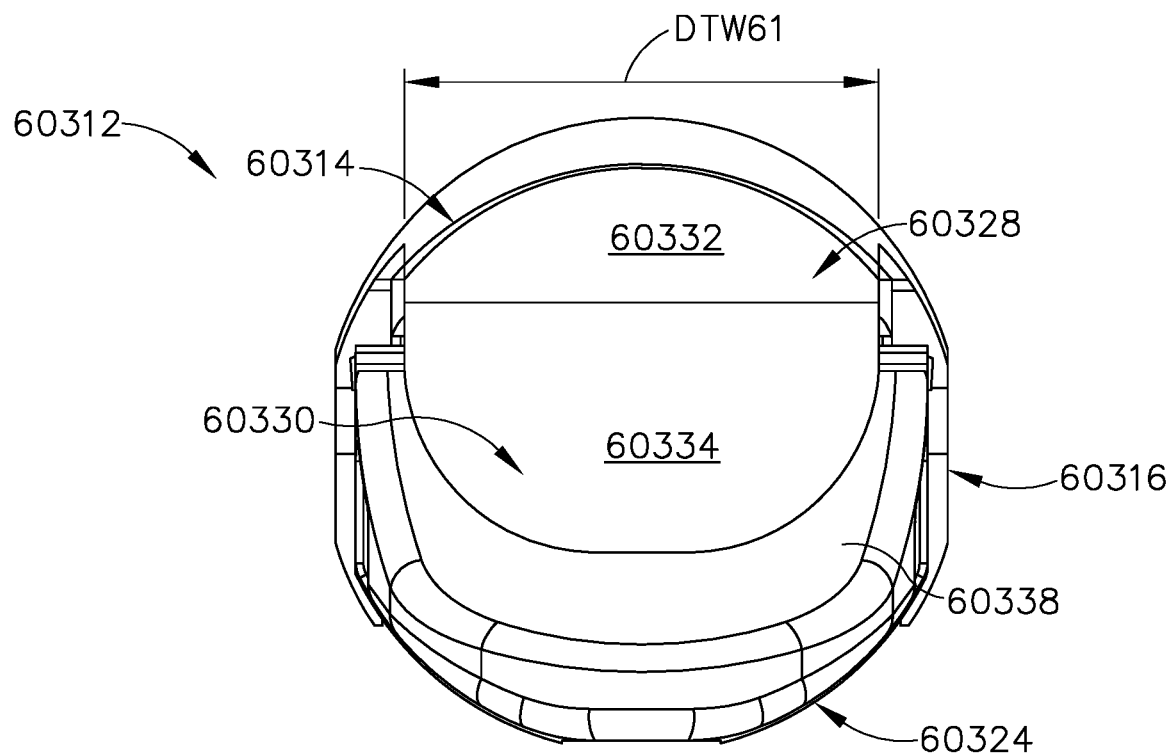
Figure 88:
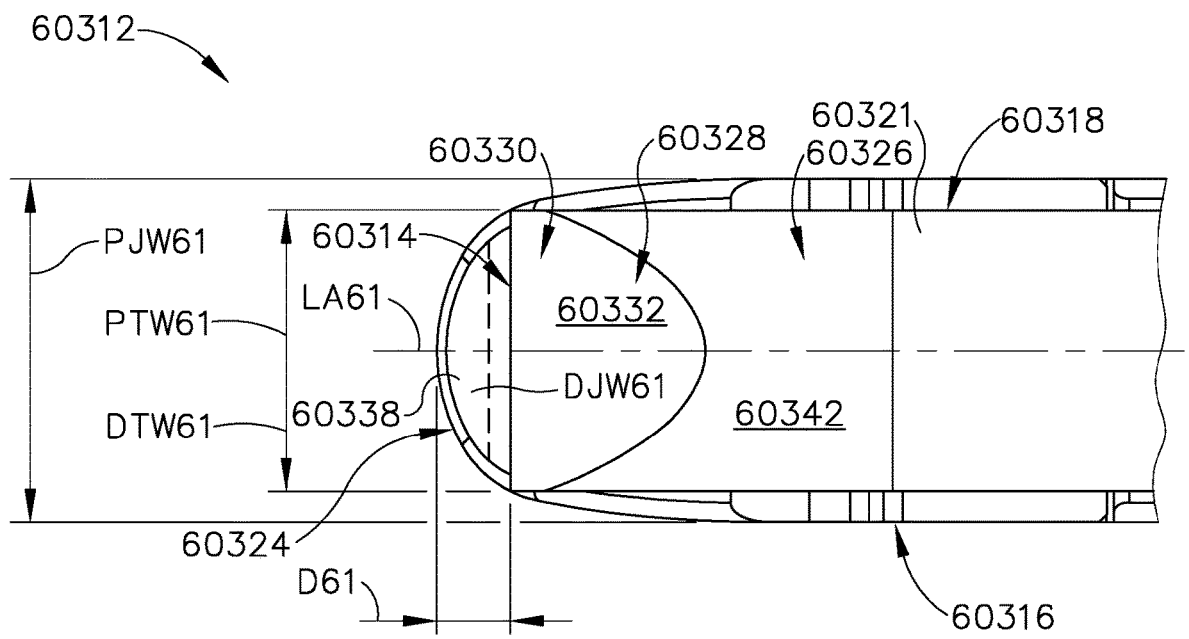
Figure 89:
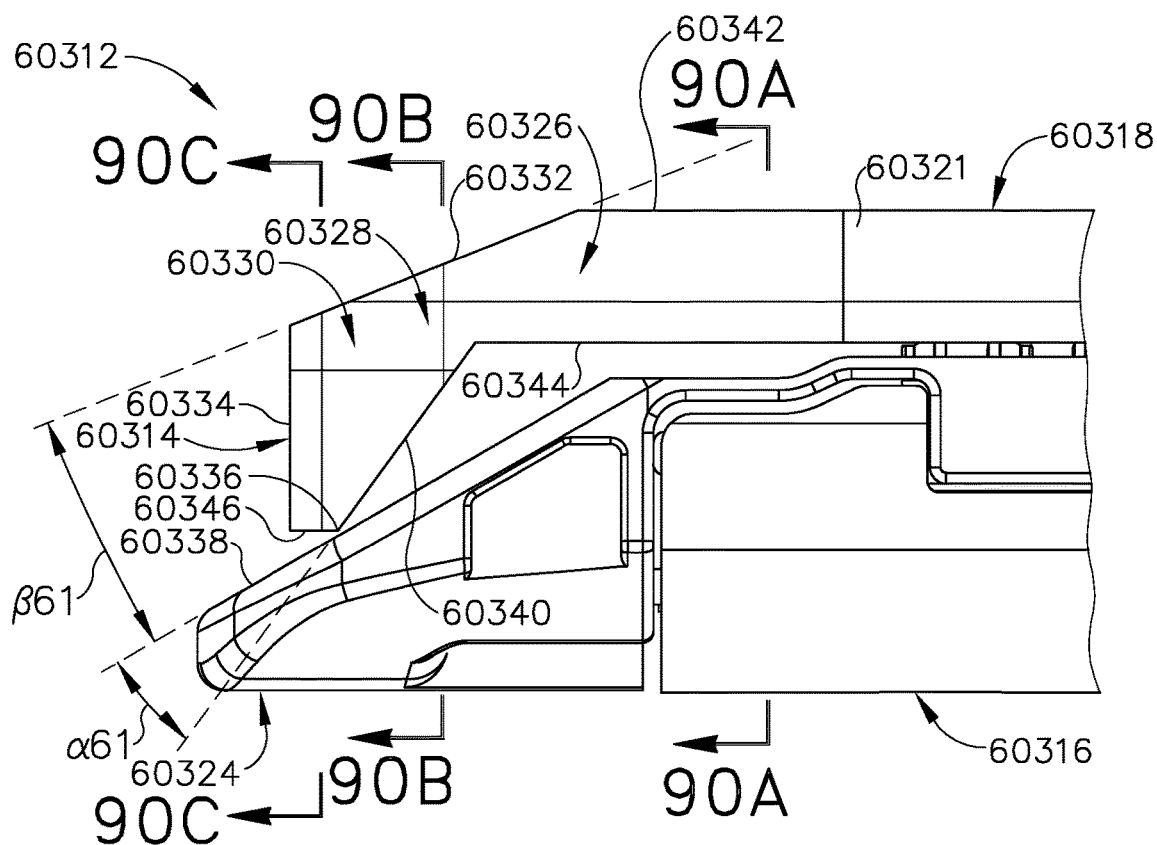

FIGS. 86, 88 and 89 each show placement tip (60314) as including a proximal portion (60326), a central portion (60328), and a distal portion (60330). Proximal portion (60326) extends distally from anvil (60318). Central portion (60328) is disposed longitudinally between proximal and distal portions (60326, 60330). Additionally, as shown in FIG. 88, placement tip (60314) is symmetric about a longitudinal axis (LA61). However, placement tip (60314) may be non-symmetric, if desired. Placement tip (60314) may be integrally formed together as unitary piece or consist of separately formed components.

FIG. 88 shows placement tip (60314) having a generally uniform width along the entire length of placement tip (60314) along longitudinal axis (LA61). In other words, the width of the transverse cross-section of placement tip (60314) is generally uniform. Distal portion (60330) of placement tip (60314) has a distal tip width (DTW1) that is greater than a distal jaw width (DJW61) of lower jaw (60316) disposed opposite placement tip (60314). However, this is not as pronounced as the examples shown in FIGS. 93 and 96. Proximal portion (60326) of placement tip (60314) has a proximal tip width (PTW61) that is less than a proximal jaw width (PJW61) of lower jaw (60316) that is disposed opposite placement tip (60314). Since placement tip (60314) has a generally uniform width, proximal tip width (PTW61) is generally equal to distal tip width (DTW61). Additionally, as shown in FIG. 88, lower jaw (60316) extends distally a distance (D61) beyond a distal tip of placement tip (60314).

FIG. 89 shows placement tip (60314) as including an angled planar upper surface (60332) abutting a planar distal surface (60334). As shown, distal portion (60330) terminates at planar distal surface (60334) that extends perpendicular to longitudinal axis (LA61) and parallel to transverse cross-section, for example, line 90A-90A, line 90B-90B, or line 90C-90C. Additionally, regarding the closed configuration, FIG. 89 shows a contacting portion (60336) that is in abutting contact with an angled surface (60338) of staple cartridge (60324). With continued reference to FIG. 89, placement tip (60314) includes an angled underside surface (60340), a top arcuate surface (60342), and a proximal underside surface (60344). FIG. 89 also shows distal portion (60330) including a distal underside surface (60346) that is non-parallel to angled underside surface (60340).

Regarding the angles shown in FIG. 89, a first angle alpha ($\alpha 61$) is defined between angled surface (60338) of staple cartridge and angled underside surface (60340) of placement tip (60314). Similarly, a first angle beta ($\beta 61$) is defined between angled surface (60338) and angled planar upper surface (60332). Since angled surface (60338) and angled planar upper surface (60332) appear generally parallel, first angle beta ($\beta 61$) is small.

Figure 90A:
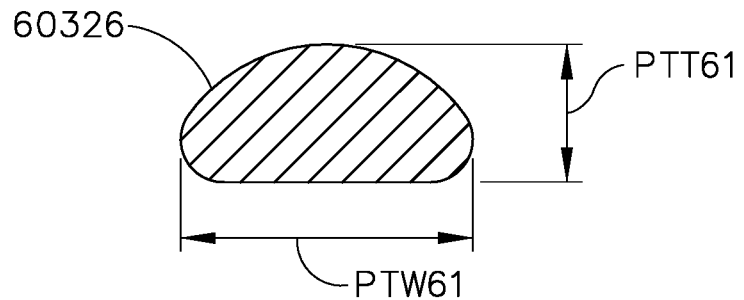
Figure 90B:
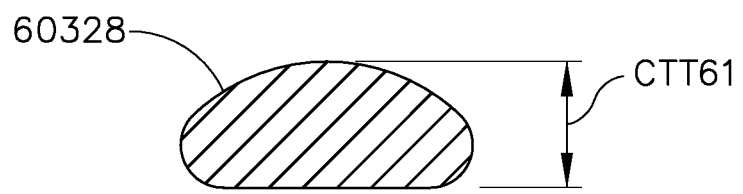
Figure 90C:
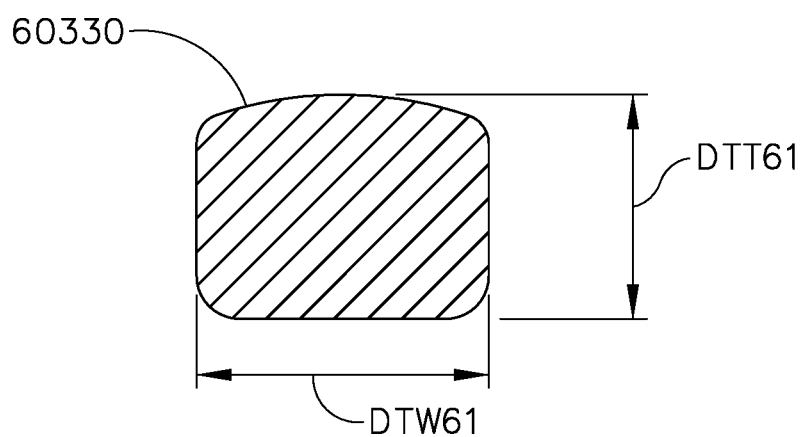

As shown in the side view of FIG. 89 and the cross-sectional views of FIGS. 90A-90C, the thickness of placement tip (60314) varies longitudinally along longitudinal axis (LA61). More specifically, FIG. 90A shows a cross-sectional view of proximal portion (60326) of placement tip (60314) of FIG. 89, taken along line 90A-90A of FIG. 89 having a proximal cross-sectional thickness (PTT61). As shown in FIG. 89, proximal cross-sectional thickness (PTT61) of placement tip (60314) is generally uniform. Proximal cross-sectional thickness (PTT61) may be assessed at a location where placement tip (60314) attaches to anvil (60318).

FIG. 90B shows a cross-sectional view of a central portion (60328) of placement tip (60314) of FIG. 89, taken along line 90B-90B of FIG. 89 having a central cross-sectional thickness (CTT61). As shown, central cross-sectional thickness (CTT61) taken along transverse cross-section is less than proximal cross-sectional thickness (PTT61).

FIG. 90C shows a cross-sectional view of distal portion (60330) of placement tip (60314) of FIG. 89, taken along line 90C-90C of FIG. 89 having a distal cross-sectional thickness (DTT61). As shown, distal cross-sectional thickness (DTT61) taken along a transverse cross-section is greater than proximal cross-sectional thickness (PTT61) of proximal portion (60326) along the transverse cross-section which is greater than central cross-sectional thickness (CTT61) of central portion (60328) along the transverse cross-section.

2. Another Exemplary Surgical Instrument Having Another Exemplary End Effector and Another Example of a Placement Tip FIGS. 91-95C show another exemplary end effector (60412) including another exemplary placement tip (60414). As shown in FIGS. 91-94, end effector (60412) of the present example comprises placement tip (60414), a lower jaw (60416), an anvil (60418), a distal end (60421) of anvil (60418), a shaft (60422), a staple cartridge (60424), a proximal portion (60426), a central portion (60428), a distal portion (60430), an angled upper surface (60432), a planar perpendicular distal surface (60434), a contacting portion (60436), an angled surface (60438) of staple cartridge (60424), an angled underside surface (60440), a top arcuate surface (60442), and a proximal underside surface (60444).

Figure 91:
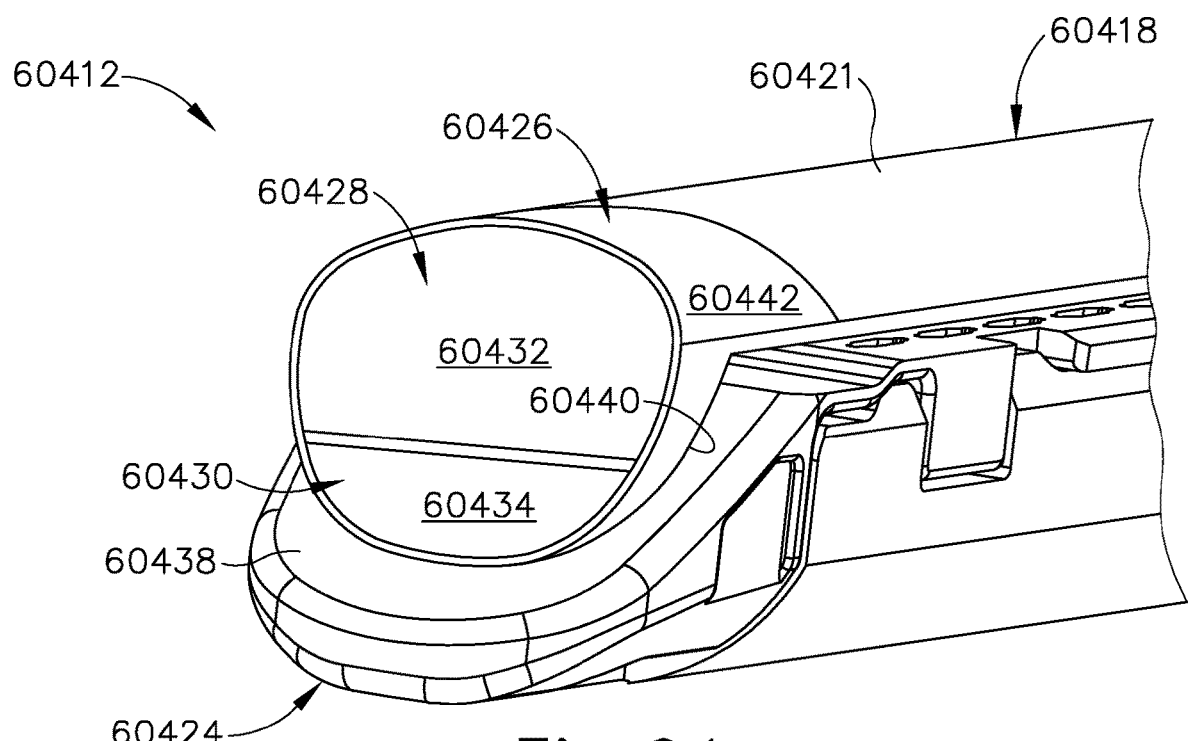
Figure 92:
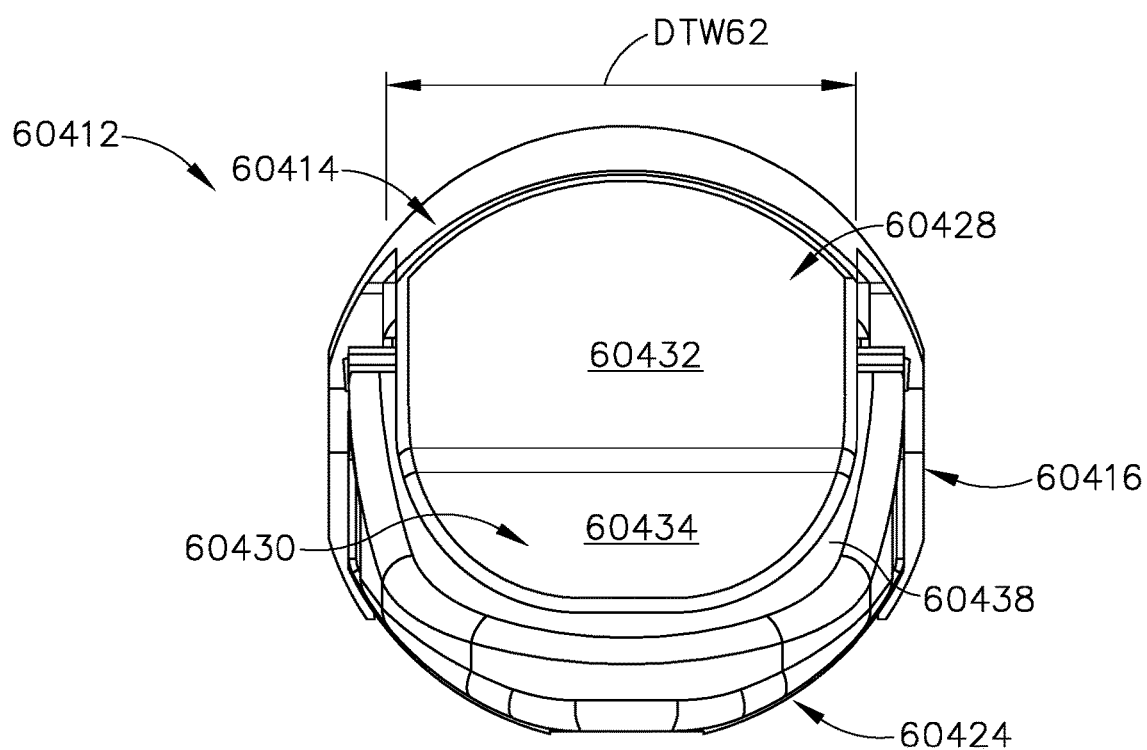
Figure 93:
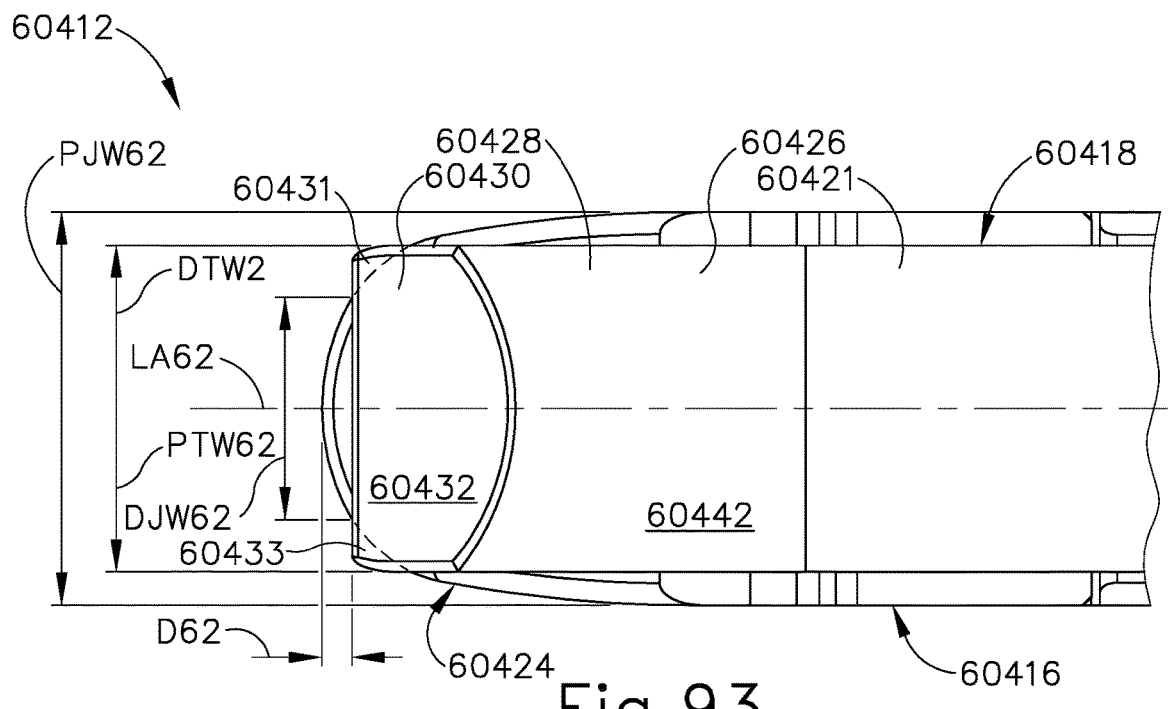

FIGS. 91, 93, and 94 each show placement tip (60414) as including proximal portion (60426), central portion (60428), and distal portion (60430). Proximal portion (60426) extends distally from and is attached to anvil (60418). As previously discussed, it is also envisioned that placement tip (60414) may be integrally formed with one of anvil (60418) or lower jaw (60416). Central portion (60428) is disposed longitudinally between proximal and distal portions (60426, 60330). Additionally, as shown in FIG. 93, placement tip (60414) is symmetric about a longitudinal axis (LA62). However, placement tip (60414) may be non-symmetric, if desired. Placement tip (60414) may be integrally formed together as unitary piece or consist of separately formed components.

FIG. 93 shows placement tip (60414) having a generally uniform width along the entire length of placement tip (60414) along longitudinal axis (LA62). In other words, the width of the transverse cross-section of placement tip (60414) is generally uniform. Distal portion (60430) of placement tip (60414) has a distal tip width (DTW62) that is greater than a distal jaw width (DTW62) of lower jaw (60416) disposed opposite placement tip (60414). As such, placement tip (60414) includes first and second overhang portions (60431, 433) that extend beyond lower jaw (60416). Proximal portion (60426) of placement tip (60414) has a proximal tip width (PTW62) that is less than a proximal jaw width (PJW62) of lower jaw (60416) that is disposed opposite placement tip (60414). Since placement tip (60414) has a generally uniform width, proximal tip width (PTW62) is generally equal to distal tip width (DTW62). Additionally, as shown in FIG. 93, lower jaw (60416) extends distally a distance (D62) beyond a distal tip of placement tip (60414).

FIG. 94 shows placement tip (60414) as including an angled planar upper surface (60432) and a planar distal surface (60434). As shown, distal portion (60430) terminates at planar distal surface (60434) that extends perpendicular to longitudinal axis (LA62) and parallel to transverse cross-section, for example, shown as line 95A-95A, line 95B-95B, or line 95C-95C. With continued reference to FIG. 94, placement tip (60414) includes an angled underside surface (60440), a top arcuate surface (60442), and a proximal underside surface (60444). Unlike placement tip (60314) shown in FIG. 94, angled underside surface (60440) of placement tip (60414) extends completely to planar distal surface (60434), and as a result, placement tip (60414) omits a separately angled distal underside surface. Additionally, regarding the closed configuration, FIG. 94 shows a contacting portion (60436) that is in abutting contact with an angled surface (60438) of staple cartridge (60424).

Regarding the angles shown in FIG. 94, a second angle alpha ($\alpha 62$) is defined between angled surface (60438) of staple cartridge and angled underside surface (60440). Since angled surface (60438) of staple cartridge and angled underside surface (60440) appear generally parallel, second angle beta ($\beta 62$) is small. Similarly, a second angle beta ($\beta 62$) is defined between angled surface (60438) and angled planar upper surface (60432).

As shown in the side view of FIG. 94 and the cross-sectional views of FIGS. 95A-95C, the thickness of placement tip (60414) varies longitudinally along the longitudinal axis (LA62). More specifically, FIG. 95A shows a cross-sectional view of proximal portion (60426) of placement tip (60414) of FIG. 94, taken along line 95A-95A of FIG. 94 having a proximal cross-sectional thickness (PTT62). As shown in FIG. 94, proximal cross-sectional thickness (PTT62) of placement tip (60414) is generally uniform. Proximal cross-sectional thickness (PTT62) may be assessed at a location where placement tip (60414) attaches to anvil (60418).

FIG. 95B shows a cross-sectional view of central portion (60428) of placement tip (60414) of FIG. 94, taken along line 95B-95B of FIG. 94 having a central cross-sectional thickness (CTT62). FIG. 95C shows a cross-sectional view of distal portion (60430) of placement tip (60414) of FIG. 94, taken along line 95C-95C of FIG. 94 having a distal cross-sectional thickness (DTT62). As shown, central cross-sectional thickness (CTT62) of central portion (60428) taken along the transverse cross-section is greater than distal cross-sectional thickness (DTT62) of distal portion (60430) along the transverse cross-section which is greater than proximal cross-sectional thickness (PTT62) of proximal portion (60426) along the transverse cross-section.

3. Another Exemplary Surgical Instrument Having an Exemplary End Effector and an Example of a Placement Tip FIGS. 96-98C show another exemplary end effector (60512) including another exemplary placement tip (60514). As shown in FIGS. 96 and 97, end effector (60512) of the present example comprises another exemplary placement tip (60514), a lower jaw (60516), an anvil (60518), a distal end (60521) of anvil (60518), a shaft (60522), a staple cartridge (60524), a proximal portion (60526), a central portion (60528), a distal portion (60530), an angled upper surface (60532), a planar perpendicular distal surface (60534), a contacting portion (60536), an angled surface (60538) of staple cartridge (60524), an angled underside surface (60540), a top arcuate surface (60542), and a proximal underside surface (60544).

FIGS. 96 and 97 each show placement tip (60514) as including proximal portion (60526), central portion (60528), and distal portion (60530). Proximal portion (60526) extends distally from anvil (60518). Central portion (60528) is disposed longitudinally between proximal and distal portions (60526, 60330). Additionally, as shown in FIG. 96, placement tip (60514) is symmetric about a longitudinal axis (LA63). However, placement tip (60514) may be non-symmetric, if desired. Placement tip (60514) may be integrally formed together as unitary piece or consist of separately formed components.

FIG. 96 shows placement tip (60514) having a generally uniform width along the entire length of placement tip (60514) along longitudinal axis (LA63). In other words, the width of the transverse cross-section of placement tip (60514) is generally uniform. Distal portion (60530) of placement tip (60514) has a distal tip width (DTW63) that is greater than a distal jaw width (DTW63) of lower jaw (60516) disposed opposite placement tip (60514). As such, placement tip (60514) includes first and second overhang portions (60531, 533) that extend beyond lower jaw (60516). Proximal portion (60526) of placement tip (60514) has a proximal tip width (PTW36) that is less than a proximal jaw width (PJW63) of lower jaw (60516) that is disposed opposite placement tip (60514). Since placement tip (60514) has a generally uniform width, proximal tip width (PTW63) is generally equal to distal tip width (DTW63). Additionally, as shown in FIG. 96, lower jaw (60516) extends distally a distance (D63) beyond a distal tip of placement tip (60514).

FIG. 97 shows distal portion (60530) of placement tip (60514) terminating at planar distal surface (60534) that extends perpendicular to longitudinal axis (LA63) and parallel to transverse cross-section, for example, shown by line 98A-98A, line 98B-98B, or line 98C-98C. Unlike placement tip (60314) shown in FIG. 97, angled underside surface (60540) of placement tip (60514) extends completely to planar distal surface (60534), and as a result, placement tip (60514) omits a separately angled distal underside surface. Additionally, regarding the closed configuration, FIG. 97 shows contacting portion (60536) in abutting contact with angled surface (60538) of staple cartridge (60524).

Regarding the angles shown in FIG. 97, a third angle alpha (α63) is defined between angled surface (60538) of staple cartridge and angled underside surface (60540) defines. Similarly, a third angle beta (β63) is defined between angled surface (60538) and angled planar upper surface (60532) defines. Since angled surface (60538) and angled planar upper surface (60532) appear generally parallel, third angle beta (β63) is small.

As shown in the side view of FIG. 97 and the cross-sectional views of FIGS. 98A-98C, the thickness of placement tip (60514) varies longitudinally along the longitudinal axis (LA63). More specifically, FIG. 98A shows a cross-sectional view of proximal portion (60526) of placement tip (60514) of FIG. 97, taken along line 98A-98A of FIG. 97 having a proximal cross-sectional thickness (PTT63). As shown in FIG. 97, proximal cross-sectional thickness (PTT63) of placement tip (60514) is generally uniform. Proximal cross-sectional thickness (PTT63) may be assessed at a location where proximal portion (60526) of placement tip (60514) attaches to anvil (60518).

FIG. 98B shows a cross-sectional view of central portion (60528) of placement tip (60514) of FIG. 94, taken along line 98B-98B of FIG. 97 having a central cross-sectional thickness (CTT63). Similarly, FIG. 98C shows a cross-sectional view of distal portion (60530) of placement tip (60514) of FIG. 97, taken along line 98C-98C of FIG. 97 having a distal cross-sectional thickness (DTT63). The thickness of placement tip (60514) continually increases moving distally along the entire length of placement tip (60514). For example, proximal cross-sectional thickness (PTT63) of proximal portion (60526) is less than central cross-sectional thickness (CTT63) of central portion (60528) which is less than distal cross-sectional thickness (DTT63) of distal portion (60530).

XI. BUTTRESS APPLIER CARTRIDGE FOR SURGICAL STAPLER HAVING END EFFECTOR WITH DEFLECTABLE CURVED TIP

A. Another Exemplary Surgical Instrument Including End Effector with Another Placement Tip FIG. 99 shows another exemplary instrument (70310) with another exemplary end effector (70312) and another exemplary placement tip (70314). Instrument (70310) may have a modular configuration such that shaft (70322) is selectively removable from, and selectively attachable to, handle portion (70320). Instrument (70310) is configured similarly to instrument (10), such that the operability and use of instrument (70310) is the same as described above for instrument (10) with the added feature of instrument (70310) having a modular configuration. With its modular configuration, instrument (70310) provides a way to change the desired end effector. Features operable for providing the modular configuration of instrument (70310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (70322) is not detachable from handle portion (70320).

End effector (70312) is provided on shaft (70322) that is detachable from handle portion (70320). End effector (70312) is operable to compress, staple, and cut tissue. End effector (70312) may be used in place of end effector (12) shown in FIG. 1. In some versions, end effector (70312) may be integrally formed with shaft (70322) or, alternatively, may be separately formed and subsequently combined. In some versions, end effector (70312) may be provided for use in robotic systems. In such robotic systems, modular shaft (70322) having any of the following end effector (70312) may be attachable to a portion of the robotic system for use such that handle portion (70320) is replaced by components of the robotic system, including a body. Other ways to incorporate end effector (70312) having any of the following placement tips (70314) into a user operated or robotic operated instrument will be apparent to those of ordinary skill in the art.

Placement tip (70314) is operable to elastically deform from a non-deflected position to a deflected position. Placement tip (70314) obtains the non-deflected position when end effector (70312) is not clamping tissue. More specifically, in this non-deflected position, end effector (70312) may be in the open configuration as shown in FIG. 99, or in the closed configuration as shown in FIGS. 8 and 9 with respect to end effector (212). In instances when end effector (70312) are in this non-deflected position, end effector (70312) may be considered in a non-loaded state or non-loaded position. Conversely, in the deflected position (not shown) when end effector (70312) is clamping tissue, end effector (70312) may be considered in a loaded state or a loaded position. In the deflected position, at least a portion of placement tip (70314) deflect upwardly. The deflected position for placement tip (70314) may be substantially straight in some versions, but may be deflected to a degree (e.g., slightly above or slightly below longitudinal (LA71)) in other versions. It should be understood that the deflected position for placement tip (70314) may be defined by the characteristics (e.g., thickness, density, etc.) of the tissue that is being captured between respective lower jaw (70316) and anvil (70318), thereby causing the deflection of placement tip (70314). In some variations, placement tip (70314) does not deflect in response to a load.

FIG. 99 shows surgical instrument (70310), configured as a surgical stapler, that comprises another exemplary end effector (70312) and another exemplary placement tip (70314). End effector (70312) includes an upper jaw and a lower jaw (70316), with the upper jaw including an anvil (70318). Instrument (70310) additionally includes a body, shown as a handle portion (70320), and a shaft (70322) that extends from handle portion (70320). As shown in FIG. 99, shaft (70322) defines a longitudinal axis (LA71) that is colinear with an end effector axis (EEA71) of end effector (70312), but which may non-colinear, and instead angled, when end effector (70312) is articulated relative to shaft (70322) using articulation joint (70323).

Placement tip (70314) is located adjacent at least one of a distal end (70321) of anvil (70318) or a distal end of lower jaw (70316). As shown in FIG. 99, placement tip (70314) is coupled with distal end (70321) of anvil (70318). Placement tip (70314) may be permanently coupled with anvil (70318), or alternatively, placement tip (70314) may be removably coupled with anvil (70318). Placement tip (70314) may be integrally formed together with anvil (70318) as unitary piece or consist of separately formed components. Placement tip (70314) may be positioned on the same jaw as staple cartridge (70324) or on the same jaw as anvil (70318). As shown in FIG. 99, upper jaw includes anvil (70318), while lower jaw (70316) is removably coupled with staple cartridge (70324). However, this relationship may be reversed if desired. Staple cartridge (70324) is configured to hold one or more staples in a manner similar to staple cartridge (37). Staple cartridge includes an angled distal portion (70326). As previously described, at least one of anvil (70318) or lower jaw (70316) is movable relative to other of anvil (70318) or lower jaw (70316) between the open configuration and the closed configuration. As shown, anvil (70318) pivotably rotates toward lower jaw (70316) in the same manner as anvil (18) as described above with respect to instrument (10). In this manner, end effector (70312) is like end effector (12), except for the laterally deflected configuration and deformability of placement tip (70314).

B. Exemplary Buttress Assembly for Surgical Stapler

In some instances, it may be desirable to equip end effectors (12, 212, 70312) with a buttress material to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (7043). In some other instances, a buttress may be provided on the surface of anvil (18, 218, 70318) that faces staple cartridge (37, 237, 70324). It should also be understood that a first buttress may be provided on upper deck (72) of staple cartridge (37, 237, 70324) while a second buttress is provided on anvil (18, 218, 70318) of the same end effector (12, 212). Various examples of forms that a buttress may take will be described in greater detail below. Various ways in which a buttress may be secured to a staple cartridge (37, 237, 70324) or an anvil (18, 218, 70318) will also be described in greater detail below. Exemplary buttress assemblies, exemplary materials and techniques for applying buttress assemblies, and exemplary buttress applier cartridges may be configured in accordance with at least some of the teachings of U.S. Pub. No. 2017/0055981 entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein.

1 Exemplary Composition of Buttress Assembly for Surgical Stapler

FIG. 100 shows an exemplary pair of buttress assemblies (70410, 70412) with a basic composition. Buttress assembly (70410) of this example comprises a buttress body (70414) and an upper adhesive layer (70416). Similarly, buttress assembly (70412) comprises a buttress body (70418) and a lower adhesive layer (70420). In the present example, each buttress body (70414, 70418) comprises a strong yet flexible material configured to structurally support a line of staples (70447). By way of example only, each buttress body (70414, 70418) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (70414, 70418).

Each buttress body (70414, 70418) may comprise a material including, for example, a hemostatic agent such as fibrin to assist in coagulating blood and reduce bleeding at the severed and/or stapled surgical site along tissue ($T_{71}$, $T_{72}$). As another merely illustrative example, each buttress body (70414, 70418) may comprise other adjuncts or hemostatic agents such as thrombin may be used such that each buttress body (70414, 70418) may assist to coagulate blood and reduce the amount of bleeding at the surgical site. Other adjuncts or reagents that may be incorporated into each buttress body (70414, 70418) may further include but are not limited to medical fluid or matrix components. Merely illustrative examples of materials that may be used to form each buttress body (70414, 70418), as well as materials that may be otherwise incorporated into each buttress body (70414, 70418), are disclosed in U.S. Pub. No. 2016/0278774, entitled "Method of Applying a Buttress to a Surgical Stapler," published Sep. 29, 2016, issued as U.S. Pat. No. 10,349,939 on Jul. 19, 2019, the disclosure of which is incorporated by reference herein. Alternatively, any other suitable materials may be used.

In the present example, adhesive layer (70416) is provided on buttress body (70414) to adhere buttress body (70414) to underside (70424) of anvil (18). Similarly, adhesive layer (70420) is provided on buttress body (70418) to adhere buttress body (70418) to upper deck (72) of staple cartridge (37). Such an adhesive material may provide proper positioning of buttress body (70414, 70418) before and during actuation of end effector (12); then allow buttress body (70414, 70418) to separate from end effector (12) after end effector (12) has been actuated, without causing damage to buttress body (70414, 70418) that is substantial enough to compromise the proper subsequent functioning of buttress body (70414, 70418). Examples of various suitable materials that may be used to form adhesive layers (70416, 70420) are disclosed in U.S. Pub. No. 2016/0278774, issued as U.S. Pat. No. 10,349,939 on Jul. 16, 2019, the disclosure of which is incorporated by reference herein.

2. Exemplary Materials and Techniques for Providing Adhesion of Buttress to Surgical Stapler FIGS. 101A-101C show a sequence where an end effector (12) that has been loaded with buttress assemblies (70410, 70412) is actuated to drive staples (47) through two opposed layers of tissue ($T_{71}$, $T_{72}$), with buttress assemblies (70410, 70412) being secured to the same layers of tissue ($T_{71}$, $T_{72}$) by staples (47). In particular, FIG. 101A shows layers of tissue ($T_{71}$, $T_{72}$) positioned between anvil (18) and staple cartridge (37), with anvil (18) in the open position. Buttress assembly (70410) is adhered to underside (70424) of anvil (18) via adhesive layer (70416); while buttress assembly (70412) is adhered to upper deck (72) of staple cartridge (37) via adhesive layer (70420). Layers of tissue ($T_{71}$, $T_{72}$) are thus interposed between buttress assemblies (70410, 70412). Next, closure trigger (26) is pivoted toward pistol grip (24) to drive closure tube (7032) and closure ring (7033) distally. This drives anvil (18) to the closed position as shown in FIG. 101B. At this stage, layers of tissue ($T_{71}$, $T_{72}$) are compressed between anvil (18) and staple cartridge (37), with buttress assemblies (70410, 70412) engaging opposite surfaces of tissue layers ($T_{71}$, $T_{72}$). End effector (12) is then actuated as described above, driving staple (47) through buttress assemblies (70410, 70412) and tissue ($T_{71}$, $T_{72}$). As shown in FIG. 101C, crown (70422) of driven staple (47) captures and retains buttress assembly (70412) against layer of tissue ($T_{72}$). Deformed legs (70426) of staple (47) capture and retain buttress assembly (70410) against layer of tissue ($T_{71}$).

A series of staples (47) will similarly capture and retain buttress assemblies (70410, 70412) against layers of tissue ($T_{71}$, $T_{72}$), thereby securing buttress assemblies (70410, 70412) to tissue ($T_{71}$, $T_{72}$) as shown in FIG. 102. As end effector (12) is pulled away from tissue ($T_{71}$, $T_{72}$) after deploying staples (47) and buttress assemblies (70410, 70412), buttress assemblies (70410, 70412) disengage end effector (12), such that buttress assemblies (70410, 70412) remain secured to tissue ($T_{71}$, $T_{72}$) with staples (47). Buttress tissue ($T_{71}$, $T_{72}$) thus provide structural reinforcement to the lines of staples (47). As can also be seen in FIG. 102, distally presented cutting edge (7048) of firing beam (14) also cuts through a centerline of buttress tissue assemblies (70410, 70412), separating each buttress assemblies (70410, 70412) into a corresponding pair of sections, such that each section remains secured to a respective severed region of tissue ($T_{71}$, $T_{72}$).

3. Exemplary Buttress Applier Cartridge with Active Retainer Arms

Because end effector (12) may be actuated many times during use of instrument (10) in a single surgical procedure, it may be desirable to enable an operator to repeatedly and easily load buttress assemblies (70410) on underside (70424) of anvil (18) during that single surgical procedure. FIGS. 103-105B show an exemplary buttress applier cartridge (70510) that may be used to support and protect buttress assemblies (70410, 70412). Cartridge (70510) may also be used to easily load buttress assemblies (70410, 70412) on end effector (12). As best seen in FIGS. 103-104, cartridge (70510) of this example comprises an open end (70512) and a closed end (70514). Open end (70512) is configured to receive end effector (12) as will be described in greater detail below. Cartridge (70510) further includes a first housing (70516a) and a second housing (70516b), which each generally define a "U" shape to present open end (70512). A platform (70518) and a sled retainer (70520) are interposed between first and second housings (70516a-b).

Platform (70518) of the present example is configured to support a pair of buttress assemblies (70410) on one side of platform (70518) and another pair of buttress assemblies (70412) on the other side of platform (70518). Platform (70518) is exposed in recesses that are formed between the prongs of the "U" configuration of first and second housings (70516a-b). Each buttress assembly (70410, 70412) is provided in a respective pair of portions that are separated to avoid spanning across slots (42, 49) of anvil (18) and staple cartridge (37), respectively, though platform (70518) may just as easily support wide versions of buttress assemblies (70410, 70412) that unitarily span across slots (42, 49) of anvil (18) and staple cartridge (37), respectively. More specifically, the outer edges of platform (70518) include retention features (70530) in the form of ridges that further engage first and second housings (70516a-b) to prevent platform (70518) from sliding relative to first and second housings (70516a-b).

First and second housings (70516a-b) include integral gripping features (70522) that have a surface geometry that is configured to promote an operator's grip of cartridge (70510) during use of cartridge (70510). Indicator plates (70524) are positioned to correspond with windows (70526) that are formed in first and second housings (70516a-b), such that indicator plates (70524) are visible through windows (70526) at different times. Arms (70528) of the present example are configured to selectively secure buttress assemblies (70410, 70412) to platform (70518). In the present example, arms (70528) are resilient and are thus configured to resiliently bear against buttress assemblies (70410, 70412), thereby pinching buttress assemblies (70410, 70412) against platform (70518). Buttress applier cartridge (70510) includes a tapered cam surface (70532) and a housing engagement feature (70534). As best seen in FIG. 104, housing engagement features (70534) are positioned to engage corresponding surfaces of first and second housings (70516a-b). As shown in FIGS. 103-104, first and second housings (70516a-b) include proximal guide features (70536) and distal guide features (70538). Guide features (70536, 70538) are configured to assist in providing proper alignment of end effector (40) with cartridge (70510). In the present example, guide features (70536, 70538) are unitarily formed features of first and second housings (70516a-b).

FIG. 105A shows cartridge (70510) in a configuration where retainer arms (70528) are positioned to hold buttress assemblies (70410, 70412) against platform (70518); while FIG. 105B shows cartridge (70510) in a configuration where retainer arms (70528) are positioned to release buttress assemblies (70410, 70412) from platform (70518). While FIGS. 105A-105B only show buttress assembly (70410) on platform (70518), buttress assembly (70412) would be retained on and released from platform (70518) in an identical fashion. To use cartridge (70510) to load end effector (12), the operator would first position cartridge (70510) and end effector (12) such that end effector is aligned with open end (70512) of cartridge (70510) as shown in FIG. 105A. The operator would then advance end effector (12) distally (and/or retract cartridge (70510) proximally) to position platform (70518) and buttress assemblies (70410, 70412) between anvil (18) and staple cartridge (37) as shown in FIG. 105B. This will ultimately result in the arrangement shown in FIG. 105A.

C. Exemplary Buttress Applier Cartridges

It may be desirable to use buttress assemblies (70410, 70412) with end effector (212, 70312). However, since end effectors (212, 70312) have curved distal tips (219, 70314), it may be difficult or impractical to use cartridge (70510) to load buttress assemblies (70410, 70412) on end effectors (212, 70312). It may therefore be desirable to provide a modified version of cartridge (70510) that accommodates curved distal tips (219, 70314), thereby facilitating loading of buttress assemblies (70410, 70412) on end effectors (212, 70312). Examples of such a buttress applier cartridge (70610, 70710) are described below. While buttress applier cartridges (70610, 70710) are described in the context of end effector (70312), buttress applier cartridges (70610, 70710) may also be used with end effector (212) and other end effectors that have curved or otherwise deflected distal tip portions.

1. Another Exemplary Buttress Applier Cartridge

FIGS. 106-108B show another exemplary buttress applier cartridge (70610) that may be used to support and protect buttress assemblies (70410, 70412). Buttress applier cartridge (70610) may also be used to easily load buttress assemblies (70410, 70412) on end effector (70312). As shown in FIG. 106, buttress applier cartridge (70610) includes an open end (70612) and a closed end (70614). Open end (70612) is configured to receive end effector (70312), in a similar manner as buttress applier cartridge (70510) shown in FIGS. 105A-105B. While buttress applier cartridge (70610) is described and shown below with relation to instrument (70310), end effector (70312), placement tip (70314), lower jaw (70316), anvil (70318) and staple cartridge (70324), principles are also applicable to other instruments have curved distal tips, such as end effector (212) that includes lower jaw (216), anvil (218), distal tip (219) and staple cartridge (37).

With continued reference to FIG. 106, buttress applier cartridge (70610) includes a first housing (70616a) and a second housing (70616b), with each generally defining a "U" shape to present open end (70612). First and second housings (70616a-b) define a gap (G70) configured to receive a portion of an end effector (70312) of a surgical stapler (70310). First and second housings (70616a-b) receive a platform (70618). First housing (70616a) includes proximal and distal portions (70620a, 70622a), while second housing (70616b) includes proximal and distal portions (70620b, 70622b). As shown, first and second housings (70616a-b) are separately formed from platform (70618) and subsequently coupled with platform (70618). Alternatively, first and second housings (70616a-b) may be integrally formed together as a unitary piece together and subsequently coupled with platform (70618), or alternatively, first and second housings (70616a-b) may be integrally formed together as a unitary piece together with platform (70618). As shown, first and second housings (70616a-b) and platform (70618) are symmetric about a plane generally defined by platform (70618). In other words, using the spatial orientation of FIG. 107, the left side of the buttress applier cartridge (70610) is symmetric to the right side of the buttress applier cartridge (70610). Similarly, using the spatial orientation of FIG. 108A-108B showing distal portions (70622a-b, 70630), the top side of the buttress applier cartridge (70610) is symmetric to the bottom side of the buttress applier cartridge (70610). The buttress applier cartridge (70610) may be non-symmetric if desired.

Platform (70618) is configured to support one or more buttress assemblies (70400, 70410) against a first side (70624) (e.g. a top side) of platform (70618) and one or more buttress assemblies (70412) against a second side (70626) (e.g. a bottom side) of platform (70618). As shown, platform (70618) includes proximal and distal portions (70628, 70630). Platform (70618) is disposed between first and second housings (70616a-b). A portion of platform (70618) is disposed within gap (G70) defined by first and second housings (70616a-b). The location of platform (70618) and buttress assemblies (70410, 70412) in the gap (G70) may prevent inadvertent contact between buttress assemblies (70410, 70412) and other devices in the operating room. In other words, first and second housings (70616a-b) may provide some degree of physical shielding of buttress assemblies (70410, 70412). Outer portions of platform (70618) may be captured between first and second housings (70616a-b) to thereby securably couple platform (70618) with first and second housings (70616a-b).

In some versions, platform (70618) is formed of a material that provides a high coefficient of friction, thereby reducing any tendency that buttress assemblies (70410, 70412) might otherwise have to slide along corresponding surfaces of platform (70618). For instance, platform (70618) may comprise an elastomeric material and/or a foam material. In some instances, platform (70618) is formed of a compressible foam material that is configured to maintain a compressed configuration after being compressed by end effector (70312). By way of example only, platform (70618) may comprise Santoprene, closed-cell polyurethane foam, any other compressible material, and/or a material that may be made compressible via geometry (e.g., a rubber material with deformable standing features). Various suitable materials and structural configurations that may be used to form platform (70618) will be apparent to those of ordinary skill in the art in view of the teachings herein.

At least one of distal portion (70630) of platform (70618) or distal portion (70622a-b) of first and second housings (70616a-b) include one or more cavities configured to receive a curved distal tip (70314) of a first jaw of end effector (70312). As shown in FIGS. 106-108B, first housing (70616a) includes a first cavity (70632) disposed adjacent first side (70624) of platform (70618). First cavity (70632) enables curved distal tip (70314) to extend below a staple deck (such as staple deck (72) of staple cartridge (37)) in the closed configuration. First cavity (70632) terminates at a top surface of platform (70618). As shown, first cavity (70632) extends generally perpendicular to platform (70618). However, first cavity (70632) may extend at various suitable angles relative to platform (70618). As shown, first cavity (70632) has a cross-sectional area that increases moving towards platform (70618). First cavity (70632) has an inner perimeter (IP70) defined by inner walls (70634) that is configured to closely accommodate an outer perimeter (OP70) of curved distal tip (70314) of end effector (70312). As shown, first cavity (70632) does not extend across the entire width of gap (G70); however, first cavity (70632) may extend across the entire width of gap (G70) if desired. As shown in FIG. 108B, curved distal tip (70314) of end effector (70312) is configured to deform against platform (70618) when end effector (70312) is in the closed configuration.

Since buttress applier cartridge (70610) is shown as being symmetric, a second cavity (70636) having inner walls (70638) is adjacent second side (70626) of platform (70618). As shown in FIG. 107, second cavity (70636) terminates at second side (70626) of platform (70618). Since first and second cavities (70632, 70636) have inner perimeter (IP70) configured to receive outer perimeter (OP70) of placement tip (70314), the particular shapes and sizes of first and second cavities (70632, 70636) may vary to correspond with the desired placement tip (70314). As such, it is envisioned that second cavity (70636) may be sized and shaped similar to first cavity (70632), or alternatively, may be sized and/or shaped differently than first cavity (70632), such that second cavity (70636) is configured to receive a different placement tip than first cavity (70632) if desired.

At least one of distal portion (70630) of platform (70618) or distal portion (70622a-b) of housings (70616a-b) include a surface configured to assist in placement of a staple cartridge (70324) of a second jaw of end effector (70312). As shown in FIGS. 107-108B, second housing (70616b) includes a first angled surface (70640) formed on an opposing side of first cavity (70632). First angled surface (70640) extends across gap (G70) adjacent second side (70626) of platform (70618). First angled surface (70640) is configured to assist in placement of a second jaw of end effector (212, 70312) adjacent second side (70626) of platform (70618). More specifically, first angled surface (70640) is configured to assist in placement of staple cartridge (37, 70324). As shown, placement tip (70314) is coupled with anvil (70318) is disposed opposite lower jaw (70316) this is configured to receive staple cartridge (70324). First angled surface (70640) is in abutting contact with a distal angled portion (70326) of staple cartridge (37, 70337) when the opposing jaws (such as lower jaw (16) and anvil (18)) are moving towards the closed configuration. Additionally, first angled surface (70640) includes ridges (70642) if desired.

As shown, first housing (70616a) includes a second angled surface (70644) formed on an opposing side of second cavity (70636). Second angled surface (70644) extends across gap (G70) adjacent first side (70624) of platform (70618). Second angled surface (70644) is configured to assist in placement of a first jaw of end effector (70312) adjacent first side (70624) of platform (70618). More specifically, second angled surface (70644) may generally assist in placement of placement tip (70314). Second angled surface (70644) may include ridges (70646).

As shown in FIGS. 106-108B, first buttress assembly (70410) is positioned on at least proximal portion (70628) of platform (70618). First buttress assembly (70410) is disposed in gap (G70) defined by housings (70616a-b). As shown in FIG. 107-108B, second buttress assembly (70412) is positioned on second side (70626) of platform (70618). Additionally, as shown with respect to FIGS. 103-105A, buttress assemblies (70410, 70412) may be provided in a respective pair of portions that are separated at a distance to avoid spanning across slots (42, 49) to support wide versions of buttress assemblies (70410, 70412) that unitarily span across slots (42, 49) of anvil (18) and staple cartridge (37) referring to instrument (10), respectively.

FIGS. 108A-108B depict an exemplary method of using cartridge (70610) to secure buttress assemblies (70410, 70412) to end effector (70312). The method includes positioning platform (70618) of buttress applier cartridge (70610) between the first and second jaws of end effector (70312), such that buttress assembly (70410) is below anvil (70318) and buttress assembly (70412) is above the deck of lower jaw (70316), while first and second jaws are in an open configuration. First cavity (70632) accommodates curved distal tip (70314) during such positioning. The method also includes driving one or both of the first or second jaws of end effector (70312) toward platform (70618) to thereby engage buttress assemblies (70410, 70412). As shown in FIG. 108B, as curved distal tip (70314) of end effector (70312) contacts and subsequently deforms against first side (70624) of platform (70618) when end effector (70312) moves to the closed configuration, the angle of curved distal tip (70314) changes. The method also includes driving one or both of the first or second jaws of end effector (70312) away from platform (70618) to thereby pull buttress assemblies (70410, 70412) off of platform (70618).

2. Another Exemplary Buttress Applier Cartridge

FIGS. 110-111B show another exemplary buttress applier cartridge (70710). Like buttress applier cartridge (70610), buttress applier cartridge (70710) of this example may be used with any end effector (12, 70312, 70412) described herein and in any of the various procedures described in the various patent references cited herein. Buttress applier cartridge (70710) is configured and operable just like buttress applier cartridge (70610), except for the differences indicated below.

Buttress applier cartridge (70710) includes an open end (70712), a closed end (70714), a first housing (70716a), a second housing (70716b), a platform (70718), a proximal portion (70720), a distal portion (70722), a first side (70724), a second side (70726), a proximal portion (70728), a distal portion (70730), a first cavity (70732), inner walls (70734), a second cavity (70736), inner walls (70738), a first angled surface (70740), ridges (70742), a second angled surface (70744), and ridges (70746). To this end, like numbers below indicate like features described above. Except as otherwise described below, certain details of buttress applier cartridge (70710) will therefore be omitted from the following description, it being understood that such details are already provided above in the description of buttress applier cartridge (70610). Other suitable ways in which various buttress applier cartridges may be used will be apparent to those of ordinary skill in the art in view of the teachings herein.

As shown in FIGS. 110-111B, first and second cavities (70732, 70736) connect, and therefore, extend completely through platform (70718). In other words, first and second cavities (70732, 70736) extend completely through first and second sides (70724, 70726) of platform (70718), defining a passageway that passes through the full thickness of cartridge (70710). First and second cavities (70732, 70736) extending completely therethrough platform (70718) allow placement tip (70314) to maintain its curved shape and not deform against platform (70718) when end effector (70312) is in the closed configuration as shown in FIG. 111B. Buttress applier cartridge (70710) may thus be used for versions where distal tip (219) or placement tip (70314) is rigid; or when it is desired that distal tip (219) or placement tip (70314) not deflect.

XII. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of surgical stapling using an apparatus comprising a body, a shaft extending from the body, and an end effector in communication with the shaft, wherein the method comprises: (a) positioning the end effector at a desired site for surgical stapling, wherein the end effector includes: (i) a pair of jaws, (ii) a cartridge configured to hold one or more staples, wherein the cartridge selectively connects with a first jaw of the pair of jaws, (iii) an anvil configured to be contacted by the one or more staples of the cartridge, wherein a second jaw of the pair of jaws comprises the anvil, and (iii) a placement tip selected from the group consisting of: (A) a placement tip that is elastically deformable, wherein the placement tip extends distally from a select one of the pair of jaws, wherein the placement tip defines a first angle with respect to an axis of the select one of the jaws from which the placement tip extends when the end effector is in the open position, and a second angle with respect the axis of the select one of the jaws from which the placement tip extends when the end effector is in a closed position, wherein the second angle differs from the first angle; (B) a placement tip that is elastically deformable, wherein the placement tip extends distally from a select one of the pair of jaws, wherein the placement tip comprises a distal end, wherein the placement tip is configured to transition from a first undeflected state to a second deflected state when the end effector is in the closed position and loaded, wherein when the placement tip is in the first undeflected state the distal end of the placement tip is located proximal to a distal-most end of the jaw opposite to the select one of the jaws from which the placement tip extends, and wherein when the placement tip is in the second deflected state the distal end of the placement tip is located distal to the distal-most end of the jaw opposite to the select one of the jaws from which the placement tip extends; (C) a placement tip comprised of a resilient material and extending distally from a select one of the pair of jaws, wherein the placement tip defines a third longitudinal axis that is oblique relative to a second longitudinal axis defined by the first jaw from which the placement tip extends, and wherein the third longitudinal axis defined by the placement tip extends in a direction towards the second jaw; (D) a placement tip extending distally from the second jaw, wherein the placement tip is comprised of a second material, wherein the second material is resilient, and wherein the placement tip comprises a lower stiffness than the first jaw; (E) a placement tip that is elastically deformable, wherein the placement tip extends distally from the second jaw, wherein the placement tip comprises an arcuate bend relative to a longitudinal axis of the anvil; (F) a placement tip that is elastically deformable and extends distally from a select one of the pair of jaws, wherein the placement tip comprises a pair of sides defining multiple distinct regions that each comprises a width, wherein as the pair of sides extend distally each width of the distinct regions is smaller than the width of the immediate proximally located distinct region; and (G) a placement tip that is elastically deformable and extends distally from the second jaw and distally beyond the cartridge, wherein the placement tip extends in a straight manner along a longitudinal axis defined by the anvil; (b) controlling one or more of the jaws of the end effector to place the end effector in an open position, wherein in the open position a gap exists between the jaws; (c) positioning the end effector, with the end effector in the open position, such that tissue is located between the jaws; (d) clamping the tissue between the jaws by moving at least one of the jaws toward the other jaw, wherein clamping the tissue places the end effector in a loaded state, wherein in the loaded state the placement tip of the second jaw deflects away from the first jaw; and (e) advancing a firing beam of the apparatus from a proximal position to a distal position, wherein advancing the firing beam causes the tissue to be cut by a cutting edge of the firing beam, and wherein advancing the firing beam further causes the tissue to be stapled by ejecting the one or more staples from the cartridge.

Example 2

The method of Example 1, wherein the placement tip extends distally from the anvil, wherein the first jaw includes an anvil coupled with the placement tip, wherein the placement tip is configured to contact the staple cartridge in the closed position, wherein the placement tip is integrally formed together as a unitary piece, wherein the placement tip is symmetric about the longitudinal axis.

Example 3

The method of any one or more of Examples 1 through 2, wherein the placement tip is elastically deformable, wherein the placement tip is comprised of a first resilient material, wherein the first jaw from which the placement tip extends is comprised of a second material, wherein the first resilient material has a lower stiffness than the second material, wherein the placement tip is configured to deflect in response to a clamping force applied to the placement tip.

Example 4

The method of any one or more of Examples 1 through 3, wherein the placement tip is configured such that, when the end effector is in a closed and unloaded state, the placement tip contacts a portion of the second jaw, and wherein when the end effector is in a loaded state with tissue between the first and second jaws, the placement tip deflects away from the second jaw, and wherein the placement tip extends distally from the first jaw in a curved manner.

Example 5

The method of any one or more of Examples 1 through 4, wherein the placement tip further comprises a distal end having a profile selected from the group comprising round, angled and pointed, toothed, flared, orb, asymmetric, and combinations thereof, or distal sides defining a width profile selected from the group comprising angled, stepped, asymmetric, scalloped, bump-out, and combinations thereof.

Example 6

The method of any one or more of Examples 1 through 5, wherein the end effector defines a plurality of zones based on (a) a first plane defined by the distal-most end of the jaw opposite to the select one of the jaws from which the placement tip extends, (b) a second plane defined by a deck of the jaw opposite to the select one of the jaws from which the placement tip extends, wherein the first and second planes are orthogonal to each other, and (c) a third plane defined by a bottom surface of the jaw opposite to the select one of the jaws from which the placement tip extends, wherein the third and first plane are orthogonal to each other, and wherein the distal end of the placement tip is configured to move from one zone of the plurality of zones when the placement tip is in the first undeflected state to another zone of the plurality of zones when the placement tip is in the second deflected state.

Example 7

The method of any one or more of Examples 1 through 6, wherein the placement tip comprises at least one of a curved longitudinal cross-sectional profile, a multi-angled longitudinal cross-sectional profile, a non-rectangular lateral cross-sectional profile, an inverted U-shaped lateral cross-sectional profile, an inverted V-shaped lateral cross-sectional profile, an H-shaped lateral cross-sectional profile, or an oval lateral cross-sectional profile.

Example 8

The method of any one or more of Examples 1 through 7, wherein the placement tip comprises a proximal lateral cross-sectional profile and a distal lateral cross-sectional profile, wherein the proximal lateral cross-sectional profile and the distal lateral cross-sectional profile have different shapes.

Example 9

The method of any one or more of Examples 1 through 8, wherein the placement tip comprises an arcuate bend relative to a longitudinal axis of the anvil.

Example 10

The method of any one or more of Examples 1 through 9, wherein the placement tip is elastically deformable, and wherein the apparatus further comprises a retention feature configured to secure the placement tip with the first jaw, wherein the retention feature is further configured to prevent removal of the placement tip when the retention feature is installed, wherein the retention feature connects a proximal portion of the placement tip with the first jaw, wherein the proximal portion of the placement tip comprises a connection member, wherein the connection member comprises an opening configured to receive the fastener, and wherein the first jaw comprises a void space having a complementary shape to the connection member of the placement tip, wherein the first jaw comprises a void space having a complementary shape to the connection member of the placement tip.

Example 11

The method of any one or more of Examples 1 through 10, wherein the first jaw comprises a surface feature at a distal end of the first jaw, wherein the surface feature is configured for overmolding attachment of the placement tip with the first jaw such that the placement tip extends distally from the first jaw, wherein the surface feature of the first jaw is further configured to prevent detachment of the overmolded placement tip, wherein the surface feature of the first jaw is at least substantially surrounded by the overmolded placement tip, wherein the surface feature is further configured to prevent edge peeling of the overmolded placement tip.

Example 12

A method of surgical stapling using an apparatus comprising a body, a shaft extending from the body, and an end effector in communication with the shaft, wherein the method comprises: (a) positioning the end effector at a desired site for surgical stapling, wherein the end effector includes: (i) a pair of jaws, (ii) a cartridge configured to hold one or more staples, wherein the cartridge selectively connects with a first jaw of the pair of jaws, (iii) an anvil configured to be contacted by the one or more staples of the cartridge, wherein a second jaw of the pair of jaws comprises the anvil, and (iv) a placement tip selected from the group consisting of: (A) a placement tip located at a distal end of the first jaw or a distal end of the second jaw, wherein the placement tip comprises: (1) first and second legs extending distally from one of the first or second jaws, wherein a void extends completely through the placement tip and separates the first and second legs, and (2) a distal portion that connects the first and second legs, wherein the distal portion has a first cross-sectional height that is greater than a second cross-sectional height of the first and second legs (B) a placement tip located at a distal end of the first jaw or a distal end of the second jaw, wherein the placement tip includes a body portion formed between an outer perimeter and an inner perimeter of the placement tip, wherein the inner perimeter is defined by a void extending through the placement tip, and wherein at least a distal end of the body portion is bent towards the opposing jaw; (C) a placement tip extending from a distal end of the first jaw or a distal end of the second jaw, wherein the placement tip extends along a curvilinear path and terminates at a tip end, wherein the placement tip is configured such that successive perimeters of the placement tip taken perpendicular to the curvilinear path decrease moving toward the tip end, and wherein the tip end extends at a non-zero angle relative to the longitudinal axis of the end effector (D) a placement tip extending from a distal end of the first jaw or a distal end of the second jaw, wherein the placement tip comprises: (1) a proximal portion having a proximal tip width, and (2) a distal portion having a distal tip width that is greater than a jaw width of the jaw disposed opposite the placement tip (E) a placement tip extending from a distal end of the first jaw or a distal end of the second jaw, wherein the placement tip includes proximal and distal portions, wherein the distal portion includes an asymmetric profile along the longitudinal axis of the shaft, and wherein the distal portion includes a tip axis defined by a tip of the distal portion; (F) a placement tip located at a distal end of the first jaw or a distal end of the second jaw, wherein the placement tip includes proximal and distal portions, wherein the distal portion has a distal cross-sectional thickness along a transverse cross-section that is greater than a proximal cross-sectional thickness of the proximal portion along the transverse cross-section; and (G) a placement tip located at a distal end of the first jaw or a distal end of the second jaw, wherein the placement tip comprises: (1) a proximal portion having a proximal tip width that is less than a proximal jaw width of the jaw disposed opposite the placement tip, and (2) a distal portion having a distal tip width that is greater than a distal jaw width of the jaw disposed opposite the placement tip; (b) controlling one or more of the jaws of the end effector to place the end effector in an open position, wherein in the open position a gap exists between the jaws; (c) positioning the end effector, with the end effector in the open position, such that tissue is located between the jaws; (d) clamping the tissue between the jaws by moving at least one of the jaws toward the other jaw, wherein clamping the tissue places the end effector in a loaded state, wherein in the loaded state the placement tip of the second jaw deflects away from the first jaw; and (e) advancing a firing beam of the apparatus from a proximal position to a distal position, wherein advancing the firing beam causes the tissue to be cut by a cutting edge of the firing beam, and wherein advancing the firing beam further causes the tissue to be stapled by ejecting the one or more staples from the cartridge.

Example 13

The method of any one or more of Examples 1 through 12, further comprising a malleable member configured to increase the rigidity of the placement tip and configured to allow an operator to customize the shape of the placement tip by producing different placement tip angles, wherein the malleable member includes first and second legs and a generally U-shaped portion configured to contact the outer perimeter of the body portion.

Example 14

The method of any one or more of Examples 1 through 13, wherein the placement tip includes proximal and distal portions, wherein the proximal portion has a proximal tip width that is less than a jaw width of the jaw disposed opposite the placement tip, and wherein the distal portion has a distal tip width that is greater than the jaw width of the jaw disposed opposite the placement tip.

Example 15

The method of any one or more of Examples 1 through 14, further comprising an articulation joint coupling the shaft with the end effector, wherein the articulation joint is configured to enable the end effector to pivot relative to the shaft, wherein the shaft axis and the tip axis define an angle that is selectively adjustable by a user using the articulation joint, wherein the angle is selectively adjustable from an acute angle along a first direction of articulation to an obtuse angle along a second direction of articulation, wherein the second direction is opposite the first direction.

Example 16

The method of any one or more of Examples 1 through 15, wherein the placement tip further comprises a central portion disposed longitudinally between the proximal and distal portions, wherein the central portion has a central cross-sectional thickness along the transverse cross-section that is less than the proximal cross-sectional thickness and less than the distal cross-sectional thickness or the central portion has a central cross-sectional thickness along the transverse cross-section that is greater than the proximal cross-sectional thickness but less than the distal cross-sectional thickness.

Example 17

The method of any one or more of Examples 1 through 16, further comprising securing a buttress assembly to the end effector, the securing step further comprises: (i) positioning a platform of a buttress applier cartridge between the first and second jaws while the first and second jaws are in an open configuration, wherein the platform has a buttress disposed thereon; (ii) driving one or both of the first and second jaws toward the platform to thereby engage the buttress assembly with one of the first and second jaws, wherein a distal portion of the buttress applier cartridge includes a cavity that is sized and shaped to receive a curved distal tip of one of the first or second jaws, wherein the curved distal tip extends beyond a staple deck of a staple cartridge of the other of first or second jaws when in the closed configuration; and (iii) driving one or both of the first or second jaws away from the platform to thereby pull the buttress assembly off of the platform.

Example 18

The method of any one or more of Examples 1 through 17, wherein the cavity terminates at a planar surface of the platform, wherein the curved distal tip of the end effector is configured to deform against the platform when the end effector is in the closed configuration, or the cavity extends completely through the platform, wherein the curved distal tip of the end effector is configured to maintain its curved shape and not deform against the platform when the end effector is in the closed configuration such that the curved distal tip is configured to extend below a staple deck of the opposing staple cartridge of the end effector in the closed configuration.

Example 19

The method of any one or more of Examples 1 through 18, wherein the end effector includes first and second opposing jaws, wherein the first jaw includes the curved distal tip and the second jaw includes a staple cartridge, wherein the distal portion of the housing or the distal portion of the platform includes a first angled surface that is configured to be in abutting contact with a distal angled portion of the staple cartridge, wherein the apparatus is symmetric about a plane defined by the platform, wherein the cavity extends perpendicular to the platform, and wherein the cavity has a cross-sectional area that increases moving towards the platform, and wherein the cavity does not extend across the entire width of the gap.

Example 20

A method of operating an instrument, the method comprising: (a) placing a placement tip of a jaw of the instrument between first and second layers of tissue that collectively define a tissue opening using only a lateral motion, wherein the placement tip is oriented along a tip axis that is laterally oriented in relation to a longitudinal axis of a proximal portion of the jaw; (b) laterally moving the placement tip of the instrument along the tip axis through the tissue opening; (c) and advancing the placement tip distally through the tissue opening.

XIII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed Feb. 17, 2017, issued as U.S. Pat. No. D833,010 on Nov. 6, 2018, the disclosure of which is incorporated by reference herein. Various suitable ways in which the teachings herein may be combined with the teachings of U.S. patent application Ser. No. 29/594,335, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed Feb. 17, 2017, issued as U.S. Pat. No. 10,729,434 on Aug. 4, 2020, the disclosure of which is incorporated by reference herein. Various suitable ways in which the teachings herein may be combined with the teachings of U.S. patent application Ser. No. 15/435,607 issued as U.S. Pat. No. 10,729,434 on Aug. 4, 2020, will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed Feb. 17, 2017, issued as U.S. Pat. No. 10,806,451 on Oct. 20, 2020, the disclosure of which is incorporated by reference herein. Various suitable ways in which the teachings herein may be combined with the teachings of U.S. patent application Ser. No. 15/435,618, issued as U.S. Pat. No. 10,806,451 on Oct. 20, 2020, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340, issued as U.S. Pat. No. D836, 199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, issued as U.S. Pat. No. 10,758,231 on Sep. 1, 2020, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled 37 Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
   (a) a housing having an open proximal end and a closed distal end, wherein the housing defines a gap that extends from the open proximal end to the closed distal end and is configured to receive a portion of an end effector of a surgical stapler;
   (b) a platform supported by the housing, wherein the platform is exposed within the gap, wherein the platform includes:
      (i) a first platform side configured to support a first buttress, and
      (ii) a second platform side configured to support a second buttress; and
   (c) a cavity arranged at a distal end of the platform, wherein the cavity opens to the first platform side and extends toward the second platform side, wherein the cavity is defined at least in part by a wall that extends transversely outwardly from the platform such that at least a portion of the cavity is disposed transversely outwardly from the platform,
   wherein the cavity is configured to receive a curved distal tip of the end effector therein when the end effector is clamped on the platform.

2. The apparatus of claim 1, wherein the cavity additionally opens to the second platform side.

3. The apparatus of claim 1, wherein the cavity extends longitudinally in alignment with a longitudinal centerline of the platform.

4. The apparatus of claim 1, wherein the cavity is located proximal to the closed distal end of the housing.

5. The apparatus of claim 1, wherein the platform is configured to support the first and second buttresses such that distal ends of the buttresses are proximal to the cavity.

6. The apparatus of claim 1, wherein the cavity is configured to receive the curved distal tip of the end effector without contacting the curved distal tip.

7. The apparatus of claim 1, further comprising an angled surface arranged at the distal end of the platform, wherein the angled surface extends along at least one lateral side of the cavity and transversely away from the distal end of the platform, wherein the angled surface is configured to engage a portion of the end effector.

8. The apparatus of claim 7, wherein the cavity opens to the first platform side and to the second platform side, wherein the apparatus further comprises: (a) a first angled surface arranged at a distal end of the first platform side; and (b) a second angled surface arranged at a distal end of the second platform side, wherein the cavity extends through the first and second angled surfaces.

9. An assembly comprising:
   (a) a surgical stapler having an end effector, wherein the end effector comprises:
      (i) a first jaw having a curved distal tip, and
      (ii) a second jaw; and
   (b) the apparatus of claim 1, wherein the cavity is configured to receive the curved distal tip therein when the end effector is clamped on the platform such that the first jaw engages the first buttress and the second jaw engages the second buttress.

10. The assembly of claim 9, wherein the cavity is configured to receive the curved distal tip therein before the first jaw fully engages the first buttress.

11. The assembly of claim 9, wherein the curved distal tip of the first jaw extends distal to a distal tip of the second jaw.

12. The assembly of claim 9, wherein the first jaw supports an anvil surface, wherein the second jaw is configured to support a staple cartridge having a deck with a plurality of staple openings, wherein the curved distal tip is configured to extend transversely beyond the deck in a direction away from the anvil surface and without contacting the staple cartridge when the end effector is clamped on the platform.

13. The apparatus of claim 1, wherein the cavity is closed in a distal direction by a portion of the housing.

14. The apparatus of claim 1, wherein the platform is recessed within the gap relative to opposed first and second outer sides of the housing, wherein the wall extends transversely between the first platform side and the first outer side of the housing.

15. The apparatus of claim 1, wherein a proximal end of the cavity has a smaller lateral width than an adjacent distal portion of the platform.

16. An apparatus comprising:
   (a) a housing having an open proximal end and a closed distal end, wherein the housing defines a gap that extends from the open proximal end to the closed distal end and is configured to receive a portion of an end effector of a surgical stapler;
   (b) a platform supported by the housing, wherein the platform is exposed within the gap;
   (c) a first buttress disposed on a first side of the platform;
   (d) a second buttress disposed on a second side of the platform; and
   (e) a cavity arranged at a distal end of the platform, wherein the cavity opens to the first side of the platform and to the second side of the platform, wherein the cavity is defined by a wall that extends transversely beyond the platform and terminates outwardly at an angled surface, wherein the angled surface is configured to engage a portion of the end effector,
   wherein the cavity is configured to receive a curved distal tip of the end effector therein when the end effector is clamped on the platform such that the end effector engages the first and second buttresses.

17. The apparatus of claim 16, wherein the cavity extends transversely through a full thickness of the apparatus.

18. The apparatus of claim 16, wherein at least a proximal end of the cavity is recessed relative to an outer surface of the housing.

19. A method of securing first and second buttresses to an end effector of a surgical stapler with a buttress applier cartridge, wherein the end effector comprises a first jaw having a curved distal tip and a second jaw, wherein the buttress applier cartridge includes a platform and a cavity disposed at a distal end of the platform, wherein the cavity is closed in a distal direction by a portion of the buttress applier cartridge and the cavity is defined at least in part by a wall that extends transversely outwardly from the platform such that at least a portion of the cavity is disposed transversely outwardly from the platform, the method comprising:
   (a) positioning the platform between the first and second jaws while the jaws are in an open state;
   (b) closing the end effector to clamp the platform between the first and second jaws, wherein in response to the clamping action of the end effector:
      (i) the first jaw engages the first buttress,
      (ii) the second jaw engages the second buttress, and
      (iii) the curved distal tip of the first jaw is received into the cavity of the buttress applier cartridge;
   (c) opening the end effector to thereby remove the first and second buttresses from the platform; and
   (d) removing the platform from between the first and second jaws while the first and second buttresses remain secured to the first and second jaws.

20. The method of claim 19, wherein the curved distal tip of the first jaw is resiliently deflectable from a preformed shape, wherein the curved distal tip is received into the cavity of the buttress applier cartridge without deflecting from the preformed shape.

* * * * *